(12) United States Patent
Chabriere et al.

(10) Patent No.: US 7,718,773 B2
(45) Date of Patent: May 18, 2010

(54) PHOSPHATE-BINDING PROTEIN, PHARMACEUTICAL COMPOSITIONS CONTAINING SAME AND USE THEREOF

(75) Inventors: Eric Chabriere, Nancy (FR); Carlos Contreras-Martel, Saint Egreve (FR); Juan Fontecilla-Camps, Les Adrets (FR)

(73) Assignees: Centre National de le Recherche Scientifique, Paris (FR); Universite Henri Poincare Nancy I, Nancy (FR)

( * ) Notice: Subject to any disclaimer, the term of this patent is extended or adjusted under 35 U.S.C. 154(b) by 231 days.

(21) Appl. No.: 10/577,658

(22) PCT Filed: Oct. 29, 2004

(86) PCT No.: PCT/FR2004/002797

§ 371 (c)(1),
(2), (4) Date: Jan. 17, 2004

(87) PCT Pub. No.: WO2005/042572

PCT Pub. Date: May 12, 2005

(65) Prior Publication Data

US 2007/0196879 A1    Aug. 23, 2007

(30) Foreign Application Priority Data

Oct. 30, 2003   (FR) .................................. 03 12729

(51) Int. Cl.
*A61K 35/14*    (2006.01)
*A61K 38/16*    (2006.01)
*A61K 38/00*    (2006.01)
*C07K 1/00*     (2006.01)
*C12P 21/06*    (2006.01)
*C12N 15/09*    (2006.01)
*G01N 33/53*    (2006.01)
*C12N 15/00*    (2006.01)

(52) U.S. Cl. ....................... 530/380; 530/350; 530/352; 514/12; 435/69.1; 435/69.2; 435/320.1; 435/7.1; 435/7.9; 435/7.92

(58) Field of Classification Search ....................... None
See application file for complete search history.

(56) References Cited

U.S. PATENT DOCUMENTS

2003/0158115 A1    8/2003   Toback et al.

OTHER PUBLICATIONS

Database Uniprot 'Online!; EB; Oct. 10, 2003; XP002275669; Database accession No. P35482 (whole document).
Kawasaki K., et al,: "Mineralized tissue and vertebrate evolution: the secretory calcium-binding phosphoprotein gene cluster," P.N.A.S., vol. 100, No. 7, Apr. 1, 2003 (Apr. 1, 2004), pp. 4060-4065, XP002275668 whole document.

*Primary Examiner*—Olga N Chernyshev
(74) *Attorney, Agent, or Firm*—Young & Thompson

(57) ABSTRACT

A protein includes or is formed by: (i) SEQ ID NO: 1; (ii) any sequence that is derived from sequence SEQ ID NO: 1, for example, by the substitution, removal or addition of one or more amino acids, on the condition that the derivative sequence binds to the phosphate; (iii) any sequence that is homologous to sequence SEQ ID NO: 1, preferably having a homology of at least approximately 80% with sequence SEQ ID NO: 1, on the condition that the homologous sequence binds to the phosphate; or (iv) any fragment of one of the aforementioned sequences on the condition that the fragment binds to the phosphate, such as any fragment comprising at least approximately 20 contiguous amino acids in sequence SEQ ID NO: 1.

18 Claims, 46 Drawing Sheets

| | | | | | | | | | | |
|---|---|---|---|---|---|---|---|---|---|---|
| ATOM | 1 | CB | SER | A | 1 | 24.666 | 45.653 | 14.370 | 1.00 | 26.15 | A |
| ATOM | 2 | OG | SER | A | 1 | 25.258 | 46.028 | 13.130 | 1.00 | 38.82 | A |
| ATOM | 3 | C | SER | A | 1 | 22.519 | 45.324 | 15.622 | 1.00 | 20.30 | A |
| ATOM | 4 | O | SER | A | 1 | 21.889 | 46.093 | 16.367 | 1.00 | 18.83 | A |
| ATOM | 5 | N | SER | A | 1 | 22.817 | 47.273 | 14.074 | 1.00 | 22.37 | A |
| ATOM | 6 | CA | SER | A | 1 | 23.146 | 45.831 | 14.317 | 1.00 | 22.87 | A |
| ATOM | 7 | N | ILE | A | 2 | 22.676 | 44.027 | 15.878 | 1.00 | 14.00 | A |
| ATOM | 8 | CA | ILE | A | 2 | 22.149 | 43.401 | 17.092 | 1.00 | 13.36 | A |
| ATOM | 9 | CB | ILE | A | 2 | 21.747 | 41.923 | 16.828 | 1.00 | 14.04 | A |
| ATOM | 10 | CG2 | ILE | A | 2 | 21.536 | 41.191 | 18.155 | 1.00 | 9.05 | A |
| ATOM | 11 | CG1 | ILE | A | 2 | 20.458 | 41.872 | 15.988 | 1.00 | 13.38 | A |
| ATOM | 12 | CD1 | ILE | A | 2 | 20.173 | 40.501 | 15.357 | 1.00 | 14.27 | A |
| ATOM | 13 | C | ILE | A | 2 | 23.303 | 43.459 | 18.083 | 1.00 | 12.32 | A |
| ATOM | 14 | O | ILE | A | 2 | 24.376 | 42.890 | 17.847 | 1.00 | 14.26 | A |
| ATOM | 15 | N | ASP | A | 3 | 23.075 | 44.122 | 19.205 | 1.00 | 13.19 | A |
| ATOM | 16 | CA | ASP | A | 3 | 24.134 | 44.331 | 20.193 | 1.00 | 11.15 | A |
| ATOM | 17 | CB | ASP | A | 3 | 24.149 | 45.830 | 20.578 | 1.00 | 12.52 | A |
| ATOM | 18 | CG | ASP | A | 3 | 24.268 | 46.744 | 19.351 | 1.00 | 11.70 | A |
| ATOM | 19 | OD1 | ASP | A | 3 | 25.289 | 46.618 | 18.642 | 1.00 | 11.97 | A |
| ATOM | 20 | OD2 | ASP | A | 3 | 23.356 | 47.569 | 19.094 | 1.00 | 13.82 | A |
| ATOM | 21 | C | ASP | A | 3 | 23.981 | 43.508 | 21.456 | 1.00 | 11.88 | A |
| ATOM | 22 | O | ASP | A | 3 | 22.947 | 43.577 | 22.116 | 1.00 | 11.48 | A |
| ATOM | 23 | N | GLY | A | 4 | 25.022 | 42.763 | 21.800 | 1.00 | 9.46 | A |
| ATOM | 24 | CA | GLY | A | 4 | 24.973 | 41.947 | 23.007 | 1.00 | 10.97 | A |
| ATOM | 25 | C | GLY | A | 4 | 26.303 | 41.966 | 23.740 | 1.00 | 8.48 | A |
| ATOM | 26 | O | GLY | A | 4 | 27.314 | 42.413 | 23.200 | 1.00 | 9.87 | A |
| ATOM | 27 | N | GLY | A | 5 | 26.296 | 41.496 | 24.987 | 1.00 | 11.77 | A |
| ATOM | 28 | CA | GLY | A | 5 | 27.511 | 41.489 | 25.785 | 1.00 | 4.85 | A |
| ATOM | 29 | C | GLY | A | 5 | 27.163 | 41.000 | 27.186 | 1.00 | 8.06 | A |
| ATOM | 30 | O | GLY | A | 5 | 26.009 | 40.610 | 27.447 | 1.00 | 9.13 | A |
| ATOM | 31 | N | GLY | A | 6 | 28.144 | 41.021 | 28.089 | 1.00 | 9.80 | A |
| ATOM | 32 | CA | GLY | A | 6 | 27.898 | 40.589 | 29.458 | 1.00 | 9.86 | A |
| ATOM | 33 | C | GLY | A | 6 | 28.970 | 39.679 | 30.014 | 1.00 | 7.11 | A |
| ATOM | 34 | O | GLY | A | 6 | 30.150 | 40.030 | 30.000 | 1.00 | 8.89 | A |
| ATOM | 35 | N | ALA | A | 7 | 28.567 | 38.518 | 30.525 | 1.00 | 9.08 | A |
| ATOM | 36 | CA | ALA | A | 7 | 29.509 | 37.540 | 31.079 | 1.00 | 8.69 | A |
| ATOM | 37 | CB | ALA | A | 7 | 28.814 | 36.168 | 31.195 | 1.00 | 7.94 | A |
| ATOM | 38 | C | ALA | A | 7 | 30.811 | 37.363 | 30.277 | 1.00 | 9.69 | A |
| ATOM | 39 | O | ALA | A | 7 | 30.781 | 37.212 | 29.050 | 1.00 | 7.30 | A |
| ATOM | 40 | N | THR | A | 8 | 31.941 | 37.367 | 30.981 | 1.00 | 7.56 | A |
| ATOM | 41 | CA | THR | A | 8 | 33.236 | 37.135 | 30.338 | 1.00 | 7.21 | A |
| ATOM | 42 | CB | THR | A | 8 | 34.402 | 37.865 | 31.065 | 1.00 | 8.00 | A |
| ATOM | 43 | OG1 | THR | A | 8 | 34.532 | 37.344 | 32.402 | 1.00 | 9.83 | A |
| ATOM | 44 | CG2 | THR | A | 8 | 34.123 | 39.388 | 31.139 | 1.00 | 10.68 | A |
| ATOM | 45 | C | THR | A | 8 | 33.542 | 35.624 | 30.340 | 1.00 | 5.67 | A |
| ATOM | 46 | O | THR | A | 8 | 34.355 | 35.168 | 29.552 | 1.00 | 8.00 | A |
| ATOM | 47 | N | LEU | A | 9 | 32.885 | 34.842 | 31.195 | 1.00 | 6.65 | A |
| ATOM | 48 | CA | LEU | A | 9 | 33.190 | 33.389 | 31.224 | 1.00 | 9.98 | A |
| ATOM | 49 | CB | LEU | A | 9 | 32.275 | 32.649 | 32.238 | 1.00 | 10.55 | A |
| ATOM | 50 | CG | LEU | A | 9 | 32.400 | 31.109 | 32.271 | 1.00 | 11.53 | A |
| ATOM | 51 | CD1 | LEU | A | 9 | 32.200 | 30.566 | 33.699 | 1.00 | 10.77 | A |
| ATOM | 52 | CD2 | LEU | A | 9 | 31.356 | 30.503 | 31.300 | 1.00 | 6.94 | A |
| ATOM | 53 | C | LEU | A | 9 | 33.103 | 32.755 | 29.817 | 1.00 | 10.91 | A |
| ATOM | 54 | O | LEU | A | 9 | 33.985 | 31.970 | 29.421 | 1.00 | 9.67 | A |
| ATOM | 55 | N | PRO | A | 10 | 32.051 | 33.088 | 29.040 | 1.00 | 6.59 | A |
| ATOM | 56 | CD | PRO | A | 10 | 30.763 | 33.664 | 29.485 | 1.00 | 8.09 | A |
| ATOM | 57 | CA | PRO | A | 10 | 31.915 | 32.521 | 27.686 | 1.00 | 7.68 | A |
| ATOM | 58 | CB | PRO | A | 10 | 30.428 | 32.218 | 27.611 | 1.00 | 11.73 | A |
| ATOM | 59 | CG | PRO | A | 10 | 29.845 | 33.467 | 28.251 | 1.00 | 8.40 | A |
| ATOM | 60 | C | PRO | A | 10 | 32.317 | 33.504 | 26.579 | 1.00 | 8.72 | A |
| ATOM | 61 | O | PRO | A | 10 | 32.040 | 33.263 | 25.396 | 1.00 | 9.01 | A |
| ATOM | 62 | N | GLU | A | 11 | 33.003 | 34.589 | 26.928 | 1.00 | 5.35 | A |
| ATOM | 63 | CA | GLU | A | 11 | 33.325 | 35.565 | 25.896 | 1.00 | 8.04 | A |
| ATOM | 64 | CB | GLU | A | 11 | 33.978 | 36.829 | 26.493 | 1.00 | 12.60 | A |
| ATOM | 65 | CG | GLU | A | 11 | 35.380 | 36.672 | 27.001 | 1.00 | 21.32 | A |
| ATOM | 66 | CD | GLU | A | 11 | 35.994 | 38.013 | 27.391 | 1.00 | 26.61 | A |
| ATOM | 67 | OE1 | GLU | A | 11 | 35.264 | 38.873 | 27.920 | 1.00 | 30.93 | A |
| ATOM | 68 | OE2 | GLU | A | 11 | 37.203 | 38.202 | 27.176 | 1.00 | 31.32 | A |
| ATOM | 69 | C | GLU | A | 11 | 34.143 | 35.066 | 24.709 | 1.00 | 10.00 | A |
| ATOM | 70 | O | GLU | A | 11 | 33.866 | 35.464 | 23.563 | 1.00 | 8.68 | A |
| ATOM | 71 | N | LYS | A | 12 | 35.134 | 34.215 | 24.957 | 1.00 | 8.65 | A |
| ATOM | 72 | CA | LYS | A | 12 | 35.935 | 33.678 | 23.850 | 1.00 | 10.43 | A |
| ATOM | 73 | CB | LYS | A | 12 | 37.081 | 32.840 | 24.374 | 1.00 | 11.05 | A |
| ATOM | 74 | CG | LYS | A | 12 | 38.151 | 33.646 | 25.090 | 1.00 | 9.26 | A |
| ATOM | 75 | CD | LYS | A | 12 | 39.117 | 32.622 | 25.673 | 1.00 | 17.64 | A |

FIGURE 5

| | | | | | | | | | | |
|---|---|---|---|---|---|---|---|---|---|---|
| ATOM | 76 | CE | LYS | A | 12 | 40.293 | 33.277 | 26.307 | 1.00 24.93 | A |
| ATOM | 77 | NZ | LYS | A | 12 | 41.298 | 32.237 | 26.600 | 1.00 25.96 | A |
| ATOM | 78 | C | LYS | A | 12 | 35.079 | 32.830 | 22.934 | 1.00 11.17 | A |
| ATOM | 79 | O | LYS | A | 12 | 35.339 | 32.726 | 21.736 | 1.00 8.79 | A |
| ATOM | 80 | N | LEU | A | 13 | 34.071 | 32.176 | 23.498 | 1.00 7.67 | A |
| ATOM | 81 | CA | LEU | A | 13 | 33.189 | 31.383 | 22.669 | 1.00 10.04 | A |
| ATOM | 82 | CB | LEU | A | 13 | 32.230 | 30.549 | 23.534 | 1.00 8.86 | A |
| ATOM | 83 | CG | LEU | A | 13 | 31.082 | 29.888 | 22.769 | 1.00 8.97 | A |
| ATOM | 84 | CD1 | LEU | A | 13 | 31.649 | 28.807 | 21.805 | 1.00 12.12 | A |
| ATOM | 85 | CD2 | LEU | A | 13 | 30.101 | 29.268 | 23.753 | 1.00 12.69 | A |
| ATOM | 86 | C | LEU | A | 13 | 32.371 | 32.292 | 21.750 | 1.00 9.01 | A |
| ATOM | 87 | O | LEU | A | 13 | 32.293 | 32.064 | 20.536 | 1.00 10.60 | A |
| ATOM | 88 | N | TYR | A | 14 | 31.761 | 33.329 | 22.305 | 1.00 10.47 | A |
| ATOM | 89 | CA | TYR | A | 14 | 30.920 | 34.195 | 21.482 | 1.00 9.03 | A |
| ATOM | 90 | CB | TYR | A | 14 | 30.029 | 35.087 | 22.352 | 1.00 8.38 | A |
| ATOM | 91 | CG | TYR | A | 14 | 29.091 | 34.293 | 23.253 | 1.00 11.48 | A |
| ATOM | 92 | CD1 | TYR | A | 14 | 28.499 | 33.109 | 22.806 | 1.00 12.01 | A |
| ATOM | 93 | CE1 | TYR | A | 14 | 27.671 | 32.341 | 23.642 | 1.00 10.45 | A |
| ATOM | 94 | CD2 | TYR | A | 14 | 28.824 | 34.706 | 24.564 | 1.00 10.30 | A |
| ATOM | 95 | CE2 | TYR | A | 14 | 27.998 | 33.948 | 25.403 | 1.00 10.35 | A |
| ATOM | 96 | CZ | TYR | A | 14 | 27.430 | 32.766 | 24.933 | 1.00 8.21 | A |
| ATOM | 97 | OH | TYR | A | 14 | 26.628 | 32.014 | 25.757 | 1.00 8.65 | A |
| ATOM | 98 | C | TYR | A | 14 | 31.715 | 35.036 | 20.489 | 1.00 9.67 | A |
| ATOM | 99 | O | TYR | A | 14 | 31.142 | 35.538 | 19.515 | 1.00 8.36 | A |
| ATOM | 100 | N | LEU | A | 15 | 33.021 | 35.184 | 20.738 | 1.00 8.53 | A |
| ATOM | 101 | CA | LEU | A | 15 | 33.904 | 35.936 | 19.838 | 1.00 9.45 | A |
| ATOM | 102 | CB | LEU | A | 15 | 35.087 | 36.564 | 20.601 | 1.00 8.09 | A |
| ATOM | 103 | CG | LEU | A | 15 | 34.742 | 37.802 | 21.433 | 1.00 14.85 | A |
| ATOM | 104 | CD1 | LEU | A | 15 | 35.932 | 38.141 | 22.306 | 1.00 16.07 | A |
| ATOM | 105 | CD2 | LEU | A | 15 | 34.364 | 38.990 | 20.510 | 1.00 12.61 | A |
| ATOM | 106 | C | LEU | A | 15 | 34.467 | 35.018 | 18.756 | 1.00 16.00 | A |
| ATOM | 107 | O | LEU | A | 15 | 35.174 | 35.466 | 17.859 | 1.00 16.13 | A |
| ATOM | 108 | N | THR | A | 16 | 34.178 | 33.729 | 18.848 | 1.00 11.70 | A |
| ATOM | 109 | CA | THR | A | 16 | 34.681 | 32.791 | 17.853 | 1.00 11.09 | A |
| ATOM | 110 | CB | THR | A | 16 | 34.523 | 31.334 | 18.371 | 1.00 11.33 | A |
| ATOM | 111 | OG1 | THR | A | 16 | 35.406 | 31.142 | 19.484 | 1.00 13.08 | A |
| ATOM | 112 | CG2 | THR | A | 16 | 34.848 | 30.314 | 17.291 | 1.00 11.23 | A |
| ATOM | 113 | C | THR | A | 16 | 33.906 | 32.997 | 16.549 | 1.00 12.10 | A |
| ATOM | 114 | O | THR | A | 16 | 32.671 | 32.996 | 16.540 | 1.00 12.20 | A |
| ATOM | 115 | N | PRO | A | 17 | 34.620 | 33.158 | 15.420 | 1.00 14.18 | A |
| ATOM | 116 | CD | PRO | A | 17 | 36.085 | 33.162 | 15.251 | 1.00 14.83 | A |
| ATOM | 117 | CA | PRO | A | 17 | 33.933 | 33.367 | 14.137 | 1.00 17.90 | A |
| ATOM | 118 | CB | PRO | A | 17 | 35.068 | 33.292 | 13.113 | 1.00 20.97 | A |
| ATOM | 119 | CG | PRO | A | 17 | 36.251 | 33.842 | 13.890 | 1.00 21.64 | A |
| ATOM | 120 | C | PRO | A | 17 | 32.830 | 32.341 | 13.854 | 1.00 14.42 | A |
| ATOM | 121 | O | PRO | A | 17 | 33.027 | 31.143 | 14.066 | 1.00 14.18 | A |
| ATOM | 122 | N | ASP | A | 18 | 31.673 | 32.836 | 13.414 | 1.00 15.17 | A |
| ATOM | 123 | CA | ASP | A | 18 | 30.515 | 32.020 | 13.058 | 1.00 19.19 | A |
| ATOM | 124 | CB | ASP | A | 18 | 30.932 | 30.829 | 12.169 | 1.00 23.04 | A |
| ATOM | 125 | CG | ASP | A | 18 | 31.649 | 31.260 | 10.885 | 1.00 30.30 | A |
| ATOM | 126 | OD1 | ASP | A | 18 | 31.214 | 32.238 | 10.239 | 1.00 30.86 | A |
| ATOM | 127 | OD2 | ASP | A | 18 | 32.645 | 30.599 | 10.511 | 1.00 39.65 | A |
| ATOM | 128 | C | ASP | A | 18 | 29.657 | 31.479 | 14.212 | 1.00 13.08 | A |
| ATOM | 129 | O | ASP | A | 18 | 28.651 | 30.833 | 13.958 | 1.00 13.28 | A |
| ATOM | 130 | N | VAL | A | 19 | 30.041 | 31.709 | 15.466 | 1.00 13.07 | A |
| ATOM | 131 | CA | VAL | A | 19 | 29.199 | 31.221 | 16.570 | 1.00 8.94 | A |
| ATOM | 132 | CB | VAL | A | 19 | 29.976 | 31.225 | 17.911 | 1.00 9.65 | A |
| ATOM | 133 | CG1 | VAL | A | 19 | 29.014 | 31.123 | 19.098 | 1.00 11.73 | A |
| ATOM | 134 | CG2 | VAL | A | 19 | 30.930 | 30.026 | 17.923 | 1.00 11.99 | A |
| ATOM | 135 | C | VAL | A | 19 | 27.971 | 32.126 | 16.613 | 1.00 11.81 | A |
| ATOM | 136 | O | VAL | A | 19 | 26.829 | 31.655 | 16.707 | 1.00 11.21 | A |
| ATOM | 137 | N | LEU | A | 20 | 28.198 | 33.434 | 16.567 | 1.00 10.93 | A |
| ATOM | 138 | CA | LEU | A | 20 | 27.077 | 34.363 | 16.486 | 1.00 8.58 | A |
| ATOM | 139 | CB | LEU | A | 20 | 27.439 | 35.730 | 17.084 | 1.00 13.44 | A |
| ATOM | 140 | CG | LEU | A | 20 | 27.677 | 35.767 | 18.601 | 1.00 14.24 | A |
| ATOM | 141 | CD1 | LEU | A | 20 | 27.863 | 37.222 | 19.084 | 1.00 13.26 | A |
| ATOM | 142 | CD2 | LEU | A | 20 | 26.480 | 35.130 | 19.315 | 1.00 11.94 | A |
| ATOM | 143 | C | LEU | A | 20 | 26.857 | 34.470 | 14.969 | 1.00 15.21 | A |
| ATOM | 144 | O | LEU | A | 20 | 27.836 | 34.550 | 14.196 | 1.00 11.72 | A |
| ATOM | 145 | N | THR | A | 21 | 25.596 | 34.455 | 14.540 | 1.00 14.05 | A |
| ATOM | 146 | CA | THR | A | 21 | 25.268 | 34.511 | 13.114 | 1.00 12.27 | A |
| ATOM | 147 | CB | THR | A | 21 | 24.006 | 33.653 | 12.865 | 1.00 16.46 | A |
| ATOM | 148 | OG1 | THR | A | 21 | 22.966 | 34.044 | 13.774 | 1.00 13.53 | A |
| ATOM | 149 | CG2 | THR | A | 21 | 24.326 | 32.173 | 13.121 | 1.00 17.80 | A |
| ATOM | 150 | C | THR | A | 21 | 25.121 | 35.937 | 12.509 | 1.00 14.67 | A |
| ATOM | 151 | O | THR | A | 21 | 25.452 | 36.928 | 13.148 | 1.00 12.04 | A |

FIGURE 5 (continued)

| | | | | | | | | | |
|---|---|---|---|---|---|---|---|---|---|
| ATOM | 152 | N | ALA | A | 22 | 24.663 | 36.037 | 11.265 | 1.00 12.98 A |
| ATOM | 153 | CA | ALA | A | 22 | 24.523 | 37.335 | 10.594 | 1.00 12.25 A |
| ATOM | 154 | CB | ALA | A | 22 | 23.913 | 37.146 | 9.208 | 1.00 15.06 A |
| ATOM | 155 | C | ALA | A | 22 | 23.749 | 38.418 | 11.337 | 1.00 10.99 A |
| ATOM | 156 | O | ALA | A | 22 | 22.688 | 38.174 | 11.916 | 1.00 15.12 A |
| ATOM | 157 | N | GLY | A | 23 | 24.285 | 39.636 | 11.292 | 1.00 13.67 A |
| ATOM | 158 | CA | GLY | A | 23 | 23.631 | 40.753 | 11.951 | 1.00 14.86 A |
| ATOM | 159 | C | GLY | A | 23 | 24.068 | 41.057 | 13.371 | 1.00 14.29 A |
| ATOM | 160 | O | GLY | A | 23 | 23.775 | 42.138 | 13.894 | 1.00 15.41 A |
| ATOM | 161 | N | PHE | A | 24 | 24.760 | 40.116 | 14.001 | 1.00 12.44 A |
| ATOM | 162 | CA | PHE | A | 24 | 25.238 | 40.283 | 15.363 | 1.00 14.48 A |
| ATOM | 163 | CB | PHE | A | 24 | 25.424 | 38.899 | 16.020 | 1.00 9.89 A |
| ATOM | 164 | CG | PHE | A | 24 | 24.156 | 38.276 | 16.527 | 1.00 12.35 A |
| ATOM | 165 | CD1 | PHE | A | 24 | 23.225 | 37.734 | 15.644 | 1.00 6.46 A |
| ATOM | 166 | CD2 | PHE | A | 24 | 23.888 | 38.237 | 17.898 | 1.00 12.73 A |
| ATOM | 167 | CE1 | PHE | A | 24 | 22.035 | 37.153 | 16.125 | 1.00 11.12 A |
| ATOM | 168 | CE2 | PHE | A | 24 | 22.695 | 37.662 | 18.397 | 1.00 7.42 A |
| ATOM | 169 | CZ | PHE | A | 24 | 21.772 | 37.118 | 17.502 | 1.00 11.79 A |
| ATOM | 170 | C | PHE | A | 24 | 26.584 | 41.030 | 15.444 | 1.00 14.36 A |
| ATOM | 171 | O | PHE | A | 24 | 27.569 | 40.592 | 14.850 | 1.00 12.41 A |
| ATOM | 172 | N | ALA | A | 25 | 26.630 | 42.141 | 16.183 | 1.00 14.60 A |
| ATOM | 173 | CA | ALA | A | 25 | 27.881 | 42.875 | 16.378 | 1.00 13.54 A |
| ATOM | 174 | CB | ALA | A | 25 | 27.606 | 44.233 | 17.024 | 1.00 15.19 A |
| ATOM | 175 | C | ALA | A | 25 | 28.752 | 42.031 | 17.315 | 1.00 12.48 A |
| ATOM | 176 | O | ALA | A | 25 | 28.240 | 41.155 | 18.023 | 1.00 12.61 A |
| ATOM | 177 | N | PRO | A | 26 | 30.067 | 42.289 | 17.348 | 1.00 11.27 A |
| ATOM | 178 | CD | PRO | A | 26 | 30.837 | 43.202 | 16.476 | 1.00 13.96 A |
| ATOM | 179 | CA | PRO | A | 26 | 30.952 | 41.507 | 18.231 | 1.00 12.70 A |
| ATOM | 180 | CB | PRO | A | 26 | 32.334 | 42.117 | 17.989 | 1.00 14.99 A |
| ATOM | 181 | CG | PRO | A | 26 | 32.241 | 42.582 | 16.519 | 1.00 19.22 A |
| ATOM | 182 | C | PRO | A | 26 | 30.536 | 41.602 | 19.699 | 1.00 10.57 A |
| ATOM | 183 | O | PRO | A | 26 | 30.222 | 42.681 | 20.192 | 1.00 10.54 A |
| ATOM | 184 | N | TYR | A | 27 | 30.529 | 40.456 | 20.367 | 1.00 8.04 A |
| ATOM | 185 | CA | TYR | A | 27 | 30.161 | 40.345 | 21.793 | 1.00 9.13 A |
| ATOM | 186 | CB | TYR | A | 27 | 30.294 | 38.886 | 22.231 | 1.00 8.74 A |
| ATOM | 187 | CG | TYR | A | 27 | 29.824 | 38.612 | 23.648 | 1.00 5.12 A |
| ATOM | 188 | CD1 | TYR | A | 27 | 28.469 | 38.512 | 23.938 | 1.00 6.81 A |
| ATOM | 189 | CE1 | TYR | A | 27 | 28.024 | 38.224 | 25.247 | 1.00 9.00 A |
| ATOM | 190 | CD2 | TYR | A | 27 | 30.741 | 38.423 | 24.682 | 1.00 5.70 A |
| ATOM | 191 | CE2 | TYR | A | 27 | 30.310 | 38.131 | 25.992 | 1.00 7.78 A |
| ATOM | 192 | CZ | TYR | A | 27 | 28.948 | 38.032 | 26.259 | 1.00 9.36 A |
| ATOM | 193 | OH | TYR | A | 27 | 28.502 | 37.709 | 27.532 | 1.00 8.37 A |
| ATOM | 194 | C | TYR | A | 27 | 31.081 | 41.207 | 22.675 | 1.00 10.49 A |
| ATOM | 195 | O | TYR | A | 27 | 32.297 | 41.207 | 22.494 | 1.00 9.91 A |
| ATOM | 196 | N | ILE | A | 28 | 30.510 | 41.931 | 23.635 | 1.00 8.97 A |
| ATOM | 197 | CA | ILE | A | 28 | 31.324 | 42.765 | 24.517 | 1.00 12.31 A |
| ATOM | 198 | CB | ILE | A | 28 | 30.801 | 44.225 | 24.521 | 1.00 13.61 A |
| ATOM | 199 | CG2 | ILE | A | 28 | 31.657 | 45.098 | 25.459 | 1.00 13.95 A |
| ATOM | 200 | CG1 | ILE | A | 28 | 30.871 | 44.793 | 23.095 | 1.00 11.91 A |
| ATOM | 201 | CD1 | ILE | A | 28 | 30.192 | 46.146 | 22.915 | 1.00 12.92 A |
| ATOM | 202 | C | ILE | A | 28 | 31.333 | 42.191 | 25.942 | 1.00 13.14 A |
| ATOM | 203 | O | ILE | A | 28 | 30.315 | 42.189 | 26.622 | 1.00 8.79 A |
| ATOM | 204 | N | GLY | A | 29 | 32.499 | 41.706 | 26.373 | 1.00 13.23 A |
| ATOM | 205 | CA | GLY | A | 29 | 32.630 | 41.105 | 27.695 | 1.00 15.83 A |
| ATOM | 206 | C | GLY | A | 29 | 32.868 | 42.127 | 28.791 | 1.00 16.10 A |
| ATOM | 207 | O | GLY | A | 29 | 33.915 | 42.794 | 28.826 | 1.00 12.27 A |
| ATOM | 208 | N | THR | A | 30 | 31.900 | 42.234 | 29.697 | 1.00 8.70 A |
| ATOM | 209 | CA | THR | A | 30 | 31.966 | 43.200 | 30.783 | 1.00 10.71 A |
| ATOM | 210 | CB | THR | A | 30 | 31.061 | 44.442 | 30.473 | 1.00 11.83 A |
| ATOM | 211 | OG1 | THR | A | 30 | 29.703 | 44.014 | 30.222 | 1.00 16.91 A |
| ATOM | 212 | CG2 | THR | A | 30 | 31.607 | 45.235 | 29.249 | 1.00 8.83 A |
| ATOM | 213 | C | THR | A | 30 | 31.538 | 42.640 | 32.147 | 1.00 11.78 A |
| ATOM | 214 | O | THR | A | 30 | 31.532 | 43.378 | 33.135 | 1.00 11.34 A |
| ATOM | 215 | N | GLY | A | 31 | 31.187 | 41.352 | 32.210 | 1.00 10.41 A |
| ATOM | 216 | CA | GLY | A | 31 | 30.729 | 40.789 | 33.473 | 1.00 8.40 A |
| ATOM | 217 | C | GLY | A | 31 | 29.208 | 40.604 | 33.467 | 1.00 9.64 A |
| ATOM | 218 | O | GLY | A | 31 | 28.478 | 41.396 | 32.862 | 1.00 8.01 A |
| ATOM | 219 | N | SER | A | 32 | 28.718 | 39.566 | 34.138 | 1.00 7.93 A |
| ATOM | 220 | CA | SER | A | 32 | 27.274 | 39.297 | 34.143 | 1.00 4.39 A |
| ATOM | 221 | CB | SER | A | 32 | 26.961 | 37.954 | 34.832 | 1.00 2.86 A |
| ATOM | 222 | OG | SER | A | 32 | 27.538 | 36.876 | 34.125 | 1.00 6.73 A |
| ATOM | 223 | C | SER | A | 32 | 26.440 | 40.386 | 34.793 | 1.00 7.61 A |
| ATOM | 224 | O | SER | A | 32 | 25.321 | 40.626 | 34.354 | 1.00 9.70 A |
| ATOM | 225 | N | GLY | A | 33 | 26.984 | 41.052 | 35.811 | 1.00 8.20 A |
| ATOM | 226 | CA | GLY | A | 33 | 26.256 | 42.121 | 36.506 | 1.00 6.91 A |

FIGURE 5 (continued)

| | | | | | | | | | | |
|---|---|---|---|---|---|---|---|---|---|---|
| ATOM | 227 | C | GLY | A | 33 | 25.942 | 43.235 | 35.524 | 1.00 9.16 | A |
| ATOM | 228 | O | GLY | A | 33 | 24.799 | 43.708 | 35.429 | 1.00 9.95 | A |
| ATOM | 229 | N | LYS | A | 34 | 26.943 | 43.633 | 34.749 | 1.00 10.60 | A |
| ATOM | 230 | CA | LYS | A | 34 | 26.710 | 44.681 | 33.758 | 1.00 8.52 | A |
| ATOM | 231 | CB | LYS | A | 34 | 28.040 | 45.240 | 33.250 | 1.00 7.07 | A |
| ATOM | 232 | CG | LYS | A | 34 | 28.667 | 46.220 | 34.250 | 1.00 12.80 | A |
| ATOM | 233 | CD | LYS | A | 34 | 29.957 | 46.854 | 33.703 | 1.00 10.66 | A |
| ATOM | 234 | CE | LYS | A | 34 | 30.597 | 47.768 | 34.748 | 1.00 10.90 | A |
| ATOM | 235 | NZ | LYS | A | 34 | 29.700 | 48.890 | 35.066 | 1.00 23.47 | A |
| ATOM | 236 | C | LYS | A | 34 | 25.848 | 44.201 | 32.601 | 1.00 12.94 | A |
| ATOM | 237 | O | LYS | A | 34 | 25.070 | 44.977 | 32.043 | 1.00 9.59 | A |
| ATOM | 238 | N | GLY | A | 35 | 25.983 | 42.928 | 32.236 | 1.00 9.69 | A |
| ATOM | 239 | CA | GLY | A | 35 | 25.158 | 42.386 | 31.162 | 1.00 7.50 | A |
| ATOM | 240 | C | GLY | A | 35 | 23.677 | 42.414 | 31.542 | 1.00 9.68 | A |
| ATOM | 241 | O | GLY | A | 35 | 22.831 | 42.767 | 30.717 | 1.00 9.00 | A |
| ATOM | 242 | N | LYS | A | 36 | 23.340 | 42.077 | 32.787 | 1.00 8.56 | A |
| ATOM | 243 | CA | LYS | A | 36 | 21.929 | 42.089 | 33.173 | 1.00 7.26 | A |
| ATOM | 244 | CB | LYS | A | 36 | 21.709 | 41.393 | 34.533 | 1.00 9.15 | A |
| ATOM | 245 | CG | LYS | A | 36 | 21.954 | 39.861 | 34.445 | 1.00 5.28 | A |
| ATOM | 246 | CD | LYS | A | 36 | 21.394 | 39.069 | 35.662 | 1.00 6.85 | A |
| ATOM | 247 | CE | LYS | A | 36 | 21.990 | 39.576 | 36.986 | 1.00 11.53 | A |
| ATOM | 248 | NZ | LYS | A | 36 | 21.397 | 38.945 | 38.221 | 1.00 11.99 | A |
| ATOM | 249 | C | LYS | A | 36 | 21.409 | 43.527 | 33.204 | 1.00 11.18 | A |
| ATOM | 250 | O | LYS | A | 36 | 20.311 | 43.787 | 32.724 | 1.00 14.03 | A |
| ATOM | 251 | N | ILE | A | 37 | 22.190 | 44.459 | 33.749 | 1.00 9.12 | A |
| ATOM | 252 | CA | ILE | A | 37 | 21.752 | 45.854 | 33.766 | 1.00 11.15 | A |
| ATOM | 253 | CB | ILE | A | 37 | 22.778 | 46.779 | 34.462 | 1.00 10.46 | A |
| ATOM | 254 | CG2 | ILE | A | 37 | 22.424 | 48.252 | 34.197 | 1.00 11.32 | A |
| ATOM | 255 | CG1 | ILE | A | 37 | 22.774 | 46.522 | 35.972 | 1.00 9.50 | A |
| ATOM | 256 | CD1 | ILE | A | 37 | 24.024 | 47.029 | 36.669 | 1.00 15.62 | A |
| ATOM | 257 | C | ILE | A | 37 | 21.563 | 46.368 | 32.325 | 1.00 11.78 | A |
| ATOM | 258 | O | ILE | A | 37 | 20.570 | 47.017 | 32.018 | 1.00 11.36 | A |
| ATOM | 259 | N | ALA | A | 38 | 22.518 | 46.071 | 31.452 | 1.00 9.31 | A |
| ATOM | 260 | CA | ALA | A | 38 | 22.438 | 46.539 | 30.063 | 1.00 10.19 | A |
| ATOM | 261 | CB | ALA | A | 38 | 23.650 | 46.016 | 29.269 | 1.00 10.93 | A |
| ATOM | 262 | C | ALA | A | 38 | 21.129 | 46.102 | 29.375 | 1.00 9.69 | A |
| ATOM | 263 | O | ALA | A | 38 | 20.447 | 46.899 | 28.712 | 1.00 8.41 | A |
| ATOM | 264 | N | PHE | A | 39 | 20.771 | 44.831 | 29.541 | 1.00 8.70 | A |
| ATOM | 265 | CA | PHE | A | 39 | 19.566 | 44.327 | 28.914 | 1.00 9.40 | A |
| ATOM | 266 | CB | PHE | A | 39 | 19.549 | 42.787 | 28.888 | 1.00 9.06 | A |
| ATOM | 267 | CG | PHE | A | 39 | 18.287 | 42.214 | 28.270 | 1.00 7.16 | A |
| ATOM | 268 | CD1 | PHE | A | 39 | 18.223 | 41.953 | 26.896 | 1.00 8.56 | A |
| ATOM | 269 | CD2 | PHE | A | 39 | 17.146 | 42.000 | 29.051 | 1.00 8.19 | A |
| ATOM | 270 | CE1 | PHE | A | 39 | 17.035 | 41.481 | 26.306 | 1.00 9.12 | A |
| ATOM | 271 | CE2 | PHE | A | 39 | 15.947 | 41.530 | 28.479 | 1.00 9.01 | A |
| ATOM | 272 | CZ | PHE | A | 39 | 15.888 | 41.269 | 27.101 | 1.00 8.28 | A |
| ATOM | 273 | C | PHE | A | 39 | 18.304 | 44.790 | 29.608 | 1.00 12.15 | A |
| ATOM | 274 | O | PHE | A | 39 | 17.398 | 45.313 | 28.972 | 1.00 10.76 | A |
| ATOM | 275 | N | LEU | A | 40 | 18.246 | 44.602 | 30.920 | 1.00 8.71 | A |
| ATOM | 276 | CA | LEU | A | 40 | 17.034 | 44.938 | 31.678 | 1.00 8.94 | A |
| ATOM | 277 | CB | LEU | A | 40 | 17.204 | 44.513 | 33.144 | 1.00 7.80 | A |
| ATOM | 278 | CG | LEU | A | 40 | 17.342 | 43.005 | 33.400 | 1.00 10.06 | A |
| ATOM | 279 | CD1 | LEU | A | 40 | 17.809 | 42.781 | 34.887 | 1.00 6.45 | A |
| ATOM | 280 | CD2 | LEU | A | 40 | 16.006 | 42.296 | 33.132 | 1.00 12.55 | A |
| ATOM | 281 | C | LEU | A | 40 | 16.626 | 46.403 | 31.632 | 1.00 10.63 | A |
| ATOM | 282 | O | LEU | A | 40 | 15.430 | 46.730 | 31.629 | 1.00 11.89 | A |
| ATOM | 283 | N | GLU | A | 41 | 17.604 | 47.291 | 31.586 | 1.00 10.88 | A |
| ATOM | 284 | CA | GLU | A | 41 | 17.294 | 48.717 | 31.551 | 1.00 9.10 | A |
| ATOM | 285 | CB | GLU | A | 41 | 18.053 | 49.436 | 32.669 | 1.00 13.20 | A |
| ATOM | 286 | CG | GLU | A | 41 | 17.802 | 48.829 | 34.036 | 1.00 11.00 | A |
| ATOM | 287 | CD | GLU | A | 41 | 18.671 | 49.429 | 35.131 | 1.00 22.54 | A |
| ATOM | 288 | OE1 | GLU | A | 41 | 18.975 | 48.713 | 36.103 | 1.00 27.36 | A |
| ATOM | 289 | OE2 | GLU | A | 41 | 19.037 | 50.616 | 35.043 | 1.00 22.49 | A |
| ATOM | 290 | C | GLU | A | 41 | 17.633 | 49.361 | 30.218 | 1.00 12.72 | A |
| ATOM | 291 | O | GLU | A | 41 | 17.505 | 50.576 | 30.066 | 1.00 13.60 | A |
| ATOM | 292 | N | ASN | A | 42 | 18.010 | 48.537 | 29.238 | 1.00 11.74 | A |
| ATOM | 293 | CA | ASN | A | 42 | 18.463 | 49.008 | 27.923 | 1.00 11.79 | A |
| ATOM | 294 | CB | ASN | A | 42 | 17.322 | 49.494 | 27.022 | 1.00 14.08 | A |
| ATOM | 295 | CG | ASN | A | 42 | 17.824 | 49.897 | 25.642 | 1.00 16.54 | A |
| ATOM | 296 | OD1 | ASN | A | 42 | 18.885 | 49.428 | 25.189 | 1.00 15.67 | A |
| ATOM | 297 | ND2 | ASN | A | 42 | 17.076 | 50.763 | 24.960 | 1.00 14.22 | A |
| ATOM | 298 | C | ASN | A | 42 | 19.486 | 50.126 | 28.091 | 1.00 16.68 | A |
| ATOM | 299 | O | ASN | A | 42 | 19.300 | 51.260 | 27.631 | 1.00 14.27 | A |
| ATOM | 300 | N | SER | A | 43 | 20.578 | 49.789 | 28.767 | 1.00 14.51 | A |

FIGURE 5 (continued)

| ATOM | 301 | CA | SER | A | 43 | 21.665 | 50.740 | 29.001 | 1.00 | 14.54 | A |
|------|-----|-----|-----|---|----|--------|--------|--------|------|-------|---|
| ATOM | 302 | CB | SER | A | 43 | 21.920 | 50.874 | 30.520 | 1.00 | 19.90 | A |
| ATOM | 303 | OG | SER | A | 43 | 20.922 | 51.662 | 31.162 | 1.00 | 26.26 | A |
| ATOM | 304 | C | SER | A | 43 | 22.965 | 50.327 | 28.302 | 1.00 | 13.78 | A |
| ATOM | 305 | O | SER | A | 43 | 23.790 | 49.633 | 28.891 | 1.00 | 10.60 | A |
| ATOM | 306 | N | TYR | A | 44 | 23.168 | 50.755 | 27.056 | 1.00 | 9.73 | A |
| ATOM | 307 | CA | TYR | A | 44 | 24.396 | 50.401 | 26.361 | 1.00 | 10.86 | A |
| ATOM | 308 | CB | TYR | A | 44 | 24.330 | 50.880 | 24.904 | 1.00 | 10.54 | A |
| ATOM | 309 | CG | TYR | A | 44 | 25.414 | 50.311 | 24.034 | 1.00 | 12.22 | A |
| ATOM | 310 | CD1 | TYR | A | 44 | 26.631 | 50.983 | 23.857 | 1.00 | 12.57 | A |
| ATOM | 311 | CE1 | TYR | A | 44 | 27.625 | 50.469 | 23.011 | 1.00 | 10.91 | A |
| ATOM | 312 | CD2 | TYR | A | 44 | 25.217 | 49.106 | 23.357 | 1.00 | 10.34 | A |
| ATOM | 313 | CE2 | TYR | A | 44 | 26.201 | 48.587 | 22.517 | 1.00 | 11.21 | A |
| ATOM | 314 | CZ | TYR | A | 44 | 27.394 | 49.267 | 22.347 | 1.00 | 14.12 | A |
| ATOM | 315 | OH | TYR | A | 44 | 28.357 | 48.725 | 21.524 | 1.00 | 11.54 | A |
| ATOM | 316 | C | TYR | A | 44 | 25.650 | 50.971 | 27.026 | 1.00 | 8.02 | A |
| ATOM | 317 | O | TYR | A | 44 | 26.775 | 50.515 | 26.756 | 1.00 | 10.36 | A |
| ATOM | 318 | N | ASN | A | 45 | 25.484 | 51.941 | 27.917 | 1.00 | 8.55 | A |
| ATOM | 319 | CA | ASN | A | 45 | 26.657 | 52.547 | 28.535 | 1.00 | 14.36 | A |
| ATOM | 320 | CB | ASN | A | 45 | 26.271 | 53.811 | 29.337 | 1.00 | 8.69 | A |
| ATOM | 321 | CG | ASN | A | 45 | 25.707 | 53.503 | 30.708 | 1.00 | 11.69 | A |
| ATOM | 322 | OD1 | ASN | A | 45 | 25.048 | 52.488 | 30.910 | 1.00 | 13.56 | A |
| ATOM | 323 | ND2 | ASN | A | 45 | 25.934 | 54.411 | 31.655 | 1.00 | 14.48 | A |
| ATOM | 324 | C | ASN | A | 45 | 27.423 | 51.535 | 29.388 | 1.00 | 13.91 | A |
| ATOM | 325 | O | ASN | A | 45 | 28.573 | 51.781 | 29.755 | 1.00 | 11.13 | A |
| ATOM | 326 | N | GLN | A | 46 | 26.788 | 50.393 | 29.681 | 1.00 | 8.83 | A |
| ATOM | 327 | CA | GLN | A | 46 | 27.462 | 49.337 | 30.435 | 1.00 | 11.62 | A |
| ATOM | 328 | CB | GLN | A | 46 | 26.421 | 48.390 | 31.080 | 1.00 | 10.13 | A |
| ATOM | 329 | CG | GLN | A | 46 | 25.487 | 49.076 | 32.083 | 1.00 | 14.66 | A |
| ATOM | 330 | CD | GLN | A | 46 | 26.259 | 49.792 | 33.170 | 1.00 | 18.72 | A |
| ATOM | 331 | OE1 | GLN | A | 46 | 26.983 | 49.165 | 33.937 | 1.00 | 18.65 | A |
| ATOM | 332 | NE2 | GLN | A | 46 | 26.133 | 51.116 | 33.228 | 1.00 | 16.99 | A |
| ATOM | 333 | C | GLN | A | 46 | 28.408 | 48.543 | 29.491 | 1.00 | 10.06 | A |
| ATOM | 334 | O | GLN | A | 46 | 29.275 | 47.818 | 29.956 | 1.00 | 10.43 | A |
| ATOM | 335 | N | PHE | A | 47 | 28.232 | 48.691 | 28.174 | 1.00 | 8.72 | A |
| ATOM | 336 | CA | PHE | A | 47 | 29.055 | 48.025 | 27.148 | 1.00 | 7.46 | A |
| ATOM | 337 | CB | PHE | A | 47 | 28.191 | 47.487 | 25.992 | 1.00 | 7.56 | A |
| ATOM | 338 | CG | PHE | A | 47 | 27.271 | 46.349 | 26.366 | 1.00 | 12.11 | A |
| ATOM | 339 | CD1 | PHE | A | 47 | 27.433 | 45.651 | 27.559 | 1.00 | 11.35 | A |
| ATOM | 340 | CD2 | PHE | A | 47 | 26.268 | 45.945 | 25.474 | 1.00 | 14.21 | A |
| ATOM | 341 | CE1 | PHE | A | 47 | 26.616 | 44.567 | 27.861 | 1.00 | 9.31 | A |
| ATOM | 342 | CE2 | PHE | A | 47 | 25.442 | 44.859 | 25.761 | 1.00 | 9.84 | A |
| ATOM | 343 | CZ | PHE | A | 47 | 25.617 | 44.167 | 26.959 | 1.00 | 10.19 | A |
| ATOM | 344 | C | PHE | A | 47 | 30.053 | 48.988 | 26.484 | 1.00 | 12.94 | A |
| ATOM | 345 | O | PHE | A | 47 | 31.109 | 48.580 | 26.022 | 1.00 | 14.11 | A |
| ATOM | 346 | N | GLY | A | 48 | 29.677 | 50.257 | 26.378 | 1.00 | 11.49 | A |
| ATOM | 347 | CA | GLY | A | 48 | 30.551 | 51.222 | 25.731 | 1.00 | 13.51 | A |
| ATOM | 348 | C | GLY | A | 48 | 30.027 | 52.642 | 25.833 | 1.00 | 15.44 | A |
| ATOM | 349 | O | GLY | A | 48 | 28.999 | 52.908 | 26.459 | 1.00 | 16.60 | A |
| ATOM | 350 | N | THR | A | 49 | 30.722 | 53.566 | 25.187 | 1.00 | 14.37 | A |
| ATOM | 351 | CA | THR | A | 49 | 30.333 | 54.967 | 25.256 | 1.00 | 13.58 | A |
| ATOM | 352 | CB | THR | A | 49 | 31.576 | 55.843 | 25.161 | 1.00 | 14.46 | A |
| ATOM | 353 | OG1 | THR | A | 49 | 32.234 | 55.567 | 23.924 | 1.00 | 15.00 | A |
| ATOM | 354 | CG2 | THR | A | 49 | 32.558 | 55.524 | 26.322 | 1.00 | 13.17 | A |
| ATOM | 355 | C | THR | A | 49 | 29.301 | 55.436 | 24.216 | 1.00 | 14.30 | A |
| ATOM | 356 | O | THR | A | 49 | 28.716 | 56.511 | 24.370 | 1.00 | 12.47 | A |
| ATOM | 357 | N | ASN | A | 50 | 29.062 | 54.659 | 23.162 | 1.00 | 13.09 | A |
| ATOM | 358 | CA | ASN | A | 50 | 28.076 | 55.116 | 22.173 | 1.00 | 14.85 | A |
| ATOM | 359 | CB | ASN | A | 50 | 28.324 | 54.519 | 20.785 | 1.00 | 15.63 | A |
| ATOM | 360 | CG | ASN | A | 50 | 27.379 | 55.096 | 19.739 | 1.00 | 18.88 | A |
| ATOM | 361 | OD1 | ASN | A | 50 | 26.472 | 55.883 | 20.059 | 1.00 | 19.28 | A |
| ATOM | 362 | ND2 | ASN | A | 50 | 27.574 | 54.707 | 18.489 | 1.00 | 19.28 | A |
| ATOM | 363 | C | ASN | A | 50 | 26.669 | 54.751 | 22.615 | 1.00 | 14.82 | A |
| ATOM | 364 | O | ASN | A | 50 | 26.099 | 53.739 | 22.187 | 1.00 | 14.58 | A |
| ATOM | 365 | N | THR | A | 51 | 26.097 | 55.608 | 23.443 | 1.00 | 13.25 | A |
| ATOM | 366 | CA | THR | A | 51 | 24.782 | 55.377 | 23.988 | 1.00 | 15.77 | A |
| ATOM | 367 | CB | THR | A | 51 | 24.595 | 56.210 | 25.242 | 1.00 | 17.96 | A |
| ATOM | 368 | OG1 | THR | A | 51 | 24.937 | 57.574 | 24.973 | 1.00 | 16.18 | A |
| ATOM | 369 | CG2 | THR | A | 51 | 25.506 | 55.684 | 26.332 | 1.00 | 18.64 | A |
| ATOM | 370 | C | THR | A | 51 | 23.581 | 55.539 | 23.053 | 1.00 | 18.71 | A |
| ATOM | 371 | O | THR | A | 51 | 22.440 | 55.436 | 23.512 | 1.00 | 19.68 | A |
| ATOM | 372 | N | THR | A | 52 | 23.820 | 55.795 | 21.761 | 1.00 | 16.82 | A |
| ATOM | 373 | CA | THR | A | 52 | 22.702 | 55.865 | 20.827 | 1.00 | 19.67 | A |
| ATOM | 374 | CB | THR | A | 52 | 23.017 | 56.666 | 19.524 | 1.00 | 22.55 | A |
| ATOM | 375 | OG1 | THR | A | 52 | 24.028 | 56.006 | 18.744 | 1.00 | 22.57 | A |

FIGURE 5 (continued)

| ATOM | 376 | CG2 | THR | A | 52 | 23.460 | 58.081 | 19.875 | 1.00 | 21.07 | A |
| --- | --- | --- | --- | --- | --- | --- | --- | --- | --- | --- | --- |
| ATOM | 377 | C | THR | A | 52 | 22.342 | 54.428 | 20.446 | 1.00 | 17.92 | A |
| ATOM | 378 | O | THR | A | 52 | 21.270 | 54.175 | 19.905 | 1.00 | 17.96 | A |
| ATOM | 379 | N | LYS | A | 53 | 23.238 | 53.488 | 20.740 | 1.00 | 14.41 | A |
| ATOM | 380 | CA | LYS | A | 53 | 22.978 | 52.080 | 20.427 | 1.00 | 12.53 | A |
| ATOM | 381 | CB | LYS | A | 53 | 24.292 | 51.292 | 20.406 | 1.00 | 14.33 | A |
| ATOM | 382 | CG | LYS | A | 53 | 25.207 | 51.573 | 19.213 | 1.00 | 17.93 | A |
| ATOM | 383 | CD | LYS | A | 53 | 26.478 | 50.731 | 19.324 | 1.00 | 18.20 | A |
| ATOM | 384 | CE | LYS | A | 53 | 27.477 | 51.052 | 18.214 | 1.00 | 21.01 | A |
| ATOM | 385 | NZ | LYS | A | 53 | 26.908 | 50.784 | 16.865 | 1.00 | 22.67 | A |
| ATOM | 386 | C | LYS | A | 53 | 22.045 | 51.470 | 21.474 | 1.00 | 12.72 | A |
| ATOM | 387 | O | LYS | A | 53 | 22.075 | 51.869 | 22.635 | 1.00 | 11.93 | A |
| ATOM | 388 | N | ASP | A | 54 | 21.223 | 50.499 | 21.064 | 1.00 | 13.58 | A |
| ATOM | 389 | CA | ASP | A | 54 | 20.298 | 49.826 | 21.982 | 1.00 | 10.96 | A |
| ATOM | 390 | CB | ASP | A | 54 | 18.887 | 49.745 | 21.380 | 1.00 | 12.81 | A |
| ATOM | 391 | CG | ASP | A | 54 | 18.249 | 51.107 | 21.218 | 1.00 | 19.07 | A |
| ATOM | 392 | OD1 | ASP | A | 54 | 18.010 | 51.529 | 20.059 | 1.00 | 17.31 | A |
| ATOM | 393 | OD2 | ASP | A | 54 | 17.997 | 51.759 | 22.260 | 1.00 | 15.46 | A |
| ATOM | 394 | C | ASP | A | 54 | 20.819 | 48.416 | 22.246 | 1.00 | 8.44 | A |
| ATOM | 395 | O | ASP | A | 54 | 21.505 | 47.837 | 21.407 | 1.00 | 14.56 | A |
| ATOM | 396 | N | VAL | A | 55 | 20.485 | 47.875 | 23.411 | 1.00 | 12.75 | A |
| ATOM | 397 | CA | VAL | A | 55 | 20.919 | 46.541 | 23.799 | 1.00 | 12.22 | A |
| ATOM | 398 | CB | VAL | A | 55 | 21.150 | 46.486 | 25.328 | 1.00 | 7.89 | A |
| ATOM | 399 | CG1 | VAL | A | 55 | 21.596 | 45.057 | 25.775 | 1.00 | 7.35 | A |
| ATOM | 400 | CG2 | VAL | A | 55 | 22.229 | 47.518 | 25.707 | 1.00 | 6.23 | A |
| ATOM | 401 | C | VAL | A | 55 | 19.840 | 45.540 | 23.386 | 1.00 | 9.36 | A |
| ATOM | 402 | O | VAL | A | 55 | 18.659 | 45.768 | 23.630 | 1.00 | 11.95 | A |
| ATOM | 403 | N | HIS | A | 56 | 20.258 | 44.441 | 22.755 | 1.00 | 9.82 | A |
| ATOM | 404 | CA | HIS | A | 56 | 19.323 | 43.432 | 22.285 | 1.00 | 8.89 | A |
| ATOM | 405 | CB | HIS | A | 56 | 19.552 | 43.218 | 20.782 | 1.00 | 8.33 | A |
| ATOM | 406 | CG | HIS | A | 56 | 19.455 | 44.485 | 19.985 | 1.00 | 9.48 | A |
| ATOM | 407 | CD2 | HIS | A | 56 | 20.414 | 45.264 | 19.430 | 1.00 | 11.14 | A |
| ATOM | 408 | ND1 | HIS | A | 56 | 18.255 | 45.121 | 19.738 | 1.00 | 13.82 | A |
| ATOM | 409 | CE1 | HIS | A | 56 | 18.483 | 46.236 | 19.064 | 1.00 | 12.14 | A |
| ATOM | 410 | NE2 | HIS | A | 56 | 19.783 | 46.345 | 18.866 | 1.00 | 12.83 | A |
| ATOM | 411 | C | HIS | A | 56 | 19.389 | 42.097 | 23.033 | 1.00 | 9.87 | A |
| ATOM | 412 | O | HIS | A | 56 | 18.419 | 41.331 | 23.039 | 1.00 | 8.84 | A |
| ATOM | 413 | N | TRP | A | 57 | 20.531 | 41.797 | 23.649 | 1.00 | 10.03 | A |
| ATOM | 414 | CA | TRP | A | 57 | 20.618 | 40.535 | 24.385 | 1.00 | 12.07 | A |
| ATOM | 415 | CB | TRP | A | 57 | 20.753 | 39.340 | 23.430 | 1.00 | 7.72 | A |
| ATOM | 416 | CG | TRP | A | 57 | 22.078 | 39.288 | 22.673 | 1.00 | 9.96 | A |
| ATOM | 417 | CD2 | TRP | A | 57 | 23.188 | 38.398 | 22.935 | 1.00 | 8.55 | A |
| ATOM | 418 | CE2 | TRP | A | 57 | 24.161 | 38.642 | 21.945 | 1.00 | 7.37 | A |
| ATOM | 419 | CE3 | TRP | A | 57 | 23.442 | 37.413 | 23.914 | 1.00 | 9.79 | A |
| ATOM | 420 | CD1 | TRP | A | 57 | 22.430 | 40.021 | 21.570 | 1.00 | 9.43 | A |
| ATOM | 421 | NE1 | TRP | A | 57 | 23.685 | 39.637 | 21.124 | 1.00 | 7.89 | A |
| ATOM | 422 | CZ2 | TRP | A | 57 | 25.381 | 37.936 | 21.895 | 1.00 | 8.66 | A |
| ATOM | 423 | CZ3 | TRP | A | 57 | 24.647 | 36.713 | 23.862 | 1.00 | 7.59 | A |
| ATOM | 424 | CH2 | TRP | A | 57 | 25.605 | 36.982 | 22.852 | 1.00 | 13.66 | A |
| ATOM | 425 | C | TRP | A | 57 | 21.830 | 40.575 | 25.286 | 1.00 | 9.35 | A |
| ATOM | 426 | O | TRP | A | 57 | 22.648 | 41.481 | 25.179 | 1.00 | 9.06 | A |
| ATOM | 427 | N | ALA | A | 58 | 21.945 | 39.579 | 26.159 | 1.00 | 6.35 | A |
| ATOM | 428 | CA | ALA | A | 58 | 23.081 | 39.523 | 27.061 | 1.00 | 8.26 | A |
| ATOM | 429 | CB | ALA | A | 58 | 22.755 | 40.280 | 28.362 | 1.00 | 10.03 | A |
| ATOM | 430 | C | ALA | A | 58 | 23.471 | 38.101 | 27.407 | 1.00 | 7.97 | A |
| ATOM | 431 | O | ALA | A | 58 | 22.638 | 37.207 | 27.401 | 1.00 | 9.27 | A |
| ATOM | 432 | N | GLY | A | 59 | 24.749 | 37.908 | 27.702 | 1.00 | 9.58 | A |
| ATOM | 433 | CA | GLY | A | 59 | 25.213 | 36.608 | 28.184 | 1.00 | 7.09 | A |
| ATOM | 434 | C | GLY | A | 59 | 25.342 | 36.791 | 29.695 | 1.00 | 9.23 | A |
| ATOM | 435 | O | GLY | A | 59 | 25.779 | 37.846 | 30.159 | 1.00 | 10.14 | A |
| ATOM | 436 | N | SER | A | 60 | 24.938 | 35.801 | 30.484 | 1.00 | 5.73 | A |
| ATOM | 437 | CA | SER | A | 60 | 25.058 | 35.917 | 31.938 | 1.00 | 5.95 | A |
| ATOM | 438 | CB | SER | A | 60 | 23.815 | 36.613 | 32.535 | 1.00 | 10.17 | A |
| ATOM | 439 | OG | SER | A | 60 | 23.896 | 36.707 | 33.966 | 1.00 | 9.12 | A |
| ATOM | 440 | C | SER | A | 60 | 25.161 | 34.540 | 32.566 | 1.00 | 8.54 | A |
| ATOM | 441 | O | SER | A | 60 | 24.437 | 33.632 | 32.146 | 1.00 | 9.12 | A |
| ATOM | 442 | N | ASP | A | 61 | 26.067 | 34.376 | 33.536 | 1.00 | 9.30 | A |
| ATOM | 443 | CA | ASP | A | 61 | 26.132 | 33.124 | 34.292 | 1.00 | 8.23 | A |
| ATOM | 444 | CB | ASP | A | 61 | 27.543 | 32.485 | 34.381 | 1.00 | 6.13 | A |
| ATOM | 445 | CG | ASP | A | 61 | 28.600 | 33.266 | 33.649 | 1.00 | 13.41 | A |
| ATOM | 446 | OD1 | ASP | A | 61 | 28.869 | 32.961 | 32.449 | 1.00 | 10.15 | A |
| ATOM | 447 | OD2 | ASP | A | 61 | 29.150 | 34.191 | 34.281 | 1.00 | 13.11 | A |
| ATOM | 448 | C | ASP | A | 61 | 25.597 | 33.456 | 35.710 | 1.00 | 10.77 | A |
| ATOM | 449 | O | ASP | A | 61 | 25.818 | 32.716 | 36.658 | 1.00 | 11.14 | A |
| ATOM | 450 | N | SER | A | 62 | 24.914 | 34.595 | 35.833 | 1.00 | 7.59 | A |
| ATOM | 451 | CA | SER | A | 62 | 24.213 | 34.995 | 37.067 | 1.00 | 10.29 | A |

FIGURE 5 (continued)

```
ATOM    452  CB   SER A  62      24.522  36.437  37.497  1.00 11.42           A
ATOM    453  OG   SER A  62      23.631  36.832  38.549  1.00 11.94           A
ATOM    454  C    SER A  62      22.721  34.944  36.706  1.00 10.70           A
ATOM    455  O    SER A  62      22.274  35.605  35.745  1.00  9.88           A
ATOM    456  N    LYS A  63      21.944  34.168  37.449  1.00  8.95           A
ATOM    457  CA   LYS A  63      20.519  34.089  37.137  1.00 10.67           A
ATOM    458  CB   LYS A  63      19.834  32.996  37.959  1.00 16.43           A
ATOM    459  CG   LYS A  63      20.046  31.605  37.461  1.00 15.34           A
ATOM    460  CD   LYS A  63      19.148  30.619  38.201  1.00 19.94           A
ATOM    461  CE   LYS A  63      17.702  30.671  37.728  1.00 16.96           A
ATOM    462  NZ   LYS A  63      16.903  29.498  38.239  1.00 14.00           A
ATOM    463  C    LYS A  63      19.786  35.392  37.399  1.00 12.40           A
ATOM    464  O    LYS A  63      20.192  36.183  38.257  1.00 10.37           A
ATOM    465  N    LEU A  64      18.699  35.604  36.659  1.00  7.10           A
ATOM    466  CA   LEU A  64      17.863  36.778  36.842  1.00  9.01           A
ATOM    467  CB   LEU A  64      16.824  36.871  35.716  1.00  6.27           A
ATOM    468  CG   LEU A  64      17.447  37.378  34.405  1.00  7.74           A
ATOM    469  CD1  LEU A  64      16.586  37.016  33.190  1.00  8.96           A
ATOM    470  CD2  LEU A  64      17.619  38.883  34.510  1.00  9.78           A
ATOM    471  C    LEU A  64      17.168  36.569  38.197  1.00 10.06           A
ATOM    472  O    LEU A  64      16.712  35.465  38.508  1.00 11.86           A
ATOM    473  N    THR A  65      17.120  37.614  39.012  1.00  6.99           A
ATOM    474  CA   THR A  65      16.503  37.481  40.334  1.00 11.54           A
ATOM    475  CB   THR A  65      17.097  38.472  41.341  1.00 13.33           A
ATOM    476  OG1  THR A  65      16.736  39.811  40.952  1.00 13.29           A
ATOM    477  CG2  THR A  65      18.644  38.331  41.395  1.00 11.42           A
ATOM    478  C    THR A  65      15.009  37.751  40.239  1.00 13.06           A
ATOM    479  O    THR A  65      14.530  38.268  39.233  1.00  9.78           A
ATOM    480  N    ALA A  66      14.272  37.374  41.281  1.00 11.93           A
ATOM    481  CA   ALA A  66      12.831  37.607  41.287  1.00 16.82           A
ATOM    482  CB   ALA A  66      12.231  37.106  42.601  1.00 17.23           A
ATOM    483  C    ALA A  66      12.527  39.104  41.105  1.00 14.69           A
ATOM    484  O    ALA A  66      11.587  39.467  40.409  1.00 12.67           A
ATOM    485  N    SER A  67      13.322  39.962  41.744  1.00 15.98           A
ATOM    486  CA   SER A  67      13.150  41.417  41.640  1.00 12.48           A
ATOM    487  CB   SER A  67      14.108  42.166  42.579  1.00 18.87           A
ATOM    488  OG   SER A  67      13.662  42.081  43.921  1.00 28.18           A
ATOM    489  C    SER A  67      13.403  41.890  40.212  1.00 12.05           A
ATOM    490  O    SER A  67      12.630  42.671  39.666  1.00 12.31           A
ATOM    491  N    GLN A  68      14.495  41.426  39.616  1.00  8.93           A
ATOM    492  CA   GLN A  68      14.796  41.803  38.237  1.00  8.58           A
ATOM    493  CB   GLN A  68      16.123  41.176  37.768  1.00 11.33           A
ATOM    494  CG   GLN A  68      17.343  41.749  38.524  1.00 12.20           A
ATOM    495  CD   GLN A  68      18.656  41.026  38.242  1.00 15.53           A
ATOM    496  OE1  GLN A  68      18.690  39.815  38.034  1.00 11.56           A
ATOM    497  NE2  GLN A  68      19.743  41.770  38.255  1.00 14.33           A
ATOM    498  C    GLN A  68      13.673  41.385  37.290  1.00 12.61           A
ATOM    499  O    GLN A  68      13.270  42.158  36.423  1.00 10.84           A
ATOM    500  N    LEU A  69      13.163  40.164  37.455  1.00 13.81           A
ATOM    501  CA   LEU A  69      12.093  39.687  36.576  1.00 13.47           A
ATOM    502  CB   LEU A  69      11.809  38.189  36.829  1.00 13.08           A
ATOM    503  CG   LEU A  69      12.989  37.268  36.496  1.00 14.83           A
ATOM    504  CD1  LEU A  69      12.772  35.862  37.071  1.00 16.18           A
ATOM    505  CD2  LEU A  69      13.140  37.233  34.981  1.00 11.50           A
ATOM    506  C    LEU A  69      10.810  40.484  36.778  1.00 13.14           A
ATOM    507  O    LEU A  69      10.138  40.860  35.814  1.00 13.07           A
ATOM    508  N    ALA A  70      10.465  40.728  38.034  1.00 12.61           A
ATOM    509  CA   ALA A  70       9.227  41.443  38.328  1.00 12.01           A
ATOM    510  CB   ALA A  70       8.951  41.453  39.841  1.00 13.19           A
ATOM    511  C    ALA A  70       9.275  42.852  37.785  1.00 12.44           A
ATOM    512  O    ALA A  70       8.297  43.334  37.240  1.00 16.48           A
ATOM    513  N    THR A  71      10.419  43.512  37.928  1.00 12.49           A
ATOM    514  CA   THR A  71      10.574  44.865  37.436  1.00 11.47           A
ATOM    515  CB   THR A  71      11.914  45.463  37.941  1.00 18.09           A
ATOM    516  OG1  THR A  71      11.834  45.621  39.370  1.00 19.27           A
ATOM    517  CG2  THR A  71      12.225  46.811  37.267  1.00 13.43           A
ATOM    518  C    THR A  71      10.501  44.905  35.902  1.00 11.57           A
ATOM    519  O    THR A  71-      9.881  45.800  35.337  1.00 15.24           A
ATOM    520  N    TYR A  72      11.116  43.941  35.223  1.00 13.13           A
ATOM    521  CA   TYR A  72      11.049  43.941  33.760  1.00 12.95           A
ATOM    522  CB   TYR A  72      11.927  42.839  33.174  1.00 11.21           A
ATOM    523  CG   TYR A  72      12.194  43.011  31.682  1.00 12.14           A
ATOM    524  CD1  TYR A  72      13.122  43.936  31.224  1.00 11.17           A
ATOM    525  CE1  TYR A  72      13.376  44.101  29.841  1.00 11.35           A
ATOM    526  CD2  TYR A  72      11.515  42.239  30.736  1.00 14.03           A
ATOM    527  CE2  TYR A  72      11.765  42.378  29.372  1.00  8.40           A
```

FIGURE 5 (continued)

| ATOM | 528 | CZ  | TYR | A | 72 | 12.689 | 43.303 | 28.928 | 1.00 | 10.19 | A |
| ATOM | 529 | OH  | TYR | A | 72 | 12.949 | 43.425 | 27.585 | 1.00 | 10.75 | A |
| ATOM | 530 | C   | TYR | A | 72 | 9.604  | 43.705 | 33.313 | 1.00 | 13.42 | A |
| ATOM | 531 | O   | TYR | A | 72 | 9.111  | 44.346 | 32.394 | 1.00 | 14.74 | A |
| ATOM | 532 | N   | ALA | A | 73 | 8.943  | 42.763 | 33.970 | 1.00 | 14.68 | A |
| ATOM | 533 | CA  | ALA | A | 73 | 7.563  | 42.423 | 33.650 | 1.00 | 15.37 | A |
| ATOM | 534 | CB  | ALA | A | 73 | 7.090  | 41.293 | 34.556 | 1.00 | 10.74 | A |
| ATOM | 535 | C   | ALA | A | 73 | 6.631  | 43.626 | 33.791 | 1.00 | 14.04 | A |
| ATOM | 536 | O   | ALA | A | 73 | 5.711  | 43.811 | 32.992 | 1.00 | 13.32 | A |
| ATOM | 537 | N   | ALA | A | 74 | 6.856  | 44.436 | 34.815 | 1.00 | 16.88 | A |
| ATOM | 538 | CA  | ALA | A | 74 | 6.006  | 45.602 | 35.032 | 1.00 | 17.08 | A |
| ATOM | 539 | CB  | ALA | A | 74 | 6.082  | 46.052 | 36.505 | 1.00 | 13.94 | A |
| ATOM | 540 | C   | ALA | A | 74 | 6.354  | 46.768 | 34.118 | 1.00 | 20.94 | A |
| ATOM | 541 | O   | ALA | A | 74 | 5.475  | 47.357 | 33.476 | 1.00 | 17.04 | A |
| ATOM | 542 | N   | ASN | A | 75 | 7.645  | 47.061 | 34.014 | 1.00 | 15.74 | A |
| ATOM | 543 | CA  | ASN | A | 75 | 8.125  | 48.203 | 33.241 | 1.00 | 17.76 | A |
| ATOM | 544 | CB  | ASN | A | 75 | 9.439  | 48.712 | 33.839 | 1.00 | 19.52 | A |
| ATOM | 545 | CG  | ASN | A | 75 | 9.308  | 49.152 | 35.289 | 1.00 | 24.86 | A |
| ATOM | 546 | OD1 | ASN | A | 75 | 10.308 | 49.485 | 35.929 | 1.00 | 26.13 | A |
| ATOM | 547 | ND2 | ASN | A | 75 | 8.084  | 49.150 | 35.816 | 1.00 | 27.41 | A |
| ATOM | 548 | C   | ASN | A | 75 | 8.356  | 48.070 | 31.741 | 1.00 | 18.90 | A |
| ATOM | 549 | O   | ASN | A | 75 | 8.049  | 48.996 | 30.986 | 1.00 | 16.37 | A |
| ATOM | 550 | N   | LYS | A | 76 | 8.910  | 46.944 | 31.304 | 1.00 | 13.20 | A |
| ATOM | 551 | CA  | LYS | A | 76 | 9.235  | 46.810 | 29.888 | 1.00 | 14.05 | A |
| ATOM | 552 | CB  | LYS | A | 76 | 10.709 | 46.412 | 29.730 | 1.00 | 11.81 | A |
| ATOM | 553 | CG  | LYS | A | 76 | 11.706 | 47.189 | 30.561 | 1.00 | 15.12 | A |
| ATOM | 554 | CD  | LYS | A | 76 | 11.710 | 48.673 | 30.208 | 1.00 | 18.17 | A |
| ATOM | 555 | CE  | LYS | A | 76 | 12.942 | 49.342 | 30.783 | 1.00 | 21.75 | A |
| ATOM | 556 | NZ  | LYS | A | 76 | 12.858 | 50.832 | 30.665 | 1.00 | 23.76 | A |
| ATOM | 557 | C   | LYS | A | 76 | 8.414  | 45.835 | 29.064 | 1.00 | 14.89 | A |
| ATOM | 558 | O   | LYS | A | 76 | 8.184  | 46.053 | 27.874 | 1.00 | 15.18 | A |
| ATOM | 559 | N   | GLN | A | 77 | 7.996  | 44.746 | 29.686 | 1.00 | 13.65 | A |
| ATOM | 560 | CA  | GLN | A | 77 | 7.240  | 43.718 | 28.978 | 1.00 | 15.70 | A |
| ATOM | 561 | CB  | GLN | A | 77 | 6.865  | 42.625 | 29.964 | 1.00 | 14.98 | A |
| ATOM | 562 | CG  | GLN | A | 77 | 6.139  | 41.438 | 29.381 | 1.00 | 18.91 | A |
| ATOM | 563 | CD  | GLN | A | 77 | 5.848  | 40.392 | 30.441 | 1.00 | 26.71 | A |
| ATOM | 564 | OE1 | GLN | A | 77 | 6.747  | 39.965 | 31.167 | 1.00 | 25.14 | A |
| ATOM | 565 | NE2 | GLN | A | 77 | 4.593  | 39.968 | 30.534 | 1.00 | 21.79 | A |
| ATOM | 566 | C   | GLN | A | 77 | 5.989  | 44.205 | 28.222 | 1.00 | 16.81 | A |
| ATOM | 567 | O   | GLN | A | 77 | 5.718  | 43.746 | 27.114 | 1.00 | 17.54 | A |
| ATOM | 568 | N   | PRO | A | 78 | 5.216  | 45.142 | 28.800 | 1.00 | 19.48 | A |
| ATOM | 569 | CD  | PRO | A | 78 | 5.255  | 45.765 | 30.134 | 1.00 | 12.68 | A |
| ATOM | 570 | CA  | PRO | A | 78 | 4.023  | 45.575 | 28.056 | 1.00 | 15.54 | A |
| ATOM | 571 | CB  | PRO | A | 78 | 3.428  | 46.654 | 28.958 | 1.00 | 19.25 | A |
| ATOM | 572 | CG  | PRO | A | 78 | 3.787  | 46.150 | 30.342 | 1.00 | 17.82 | A |
| ATOM | 573 | C   | PRO | A | 78 | 4.325  | 46.080 | 26.646 | 1.00 | 20.10 | A |
| ATOM | 574 | O   | PRO | A | 78 | 3.614  | 45.748 | 25.692 | 1.00 | 18.30 | A |
| ATOM | 575 | N   | GLY | A | 79 | 5.393  | 46.860 | 26.512 | 1.00 | 15.27 | A |
| ATOM | 576 | CA  | GLY | A | 79 | 5.745  | 47.379 | 25.210 | 1.00 | 17.02 | A |
| ATOM | 577 | C   | GLY | A | 79 | 6.802  | 46.616 | 24.427 | 1.00 | 20.02 | A |
| ATOM | 578 | O   | GLY | A | 79 | 6.839  | 46.731 | 23.199 | 1.00 | 15.38 | A |
| ATOM | 579 | N   | TRP | A | 80 | 7.639  | 45.830 | 25.111 | 1.00 | 13.75 | A |
| ATOM | 580 | CA  | TRP | A | 80 | 8.723  | 45.092 | 24.440 | 1.00 | 14.43 | A |
| ATOM | 581 | CB  | TRP | A | 80 | 10.062 | 45.359 | 25.136 | 1.00 | 11.39 | A |
| ATOM | 582 | CG  | TRP | A | 80 | 10.549 | 46.780 | 25.071 | 1.00 | 15.13 | A |
| ATOM | 583 | CD2 | TRP | A | 80 | 11.672 | 47.329 | 25.767 | 1.00 | 13.37 | A |
| ATOM | 584 | CE2 | TRP | A | 80 | 11.823 | 48.666 | 25.332 | 1.00 | 13.52 | A |
| ATOM | 585 | CE3 | TRP | A | 80 | 12.573 | 46.817 | 26.716 | 1.00 | 12.51 | A |
| ATOM | 586 | CD1 | TRP | A | 80 | 10.068 | 47.779 | 24.271 | 1.00 | 19.04 | A |
| ATOM | 587 | NE1 | TRP | A | 80 | 10.831 | 48.919 | 24.418 | 1.00 | 16.58 | A |
| ATOM | 588 | CZ2 | TRP | A | 80 | 12.840 | 49.502 | 25.812 | 1.00 | 15.28 | A |
| ATOM | 589 | CZ3 | TRP | A | 80 | 13.586 | 47.645 | 27.197 | 1.00 | 13.05 | A |
| ATOM | 590 | CH2 | TRP | A | 80 | 13.710 | 48.979 | 26.739 | 1.00 | 16.82 | A |
| ATOM | 591 | C   | TRP | A | 80 | 8.560  | 43.580 | 24.349 | 1.00 | 16.83 | A |
| ATOM | 592 | O   | TRP | A | 80 | 9.361  | 42.909 | 23.685 | 1.00 | 16.92 | A |
| ATOM | 593 | N   | GLY | A | 81 | 7.562  | 43.031 | 25.033 | 1.00 | 15.56 | A |
| ATOM | 594 | CA  | GLY | A | 81 | 7.380  | 41.584 | 25.001 | 1.00 | 11.72 | A |
| ATOM | 595 | C   | GLY | A | 81 | 8.071  | 40.921 | 26.186 | 1.00 | 13.05 | A |
| ATOM | 596 | O   | GLY | A | 81 | 8.856  | 41.557 | 26.894 | 1.00 | 8.85  | A |
| ATOM | 597 | N   | LYS | A | 82 | 7.784  | 39.638 | 26.395 | 1.00 | 10.46 | A |
| ATOM | 598 | CA  | LYS | A | 82 | 8.374  | 38.882 | 27.499 | 1.00 | 11.96 | A |
| ATOM | 599 | CB  | LYS | A | 82 | 7.702  | 37.506 | 27.608 | 1.00 | 11.82 | A |
| ATOM | 600 | CG  | LYS | A | 82 | 6.341  | 37.497 | 28.315 | 1.00 | 12.27 | A |
| ATOM | 601 | CD  | LYS | A | 82 | 5.578  | 36.167 | 28.137 | 1.00 | 15.83 | A |
| ATOM | 602 | CE  | LYS | A | 82 | 6.296  | 34.971 | 28.782 | 1.00 | 21.44 | A |
| ATOM | 603 | NZ  | LYS | A | 82 | 6.571  | 35.179 | 30.234 | 1.00 | 18.30 | A |

FIGURE 5 (continued)

| | | | | | | | | | | |
|---|---|---|---|---|---|---|---|---|---|---|
| ATOM | 604 | C | LYS | A | 82 | 9.868 | 38.658 | 27.275 | 1.00 12.45 | A |
| ATOM | 605 | O | LYS | A | 82 | 10.313 | 38.530 | 26.126 | 1.00 11.99 | A |
| ATOM | 606 | N | LEU | A | 83 | 10.649 | 38.598 | 28.357 | 1.00 10.87 | A |
| ATOM | 607 | CA | LEU | A | 83 | 12.057 | 38.305 | 28.161 | 1.00 10.47 | A |
| ATOM | 608 | CB | LEU | A | 83 | 12.955 | 38.929 | 29.248 | 1.00 16.59 | A |
| ATOM | 609 | CG | LEU | A | 83 | 13.059 | 38.501 | 30.707 | 1.00 13.98 | A |
| ATOM | 610 | CD1 | LEU | A | 83 | 13.627 | 37.083 | 30.856 | 1.00 13.97 | A |
| ATOM | 611 | CD2 | LEU | A | 83 | 14.010 | 39.508 | 31.412 | 1.00 12.95 | A |
| ATOM | 612 | C | LEU | A | 83 | 12.191 | 36.790 | 28.142 | 1.00 8.84 | A |
| ATOM | 613 | O | LEU | A | 83 | 11.288 | 36.062 | 28.604 | 1.00 12.14 | A |
| ATOM | 614 | N | ILE | A | 84 | 13.294 | 36.330 | 27.567 | 1.00 9.04 | A |
| ATOM | 615 | CA | ILE | A | 84 | 13.606 | 34.912 | 27.467 | 1.00 7.94 | A |
| ATOM | 616 | CB | ILE | A | 84 | 13.734 | 34.492 | 25.986 | 1.00 11.27 | A |
| ATOM | 617 | CG2 | ILE | A | 84 | 14.322 | 33.075 | 25.875 | 1.00 15.02 | A |
| ATOM | 618 | CG1 | ILE | A | 84 | 12.356 | 34.567 | 25.306 | 1.00 13.46 | A |
| ATOM | 619 | CD1 | ILE | A | 84 | 12.407 | 34.310 | 23.806 | 1.00 10.66 | A |
| ATOM | 620 | C | ILE | A | 84 | 14.957 | 34.682 | 28.151 | 1.00 9.44 | A |
| ATOM | 621 | O | ILE | A | 84 | 15.918 | 35.410 | 27.891 | 1.00 9.33 | A |
| ATOM | 622 | N | GLU | A | 85 | 15.018 | 33.686 | 29.023 | 1.00 7.70 | A |
| ATOM | 623 | CA | GLU | A | 85 | 16.269 | 33.331 | 29.683 | 1.00 8.79 | A |
| ATOM | 624 | CB | GLU | A | 85 | 16.211 | 33.631 | 31.196 | 1.00 7.98 | A |
| ATOM | 625 | CG | GLU | A | 85 | 17.532 | 33.291 | 31.922 | 1.00 8.35 | A |
| ATOM | 626 | CD | GLU | A | 85 | 17.472 | 33.466 | 33.442 | 1.00 9.44 | A |
| ATOM | 627 | OE1 | GLU | A | 85 | 16.520 | 32.969 | 34.103 | 1.00 13.35 | A |
| ATOM | 628 | OE2 | GLU | A | 85 | 18.408 | 34.077 | 33.998 | 1.00 10.18 | A |
| ATOM | 629 | C | GLU | A | 85 | 16.452 | 31.832 | 29.442 | 1.00 9.15 | A |
| ATOM | 630 | O | GLU | A | 85 | 15.614 | 31.047 | 29.870 | 1.00 10.73 | A |
| ATOM | 631 | N | VAL | A | 86 | 17.513 | 31.438 | 28.733 | 1.00 9.15 | A |
| ATOM | 632 | CA | VAL | A | 86 | 17.772 | 30.021 | 28.458 | 1.00 9.61 | A |
| ATOM | 633 | CB | VAL | A | 86 | 17.394 | 29.631 | 26.987 | 1.00 8.48 | A |
| ATOM | 634 | CG1 | VAL | A | 86 | 15.866 | 29.641 | 26.795 | 1.00 11.82 | A |
| ATOM | 635 | CG2 | VAL | A | 86 | 18.062 | 30.587 | 25.998 | 1.00 8.25 | A |
| ATOM | 636 | C | VAL | A | 86 | 19.247 | 29.653 | 28.653 | 1.00 12.36 | A |
| ATOM | 637 | O | VAL | A | 86 | 20.135 | 30.490 | 28.488 | 1.00 7.65 | A |
| ATOM | 638 | N | PRO | A | 87 | 19.530 | 28.392 | 29.034 | 1.00 7.50 | A |
| ATOM | 639 | CD | PRO | A | 87 | 18.611 | 27.261 | 29.245 | 1.00 11.19 | A |
| ATOM | 640 | CA | PRO | A | 87 | 20.927 | 27.986 | 29.213 | 1.00 8.03 | A |
| ATOM | 641 | CB | PRO | A | 87 | 20.806 | 26.551 | 29.747 | 1.00 11.47 | A |
| ATOM | 642 | CG | PRO | A | 87 | 19.531 | 26.065 | 29.123 | 1.00 18.08 | A |
| ATOM | 643 | C | PRO | A | 87 | 21.551 | 28.031 | 27.803 | 1.00 12.05 | A |
| ATOM | 644 | O | PRO | A | 87 | 20.845 | 27.799 | 26.798 | 1.00 11.64 | A |
| ATOM | 645 | N | SER | A | 88 | 22.844 | 28.346 | 27.739 | 1.00 10.05 | A |
| ATOM | 646 | CA | SER | A | 88 | 23.607 | 28.427 | 26.480 | 1.00 8.91 | A |
| ATOM | 647 | CB | SER | A | 88 | 24.472 | 29.695 | 26.471 | 1.00 6.92 | A |
| ATOM | 648 | OG | SER | A | 88 | 25.266 | 29.787 | 25.294 | 1.00 11.36 | A |
| ATOM | 649 | C | SER | A | 88 | 24.484 | 27.177 | 26.379 | 1.00 7.85 | A |
| ATOM | 650 | O | SER | A | 88 | 24.385 | 26.432 | 25.401 | 1.00 7.71 | A |
| ATOM | 651 | N | VAL | A | 89 | 25.365 | 26.993 | 27.368 | 1.00 7.73 | A |
| ATOM | 652 | CA | VAL | A | 89 | 26.218 | 25.802 | 27.481 | 1.00 8.66 | A |
| ATOM | 653 | CB | VAL | A | 89 | 27.639 | 26.010 | 26.874 | 1.00 5.11 | A |
| ATOM | 654 | CG1 | VAL | A | 89 | 27.522 | 26.503 | 25.400 | 1.00 7.72 | A |
| ATOM | 655 | CG2 | VAL | A | 89 | 28.444 | 27.016 | 27.744 | 1.00 8.02 | A |
| ATOM | 656 | C | VAL | A | 89 | 26.407 | 25.527 | 28.980 | 1.00 10.90 | A |
| ATOM | 657 | O | VAL | A | 89 | 26.037 | 26.356 | 29.809 | 1.00 9.82 | A |
| ATOM | 658 | N | ALA | A | 90 | 26.982 | 24.369 | 29.325 | 1.00 10.64 | A |
| ATOM | 659 | CA | ALA | A | 90 | 27.242 | 24.059 | 30.722 | 1.00 8.29 | A |
| ATOM | 660 | CB | ALA | A | 90 | 26.792 | 22.616 | 31.077 | 1.00 8.16 | A |
| ATOM | 661 | C | ALA | A | 90 | 28.764 | 24.190 | 30.863 | 1.00 7.63 | A |
| ATOM | 662 | O | ALA | A | 90 | 29.498 | 24.095 | 29.880 | 1.00 7.66 | A |
| ATOM | 663 | N | THR | A | 91 | 29.233 | 24.345 | 32.091 | 1.00 7.77 | A |
| ATOM | 664 | CA | THR | A | 91 | 30.651 | 24.559 | 32.300 | 1.00 9.18 | A |
| ATOM | 665 | CB | THR | A | 91 | 30.945 | 26.074 | 32.165 | 1.00 10.09 | A |
| ATOM | 666 | OG1 | THR | A | 91 | 32.337 | 26.323 | 32.365 | 1.00 11.79 | A |
| ATOM | 667 | CG2 | THR | A | 91 | 30.156 | 26.862 | 33.214 | 1.00 11.41 | A |
| ATOM | 668 | C | THR | A | 91 | 31.116 | 24.140 | 33.686 | 1.00 10.91 | A |
| ATOM | 669 | O | THR | A | 91 | 30.326 | 24.055 | 34.614 | 1.00 9.96 | A |
| ATOM | 670 | N | SER | A | 92 | 32.409 | 23.858 | 33.811 | 1.00 11.52 | A |
| ATOM | 671 | CA | SER | A | 92 | 32.972 | 23.598 | 35.122 | 1.00 9.75 | A |
| ATOM | 672 | CB | SER | A | 92 | 34.167 | 22.642 | 35.011 | 1.00 12.03 | A |
| ATOM | 673 | OG | SER | A | 92 | 35.213 | 23.181 | 34.186 | 1.00 10.62 | A |
| ATOM | 674 | C | SER | A | 92 | 33.490 | 24.962 | 35.601 | 1.00 10.73 | A |
| ATOM | 675 | O | SER | A | 92 | 33.397 | 25.974 | 34.883 | 1.00 8.53 | A |
| ATOM | 676 | N | VAL | A | 93 | 33.980 | 25.003 | 36.837 | 1.00 8.68 | A |
| ATOM | 677 | CA | VAL | A | 93 | 34.640 | 26.197 | 37.369 | 1.00 7.08 | A |
| ATOM | 678 | CB | VAL | A | 93 | 34.010 | 26.736 | 38.667 | 1.00 7.09 | A |
| ATOM | 679 | CG1 | VAL | A | 93 | 34.896 | 27.906 | 39.215 | 1.00 10.40 | A |

FIGURE 5 (continued)

```
ATOM    680  CG2 VAL A  93      32.592  27.269  38.376  1.00 10.45           A
ATOM    681  C   VAL A  93      36.033  25.643  37.694  1.00  9.49           A
ATOM    682  O   VAL A  93      36.162  24.745  38.527  1.00 12.26           A
ATOM    683  N   ALA A  94      37.064  26.148  37.025  1.00  8.00           A
ATOM    684  CA  ALA A  94      38.425  25.645  37.236  1.00  8.64           A
ATOM    685  CB  ALA A  94      39.204  25.722  35.921  1.00  7.88           A
ATOM    686  C   ALA A  94      39.197  26.374  38.329  1.00  7.97           A
ATOM    687  O   ALA A  94      38.906  27.530  38.625  1.00  8.61           A
ATOM    688  N   ILE A  95      40.210  25.709  38.894  1.00  5.77           A
ATOM    689  CA  ILE A  95      41.016  26.290  39.963  1.00  7.30           A
ATOM    690  CB  ILE A  95      40.870  25.486  41.307  1.00  9.66           A
ATOM    691  CG2 ILE A  95      41.522  26.261  42.465  1.00  6.29           A
ATOM    692  CG1 ILE A  95      39.401  25.218  41.641  1.00 10.13           A
ATOM    693  CD1 ILE A  95      38.566  26.491  41.909  1.00 13.60           A
ATOM    694  C   ILE A  95      42.496  26.263  39.572  1.00  8.10           A
ATOM    695  O   ILE A  95      43.261  25.373  40.001  1.00 10.23           A
ATOM    696  N   PRO A  96      42.923  27.216  38.742  1.00  6.65           A
ATOM    697  CD  PRO A  96      42.133  28.263  38.063  1.00  6.16           A
ATOM    698  CA  PRO A  96      44.330  27.265  38.326  1.00  7.43           A
ATOM    699  CB  PRO A  96      44.275  28.107  37.054  1.00  9.06           A
ATOM    700  CG  PRO A  96      43.207  29.147  37.446  1.00  8.84           A
ATOM    701  C   PRO A  96      45.133  27.938  39.434  1.00 10.94           A
ATOM    702  O   PRO A  96      44.574  28.645  40.277  1.00  8.21           A
ATOM    703  N   PHE A  97      46.441  27.715  39.447  1.00  9.05           A
ATOM    704  CA  PHE A  97      47.276  28.302  40.480  1.00  8.97           A
ATOM    705  CB  PHE A  97      47.259  27.414  41.732  1.00 10.70           A
ATOM    706  CG  PHE A  97      47.748  26.015  41.477  1.00  9.86           A
ATOM    707  CD1 PHE A  97      49.114  25.720  41.524  1.00 10.13           A
ATOM    708  CD2 PHE A  97      46.862  25.010  41.121  1.00  7.97           A
ATOM    709  CE1 PHE A  97      49.589  24.436  41.211  1.00  9.97           A
ATOM    710  CE2 PHE A  97      47.326  23.704  40.802  1.00  8.94           A
ATOM    711  CZ  PHE A  97      48.709  23.433  40.852  1.00  7.63           A
ATOM    712  C   PHE A  97      48.698  28.418  39.949  1.00  9.55           A
ATOM    713  O   PHE A  97      49.054  27.761  38.962  1.00  9.51           A
ATOM    714  N   ARG A  98      49.498  29.260  40.597  1.00  8.26           A
ATOM    715  CA  ARG A  98      50.900  29.457  40.205  1.00 11.26           A
ATOM    716  CB  ARG A  98      51.149  30.927  39.808  1.00 13.41           A
ATOM    717  CG  ARG A  98      52.624  31.218  39.452  1.00 12.41           A
ATOM    718  CD  ARG A  98      52.902  32.648  39.002  1.00 15.00           A
ATOM    719  NE  ARG A  98      54.350  32.871  38.907  1.00 20.95           A
ATOM    720  CZ  ARG A  98      55.048  33.714  39.670  1.00 19.61           A
ATOM    721  NH1 ARG A  98      54.454  34.446  40.606  1.00 16.05           A
ATOM    722  NH2 ARG A  98      56.361  33.824  39.500  1.00 22.95           A
ATOM    723  C   ARG A  98      51.765  29.079  41.415  1.00  9.82           A
ATOM    724  O   ARG A  98      51.955  29.881  42.327  1.00 12.72           A
ATOM    725  N   LYS A  99      52.258  27.838  41.417  1.00 13.72           A
ATOM    726  CA  LYS A  99      53.081  27.314  42.510  1.00 14.88           A
ATOM    727  CB  LYS A  99      52.179  26.922  43.688  1.00 10.80           A
ATOM    728  CG  LYS A  99      52.899  26.401  44.919  1.00  8.32           A
ATOM    729  CD  LYS A  99      53.744  27.518  45.557  1.00 10.62           A
ATOM    730  CE  LYS A  99      54.525  27.007  46.790  1.00 10.76           A
ATOM    731  NZ  LYS A  99      55.346  28.125  47.368  1.00 13.56           A
ATOM    732  C   LYS A  99      53.809  26.095  41.956  1.00 14.43           A
ATOM    733  O   LYS A  99      53.200  25.056  41.701  1.00 15.34           A
ATOM    734  N   ALA A 100      55.120  26.226  41.769  1.00 12.67           A
ATOM    735  CA  ALA A 100      55.911  25.143  41.202  1.00 14.53           A
ATOM    736  CB  ALA A 100      57.354  25.629  40.914  1.00 14.12           A
ATOM    737  C   ALA A 100      55.960  23.900  42.072  1.00 14.42           A
ATOM    738  O   ALA A 100      55.929  23.987  43.303  1.00 16.53           A
ATOM    739  N   GLY A 101      56.061  22.751  41.409  1.00 10.16           A
ATOM    740  CA  GLY A 101      56.133  21.476  42.096  1.00 11.78           A
ATOM    741  C   GLY A 101      55.786  20.360  41.136  1.00 17.78           A
ATOM    742  O   GLY A 101      54.853  20.479  40.338  1.00 14.78           A
ATOM    743  N   GLY A 102      56.543  19.274  41.195  1.00 13.81           A
ATOM    744  CA  GLY A 102      56.273  18.156  40.313  1.00 20.81           A
ATOM    745  C   GLY A 102      55.051  17.348  40.720  1.00 16.58           A
ATOM    746  O   GLY A 102      54.498  16.627  39.898  1.00 16.24           A
ATOM    747  N   ASN A 103      54.624  17.451  41.976  1.00 17.72           A
ATOM    748  CA  ASN A 103      53.465  16.675  42.434  1.00 16.85           A
ATOM    749  CB  ASN A 103      53.372  16.694  43.963  1.00 15.22           A
ATOM    750  CG  ASN A 103      54.365  15.760  44.615  1.00 23.02           A
ATOM    751  OD1 ASN A 103      55.279  15.249  43.955  1.00 19.32           A
ATOM    752  ND2 ASN A 103      54.205  15.535  45.916  1.00 15.75           A
ATOM    753  C   ASN A 103      52.145  17.197  41.885  1.00 15.38           A
ATOM    754  O   ASN A 103      51.991  18.390  41.666  1.00 11.02           A
ATOM    755  N   ALA A 104      51.183  16.306  41.693  1.00 16.02           A
```

FIGURE 5 (continued)

| ATOM | 756 | CA | ALA | A | 104 | 49.880 | 16.744 | 41.219 | 1.00 | 16.65 | A |
|------|-----|-----|-----|---|-----|--------|--------|--------|------|-------|---|
| ATOM | 757 | CB | ALA | A | 104 | 49.068 | 15.538 | 40.741 | 1.00 | 20.27 | A |
| ATOM | 758 | C | ALA | A | 104 | 49.170 | 17.427 | 42.395 | 1.00 | 15.98 | A |
| ATOM | 759 | O | ALA | A | 104 | 49.298 | 16.986 | 43.531 | 1.00 | 15.25 | A |
| ATOM | 760 | N | VAL | A | 105 | 48.470 | 18.530 | 42.127 | 1.00 | 13.62 | A |
| ATOM | 761 | CA | VAL | A | 105 | 47.701 | 19.227 | 43.157 | 1.00 | 13.77 | A |
| ATOM | 762 | CB | VAL | A | 105 | 47.708 | 20.756 | 42.945 | 1.00 | 15.80 | A |
| ATOM | 763 | CG1 | VAL | A | 105 | 46.645 | 21.409 | 43.814 | 1.00 | 16.24 | A |
| ATOM | 764 | CG2 | VAL | A | 105 | 49.081 | 21.310 | 43.295 | 1.00 | 15.48 | A |
| ATOM | 765 | C | VAL | A | 105 | 46.273 | 18.699 | 43.026 | 1.00 | 13.93 | A |
| ATOM | 766 | O | VAL | A | 105 | 45.634 | 18.867 | 41.982 | 1.00 | 11.00 | A |
| ATOM | 767 | N | ASP | A | 106 | 45.781 | 18.059 | 44.085 | 1.00 | 11.30 | A |
| ATOM | 768 | CA | ASP | A | 106 | 44.446 | 17.447 | 44.087 | 1.00 | 13.33 | A |
| ATOM | 769 | CB | ASP | A | 106 | 44.594 | 15.914 | 44.007 | 1.00 | 15.23 | A |
| ATOM | 770 | CG | ASP | A | 106 | 43.266 | 15.181 | 43.763 | 1.00 | 18.75 | A |
| ATOM | 771 | OD1 | ASP | A | 106 | 43.294 | 13.932 | 43.636 | 1.00 | 20.08 | A |
| ATOM | 772 | OD2 | ASP | A | 106 | 42.201 | 15.832 | 43.705 | 1.00 | 16.37 | A |
| ATOM | 773 | C | ASP | A | 106 | 43.748 | 17.854 | 45.371 | 1.00 | 13.44 | A |
| ATOM | 774 | O | ASP | A | 106 | 44.013 | 17.312 | 46.441 | 1.00 | 12.47 | A |
| ATOM | 775 | N | LEU | A | 107 | 42.838 | 18.809 | 45.256 | 1.00 | 12.47 | A |
| ATOM | 776 | CA | LEU | A | 107 | 42.126 | 19.322 | 46.424 | 1.00 | 10.60 | A |
| ATOM | 777 | CB | LEU | A | 107 | 41.608 | 20.743 | 46.139 | 1.00 | 9.94 | A |
| ATOM | 778 | CG | LEU | A | 107 | 42.656 | 21.830 | 45.874 | 1.00 | 15.11 | A |
| ATOM | 779 | CD1 | LEU | A | 107 | 41.992 | 23.049 | 45.233 | 1.00 | 12.77 | A |
| ATOM | 780 | CD2 | LEU | A | 107 | 43.332 | 22.222 | 47.191 | 1.00 | 15.50 | A |
| ATOM | 781 | C | LEU | A | 107 | 40.936 | 18.504 | 46.860 | 1.00 | 11.58 | A |
| ATOM | 782 | O | LEU | A | 107 | 40.118 | 18.134 | 46.029 | 1.00 | 11.26 | A |
| ATOM | 783 | N | SER | A | 108 | 40.840 | 18.205 | 48.157 | 1.00 | 10.03 | A |
| ATOM | 784 | CA | SER | A | 108 | 39.632 | 17.555 | 48.632 | 1.00 | 9.49 | A |
| ATOM | 785 | CB | SER | A | 108 | 39.823 | 16.938 | 50.026 | 1.00 | 11.45 | A |
| ATOM | 786 | OG | SER | A | 108 | 40.112 | 17.944 | 50.988 | 1.00 | 10.62 | A |
| ATOM | 787 | C | SER | A | 108 | 38.686 | 18.762 | 48.734 | 1.00 | 13.88 | A |
| ATOM | 788 | O | SER | A | 108 | 39.137 | 19.909 | 48.733 | 1.00 | 9.31 | A |
| ATOM | 789 | N | VAL | A | 109 | 37.384 | 18.528 | 48.795 | 1.00 | 11.62 | A |
| ATOM | 790 | CA | VAL | A | 109 | 36.456 | 19.648 | 48.915 | 1.00 | 12.52 | A |
| ATOM | 791 | CB | VAL | A | 109 | 34.997 | 19.149 | 48.822 | 1.00 | 14.25 | A |
| ATOM | 792 | CG1 | VAL | A | 109 | 34.022 | 20.273 | 49.172 | 1.00 | 10.43 | A |
| ATOM | 793 | CG2 | VAL | A | 109 | 34.738 | 18.624 | 47.385 | 1.00 | 9.95 | A |
| ATOM | 794 | C | VAL | A | 109 | 36.705 | 20.397 | 50.228 | 1.00 | 8.60 | A |
| ATOM | 795 | O | VAL | A | 109 | 36.646 | 21.622 | 50.265 | 1.00 | 9.21 | A |
| ATOM | 796 | N | LYS | A | 110 | 36.995 | 19.666 | 51.301 | 1.00 | 9.28 | A |
| ATOM | 797 | CA | LYS | A | 110 | 37.307 | 20.306 | 52.593 | 1.00 | 7.04 | A |
| ATOM | 798 | CB | LYS | A | 110 | 37.597 | 19.237 | 53.650 | 1.00 | 7.60 | A |
| ATOM | 799 | CG | LYS | A | 110 | 38.038 | 19.793 | 55.030 | 1.00 | 9.51 | A |
| ATOM | 800 | CD | LYS | A | 110 | 36.987 | 20.726 | 55.655 | 1.00 | 7.71 | A |
| ATOM | 801 | CE | LYS | A | 110 | 37.436 | 21.170 | 57.033 | 1.00 | 15.09 | A |
| ATOM | 802 | NZ | LYS | A | 110 | 36.482 | 22.129 | 57.688 | 1.00 | 11.10 | A |
| ATOM | 803 | C | LYS | A | 110 | 38.532 | 21.234 | 52.452 | 1.00 | 8.55 | A |
| ATOM | 804 | O | LYS | A | 110 | 38.588 | 22.313 | 53.040 | 1.00 | 9.65 | A |
| ATOM | 805 | N | GLU | A | 111 | 39.530 | 20.803 | 51.696 | 1.00 | 8.56 | A |
| ATOM | 806 | CA | GLU | A | 111 | 40.711 | 21.640 | 51.495 | 1.00 | 11.39 | A |
| ATOM | 807 | CB | GLU | A | 111 | 41.817 | 20.836 | 50.800 | 1.00 | 13.45 | A |
| ATOM | 808 | CG | GLU | A | 111 | 42.582 | 19.940 | 51.784 | 1.00 | 15.25 | A |
| ATOM | 809 | CD | GLU | A | 111 | 43.527 | 18.960 | 51.098 | 1.00 | 16.99 | A |
| ATOM | 810 | OE1 | GLU | A | 111 | 44.310 | 18.296 | 51.808 | 1.00 | 12.70 | A |
| ATOM | 811 | OE2 | GLU | A | 111 | 43.477 | 18.851 | 49.860 | 1.00 | 13.80 | A |
| ATOM | 812 | C | GLU | A | 111 | 40.342 | 22.881 | 50.663 | 1.00 | 12.16 | A |
| ATOM | 813 | O | GLU | A | 111 | 40.751 | 23.998 | 50.983 | 1.00 | 8.45 | A |
| ATOM | 814 | N | LEU | A | 112 | 39.586 | 22.680 | 49.587 | 1.00 | 11.50 | A |
| ATOM | 815 | CA | LEU | A | 112 | 39.157 | 23.802 | 48.753 | 1.00 | 11.60 | A |
| ATOM | 816 | CB | LEU | A | 112 | 38.127 | 23.339 | 47.728 | 1.00 | 12.29 | A |
| ATOM | 817 | CG | LEU | A | 112 | 37.520 | 24.486 | 46.906 | 1.00 | 13.68 | A |
| ATOM | 818 | CD1 | LEU | A | 112 | 38.486 | 24.835 | 45.793 | 1.00 | 14.87 | A |
| ATOM | 819 | CD2 | LEU | A | 112 | 36.183 | 24.067 | 46.307 | 1.00 | 23.81 | A |
| ATOM | 820 | C | LEU | A | 112 | 38.491 | 24.845 | 49.648 | 1.00 | 11.64 | A |
| ATOM | 821 | O | LEU | A | 112 | 38.782 | 26.036 | 49.569 | 1.00 | 9.35 | A |
| ATOM | 822 | N | CYS | A | 113 | 37.598 | 24.370 | 50.511 | 1.00 | 9.13 | A |
| ATOM | 823 | CA | CYS | A | 113 | 36.869 | 25.251 | 51.407 | 1.00 | 10.02 | A |
| ATOM | 824 | C | CYS | A | 113 | 37.806 | 26.040 | 52.332 | 1.00 | 10.42 | A |
| ATOM | 825 | O | CYS | A | 113 | 37.620 | 27.243 | 52.550 | 1.00 | 9.94 | A |
| ATOM | 826 | CB | CYS | A | 113 | 35.881 | 24.414 | 52.215 | 1.00 | 7.06 | A |
| ATOM | 827 | SG | CYS | A | 113 | 34.495 | 23.714 | 51.225 | 1.00 | 12.97 | A |
| ATOM | 828 | N | GLY | A | 114 | 38.815 | 25.357 | 52.854 | 1.00 | 8.53 | A |
| ATOM | 829 | CA | GLY | A | 114 | 39.774 | 25.979 | 53.746 | 1.00 | 8.15 | A |
| ATOM | 830 | C | GLY | A | 114 | 40.615 | 27.023 | 53.048 | 1.00 | 8.58 | A |
| ATOM | 831 | O | GLY | A | 114 | 40.974 | 28.045 | 53.660 | 1.00 | 9.42 | A |

FIGURE 5 (continued)

| | | | | | | | | | | |
|---|---|---|---|---|---|---|---|---|---|---|
| ATOM | 832 | N   | VAL | A | 115 | 40.929 | 26.780 | 51.773 | 1.00 8.91  | A |
| ATOM | 833 | CA  | VAL | A | 115 | 41.724 | 27.727 | 51.001 | 1.00 11.99 | A |
| ATOM | 834 | CB  | VAL | A | 115 | 42.142 | 27.154 | 49.611 | 1.00 10.97 | A |
| ATOM | 835 | CG1 | VAL | A | 115 | 42.754 | 28.274 | 48.736 | 1.00 12.08 | A |
| ATOM | 836 | CG2 | VAL | A | 115 | 43.175 | 26.034 | 49.794 | 1.00 9.96  | A |
| ATOM | 837 | C   | VAL | A | 115 | 40.933 | 28.999 | 50.769 | 1.00 10.50 | A |
| ATOM | 838 | O   | VAL | A | 115 | 41.450 | 30.107 | 50.958 | 1.00 10.53 | A |
| ATOM | 839 | N   | PHE | A | 116 | 39.672 | 28.856 | 50.383 | 1.00 10.04 | A |
| ATOM | 840 | CA  | PHE | A | 116 | 38.885 | 30.046 | 50.123 | 1.00 12.53 | A |
| ATOM | 841 | CB  | PHE | A | 116 | 37.891 | 29.774 | 49.000 | 1.00 8.51  | A |
| ATOM | 842 | CG  | PHE | A | 116 | 38.564 | 29.656 | 47.664 | 1.00 8.77  | A |
| ATOM | 843 | CD1 | PHE | A | 116 | 39.041 | 28.429 | 47.220 | 1.00 7.52  | A |
| ATOM | 844 | CD2 | PHE | A | 116 | 38.792 | 30.791 | 46.892 | 1.00 10.79 | A |
| ATOM | 845 | CE1 | PHE | A | 116 | 39.742 | 28.319 | 46.019 | 1.00 11.26 | A |
| ATOM | 846 | CE2 | PHE | A | 116 | 39.494 | 30.708 | 45.682 | 1.00 12.98 | A |
| ATOM | 847 | CZ  | PHE | A | 116 | 39.971 | 29.463 | 45.244 | 1.00 12.19 | A |
| ATOM | 848 | C   | PHE | A | 116 | 38.236 | 30.713 | 51.319 | 1.00 11.72 | A |
| ATOM | 849 | O   | PHE | A | 116 | 37.688 | 31.802 | 51.180 | 1.00 10.01 | A |
| ATOM | 850 | N   | SER | A | 117 | 38.323 | 30.077 | 52.493 | 1.00 7.36  | A |
| ATOM | 851 | CA  | SER | A | 117 | 37.802 | 30.669 | 53.722 | 1.00 12.12 | A |
| ATOM | 852 | CB  | SER | A | 117 | 37.217 | 29.605 | 54.654 | 1.00 11.41 | A |
| ATOM | 853 | OG  | SER | A | 117 | 38.251 | 28.827 | 55.231 | 1.00 12.73 | A |
| ATOM | 854 | C   | SER | A | 117 | 38.935 | 31.372 | 54.474 | 1.00 12.93 | A |
| ATOM | 855 | O   | SER | A | 117 | 38.693 | 32.241 | 55.316 | 1.00 9.90  | A |
| ATOM | 856 | N   | GLY | A | 118 | 40.169 | 30.988 | 54.174 | 1.00 14.10 | A |
| ATOM | 857 | CA  | GLY | A | 118 | 41.312 | 31.576 | 54.860 | 1.00 13.07 | A |
| ATOM | 858 | C   | GLY | A | 118 | 41.850 | 30.640 | 55.931 | 1.00 15.32 | A |
| ATOM | 859 | O   | GLY | A | 118 | 42.935 | 30.873 | 56.484 | 1.00 15.65 | A |
| ATOM | 860 | N   | ARG | A | 119 | 41.107 | 29.575 | 56.241 | 1.00 15.32 | A |
| ATOM | 861 | CA  | ARG | A | 119 | 41.550 | 28.622 | 57.266 | 1.00 15.10 | A |
| ATOM | 862 | CB  | ARG | A | 119 | 40.503 | 27.518 | 57.485 | 1.00 17.52 | A |
| ATOM | 863 | CG  | ARG | A | 119 | 40.986 | 26.359 | 58.390 | 1.00 19.04 | A |
| ATOM | 864 | CD  | ARG | A | 119 | 39.880 | 25.325 | 58.628 | 1.00 17.23 | A |
| ATOM | 865 | NE  | ARG | A | 119 | 39.338 | 24.771 | 57.377 | 1.00 11.41 | A |
| ATOM | 866 | CZ  | ARG | A | 119 | 39.828 | 23.717 | 56.727 | 1.00 13.77 | A |
| ATOM | 867 | NH1 | ARG | A | 119 | 40.895 | 23.061 | 57.188 | 1.00 9.19  | A |
| ATOM | 868 | NH2 | ARG | A | 119 | 39.239 | 23.317 | 55.607 | 1.00 10.56 | A |
| ATOM | 869 | C   | ARG | A | 119 | 42.896 | 27.990 | 56.896 | 1.00 14.09 | A |
| ATOM | 870 | O   | ARG | A | 119 | 43.749 | 27.784 | 57.757 | 1.00 12.49 | A |
| ATOM | 871 | N   | ILE | A | 120 | 43.074 | 27.672 | 55.620 | 1.00 14.25 | A |
| ATOM | 872 | CA  | ILE | A | 120 | 44.327 | 27.088 | 55.134 | 1.00 11.87 | A |
| ATOM | 873 | CB  | ILE | A | 120 | 44.066 | 25.956 | 54.113 | 1.00 13.86 | A |
| ATOM | 874 | CG2 | ILE | A | 120 | 45.373 | 25.443 | 53.529 | 1.00 12.88 | A |
| ATOM | 875 | CG1 | ILE | A | 120 | 43.349 | 24.796 | 54.812 | 1.00 12.97 | A |
| ATOM | 876 | CD1 | ILE | A | 120 | 42.920 | 23.638 | 53.863 | 1.00 12.93 | A |
| ATOM | 877 | C   | ILE | A | 120 | 45.042 | 28.241 | 54.445 | 1.00 16.50 | A |
| ATOM | 878 | O   | ILE | A | 120 | 44.606 | 28.704 | 53.391 | 1.00 15.43 | A |
| ATOM | 879 | N   | ALA | A | 121 | 46.131 | 28.706 | 55.051 | 1.00 15.30 | A |
| ATOM | 880 | CA  | ALA | A | 121 | 46.884 | 29.848 | 54.529 | 1.00 14.70 | A |
| ATOM | 881 | CB  | ALA | A | 121 | 47.111 | 30.850 | 55.640 | 1.00 21.39 | A |
| ATOM | 882 | C   | ALA | A | 121 | 48.211 | 29.482 | 53.904 | 1.00 15.45 | A |
| ATOM | 883 | O   | ALA | A | 121 | 48.868 | 30.329 | 53.284 | 1.00 16.44 | A |
| ATOM | 884 | N   | ASN | A | 122 | 48.608 | 28.227 | 54.056 | 1.00 12.07 | A |
| ATOM | 885 | CA  | ASN | A | 122 | 49.887 | 27.789 | 53.507 | 1.00 12.53 | A |
| ATOM | 886 | CB  | ASN | A | 122 | 50.853 | 27.467 | 54.660 | 1.00 13.64 | A |
| ATOM | 887 | CG  | ASN | A | 122 | 52.279 | 27.293 | 54.188 | 1.00 16.68 | A |
| ATOM | 888 | OD1 | ASN | A | 122 | 52.666 | 26.224 | 53.725 | 1.00 18.01 | A |
| ATOM | 889 | ND2 | ASN | A | 122 | 53.063 | 28.363 | 54.279 | 1.00 14.68 | A |
| ATOM | 890 | C   | ASN | A | 122 | 49.681 | 26.568 | 52.608 | 1.00 11.32 | A |
| ATOM | 891 | O   | ASN | A | 122 | 48.809 | 25.737 | 52.865 | 1.00 11.94 | A |
| ATOM | 892 | N   | TRP | A | 123 | 50.454 | 26.499 | 51.528 | 1.00 12.38 | A |
| ATOM | 893 | CA  | TRP | A | 123 | 50.365 | 25.390 | 50.580 | 1.00 10.94 | A |
| ATOM | 894 | CB  | TRP | A | 123 | 51.330 | 25.597 | 49.406 | 1.00 10.33 | A |
| ATOM | 895 | CG  | TRP | A | 123 | 50.761 | 26.503 | 48.337 | 1.00 12.83 | A |
| ATOM | 896 | CD2 | TRP | A | 123 | 49.900 | 26.108 | 47.261 | 1.00 10.58 | A |
| ATOM | 897 | CE2 | TRP | A | 123 | 49.568 | 27.279 | 46.533 | 1.00 12.26 | A |
| ATOM | 898 | CE3 | TRP | A | 123 | 49.381 | 24.884 | 46.841 | 1.00 12.52 | A |
| ATOM | 899 | CD1 | TRP | A | 123 | 50.916 | 27.862 | 48.227 | 1.00 15.24 | A |
| ATOM | 900 | NE1 | TRP | A | 123 | 50.198 | 28.334 | 47.140 | 1.00 12.70 | A |
| ATOM | 901 | CZ2 | TRP | A | 123 | 48.732 | 27.256 | 45.403 | 1.00 10.92 | A |
| ATOM | 902 | CZ3 | TRP | A | 123 | 48.547 | 24.863 | 45.710 | 1.00 16.36 | A |
| ATOM | 903 | CH2 | TRP | A | 123 | 48.237 | 26.043 | 45.012 | 1.00 9.72  | A |
| ATOM | 904 | C   | TRP | A | 123 | 50.661 | 24.045 | 51.213 | 1.00 13.55 | A |
| ATOM | 905 | O   | TRP | A | 123 | 50.284 | 23.006 | 50.676 | 1.00 13.98 | A |
| ATOM | 906 | N   | SER | A | 124 | 51.346 | 24.054 | 52.349 | 1.00 13.10 | A |
| ATOM | 907 | CA  | SER | A | 124 | 51.654 | 22.801 | 53.010 | 1.00 11.36 | A |

FIGURE 5 (continued)

```
ATOM    908  CB   SER A 124      52.670  23.038  54.135  1.00 11.89      A
ATOM    909  OG   SER A 124      52.130  23.884  55.132  1.00 14.19      A
ATOM    910  C    SER A 124      50.361  22.161  53.564  1.00 17.25      A
ATOM    911  O    SER A 124      50.354  20.974  53.924  1.00 13.81      A
ATOM    912  N    GLY A 125      49.273  22.937  53.617  1.00 13.73      A
ATOM    913  CA   GLY A 125      47.999  22.416  54.117  1.00 13.26      A
ATOM    914  C    GLY A 125      47.216  21.569  53.101  1.00 19.05      A
ATOM    915  O    GLY A 125      46.116  21.066  53.404  1.00 15.82      A
ATOM    916  N    ILE A 126      47.759  21.413  51.892  1.00 11.57      A
ATOM    917  CA   ILE A 126      47.111  20.590  50.866  1.00 13.57      A
ATOM    918  CB   ILE A 126      47.116  21.338  49.499  1.00 10.65      A
ATOM    919  CG2  ILE A 126      46.584  20.440  48.369  1.00 10.73      A
ATOM    920  CG1  ILE A 126      46.244  22.598  49.639  1.00 14.04      A
ATOM    921  CD1  ILE A 126      46.355  23.571  48.474  1.00 21.47      A
ATOM    922  C    ILE A 126      47.886  19.270  50.794  1.00 14.42      A
ATOM    923  O    ILE A 126      49.012  19.228  50.299  1.00 12.48      A
ATOM    924  N    THR A 127      47.287  18.199  51.310  1.00 14.33      A
ATOM    925  CA   THR A 127      47.974  16.918  51.341  1.00 15.70      A
ATOM    926  CB   THR A 127      47.144  15.848  52.079  1.00 20.78      A
ATOM    927  OG1  THR A 127      45.978  15.519  51.309  1.00 21.71      A
ATOM    928  CG2  THR A 127      46.719  16.379  53.462  1.00 19.06      A
ATOM    929  C    THR A 127      48.389  16.389  49.978  1.00 15.85      A
ATOM    930  O    THR A 127      47.628  16.442  49.011  1.00 15.48      A
ATOM    931  N    GLY A 128      49.627  15.907  49.925  1.00 11.25      A
ATOM    932  CA   GLY A 128      50.202  15.348  48.719  1.00 13.92      A
ATOM    933  C    GLY A 128      50.726  16.299  47.655  1.00 15.93      A
ATOM    934  O    GLY A 128      51.360  15.837  46.718  1.00 18.28      A
ATOM    935  N    ALA A 129      50.491  17.610  47.788  1.00 13.36      A
ATOM    936  CA   ALA A 129      50.929  18.558  46.765  1.00 14.53      A
ATOM    937  CB   ALA A 129      50.138  19.873  46.886  1.00 13.51      A
ATOM    938  C    ALA A 129      52.428  18.856  46.777  1.00 20.08      A
ATOM    939  O    ALA A 129      52.954  19.427  45.811  1.00 13.92      A
ATOM    940  N    GLY A 130      53.110  18.489  47.863  1.00 15.72      A
ATOM    941  CA   GLY A 130      54.552  18.715  47.931  1.00 18.22      A
ATOM    942  C    GLY A 130      54.937  20.167  47.720  1.00 17.01      A
ATOM    943  O    GLY A 130      55.944  20.485  47.088  1.00 16.95      A
ATOM    944  N    ARG A 131      54.130  21.059  48.274  1.00 14.88      A
ATOM    945  CA   ARG A 131      54.361  22.500  48.142  1.00 14.67      A
ATOM    946  CB   ARG A 131      53.312  23.102  47.190  1.00 10.65      A
ATOM    947  CG   ARG A 131      53.506  22.713  45.730  1.00 14.78      A
ATOM    948  CD   ARG A 131      52.234  22.985  44.895  1.00 13.27      A
ATOM    949  NE   ARG A 131      52.479  22.959  43.441  1.00 13.40      A
ATOM    950  CZ   ARG A 131      52.670  21.873  42.695  1.00 12.12      A
ATOM    951  NH1  ARG A 131      52.880  22.010  41.383  1.00 12.83      A
ATOM    952  NH2  ARG A 131      52.656  20.660  43.233  1.00 13.76      A
ATOM    953  C    ARG A 131      54.217  23.171  49.502  1.00 14.12      A
ATOM    954  O    ARG A 131      53.451  22.703  50.329  1.00 15.12      A
ATOM    955  N    SER A 132      54.948  24.258  49.730  1.00 12.39      A
ATOM    956  CA   SER A 132      54.830  24.987  50.990  1.00 15.94      A
ATOM    957  CB   SER A 132      55.817  24.450  52.046  1.00 22.25      A
ATOM    958  OG   SER A 132      57.143  24.690  51.644  1.00 25.99      A
ATOM    959  C    SER A 132      55.070  26.468  50.735  1.00 12.92      A
ATOM    960  O    SER A 132      55.695  26.857  49.746  1.00 16.84      A
ATOM    961  N    GLY A 133      54.570  27.300  51.634  1.00 14.33      A
ATOM    962  CA   GLY A 133      54.695  28.734  51.442  1.00 14.73      A
ATOM    963  C    GLY A 133      53.295  29.318  51.394  1.00 14.56      A
ATOM    964  O    GLY A 133      52.320  28.589  51.183  1.00 12.31      A
ATOM    965  N    PRO A 134      53.162  30.633  51.561  1.00 15.09      A
ATOM    966  CD   PRO A 134      54.254  31.607  51.743  1.00 16.35      A
ATOM    967  CA   PRO A 134      51.854  31.291  51.548  1.00 14.55      A
ATOM    968  CB   PRO A 134      52.196  32.760  51.828  1.00 20.54      A
ATOM    969  CG   PRO A 134      53.623  32.900  51.266  1.00 21.58      A
ATOM    970  C    PRO A 134      50.997  31.143  50.299  1.00 16.29      A
ATOM    971  O    PRO A 134      51.509  31.105  49.180  1.00 12.69      A
ATOM    972  N    ILE A 135      49.685  31.057  50.527  1.00 13.39      A
ATOM    973  CA   ILE A 135      48.688  30.973  49.454  1.00 13.74      A
ATOM    974  CB   ILE A 135      47.523  30.010  49.801  1.00 15.95      A
ATOM    975  CG2  ILE A 135      46.417  30.115  48.727  1.00 13.97      A
ATOM    976  CG1  ILE A 135      48.032  28.582  49.918  1.00 15.73      A
ATOM    977  CD1  ILE A 135      46.988  27.607  50.453  1.00 15.61      A
ATOM    978  C    ILE A 135      48.077  32.366  49.353  1.00 13.04      A
ATOM    979  O    ILE A 135      47.757  32.983  50.372  1.00 15.69      A
ATOM    980  N    GLN A 136      47.918  32.872  48.136  1.00 11.91      A
ATOM    981  CA   GLN A 136      47.319  34.190  47.958  1.00 11.20      A
ATOM    982  CB   GLN A 136      48.317  35.145  47.306  1.00 12.71      A
ATOM    983  CG   GLN A 136      47.892  36.594  47.337  1.00 19.42      A
```

FIGURE 5 (continued)

```
ATOM    984  CD   GLN A 136      48.999  37.566  46.905  1.00  23.10           A
ATOM    985  OE1  GLN A 136      49.620  37.403  45.858  1.00  23.52           A
ATOM    986  NE2  GLN A 136      49.233  38.585  47.714  1.00  30.84           A
ATOM    987  C    GLN A 136      46.105  34.023  47.053  1.00   9.51           A
ATOM    988  O    GLN A 136      46.254  33.639  45.921  1.00   9.81           A
ATOM    989  N    VAL A 137      44.911  34.303  47.552  1.00   8.18           A
ATOM    990  CA   VAL A 137      43.717  34.161  46.733  1.00   4.96           A
ATOM    991  CB   VAL A 137      42.470  33.907  47.657  1.00   8.36           A
ATOM    992  CG1  VAL A 137      41.176  34.014  46.855  1.00   5.20           A
ATOM    993  CG2  VAL A 137      42.589  32.543  48.294  1.00  10.61           A
ATOM    994  C    VAL A 137      43.442  35.380  45.837  1.00   9.91           A
ATOM    995  O    VAL A 137      43.555  36.534  46.284  1.00   9.14           A
ATOM    996  N    VAL A 138      43.124  35.114  44.566  1.00   7.01           A
ATOM    997  CA   VAL A 138      42.735  36.134  43.600  1.00   8.67           A
ATOM    998  CB   VAL A 138      43.437  35.976  42.226  1.00   9.91           A
ATOM    999  CG1  VAL A 138      42.983  37.092  41.301  1.00  11.71           A
ATOM   1000  CG2  VAL A 138      44.947  36.068  42.394  1.00  18.67           A
ATOM   1001  C    VAL A 138      41.237  35.914  43.386  1.00   7.40           A
ATOM   1002  O    VAL A 138      40.791  34.775  43.196  1.00   7.75           A
ATOM   1003  N    TYR A 139      40.452  36.987  43.435  1.00   9.87           A
ATOM   1004  CA   TYR A 139      39.009  36.871  43.256  1.00   9.42           A
ATOM   1005  CB   TYR A 139      38.303  36.902  44.625  1.00   8.26           A
ATOM   1006  CG   TYR A 139      38.509  38.192  45.389  1.00   9.37           A
ATOM   1007  CD1  TYR A 139      37.570  39.211  45.322  1.00   8.61           A
ATOM   1008  CE1  TYR A 139      37.748  40.424  46.013  1.00   9.72           A
ATOM   1009  CD2  TYR A 139      39.659  38.397  46.177  1.00   9.71           A
ATOM   1010  CE2  TYR A 139      39.853  39.616  46.878  1.00  12.90           A
ATOM   1011  CZ   TYR A 139      38.890  40.623  46.786  1.00  15.66           A
ATOM   1012  OH   TYR A 139      39.045  41.829  47.459  1.00   8.23           A
ATOM   1013  C    TYR A 139      38.507  38.006  42.381  1.00   8.45           A
ATOM   1014  O    TYR A 139      39.246  38.947  42.099  1.00   8.15           A
ATOM   1015  N    ARG A 140      37.259  37.899  41.935  1.00   8.93           A
ATOM   1016  CA   ARG A 140      36.660  38.903  41.070  1.00   7.41           A
ATOM   1017  CB   ARG A 140      35.514  38.296  40.243  1.00  10.32           A
ATOM   1018  CG   ARG A 140      35.991  37.317  39.148  1.00   5.86           A
ATOM   1019  CD   ARG A 140      36.556  38.103  37.948  1.00   5.80           A
ATOM   1020  NE   ARG A 140      35.502  38.821  37.218  1.00   7.23           A
ATOM   1021  CZ   ARG A 140      34.659  38.232  36.376  1.00  11.87           A
ATOM   1022  NH1  ARG A 140      34.748  36.918  36.152  1.00   5.93           A
ATOM   1023  NH2  ARG A 140      33.715  38.952  35.769  1.00   8.31           A
ATOM   1024  C    ARG A 140      36.129  40.063  41.895  1.00   8.44           A
ATOM   1025  O    ARG A 140      35.327  39.896  42.832  1.00   8.91           A
ATOM   1026  N    ALA A 141      36.583  41.242  41.523  1.00   8.44           A
ATOM   1027  CA   ALA A 141      36.198  42.471  42.206  1.00   8.99           A
ATOM   1028  CB   ALA A 141      37.121  43.579  41.761  1.00  12.40           A
ATOM   1029  C    ALA A 141      34.748  42.895  41.975  1.00  11.15           A
ATOM   1030  O    ALA A 141      34.091  43.421  42.878  1.00   9.17           A
ATOM   1031  N    GLU A 142      34.258  42.679  40.765  1.00  10.41           A
ATOM   1032  CA   GLU A 142      32.912  43.110  40.401  1.00  11.28           A
ATOM   1033  CB   GLU A 142      32.944  43.735  38.995  1.00  11.17           A
ATOM   1034  CG   GLU A 142      32.968  42.720  37.800  1.00  16.02           A
ATOM   1035  CD   GLU A 142      34.319  41.984  37.551  1.00  14.71           A
ATOM   1036  OE1  GLU A 142      35.102  41.758  38.492  1.00  20.26           A
ATOM   1037  OE2  GLU A 142      34.582  41.608  36.382  1.00  15.07           A
ATOM   1038  C    GLU A 142      31.854  42.001  40.428  1.00  15.45           A
ATOM   1039  O    GLU A 142      32.160  40.827  40.689  1.00  11.17           A
ATOM   1040  N    VAL A 143      30.604  42.399  40.170  1.00  13.82           A
ATOM   1041  CA   VAL A 143      29.474  41.461  40.114  1.00  12.65           A
ATOM   1042  CB   VAL A 143      28.155  42.192  39.792  1.00  12.26           A
ATOM   1043  CG1  VAL A 143      27.052  41.196  39.668  1.00  17.81           A
ATOM   1044  CG2  VAL A 143      27.822  43.174  40.870  1.00  18.80           A
ATOM   1045  C    VAL A 143      29.770  40.456  38.996  1.00  12.06           A
ATOM   1046  O    VAL A 143      29.785  40.814  37.811  1.00  10.75           A
ATOM   1047  N    SER A 144      29.972  39.198  39.388  1.00  10.21           A
ATOM   1048  CA   SER A 144      30.352  38.119  38.462  1.00   6.60           A
ATOM   1049  CB   SER A 144      31.822  37.764  38.758  1.00   8.21           A
ATOM   1050  OG   SER A 144      32.188  36.468  38.328  1.00   8.64           A
ATOM   1051  C    SER A 144      29.499  36.834  38.512  1.00   7.57           A
ATOM   1052  O    SER A 144      29.166  36.346  39.601  1.00   8.05           A
ATOM   1053  N    GLY A 145      29.168  36.303  37.330  1.00   5.34           A
ATOM   1054  CA   GLY A 145      28.437  35.047  37.226  1.00   7.72           A
ATOM   1055  C    GLY A 145      29.335  33.884  37.638  1.00   7.84           A
ATOM   1056  O    GLY A 145      28.873  32.870  38.197  1.00   6.69           A
ATOM   1057  N    THR A 146      30.628  34.001  37.357  1.00   6.57           A
ATOM   1058  CA   THR A 146      31.574  32.953  37.758  1.00   6.39           A
ATOM   1059  CB   THR A 146      33.012  33.263  37.279  1.00   9.37           A
```

FIGURE 5 (continued)

```
ATOM   1060  OG1  THR A 146      33.026  33.463  35.855  1.00   8.49      A
ATOM   1061  CG2  THR A 146      33.928  32.087  37.613  1.00  11.25      A
ATOM   1062  C    THR A 146      31.569  32.892  39.294  1.00   8.02      A
ATOM   1063  O    THR A 146      31.601  31.802  39.888  1.00   8.00      A
ATOM   1064  N    THR A 147      31.551  34.064  39.930  1.00   6.33      A
ATOM   1065  CA   THR A 147      31.483  34.131  41.394  1.00   8.35      A
ATOM   1066  CB   THR A 147      31.554  35.591  41.921  1.00   6.29      A
ATOM   1067  OG1  THR A 147      32.834  36.161  41.624  1.00   7.92      A
ATOM   1068  CG2  THR A 147      31.373  35.602  43.450  1.00   8.46      A
ATOM   1069  C    THR A 147      30.175  33.486  41.885  1.00   5.86      A
ATOM   1070  O    THR A 147      30.172  32.745  42.883  1.00   7.90      A
ATOM   1071  N    GLU A 148      29.059  33.751  41.198  1.00   5.81      A
ATOM   1072  CA   GLU A 148      27.786  33.131  41.592  1.00   5.50      A
ATOM   1073  CB   GLU A 148      26.644  33.653  40.710  1.00   6.06      A
ATOM   1074  CG   GLU A 148      25.284  33.004  41.058  1.00  10.99      A
ATOM   1075  CD   GLU A 148      24.076  33.737  40.457  1.00  12.04      A
ATOM   1076  OE1  GLU A 148      23.920  34.966  40.685  1.00   9.92      A
ATOM   1077  OE2  GLU A 148      23.271  33.078  39.765  1.00  13.03      A
ATOM   1078  C    GLU A 148      27.846  31.591  41.491  1.00   6.20      A
ATOM   1079  O    GLU A 148      27.419  30.866  42.408  1.00   7.44      A
ATOM   1080  N    LEU A 149      28.318  31.077  40.359  1.00   4.66      A
ATOM   1081  CA   LEU A 149      28.442  29.616  40.196  1.00   6.87      A
ATOM   1082  CB   LEU A 149      29.011  29.301  38.807  1.00   7.74      A
ATOM   1083  CG   LEU A 149      28.105  29.569  37.591  1.00   8.75      A
ATOM   1084  CD1  LEU A 149      28.878  29.218  36.342  1.00  10.50      A
ATOM   1085  CD2  LEU A 149      26.804  28.721  37.678  1.00   9.52      A
ATOM   1086  C    LEU A 149      29.376  28.980  41.254  1.00   7.07      A
ATOM   1087  O    LEU A 149      29.127  27.865  41.754  1.00   7.65      A
ATOM   1088  N    PHE A 150      30.473  29.670  41.568  1.00   8.71      A
ATOM   1089  CA   PHE A 150      31.459  29.183  42.540  1.00   7.06      A
ATOM   1090  CB   PHE A 150      32.752  30.021  42.427  1.00   6.97      A
ATOM   1091  CG   PHE A 150      33.884  29.551  43.325  1.00   9.24      A
ATOM   1092  CD1  PHE A 150      34.313  28.225  43.305  1.00  10.27      A
ATOM   1093  CD2  PHE A 150      34.557  30.455  44.138  1.00  12.03      A
ATOM   1094  CE1  PHE A 150      35.411  27.803  44.081  1.00  12.21      A
ATOM   1095  CE2  PHE A 150      35.657  30.050  44.920  1.00  11.31      A
ATOM   1096  CZ   PHE A 150      36.083  28.721  44.890  1.00  10.56      A
ATOM   1097  C    PHE A 150      30.936  29.217  43.987  1.00   7.58      A
ATOM   1098  O    PHE A 150      31.060  28.236  44.709  1.00   6.52      A
ATOM   1099  N    THR A 151      30.350  30.334  44.409  1.00   7.57      A
ATOM   1100  CA   THR A 151      29.836  30.437  45.770  1.00   8.97      A
ATOM   1101  CB   THR A 151      29.548  31.938  46.193  1.00   9.78      A
ATOM   1102  OG1  THR A 151      28.580  32.526  45.314  1.00   8.77      A
ATOM   1103  CG2  THR A 151      30.826  32.744  46.152  1.00   7.96      A
ATOM   1104  C    THR A 151      28.588  29.588  45.988  1.00   7.22      A
ATOM   1105  O    THR A 151      28.274  29.245  47.131  1.00   7.49      A
ATOM   1106  N    ARG A 152      27.873  29.229  44.916  1.00   5.13      A
ATOM   1107  CA   ARG A 152      26.715  28.351  45.099  1.00   9.17      A
ATOM   1108  CB   ARG A 152      25.914  28.189  43.796  1.00   9.15      A
ATOM   1109  CG   ARG A 152      24.606  27.376  43.974  1.00  10.79      A
ATOM   1110  CD   ARG A 152      23.671  27.529  42.755  1.00  17.61      A
ATOM   1111  NE   ARG A 152      23.071  28.868  42.641  1.00  14.93      A
ATOM   1112  CZ   ARG A 152      23.188  29.662  41.577  1.00  16.78      A
ATOM   1113  NH1  ARG A 152      22.605  30.860  41.565  1.00  11.71      A
ATOM   1114  NH2  ARG A 152      23.885  29.265  40.518  1.00  11.02      A
ATOM   1115  C    ARG A 152      27.274  27.007  45.557  1.00   7.79      A
ATOM   1116  O    ARG A 152      26.671  26.313  46.389  1.00   5.08      A
ATOM   1117  N    PHE A 153      28.436  26.639  45.017  1.00   6.70      A
ATOM   1118  CA   PHE A 153      29.101  25.395  45.413  1.00   9.70      A
ATOM   1119  CB   PHE A 153      30.280  25.059  44.478  1.00   7.27      A
ATOM   1120  CG   PHE A 153      30.974  23.747  44.812  1.00   6.93      A
ATOM   1121  CD1  PHE A 153      30.451  22.532  44.389  1.00   9.41      A
ATOM   1122  CD2  PHE A 153      32.134  23.738  45.592  1.00   9.61      A
ATOM   1123  CE1  PHE A 153      31.069  21.315  44.747  1.00  11.43      A
ATOM   1124  CE2  PHE A 153      32.764  22.534  45.959  1.00  13.90      A
ATOM   1125  CZ   PHE A 153      32.229  21.323  45.537  1.00  11.19      A
ATOM   1126  C    PHE A 153      29.640  25.503  46.842  1.00   8.50      A
ATOM   1127  O    PHE A 153      29.455  24.586  47.638  1.00   8.41      A
ATOM   1128  N    LEU A 154      30.320  26.599  47.167  1.00   6.84      A
ATOM   1129  CA   LEU A 154      30.877  26.752  48.521  1.00   6.20      A
ATOM   1130  CB   LEU A 154      31.672  28.060  48.657  1.00   6.23      A
ATOM   1131  CG   LEU A 154      32.876  28.250  47.720  1.00   6.30      A
ATOM   1132  CD1  LEU A 154      33.543  29.583  48.020  1.00   9.48      A
ATOM   1133  CD2  LEU A 154      33.893  27.117  47.886  1.00   6.15      A
ATOM   1134  C    LEU A 154      29.762  26.737  49.564  1.00   6.13      A
ATOM   1135  O    LEU A 154      29.912  26.170  50.641  1.00   9.16      A
```

FIGURE 5 (continued)

| | | | | | | | | | |
|---|---|---|---|---|---|---|---|---|---|
| ATOM | 1136 | N | ASN | A | 155 | 28.652 | 27.376 | 49.233 | 1.00 | 5.19 | A |
| ATOM | 1137 | CA | ASN | A | 155 | 27.493 | 27.430 | 50.116 | 1.00 | 6.32 | A |
| ATOM | 1138 | CB | ASN | A | 155 | 26.406 | 28.314 | 49.486 | 1.00 | 11.33 | A |
| ATOM | 1139 | CG | ASN | A | 155 | 25.093 | 28.294 | 50.274 | 1.00 | 14.59 | A |
| ATOM | 1140 | OD1 | ASN | A | 155 | 24.149 | 27.596 | 49.906 | 1.00 | 9.21 | A |
| ATOM | 1141 | ND2 | ASN | A | 155 | 25.034 | 29.062 | 51.361 | 1.00 | 8.23 | A |
| ATOM | 1142 | C | ASN | A | 155 | 26.929 | 26.042 | 50.363 | 1.00 | 8.76 | A |
| ATOM | 1143 | O | ASN | A | 155 | 26.465 | 25.712 | 51.465 | 1.00 | 8.00 | A |
| ATOM | 1144 | N | ALA | A | 156 | 26.965 | 25.203 | 49.336 | 1.00 | 8.80 | A |
| ATOM | 1145 | CA | ALA | A | 156 | 26.418 | 23.867 | 49.493 | 1.00 | 7.63 | A |
| ATOM | 1146 | CB | ALA | A | 156 | 26.068 | 23.300 | 48.119 | 1.00 | 8.06 | A |
| ATOM | 1147 | C | ALA | A | 156 | 27.336 | 22.882 | 50.222 | 1.00 | 12.23 | A |
| ATOM | 1148 | O | ALA | A | 156 | 26.854 | 22.037 | 50.994 | 1.00 | 9.62 | A |
| ATOM | 1149 | N | LYS | A | 157 | 28.646 | 23.029 | 50.015 | 1.00 | 9.93 | A |
| ATOM | 1150 | CA | LYS | A | 157 | 29.623 | 22.064 | 50.537 | 1.00 | 10.69 | A |
| ATOM | 1151 | CB | LYS | A | 157 | 30.437 | 21.527 | 49.352 | 1.00 | 14.97 | A |
| ATOM | 1152 | CG | LYS | A | 157 | 29.604 | 20.877 | 48.227 | 1.00 | 13.56 | A |
| ATOM | 1153 | CD | LYS | A | 157 | 28.855 | 19.640 | 48.729 | 1.00 | 16.77 | A |
| ATOM | 1154 | CE | LYS | A | 157 | 28.357 | 18.784 | 47.575 | 1.00 | 22.67 | A |
| ATOM | 1155 | NZ | LYS | A | 157 | 27.652 | 17.546 | 48.069 | 1.00 | 21.73 | A |
| ATOM | 1156 | C | LYS | A | 157 | 30.611 | 22.438 | 51.638 | 1.00 | 8.73 | A |
| ATOM | 1157 | O | LYS | A | 157 | 31.215 | 21.552 | 52.245 | 1.00 | 11.63 | A |
| ATOM | 1158 | N | CYS | A | 158 | 30.821 | 23.725 | 51.876 | 1.00 | 8.12 | A |
| ATOM | 1159 | CA | CYS | A | 158 | 31.759 | 24.132 | 52.916 | 1.00 | 8.20 | A |
| ATOM | 1160 | C | CYS | A | 158 | 30.974 | 24.252 | 54.207 | 1.00 | 9.14 | A |
| ATOM | 1161 | O | CYS | A | 158 | 30.648 | 25.349 | 54.661 | 1.00 | 10.53 | A |
| ATOM | 1162 | CB | CYS | A | 158 | 32.390 | 25.464 | 52.537 | 1.00 | 10.13 | A |
| ATOM | 1163 | SG | CYS | A | 158 | 33.331 | 25.358 | 50.982 | 1.00 | 11.82 | A |
| ATOM | 1164 | N | THR | A | 159 | 30.699 | 23.108 | 54.822 | 1.00 | 8.92 | A |
| ATOM | 1165 | CA | THR | A | 159 | 29.856 | 23.091 | 56.017 | 1.00 | 6.75 | A |
| ATOM | 1166 | CB | THR | A | 159 | 28.850 | 21.933 | 55.903 | 1.00 | 10.13 | A |
| ATOM | 1167 | OG1 | THR | A | 159 | 29.551 | 20.690 | 55.987 | 1.00 | 12.88 | A |
| ATOM | 1168 | CG2 | THR | A | 159 | 28.146 | 21.989 | 54.527 | 1.00 | 14.84 | A |
| ATOM | 1169 | C | THR | A | 159 | 30.545 | 23.021 | 57.361 | 1.00 | 8.62 | A |
| ATOM | 1170 | O | THR | A | 159 | 29.878 | 22.956 | 58.398 | 1.00 | 7.39 | A |
| ATOM | 1171 | N | THR | A | 160 | 31.875 | 23.038 | 57.358 | 1.00 | 8.39 | A |
| ATOM | 1172 | CA | THR | A | 160 | 32.603 | 22.980 | 58.612 | 1.00 | 9.53 | A |
| ATOM | 1173 | CB | THR | A | 160 | 33.194 | 21.558 | 58.889 | 1.00 | 8.99 | A |
| ATOM | 1174 | OG1 | THR | A | 160 | 34.011 | 21.140 | 57.788 | 1.00 | 12.55 | A |
| ATOM | 1175 | CG2 | THR | A | 160 | 32.083 | 20.559 | 59.114 | 1.00 | 11.60 | A |
| ATOM | 1176 | C | THR | A | 160 | 33.727 | 24.010 | 58.712 | 1.00 | 10.20 | A |
| ATOM | 1177 | O | THR | A | 160 | 34.774 | 23.739 | 59.314 | 1.00 | 8.76 | A |
| ATOM | 1178 | N | GLN | A | 161 | 33.523 | 25.189 | 58.121 | 1.00 | 8.66 | A |
| ATOM | 1179 | CA | GLN | A | 161 | 34.525 | 26.260 | 58.254 | 1.00 | 9.46 | A |
| ATOM | 1180 | CB | GLN | A | 161 | 34.564 | 27.121 | 56.989 | 1.00 | 9.58 | A |
| ATOM | 1181 | CG | GLN | A | 161 | 34.956 | 26.309 | 55.742 | 1.00 | 7.83 | A |
| ATOM | 1182 | CD | GLN | A | 161 | 36.305 | 25.608 | 55.936 | 1.00 | 10.81 | A |
| ATOM | 1183 | OE1 | GLN | A | 161 | 36.429 | 24.396 | 55.758 | 1.00 | 12.80 | A |
| ATOM | 1184 | NE2 | GLN | A | 161 | 37.306 | 26.374 | 56.313 | 1.00 | 10.64 | A |
| ATOM | 1185 | C | GLN | A | 161 | 34.058 | 27.096 | 59.449 | 1.00 | 8.71 | A |
| ATOM | 1186 | O | GLN | A | 161 | 32.979 | 26.866 | 59.960 | 1.00 | 8.58 | A |
| ATOM | 1187 | N | PRO | A | 162 | 34.870 | 28.047 | 59.928 | 1.00 | 11.51 | A |
| ATOM | 1188 | CD | PRO | A | 162 | 36.316 | 28.193 | 59.693 | 1.00 | 10.65 | A |
| ATOM | 1189 | CA | PRO | A | 162 | 34.433 | 28.869 | 61.071 | 1.00 | 9.23 | A |
| ATOM | 1190 | CB | PRO | A | 162 | 35.631 | 29.780 | 61.326 | 1.00 | 11.89 | A |
| ATOM | 1191 | CG | PRO | A | 162 | 36.786 | 28.884 | 60.979 | 1.00 | 14.39 | A |
| ATOM | 1192 | C | PRO | A | 162 | 33.171 | 29.660 | 60.727 | 1.00 | 10.67 | A |
| ATOM | 1193 | O | PRO | A | 162 | 32.280 | 29.838 | 61.567 | 1.00 | 12.32 | A |
| ATOM | 1194 | N | GLY | A | 163 | 33.112 | 30.158 | 59.492 | 1.00 | 8.94 | A |
| ATOM | 1195 | CA | GLY | A | 163 | 31.943 | 30.903 | 59.040 | 1.00 | 11.83 | A |
| ATOM | 1196 | C | GLY | A | 163 | 31.307 | 30.149 | 57.883 | 1.00 | 11.53 | A |
| ATOM | 1197 | O | GLY | A | 163 | 31.687 | 28.989 | 57.628 | 1.00 | 9.27 | A |
| ATOM | 1198 | N | THR | A | 164 | 30.359 | 30.781 | 57.178 | 1.00 | 7.79 | A |
| ATOM | 1199 | CA | THR | A | 164 | 29.698 | 30.140 | 56.039 | 1.00 | 10.06 | A |
| ATOM | 1200 | CB | THR | A | 164 | 28.213 | 29.775 | 56.347 | 1.00 | 9.77 | A |
| ATOM | 1201 | OG1 | THR | A | 164 | 27.565 | 30.914 | 56.934 | 1.00 | 12.97 | A |
| ATOM | 1202 | CG2 | THR | A | 164 | 28.119 | 28.585 | 57.328 | 1.00 | 7.94 | A |
| ATOM | 1203 | C | THR | A | 164 | 29.696 | 31.081 | 54.837 | 1.00 | 10.41 | A |
| ATOM | 1204 | O | THR | A | 164 | 29.786 | 32.301 | 55.001 | 1.00 | 7.96 | A |
| ATOM | 1205 | N | PHE | A | 165 | 29.571 | 30.507 | 53.637 | 1.00 | 7.32 | A |
| ATOM | 1206 | CA | PHE | A | 165 | 29.551 | 31.275 | 52.395 | 1.00 | 9.34 | A |
| ATOM | 1207 | CB | PHE | A | 165 | 30.321 | 30.541 | 51.299 | 1.00 | 8.51 | A |
| ATOM | 1208 | CG | PHE | A | 165 | 31.799 | 30.451 | 51.539 | 1.00 | 7.69 | A |
| ATOM | 1209 | CD1 | PHE | A | 165 | 32.659 | 31.455 | 51.096 | 1.00 | 8.05 | A |
| ATOM | 1210 | CD2 | PHE | A | 165 | 32.338 | 29.338 | 52.181 | 1.00 | 10.52 | A |
| ATOM | 1211 | CE1 | PHE | A | 165 | 34.062 | 31.349 | 51.288 | 1.00 | 6.48 | A |

FIGURE 5 (continued)

```
ATOM   1212  CE2  PHE A 165      33.720  29.214  52.385  1.00  6.44         A
ATOM   1213  CZ   PHE A 165      34.591  30.221  51.935  1.00  7.86         A
ATOM   1214  C    PHE A 165      28.135  31.467  51.854  1.00 10.39         A
ATOM   1215  O    PHE A 165      27.428  30.485  51.648  1.00 11.83         A
ATOM   1216  N    ALA A 166      27.738  32.712  51.601  1.00  8.80         A
ATOM   1217  CA   ALA A 166      26.424  33.000  51.006  1.00 10.97         A
ATOM   1218  CB   ALA A 166      25.942  34.397  51.423  1.00 10.57         A
ATOM   1219  C    ALA A 166      26.593  32.960  49.483  1.00 10.58         A
ATOM   1220  O    ALA A 166      27.694  33.182  48.968  1.00  7.60         A
ATOM   1221  N    VAL A 167      25.516  32.668  48.766  1.00  9.26         A
ATOM   1222  CA   VAL A 167      25.572  32.658  47.303  1.00  7.71         A
ATOM   1223  CB   VAL A 167      24.384  31.924  46.686  1.00  7.77         A
ATOM   1224  CG1  VAL A 167      24.546  31.870  45.159  1.00  8.04         A
ATOM   1225  CG2  VAL A 167      24.283  30.511  47.265  1.00 10.61         A
ATOM   1226  C    VAL A 167      25.473  34.123  46.875  1.00  8.91         A
ATOM   1227  O    VAL A 167      24.523  34.816  47.244  1.00  7.79         A
ATOM   1228  N    THR A 168      26.408  34.580  46.048  1.00  8.13         A
ATOM   1229  CA   THR A 168      26.411  35.974  45.653  1.00  6.66         A
ATOM   1230  CB   THR A 168      27.060  36.810  46.769  1.00 13.46         A
ATOM   1231  OG1  THR A 168      27.129  38.188  46.370  1.00 12.35         A
ATOM   1232  CG2  THR A 168      28.478  36.311  47.040  1.00 12.28         A
ATOM   1233  C    THR A 168      27.228  36.178  44.375  1.00 11.69         A
ATOM   1234  O    THR A 168      27.960  35.282  43.947  1.00 11.22         A
ATOM   1235  N    THR A 169      27.106  37.352  43.770  1.00  9.36         A
ATOM   1236  CA   THR A 169      27.888  37.641  42.580  1.00  5.90         A
ATOM   1237  CB   THR A 169      27.074  38.484  41.565  1.00 11.79         A
ATOM   1238  OG1  THR A 169      26.724  39.739  42.169  1.00  9.77         A
ATOM   1239  CG2  THR A 169      25.811  37.747  41.128  1.00 12.13         A
ATOM   1240  C    THR A 169      29.156  38.450  42.953  1.00  9.03         A
ATOM   1241  O    THR A 169      30.000  38.712  42.099  1.00  8.64         A
ATOM   1242  N    VAL A 170      29.279  38.848  44.224  1.00 11.21         A
ATOM   1243  CA   VAL A 170      30.430  39.641  44.680  1.00 11.07         A
ATOM   1244  CB   VAL A 170      29.944  41.003  45.248  1.00  8.64         A
ATOM   1245  CG1  VAL A 170      29.433  41.863  44.106  1.00  8.12         A
ATOM   1246  CG2  VAL A 170      28.802  40.805  46.208  1.00 14.20         A
ATOM   1247  C    VAL A 170      31.158  38.830  45.741  1.00 10.94         A
ATOM   1248  O    VAL A 170      30.694  38.747  46.859  1.00 11.12         A
ATOM   1249  N    PHE A 171      32.305  38.247  45.386  1.00 11.66         A
ATOM   1250  CA   PHE A 171      33.003  37.367  46.312  1.00  9.52         A
ATOM   1251  CB   PHE A 171      34.279  36.775  45.677  1.00  8.67         A
ATOM   1252  CG   PHE A 171      34.940  35.686  46.519  1.00 10.69         A
ATOM   1253  CD1  PHE A 171      36.009  35.978  47.358  1.00  9.84         A
ATOM   1254  CD2  PHE A 171      34.457  34.377  46.502  1.00 14.44         A
ATOM   1255  CE1  PHE A 171      36.593  34.986  48.184  1.00  8.85         A
ATOM   1256  CE2  PHE A 171      35.024  33.377  47.311  1.00 12.76         A
ATOM   1257  CZ   PHE A 171      36.096  33.686  48.158  1.00 12.60         A
ATOM   1258  C    PHE A 171      33.353  37.977  47.661  1.00 12.55         A
ATOM   1259  O    PHE A 171      33.292  37.294  48.679  1.00  7.64         A
ATOM   1260  N    ALA A 172      33.704  39.257  47.677  1.00  6.57         A
ATOM   1261  CA   ALA A 172      34.088  39.865  48.946  1.00  9.02         A
ATOM   1262  CB   ALA A 172      34.655  41.279  48.721  1.00  9.26         A
ATOM   1263  C    ALA A 172      32.948  39.885  49.957  1.00 11.22         A
ATOM   1264  O    ALA A 172      33.188  40.071  51.155  1.00 10.96         A
ATOM   1265  N    ASN A 173      31.714  39.677  49.493  1.00  8.23         A
ATOM   1266  CA   ASN A 173      30.563  39.651  50.409  1.00 10.55         A
ATOM   1267  CB   ASN A 173      29.361  40.396  49.822  1.00 11.87         A
ATOM   1268  CG   ASN A 173      29.628  41.862  49.606  1.00 13.88         A
ATOM   1269  OD1  ASN A 173      30.289  42.512  50.412  1.00 13.36         A
ATOM   1270  ND2  ASN A 173      29.098  42.398  48.515  1.00 16.29         A
ATOM   1271  C    ASN A 173      30.062  38.245  50.759  1.00 13.21         A
ATOM   1272  O    ASN A 173      29.077  38.109  51.498  1.00 10.89         A
ATOM   1273  N    SER A 174      30.716  37.212  50.238  1.00  7.67         A
ATOM   1274  CA   SER A 174      30.250  35.859  50.468  1.00  9.24         A
ATOM   1275  CB   SER A 174      30.869  34.905  49.429  1.00  9.01         A
ATOM   1276  OG   SER A 174      30.359  33.580  49.598  1.00  8.15         A
ATOM   1277  C    SER A 174      30.440  35.250  51.863  1.00  7.73         A
ATOM   1278  O    SER A 174      29.480  34.822  52.506  1.00  8.54         A
ATOM   1279  N    TYR A 175      31.684  35.160  52.303  1.00  6.67         A
ATOM   1280  CA   TYR A 175      31.978  34.535  53.599  1.00  6.35         A
ATOM   1281  CB   TYR A 175      33.493  34.371  53.735  1.00  7.83         A
ATOM   1282  CG   TYR A 175      33.928  33.429  54.847  1.00  6.19         A
ATOM   1283  CD1  TYR A 175      34.845  33.842  55.825  1.00  9.13         A
ATOM   1284  CE1  TYR A 175      35.315  32.938  56.811  1.00  7.78         A
ATOM   1285  CD2  TYR A 175      33.481  32.102  54.879  1.00  6.63         A
ATOM   1286  CE2  TYR A 175      33.939  31.206  55.856  1.00  9.07         A
ATOM   1287  CZ   TYR A 175      34.859  31.633  56.812  1.00 11.83         A
```

FIGURE 5 (continued)

| ATOM | 1288 | OH  | TYR A 175 | 35.348 | 30.731 | 57.746 | 1.00 | 8.85  | A |
|------|------|-----|-----------|--------|--------|--------|------|-------|---|
| ATOM | 1289 | C   | TYR A 175 | 31.424 | 35.365 | 54.761 | 1.00 | 12.71 | A |
| ATOM | 1290 | O   | TYR A 175 | 31.649 | 36.556 | 54.806 | 1.00 | 7.92  | A |
| ATOM | 1291 | N   | SER A 176 | 30.695 | 34.727 | 55.683 | 1.00 | 9.13  | A |
| ATOM | 1292 | CA  | SER A 176 | 30.104 | 35.431 | 56.828 | 1.00 | 9.94  | A |
| ATOM | 1293 | CB  | SER A 176 | 29.372 | 34.433 | 57.737 | 1.00 | 11.72 | A |
| ATOM | 1294 | OG  | SER A 176 | 30.248 | 33.426 | 58.245 | 1.00 | 9.80  | A |
| ATOM | 1295 | C   | SER A 176 | 31.092 | 36.247 | 57.659 | 1.00 | 11.68 | A |
| ATOM | 1296 | O   | SER A 176 | 30.737 | 37.302 | 58.184 | 1.00 | 12.94 | A |
| ATOM | 1297 | N   | LEU A 177 | 32.332 | 35.787 | 57.788 | 1.00 | 10.90 | A |
| ATOM | 1298 | CA  | LEU A 177 | 33.303 | 36.559 | 58.561 | 1.00 | 12.59 | A |
| ATOM | 1299 | CB  | LEU A 177 | 34.231 | 35.613 | 59.349 | 1.00 | 14.55 | A |
| ATOM | 1300 | CG  | LEU A 177 | 33.537 | 34.649 | 60.324 | 1.00 | 15.21 | A |
| ATOM | 1301 | CD1 | LEU A 177 | 34.579 | 33.649 | 60.872 | 1.00 | 18.41 | A |
| ATOM | 1302 | CD2 | LEU A 177 | 32.856 | 35.452 | 61.476 | 1.00 | 11.73 | A |
| ATOM | 1303 | C   | LEU A 177 | 34.139 | 37.522 | 57.692 | 1.00 | 13.68 | A |
| ATOM | 1304 | O   | LEU A 177 | 35.126 | 38.104 | 58.163 | 1.00 | 12.71 | A |
| ATOM | 1305 | N   | GLY A 178 | 33.754 | 37.680 | 56.434 | 1.00 | 9.18  | A |
| ATOM | 1306 | CA  | GLY A 178 | 34.475 | 38.585 | 55.541 | 1.00 | 12.34 | A |
| ATOM | 1307 | C   | GLY A 178 | 35.803 | 38.098 | 54.975 | 1.00 | 12.74 | A |
| ATOM | 1308 | O   | GLY A 178 | 36.205 | 36.939 | 55.208 | 1.00 | 13.97 | A |
| ATOM | 1309 | N   | LEU A 179 | 36.492 | 38.974 | 54.224 | 1.00 | 9.84  | A |
| ATOM | 1310 | CA  | LEU A 179 | 37.787 | 38.610 | 53.621 | 1.00 | 10.63 | A |
| ATOM | 1311 | CB  | LEU A 179 | 38.078 | 39.437 | 52.350 | 1.00 | 11.33 | A |
| ATOM | 1312 | CG  | LEU A 179 | 37.189 | 39.202 | 51.120 | 1.00 | 10.67 | A |
| ATOM | 1313 | CD1 | LEU A 179 | 37.729 | 40.017 | 49.934 | 1.00 | 12.85 | A |
| ATOM | 1314 | CD2 | LEU A 179 | 37.134 | 37.692 | 50.787 | 1.00 | 15.70 | A |
| ATOM | 1315 | C   | LEU A 179 | 38.986 | 38.779 | 54.555 | 1.00 | 12.52 | A |
| ATOM | 1316 | O   | LEU A 179 | 40.096 | 38.319 | 54.233 | 1.00 | 13.43 | A |
| ATOM | 1317 | N   | SER A 180 | 38.788 | 39.426 | 55.702 | 1.00 | 13.88 | A |
| ATOM | 1318 | CA  | SER A 180 | 39.910 | 39.635 | 56.612 | 1.00 | 17.84 | A |
| ATOM | 1319 | CB  | SER A 180 | 39.438 | 40.187 | 57.954 | 1.00 | 23.37 | A |
| ATOM | 1320 | OG  | SER A 180 | 39.006 | 41.521 | 57.770 | 1.00 | 30.75 | A |
| ATOM | 1321 | C   | SER A 180 | 40.776 | 38.411 | 56.839 | 1.00 | 18.97 | A |
| ATOM | 1322 | O   | SER A 180 | 41.990 | 38.527 | 56.856 | 1.00 | 16.57 | A |
| ATOM | 1323 | N   | PRO A 181 | 40.170 | 37.223 | 57.010 | 1.00 | 17.96 | A |
| ATOM | 1324 | CD  | PRO A 181 | 38.739 | 36.923 | 57.219 | 1.00 | 18.24 | A |
| ATOM | 1325 | CA  | PRO A 181 | 40.989 | 36.023 | 57.228 | 1.00 | 19.35 | A |
| ATOM | 1326 | CB  | PRO A 181 | 39.948 | 34.925 | 57.436 | 1.00 | 20.22 | A |
| ATOM | 1327 | CG  | PRO A 181 | 38.804 | 35.657 | 58.063 | 1.00 | 20.57 | A |
| ATOM | 1328 | C   | PRO A 181 | 41.927 | 35.697 | 56.063 | 1.00 | 24.47 | A |
| ATOM | 1329 | O   | PRO A 181 | 42.893 | 34.943 | 56.237 | 1.00 | 26.18 | A |
| ATOM | 1330 | N   | LEU A 182 | 41.646 | 36.251 | 54.880 | 1.00 | 17.84 | A |
| ATOM | 1331 | CA  | LEU A 182 | 42.470 | 36.002 | 53.688 | 1.00 | 21.43 | A |
| ATOM | 1332 | CB  | LEU A 182 | 41.615 | 36.019 | 52.410 | 1.00 | 20.15 | A |
| ATOM | 1333 | CG  | LEU A 182 | 40.748 | 34.780 | 52.178 | 1.00 | 20.14 | A |
| ATOM | 1334 | CD1 | LEU A 182 | 39.849 | 34.968 | 50.952 | 1.00 | 17.30 | A |
| ATOM | 1335 | CD2 | LEU A 182 | 41.679 | 33.580 | 52.004 | 1.00 | 15.09 | A |
| ATOM | 1336 | C   | LEU A 182 | 43.614 | 36.985 | 53.490 | 1.00 | 27.88 | A |
| ATOM | 1337 | O   | LEU A 182 | 43.499 | 37.909 | 52.682 | 1.00 | 31.51 | A |
| ATOM | 1338 | N   | ALA A 183 | 44.726 | 36.761 | 54.185 | 1.00 | 23.49 | A |
| ATOM | 1339 | CA  | ALA A 183 | 45.893 | 37.639 | 54.073 | 1.00 | 26.24 | A |
| ATOM | 1340 | CB  | ALA A 183 | 47.066 | 37.047 | 54.860 | 1.00 | 22.25 | A |
| ATOM | 1341 | C   | ALA A 183 | 46.325 | 37.920 | 52.629 | 1.00 | 20.58 | A |
| ATOM | 1342 | O   | ALA A 183 | 46.623 | 37.001 | 51.856 | 1.00 | 17.37 | A |
| ATOM | 1343 | N   | GLY A 184 | 46.354 | 39.202 | 52.278 | 1.00 | 17.97 | A |
| ATOM | 1344 | CA  | GLY A 184 | 46.762 | 39.603 | 50.949 | 1.00 | 17.46 | A |
| ATOM | 1345 | C   | GLY A 184 | 45.908 | 39.186 | 49.755 | 1.00 | 12.78 | A |
| ATOM | 1346 | O   | GLY A 184 | 46.413 | 39.159 | 48.636 | 1.00 | 15.39 | A |
| ATOM | 1347 | N   | ALA A 185 | 44.634 | 38.878 | 49.956 | 1.00 | 12.15 | A |
| ATOM | 1348 | CA  | ALA A 185 | 43.798 | 38.500 | 48.811 | 1.00 | 14.55 | A |
| ATOM | 1349 | CB  | ALA A 185 | 42.374 | 38.212 | 49.271 | 1.00 | 14.22 | A |
| ATOM | 1350 | C   | ALA A 185 | 43.812 | 39.649 | 47.795 | 1.00 | 16.74 | A |
| ATOM | 1351 | O   | ALA A 185 | 43.780 | 40.826 | 48.181 | 1.00 | 15.66 | A |
| ATOM | 1352 | N   | VAL A 186 | 43.836 | 39.300 | 46.507 | 1.00 | 9.90  | A |
| ATOM | 1353 | CA  | VAL A 186 | 43.880 | 40.276 | 45.419 | 1.00 | 11.92 | A |
| ATOM | 1354 | CB  | VAL A 186 | 45.093 | 39.969 | 44.484 | 1.00 | 14.98 | A |
| ATOM | 1355 | CG1 | VAL A 186 | 45.026 | 40.816 | 43.229 | 1.00 | 13.29 | A |
| ATOM | 1356 | CG2 | VAL A 186 | 46.398 | 40.226 | 45.244 | 1.00 | 19.64 | A |
| ATOM | 1357 | C   | VAL A 186 | 42.608 | 40.254 | 44.571 | 1.00 | 11.79 | A |
| ATOM | 1358 | O   | VAL A 186 | 42.152 | 39.182 | 44.149 | 1.00 | 11.34 | A |
| ATOM | 1359 | N   | ALA A 187 | 42.035 | 41.430 | 44.331 | 1.00 | 11.06 | A |
| ATOM | 1360 | CA  | ALA A 187 | 40.829 | 41.543 | 43.508 | 1.00 | 10.57 | A |
| ATOM | 1361 | CB  | ALA A 187 | 39.897 | 42.606 | 44.096 | 1.00 | 12.53 | A |
| ATOM | 1362 | C   | ALA A 187 | 41.211 | 41.923 | 42.079 | 1.00 | 13.16 | A |
| ATOM | 1363 | O   | ALA A 187 | 42.128 | 42.736 | 41.876 | 1.00 | 14.58 | A |

FIGURE 5 (continued)

| | | | | | | | | | | |
|---|---|---|---|---|---|---|---|---|---|---|
| ATOM | 1364 | N   | ALA | A | 188 | 40.543 | 41.328 | 41.085 | 1.00  8.38 | A |
| ATOM | 1365 | CA  | ALA | A | 188 | 40.832 | 41.672 | 39.672 | 1.00  8.09 | A |
| ATOM | 1366 | CB  | ALA | A | 188 | 41.725 | 40.609 | 39.018 | 1.00 10.94 | A |
| ATOM | 1367 | C   | ALA | A | 188 | 39.515 | 41.759 | 38.913 | 1.00  9.75 | A |
| ATOM | 1368 | O   | ALA | A | 188 | 38.510 | 41.196 | 39.349 | 1.00 10.74 | A |
| ATOM | 1369 | N   | ILE | A | 189 | 39.543 | 42.434 | 37.766 | 1.00 10.19 | A |
| ATOM | 1370 | CA  | ILE | A | 189 | 38.355 | 42.646 | 36.936 | 1.00  9.71 | A |
| ATOM | 1371 | CB  | ILE | A | 189 | 38.300 | 44.126 | 36.487 | 1.00 14.84 | A |
| ATOM | 1372 | CG2 | ILE | A | 189 | 37.056 | 44.394 | 35.606 | 1.00 12.56 | A |
| ATOM | 1373 | CG1 | ILE | A | 189 | 38.247 | 45.007 | 37.720 | 1.00 13.85 | A |
| ATOM | 1374 | CD1 | ILE | A | 189 | 36.964 | 44.848 | 38.520 | 1.00 20.17 | A |
| ATOM | 1375 | C   | ILE | A | 189 | 38.307 | 41.760 | 35.705 | 1.00 11.18 | A |
| ATOM | 1376 | O   | ILE | A | 189 | 39.260 | 41.715 | 34.930 | 1.00 12.80 | A |
| ATOM | 1377 | N   | GLY | A | 190 | 37.185 | 41.062 | 35.518 | 1.00 12.93 | A |
| ATOM | 1378 | CA  | GLY | A | 190 | 37.039 | 40.181 | 34.368 | 1.00  9.66 | A |
| ATOM | 1379 | C   | GLY | A | 190 | 37.836 | 38.881 | 34.432 | 1.00 11.20 | A |
| ATOM | 1380 | O   | GLY | A | 190 | 38.763 | 38.745 | 35.238 | 1.00 12.00 | A |
| ATOM | 1381 | N   | SER | A | 191 | 37.494 | 37.919 | 33.570 | 1.00 12.31 | A |
| ATOM | 1382 | CA  | SER | A | 191 | 38.216 | 36.644 | 33.539 | 1.00 11.69 | A |
| ATOM | 1383 | CB  | SER | A | 191 | 37.530 | 35.671 | 32.568 | 1.00  8.59 | A |
| ATOM | 1384 | OG  | SER | A | 191 | 36.224 | 35.299 | 33.026 | 1.00 10.08 | A |
| ATOM | 1385 | C   | SER | A | 191 | 39.678 | 36.896 | 33.104 | 1.00 14.30 | A |
| ATOM | 1386 | O   | SER | A | 191 | 40.612 | 36.295 | 33.638 | 1.00 11.39 | A |
| ATOM | 1387 | N   | VAL | A | 192 | 39.880 | 37.809 | 32.156 | 1.00 11.76 | A |
| ATOM | 1388 | CA  | VAL | A | 192 | 41.235 | 38.101 | 31.704 | 1.00 14.84 | A |
| ATOM | 1389 | CB  | VAL | A | 192 | 41.273 | 39.029 | 30.449 | 1.00 13.34 | A |
| ATOM | 1390 | CG1 | VAL | A | 192 | 40.838 | 38.252 | 29.213 | 1.00 24.13 | A |
| ATOM | 1391 | CG2 | VAL | A | 192 | 40.396 | 40.246 | 30.678 | 1.00 29.05 | A |
| ATOM | 1392 | C   | VAL | A | 192 | 42.056 | 38.767 | 32.804 | 1.00 11.65 | A |
| ATOM | 1393 | O   | VAL | A | 192 | 43.247 | 38.485 | 32.940 | 1.00 14.10 | A |
| ATOM | 1394 | N   | GLY | A | 193 | 41.431 | 39.670 | 33.559 | 1.00 12.08 | A |
| ATOM | 1395 | CA  | GLY | A | 193 | 42.149 | 40.344 | 34.626 | 1.00 12.16 | A |
| ATOM | 1396 | C   | GLY | A | 193 | 42.575 | 39.354 | 35.700 | 1.00 14.30 | A |
| ATOM | 1397 | O   | GLY | A | 193 | 43.652 | 39.486 | 36.291 | 1.00  9.20 | A |
| ATOM | 1398 | N   | VAL | A | 194 | 41.725 | 38.369 | 35.976 | 1.00  9.32 | A |
| ATOM | 1399 | CA  | VAL | A | 194 | 42.069 | 37.370 | 36.992 | 1.00  9.16 | A |
| ATOM | 1400 | CB  | VAL | A | 194 | 40.845 | 36.459 | 37.341 | 1.00  7.74 | A |
| ATOM | 1401 | CG1 | VAL | A | 194 | 41.309 | 35.168 | 38.071 | 1.00  8.55 | A |
| ATOM | 1402 | CG2 | VAL | A | 194 | 39.873 | 37.247 | 38.259 | 1.00 11.33 | A |
| ATOM | 1403 | C   | VAL | A | 194 | 43.256 | 36.524 | 36.530 | 1.00 10.65 | A |
| ATOM | 1404 | O   | VAL | A | 194 | 44.158 | 36.255 | 37.318 | 1.00 10.00 | A |
| ATOM | 1405 | N   | MET | A | 195 | 43.261 | 36.090 | 35.265 | 1.00  9.82 | A |
| ATOM | 1406 | CA  | MET | A | 195 | 44.391 | 35.306 | 34.775 | 1.00 11.27 | A |
| ATOM | 1407 | CB  | MET | A | 195 | 44.125 | 34.727 | 33.381 | 1.00 13.33 | A |
| ATOM | 1408 | CG  | MET | A | 195 | 43.342 | 33.449 | 33.381 | 1.00 16.98 | A |
| ATOM | 1409 | SD  | MET | A | 195 | 43.794 | 32.237 | 34.698 | 1.00 19.79 | A |
| ATOM | 1410 | CE  | MET | A | 195 | 45.205 | 31.419 | 34.043 | 1.00 16.46 | A |
| ATOM | 1411 | C   | MET | A | 195 | 45.672 | 36.118 | 34.719 | 1.00 12.67 | A |
| ATOM | 1412 | O   | MET | A | 195 | 46.757 | 35.579 | 34.948 | 1.00 15.56 | A |
| ATOM | 1413 | N   | ALA | A | 196 | 45.566 | 37.401 | 34.385 | 1.00 11.82 | A |
| ATOM | 1414 | CA  | ALA | A | 196 | 46.750 | 38.239 | 34.346 | 1.00 15.74 | A |
| ATOM | 1415 | CB  | ALA | A | 196 | 46.404 | 39.633 | 33.833 | 1.00 14.20 | A |
| ATOM | 1416 | C   | ALA | A | 196 | 47.331 | 38.323 | 35.768 | 1.00 16.81 | A |
| ATOM | 1417 | O   | ALA | A | 196 | 48.544 | 38.245 | 35.945 | 1.00 15.03 | A |
| ATOM | 1418 | N   | ALA | A | 197 | 46.464 | 38.468 | 36.778 | 1.00 13.86 | A |
| ATOM | 1419 | CA  | ALA | A | 197 | 46.939 | 38.538 | 38.151 | 1.00 13.25 | A |
| ATOM | 1420 | CB  | ALA | A | 197 | 45.790 | 38.865 | 39.108 | 1.00 13.70 | A |
| ATOM | 1421 | C   | ALA | A | 197 | 47.547 | 37.203 | 38.542 | 1.00 13.49 | A |
| ATOM | 1422 | O   | ALA | A | 197 | 48.618 | 37.159 | 39.147 | 1.00 13.32 | A |
| ATOM | 1423 | N   | ASP | A | 198 | 46.853 | 36.119 | 38.202 | 1.00 12.41 | A |
| ATOM | 1424 | CA  | ASP | A | 198 | 47.326 | 34.777 | 38.547 | 1.00 16.61 | A |
| ATOM | 1425 | CB  | ASP | A | 198 | 46.311 | 33.719 | 38.074 | 1.00 18.96 | A |
| ATOM | 1426 | CG  | ASP | A | 198 | 46.605 | 32.327 | 38.629 | 1.00 29.19 | A |
| ATOM | 1427 | OD1 | ASP | A | 198 | 46.440 | 32.107 | 39.857 | 1.00 32.24 | A |
| ATOM | 1428 | OD2 | ASP | A | 198 | 47.004 | 31.449 | 37.834 | 1.00 34.04 | A |
| ATOM | 1429 | C   | ASP | A | 198 | 48.699 | 34.509 | 37.928 | 1.00 17.95 | A |
| ATOM | 1430 | O   | ASP | A | 198 | 49.570 | 33.942 | 38.585 | 1.00 18.27 | A |
| ATOM | 1431 | N   | ASN | A | 199 | 48.900 | 34.941 | 36.684 | 1.00 16.24 | A |
| ATOM | 1432 | CA  | ASN | A | 199 | 50.173 | 34.733 | 35.980 | 1.00 17.75 | A |
| ATOM | 1433 | CB  | ASN | A | 199 | 49.941 | 34.565 | 34.478 | 1.00 19.50 | A |
| ATOM | 1434 | CG  | ASN | A | 199 | 49.270 | 33.263 | 34.122 | 1.00 21.16 | A |
| ATOM | 1435 | OD1 | ASN | A | 199 | 49.454 | 32.254 | 34.786 | 1.00 29.31 | A |
| ATOM | 1436 | ND2 | ASN | A | 199 | 48.504 | 33.275 | 33.041 | 1.00 24.39 | A |
| ATOM | 1437 | C   | ASN | A | 199 | 51.227 | 35.832 | 36.144 | 1.00 20.64 | A |
| ATOM | 1438 | O   | ASN | A | 199 | 52.272 | 35.762 | 35.507 | 1.00 27.47 | A |
| ATOM | 1439 | N   | ASP | A | 200 | 50.973 | 36.838 | 36.970 | 1.00 19.22 | A |

FIGURE 5 (continued)

| | | | | | | | | | | |
|---|---|---|---|---|---|---|---|---|---|---|
| ATOM | 1440 | CA | ASP | A | 200 | 51.925 | 37.937 | 37.148 | 1.00 | 20.54 | A |
| ATOM | 1441 | CB | ASP | A | 200 | 51.350 | 38.985 | 38.092 | 1.00 | 22.32 | A |
| ATOM | 1442 | CG | ASP | A | 200 | 52.166 | 40.271 | 38.105 | 1.00 | 23.11 | A |
| ATOM | 1443 | OD1 | ASP | A | 200 | 53.356 | 40.256 | 37.713 | 1.00 | 21.11 | A |
| ATOM | 1444 | OD2 | ASP | A | 200 | 51.612 | 41.296 | 38.526 | 1.00 | 26.57 | A |
| ATOM | 1445 | C | ASP | A | 200 | 53.252 | 37.431 | 37.716 | 1.00 | 21.98 | A |
| ATOM | 1446 | O | ASP | A | 200 | 53.315 | 36.967 | 38.855 | 1.00 | 19.25 | A |
| ATOM | 1447 | N | VAL | A | 201 | 54.315 | 37.511 | 36.922 | 1.00 | 21.71 | A |
| ATOM | 1448 | CA | VAL | A | 201 | 55.611 | 37.033 | 37.390 | 1.00 | 24.01 | A |
| ATOM | 1449 | CB | VAL | A | 201 | 56.519 | 36.597 | 36.216 | 1.00 | 23.59 | A |
| ATOM | 1450 | CG1 | VAL | A | 201 | 55.910 | 35.377 | 35.519 | 1.00 | 25.93 | A |
| ATOM | 1451 | CG2 | VAL | A | 201 | 56.710 | 37.754 | 35.246 | 1.00 | 26.53 | A |
| ATOM | 1452 | C | VAL | A | 201 | 56.370 | 38.046 | 38.222 | 1.00 | 24.27 | A |
| ATOM | 1453 | O | VAL | A | 201 | 57.451 | 37.744 | 38.715 | 1.00 | 30.90 | A |
| ATOM | 1454 | N | THR | A | 202 | 55.817 | 39.241 | 38.402 | 1.00 | 23.14 | A |
| ATOM | 1455 | CA | THR | A | 202 | 56.511 | 40.251 | 39.190 | 1.00 | 23.53 | A |
| ATOM | 1456 | CB | THR | A | 202 | 56.216 | 41.664 | 38.696 | 1.00 | 22.33 | A |
| ATOM | 1457 | OG1 | THR | A | 202 | 54.846 | 41.999 | 38.979 | 1.00 | 24.30 | A |
| ATOM | 1458 | CG2 | THR | A | 202 | 56.489 | 41.759 | 37.210 | 1.00 | 25.94 | A |
| ATOM | 1459 | C | THR | A | 202 | 56.171 | 40.184 | 40.677 | 1.00 | 24.49 | A |
| ATOM | 1460 | O | THR | A | 202 | 56.543 | 41.073 | 41.444 | 1.00 | 25.68 | A |
| ATOM | 1461 | N | THR | A | 203 | 55.440 | 39.147 | 41.076 | 1.00 | 19.97 | A |
| ATOM | 1462 | CA | THR | A | 203 | 55.116 | 38.957 | 42.484 | 1.00 | 20.69 | A |
| ATOM | 1463 | CB | THR | A | 203 | 53.608 | 39.167 | 42.768 | 1.00 | 26.13 | A |
| ATOM | 1464 | OG1 | THR | A | 203 | 52.825 | 38.196 | 42.047 | 1.00 | 25.13 | A |
| ATOM | 1465 | CG2 | THR | A | 203 | 53.202 | 40.581 | 42.363 | 1.00 | 26.59 | A |
| ATOM | 1466 | C | THR | A | 203 | 55.523 | 37.521 | 42.834 | 1.00 | 17.47 | A |
| ATOM | 1467 | O | THR | A | 203 | 55.771 | 36.703 | 41.947 | 1.00 | 18.21 | A |
| ATOM | 1468 | N | ALA | A | 204 | 55.624 | 37.217 | 44.116 | 1.00 | 16.96 | A |
| ATOM | 1469 | CA | ALA | A | 204 | 56.011 | 35.867 | 44.528 | 1.00 | 16.26 | A |
| ATOM | 1470 | CB | ALA | A | 204 | 56.175 | 35.825 | 46.065 | 1.00 | 18.50 | A |
| ATOM | 1471 | C | ALA | A | 204 | 54.978 | 34.832 | 44.092 | 1.00 | 14.92 | A |
| ATOM | 1472 | O | ALA | A | 204 | 53.806 | 35.157 | 43.906 | 1.00 | 16.09 | A |
| ATOM | 1473 | N | GLN | A | 205 | 55.409 | 33.582 | 43.921 | 1.00 | 16.21 | A |
| ATOM | 1474 | CA | GLN | A | 205 | 54.483 | 32.501 | 43.560 | 1.00 | 16.27 | A |
| ATOM | 1475 | CB | GLN | A | 205 | 55.232 | 31.191 | 43.316 | 1.00 | 15.65 | A |
| ATOM | 1476 | CG | GLN | A | 205 | 56.103 | 31.148 | 42.097 | 1.00 | 22.41 | A |
| ATOM | 1477 | CD | GLN | A | 205 | 56.469 | 29.716 | 41.717 | 1.00 | 29.28 | A |
| ATOM | 1478 | OE1 | GLN | A | 205 | 56.446 | 28.801 | 42.565 | 1.00 | 20.67 | A |
| ATOM | 1479 | NE2 | GLN | A | 205 | 56.813 | 29.510 | 40.442 | 1.00 | 25.77 | A |
| ATOM | 1480 | C | GLN | A | 205 | 53.529 | 32.262 | 44.728 | 1.00 | 14.53 | A |
| ATOM | 1481 | O | GLN | A | 205 | 53.783 | 32.717 | 45.846 | 1.00 | 14.81 | A |
| ATOM | 1482 | N | GLY | A | 206 | 52.438 | 31.540 | 44.478 | 1.00 | 11.64 | A |
| ATOM | 1483 | CA | GLY | A | 206 | 51.509 | 31.236 | 45.554 | 1.00 | 11.46 | A |
| ATOM | 1484 | C | GLY | A | 206 | 50.042 | 31.518 | 45.284 | 1.00 | 11.44 | A |
| ATOM | 1485 | O | GLY | A | 206 | 49.162 | 31.067 | 46.046 | 1.00 | 9.87 | A |
| ATOM | 1486 | N | ARG | A | 207 | 49.764 | 32.236 | 44.199 | 1.00 | 7.71 | A |
| ATOM | 1487 | CA | ARG | A | 207 | 48.383 | 32.606 | 43.878 | 1.00 | 7.50 | A |
| ATOM | 1488 | CB | ARG | A | 207 | 48.364 | 33.763 | 42.863 | 1.00 | 9.66 | A |
| ATOM | 1489 | CG | ARG | A | 207 | 48.719 | 35.114 | 43.493 | 1.00 | 7.35 | A |
| ATOM | 1490 | CD | ARG | A | 207 | 48.774 | 36.286 | 42.497 | 1.00 | 6.76 | A |
| ATOM | 1491 | NE | ARG | A | 207 | 49.079 | 37.532 | 43.221 | 1.00 | 10.86 | A |
| ATOM | 1492 | CZ | ARG | A | 207 | 49.156 | 38.738 | 42.654 | 1.00 | 13.78 | A |
| ATOM | 1493 | NH1 | ARG | A | 207 | 48.957 | 38.881 | 41.350 | 1.00 | 9.77 | A |
| ATOM | 1494 | NH2 | ARG | A | 207 | 49.415 | 39.811 | 43.398 | 1.00 | 15.04 | A |
| ATOM | 1495 | C | ARG | A | 207 | 47.500 | 31.475 | 43.389 | 1.00 | 11.20 | A |
| ATOM | 1496 | O | ARG | A | 207 | 47.959 | 30.549 | 42.713 | 1.00 | 12.10 | A |
| ATOM | 1497 | N | ILE | A | 208 | 46.214 | 31.572 | 43.721 | 1.00 | 8.65 | A |
| ATOM | 1498 | CA | ILE | A | 208 | 45.245 | 30.557 | 43.331 | 1.00 | 8.62 | A |
| ATOM | 1499 | CB | ILE | A | 208 | 45.073 | 29.491 | 44.476 | 1.00 | 11.42 | A |
| ATOM | 1500 | CG2 | ILE | A | 208 | 44.533 | 30.157 | 45.766 | 1.00 | 8.84 | A |
| ATOM | 1501 | CG1 | ILE | A | 208 | 44.158 | 28.359 | 43.984 | 1.00 | 12.09 | A |
| ATOM | 1502 | CD1 | ILE | A | 208 | 44.207 | 27.094 | 44.823 | 1.00 | 11.77 | A |
| ATOM | 1503 | C | ILE | A | 208 | 43.924 | 31.286 | 43.056 | 1.00 | 10.31 | A |
| ATOM | 1504 | O | ILE | A | 208 | 43.664 | 32.335 | 43.649 | 1.00 | 12.81 | A |
| ATOM | 1505 | N | THR | A | 209 | 43.098 | 30.776 | 42.145 | 1.00 | 7.78 | A |
| ATOM | 1506 | CA | THR | A | 209 | 41.825 | 31.470 | 41.864 | 1.00 | 9.01 | A |
| ATOM | 1507 | CB | THR | A | 209 | 42.055 | 32.610 | 40.849 | 1.00 | 11.48 | A |
| ATOM | 1508 | OG1 | THR | A | 209 | 40.906 | 33.455 | 40.789 | 1.00 | 11.18 | A |
| ATOM | 1509 | CG2 | THR | A | 209 | 42.310 | 32.030 | 39.460 | 1.00 | 12.27 | A |
| ATOM | 1510 | C | THR | A | 209 | 40.751 | 30.534 | 41.319 | 1.00 | 10.48 | A |
| ATOM | 1511 | O | THR | A | 209 | 40.978 | 29.326 | 41.215 | 1.00 | 10.85 | A |
| ATOM | 1512 | N | TYR | A | 210 | 39.577 | 31.087 | 40.997 | 1.00 | 8.58 | A |
| ATOM | 1513 | CA | TYR | A | 210 | 38.476 | 30.303 | 40.422 | 1.00 | 8.34 | A |
| ATOM | 1514 | CB | TYR | A | 210 | 37.244 | 30.304 | 41.350 | 1.00 | 4.35 | A |
| ATOM | 1515 | CG | TYR | A | 210 | 36.685 | 31.664 | 41.695 | 1.00 | 7.98 | A |

FIGURE 5 (continued)

| ATOM | 1516 | CD1 | TYR | A | 210 | 35.656 | 32.240 | 40.927 | 1.00 | 6.11 | A |
|------|------|-----|-----|---|-----|--------|--------|--------|------|------|---|
| ATOM | 1517 | CE1 | TYR | A | 210 | 35.153 | 33.509 | 41.235 | 1.00 | 7.73 | A |
| ATOM | 1518 | CD2 | TYR | A | 210 | 37.188 | 32.386 | 42.778 | 1.00 | 6.57 | A |
| ATOM | 1519 | CE2 | TYR | A | 210 | 36.699 | 33.643 | 43.086 | 1.00 | 5.93 | A |
| ATOM | 1520 | CZ  | TYR | A | 210 | 35.687 | 34.203 | 42.313 | 1.00 | 8.47 | A |
| ATOM | 1521 | OH  | TYR | A | 210 | 35.242 | 35.475 | 42.598 | 1.00 | 8.24 | A |
| ATOM | 1522 | C   | TYR | A | 210 | 38.169 | 30.983 | 39.087 | 1.00 | 5.52 | A |
| ATOM | 1523 | O   | TYR | A | 210 | 38.184 | 32.222 | 39.010 | 1.00 | 9.37 | A |
| ATOM | 1524 | N   | ILE | A | 211 | 37.934 | 30.201 | 38.032 | 1.00 | 6.28 | A |
| ATOM | 1525 | CA  | ILE | A | 211 | 37.720 | 30.832 | 36.735 | 1.00 | 7.52 | A |
| ATOM | 1526 | CB  | ILE | A | 211 | 39.085 | 31.384 | 36.235 | 1.00 | 11.97 | A |
| ATOM | 1527 | CG2 | ILE | A | 211 | 39.990 | 30.231 | 35.830 | 1.00 | 10.21 | A |
| ATOM | 1528 | CG1 | ILE | A | 211 | 38.902 | 32.361 | 35.075 | 1.00 | 14.62 | A |
| ATOM | 1529 | CD1 | ILE | A | 211 | 40.159 | 33.203 | 34.806 | 1.00 | 15.71 | A |
| ATOM | 1530 | C   | ILE | A | 211 | 37.132 | 29.936 | 35.648 | 1.00 | 8.22 | A |
| ATOM | 1531 | O   | ILE | A | 211 | 37.080 | 28.703 | 35.778 | 1.00 | 8.13 | A |
| ATOM | 1532 | N   | SER | A | 212 | 36.634 | 30.590 | 34.602 | 1.00 | 9.06 | A |
| ATOM | 1533 | CA  | SER | A | 212 | 36.140 | 29.913 | 33.394 | 1.00 | 9.98 | A |
| ATOM | 1534 | CB  | SER | A | 212 | 35.984 | 30.934 | 32.256 | 1.00 | 8.45 | A |
| ATOM | 1535 | OG  | SER | A | 212 | 35.637 | 30.283 | 31.037 | 1.00 | 9.53 | A |
| ATOM | 1536 | C   | SER | A | 212 | 37.181 | 28.904 | 32.914 | 1.00 | 10.00 | A |
| ATOM | 1537 | O   | SER | A | 212 | 38.361 | 29.234 | 32.812 | 1.00 | 7.50 | A |
| ATOM | 1538 | N   | PRO | A | 213 | 36.761 | 27.668 | 32.585 | 1.00 | 8.50 | A |
| ATOM | 1539 | CD  | PRO | A | 213 | 35.436 | 27.030 | 32.686 | 1.00 | 4.78 | A |
| ATOM | 1540 | CA  | PRO | A | 213 | 37.781 | 26.728 | 32.117 | 1.00 | 8.39 | A |
| ATOM | 1541 | CB  | PRO | A | 213 | 37.035 | 25.392 | 32.059 | 1.00 | 10.29 | A |
| ATOM | 1542 | CG  | PRO | A | 213 | 35.578 | 25.849 | 31.743 | 1.00 | 9.33 | A |
| ATOM | 1543 | C   | PRO | A | 213 | 38.360 | 27.149 | 30.777 | 1.00 | 10.79 | A |
| ATOM | 1544 | O   | PRO | A | 213 | 39.433 | 26.698 | 30.390 | 1.00 | 10.83 | A |
| ATOM | 1545 | N   | ASP | A | 214 | 37.668 | 28.038 | 30.074 | 1.00 | 5.80 | A |
| ATOM | 1546 | CA  | ASP | A | 214 | 38.164 | 28.514 | 28.775 | 1.00 | 8.50 | A |
| ATOM | 1547 | CB  | ASP | A | 214 | 37.033 | 29.175 | 27.997 | 1.00 | 7.35 | A |
| ATOM | 1548 | CG  | ASP | A | 214 | 37.248 | 29.146 | 26.497 | 1.00 | 11.12 | A |
| ATOM | 1549 | OD1 | ASP | A | 214 | 36.479 | 29.849 | 25.801 | 1.00 | 11.42 | A |
| ATOM | 1550 | OD2 | ASP | A | 214 | 38.159 | 28.428 | 26.007 | 1.00 | 10.72 | A |
| ATOM | 1551 | C   | ASP | A | 214 | 39.314 | 29.526 | 28.935 | 1.00 | 12.08 | A |
| ATOM | 1552 | O   | ASP | A | 214 | 39.933 | 29.931 | 27.943 | 1.00 | 13.08 | A |
| ATOM | 1553 | N   | PHE | A | 215 | 39.572 | 29.958 | 30.170 | 1.00 | 9.47 | A |
| ATOM | 1554 | CA  | PHE | A | 215 | 40.662 | 30.901 | 30.459 | 1.00 | 9.63 | A |
| ATOM | 1555 | CB  | PHE | A | 215 | 40.121 | 32.106 | 31.233 | 1.00 | 12.63 | A |
| ATOM | 1556 | CG  | PHE | A | 215 | 39.375 | 33.081 | 30.402 | 1.00 | 9.86 | A |
| ATOM | 1557 | CD1 | PHE | A | 215 | 39.957 | 34.301 | 30.067 | 1.00 | 11.72 | A |
| ATOM | 1558 | CD2 | PHE | A | 215 | 38.074 | 32.812 | 29.986 | 1.00 | 11.34 | A |
| ATOM | 1559 | CE1 | PHE | A | 215 | 39.250 | 35.250 | 29.332 | 1.00 | 11.89 | A |
| ATOM | 1560 | CE2 | PHE | A | 215 | 37.357 | 33.759 | 29.245 | 1.00 | 6.37 | A |
| ATOM | 1561 | CZ  | PHE | A | 215 | 37.949 | 34.976 | 28.921 | 1.00 | 13.90 | A |
| ATOM | 1562 | C   | PHE | A | 215 | 41.748 | 30.286 | 31.356 | 1.00 | 13.88 | A |
| ATOM | 1563 | O   | PHE | A | 215 | 42.837 | 30.865 | 31.480 | 1.00 | 12.28 | A |
| ATOM | 1564 | N   | ALA | A | 216 | 41.463 | 29.131 | 31.976 | 1.00 | 9.02 | A |
| ATOM | 1565 | CA  | ALA | A | 216 | 42.404 | 28.535 | 32.936 | 1.00 | 9.41 | A |
| ATOM | 1566 | CB  | ALA | A | 216 | 41.705 | 27.432 | 33.753 | 1.00 | 9.18 | A |
| ATOM | 1567 | C   | ALA | A | 216 | 43.727 | 28.007 | 32.406 | 1.00 | 13.18 | A |
| ATOM | 1568 | O   | ALA | A | 216 | 44.679 | 27.844 | 33.178 | 1.00 | 16.82 | A |
| ATOM | 1569 | N   | ALA | A | 217 | 43.790 | 27.719 | 31.106 | 1.00 | 12.39 | A |
| ATOM | 1570 | CA  | ALA | A | 217 | 45.031 | 27.224 | 30.522 | 1.00 | 14.59 | A |
| ATOM | 1571 | CB  | ALA | A | 217 | 45.094 | 25.693 | 30.625 | 1.00 | 15.34 | A |
| ATOM | 1572 | C   | ALA | A | 217 | 45.136 | 27.660 | 29.063 | 1.00 | 16.52 | A |
| ATOM | 1573 | O   | ALA | A | 217 | 44.128 | 27.958 | 28.418 | 1.00 | 14.71 | A |
| ATOM | 1574 | N   | PRO | A | 218 | 46.358 | 27.690 | 28.517 | 1.00 | 18.85 | A |
| ATOM | 1575 | CD  | PRO | A | 218 | 47.657 | 27.532 | 29.194 | 1.00 | 19.53 | A |
| ATOM | 1576 | CA  | PRO | A | 218 | 46.533 | 28.101 | 27.111 | 1.00 | 17.17 | A |
| ATOM | 1577 | CB  | PRO | A | 218 | 48.053 | 28.171 | 26.952 | 1.00 | 22.03 | A |
| ATOM | 1578 | CG  | PRO | A | 218 | 48.553 | 28.433 | 28.357 | 1.00 | 24.10 | A |
| ATOM | 1579 | C   | PRO | A | 218 | 45.889 | 27.162 | 26.076 | 1.00 | 17.95 | A |
| ATOM | 1580 | O   | PRO | A | 218 | 45.490 | 27.606 | 24.986 | 1.00 | 20.60 | A |
| ATOM | 1581 | N   | SER | A | 219 | 45.804 | 25.872 | 26.395 | 1.00 | 12.39 | A |
| ATOM | 1582 | CA  | SER | A | 219 | 45.212 | 24.883 | 25.490 | 1.00 | 11.61 | A |
| ATOM | 1583 | CB  | SER | A | 219 | 46.308 | 24.053 | 24.816 | 1.00 | 17.69 | A |
| ATOM | 1584 | OG  | SER | A | 219 | 46.870 | 23.140 | 25.749 | 1.00 | 17.25 | A |
| ATOM | 1585 | C   | SER | A | 219 | 44.341 | 23.942 | 26.324 | 1.00 | 14.52 | A |
| ATOM | 1586 | O   | SER | A | 219 | 44.454 | 23.896 | 27.559 | 1.00 | 15.86 | A |
| ATOM | 1587 | N   | LEU | A | 220 | 43.479 | 23.180 | 25.664 | 1.00 | 13.85 | A |
| ATOM | 1588 | CA  | LEU | A | 220 | 42.614 | 22.250 | 26.389 | 1.00 | 13.63 | A |
| ATOM | 1589 | CB  | LEU | A | 220 | 41.705 | 21.491 | 25.401 | 1.00 | 15.59 | A |
| ATOM | 1590 | CG  | LEU | A | 220 | 40.632 | 22.337 | 24.707 | 1.00 | 16.07 | A |
| ATOM | 1591 | CD1 | LEU | A | 220 | 39.908 | 21.517 | 23.646 | 1.00 | 15.58 | A |

FIGURE 5 (continued)

| | | | | | | | | | | |
|---|---|---|---|---|---|---|---|---|---|---|
| ATOM | 1592 | CD2 | LEU | A | 220 | 39.635 | 22.855 | 25.752 | 1.00 | 16.33 | A |
| ATOM | 1593 | C | LEU | A | 220 | 43.401 | 21.251 | 27.245 | 1.00 | 15.71 | A |
| ATOM | 1594 | O | LEU | A | 220 | 43.034 | 20.986 | 28.395 | 1.00 | 15.65 | A |
| ATOM | 1595 | N | ALA | A | 221 | 44.481 | 20.693 | 26.698 | 1.00 | 15.60 | A |
| ATOM | 1596 | CA | ALA | A | 221 | 45.283 | 19.714 | 27.452 | 1.00 | 18.03 | A |
| ATOM | 1597 | CB | ALA | A | 221 | 46.452 | 19.175 | 26.604 | 1.00 | 17.58 | A |
| ATOM | 1598 | C | ALA | A | 221 | 45.834 | 20.298 | 28.738 | 1.00 | 11.01 | A |
| ATOM | 1599 | O | ALA | A | 221 | 46.085 | 19.573 | 29.687 | 1.00 | 15.45 | A |
| ATOM | 1600 | N | GLY | A | 222 | 46.038 | 21.612 | 28.754 | 1.00 | 15.25 | A |
| ATOM | 1601 | CA | GLY | A | 222 | 46.561 | 22.267 | 29.947 | 1.00 | 11.71 | A |
| ATOM | 1602 | C | GLY | A | 222 | 45.641 | 22.101 | 31.144 | 1.00 | 10.72 | A |
| ATOM | 1603 | O | GLY | A | 222 | 46.105 | 22.139 | 32.280 | 1.00 | 14.13 | A |
| ATOM | 1604 | N | LEU | A | 223 | 44.340 | 21.938 | 30.914 | 1.00 | 11.19 | A |
| ATOM | 1605 | CA | LEU | A | 223 | 43.406 | 21.751 | 32.033 | 1.00 | 8.14 | A |
| ATOM | 1606 | CB | LEU | A | 223 | 41.946 | 21.728 | 31.525 | 1.00 | 9.90 | A |
| ATOM | 1607 | CG | LEU | A | 223 | 41.481 | 23.046 | 30.874 | 1.00 | 9.91 | A |
| ATOM | 1608 | CD1 | LEU | A | 223 | 40.035 | 22.918 | 30.331 | 1.00 | 9.85 | A |
| ATOM | 1609 | CD2 | LEU | A | 223 | 41.570 | 24.153 | 31.926 | 1.00 | 9.05 | A |
| ATOM | 1610 | C | LEU | A | 223 | 43.720 | 20.444 | 32.773 | 1.00 | 11.22 | A |
| ATOM | 1611 | O | LEU | A | 223 | 43.369 | 20.297 | 33.939 | 1.00 | 7.21 | A |
| ATOM | 1612 | N | ASN | A | 224 | 44.389 | 19.505 | 32.100 | 1.00 | 9.60 | A |
| ATOM | 1613 | CA | ASN | A | 224 | 44.742 | 18.231 | 32.727 | 1.00 | 10.35 | A |
| ATOM | 1614 | CB | ASN | A | 224 | 44.651 | 17.078 | 31.706 | 1.00 | 13.70 | A |
| ATOM | 1615 | CG | ASN | A | 224 | 43.214 | 16.768 | 31.301 | 1.00 | 15.75 | A |
| ATOM | 1616 | OD1 | ASN | A | 224 | 42.347 | 16.610 | 32.146 | 1.00 | 21.72 | A |
| ATOM | 1617 | ND2 | ASN | A | 224 | 42.968 | 16.666 | 30.012 | 1.00 | 14.86 | A |
| ATOM | 1618 | C | ASN | A | 224 | 46.138 | 18.239 | 33.359 | 1.00 | 12.93 | A |
| ATOM | 1619 | O | ASN | A | 224 | 46.580 | 17.226 | 33.898 | 1.00 | 14.86 | A |
| ATOM | 1620 | N | ASP | A | 225 | 46.833 | 19.370 | 33.308 | 1.00 | 8.74 | A |
| ATOM | 1621 | CA | ASP | A | 225 | 48.163 | 19.437 | 33.932 | 1.00 | 12.69 | A |
| ATOM | 1622 | CB | ASP | A | 225 | 49.031 | 20.467 | 33.199 | 1.00 | 11.40 | A |
| ATOM | 1623 | CG | ASP | A | 225 | 50.402 | 20.654 | 33.843 | 1.00 | 15.89 | A |
| ATOM | 1624 | OD1 | ASP | A | 225 | 50.673 | 20.076 | 34.922 | 1.00 | 14.10 | A |
| ATOM | 1625 | OD2 | ASP | A | 225 | 51.211 | 21.401 | 33.261 | 1.00 | 16.19 | A |
| ATOM | 1626 | C | ASP | A | 225 | 47.960 | 19.844 | 35.398 | 1.00 | 13.53 | A |
| ATOM | 1627 | O | ASP | A | 225 | 47.776 | 21.016 | 35.691 | 1.00 | 10.79 | A |
| ATOM | 1628 | N | ALA | A | 226 | 48.035 | 18.882 | 36.317 | 1.00 | 10.49 | A |
| ATOM | 1629 | CA | ALA | A | 226 | 47.792 | 19.178 | 37.720 | 1.00 | 9.18 | A |
| ATOM | 1630 | CB | ALA | A | 226 | 47.424 | 17.889 | 38.478 | 1.00 | 13.20 | A |
| ATOM | 1631 | C | ALA | A | 226 | 48.881 | 19.939 | 38.461 | 1.00 | 12.23 | A |
| ATOM | 1632 | O | ALA | A | 226 | 48.773 | 20.144 | 39.678 | 1.00 | 13.15 | A |
| ATOM | 1633 | N | THR | A | 227 | 49.935 | 20.347 | 37.762 | 1.00 | 10.64 | A |
| ATOM | 1634 | CA | THR | A | 227 | 50.955 | 21.148 | 38.426 | 1.00 | 10.50 | A |
| ATOM | 1635 | CB | THR | A | 227 | 52.405 | 20.854 | 37.917 | 1.00 | 15.63 | A |
| ATOM | 1636 | OG1 | THR | A | 227 | 52.541 | 21.287 | 36.561 | 1.00 | 13.88 | A |
| ATOM | 1637 | CG2 | THR | A | 227 | 52.718 | 19.374 | 38.009 | 1.00 | 16.59 | A |
| ATOM | 1638 | C | THR | A | 227 | 50.620 | 22.628 | 38.154 | 1.00 | 9.17 | A |
| ATOM | 1639 | O | THR | A | 227 | 51.320 | 23.509 | 38.626 | 1.00 | 10.52 | A |
| ATOM | 1640 | N | LYS | A | 228 | 49.530 | 22.876 | 37.414 | 1.00 | 9.27 | A |
| ATOM | 1641 | CA | LYS | A | 228 | 49.079 | 24.226 | 37.069 | 1.00 | 12.05 | A |
| ATOM | 1642 | CB | LYS | A | 228 | 49.378 | 24.511 | 35.594 | 1.00 | 15.38 | A |
| ATOM | 1643 | CG | LYS | A | 228 | 50.877 | 24.607 | 35.272 | 1.00 | 22.71 | A |
| ATOM | 1644 | CD | LYS | A | 228 | 51.125 | 24.652 | 33.758 | 1.00 | 20.66 | A |
| ATOM | 1645 | CE | LYS | A | 228 | 52.613 | 24.720 | 33.447 | 1.00 | 26.84 | A |
| ATOM | 1646 | NZ | LYS | A | 228 | 53.205 | 25.974 | 33.986 | 1.00 | 37.16 | A |
| ATOM | 1647 | C | LYS | A | 228 | 47.576 | 24.453 | 37.313 | 1.00 | 8.78 | A |
| ATOM | 1648 | O | LYS | A | 228 | 47.153 | 25.574 | 37.634 | 1.00 | 9.99 | A |
| ATOM | 1649 | N | VAL | A | 229 | 46.777 | 23.407 | 37.100 | 1.00 | 9.98 | A |
| ATOM | 1650 | CA | VAL | A | 229 | 45.327 | 23.465 | 37.282 | 1.00 | 6.71 | A |
| ATOM | 1651 | CB | VAL | A | 229 | 44.611 | 23.300 | 35.939 | 1.00 | 8.87 | A |
| ATOM | 1652 | CG1 | VAL | A | 229 | 43.082 | 23.303 | 36.150 | 1.00 | 10.77 | A |
| ATOM | 1653 | CG2 | VAL | A | 229 | 45.019 | 24.468 | 34.988 | 1.00 | 10.90 | A |
| ATOM | 1654 | C | VAL | A | 229 | 44.913 | 22.339 | 38.245 | 1.00 | 10.51 | A |
| ATOM | 1655 | O | VAL | A | 229 | 45.107 | 21.154 | 37.967 | 1.00 | 8.04 | A |
| ATOM | 1656 | N | ALA | A | 230 | 44.343 | 22.706 | 39.383 | 1.00 | 10.29 | A |
| ATOM | 1657 | CA | ALA | A | 230 | 43.985 | 21.696 | 40.387 | 1.00 | 8.30 | A |
| ATOM | 1658 | CB | ALA | A | 230 | 43.612 | 22.380 | 41.677 | 1.00 | 10.71 | A |
| ATOM | 1659 | C | ALA | A | 230 | 42.900 | 20.691 | 40.064 | 1.00 | 12.18 | A |
| ATOM | 1660 | O | ALA | A | 230 | 41.884 | 21.020 | 39.435 | 1.00 | 12.58 | A |
| ATOM | 1661 | N | ARG | A | 231 | 43.120 | 19.452 | 40.501 | 1.00 | 8.23 | A |
| ATOM | 1662 | CA | ARG | A | 231 | 42.080 | 18.436 | 40.382 | 1.00 | 8.98 | A |
| ATOM | 1663 | CB | ARG | A | 231 | 42.656 | 17.021 | 40.495 | 1.00 | 11.67 | A |
| ATOM | 1664 | CG | ARG | A | 231 | 43.433 | 16.581 | 39.265 | 1.00 | 14.58 | A |
| ATOM | 1665 | CD | ARG | A | 231 | 44.130 | 15.244 | 39.487 | 1.00 | 18.76 | A |
| ATOM | 1666 | NE | ARG | A | 231 | 44.972 | 14.941 | 38.336 | 1.00 | 19.63 | A |
| ATOM | 1667 | CZ | ARG | A | 231 | 45.931 | 14.029 | 38.331 | 1.00 | 26.24 | A |

FIGURE 5 (continued)

```
ATOM   1668  NH1 ARG A 231      46.184  13.312  39.426  1.00 22.17           A
ATOM   1669  NH2 ARG A 231      46.649  13.848  37.228  1.00 31.31           A
ATOM   1670  C   ARG A 231      41.271  18.738  41.632  1.00  8.66           A
ATOM   1671  O   ARG A 231      41.801  19.332  42.582  1.00 13.24           A
ATOM   1672  N   THR A 232      39.997  18.371  41.640  1.00  9.11           A
ATOM   1673  CA  THR A 232      39.180  18.607  42.822  1.00 11.84           A
ATOM   1674  CB  THR A 232      38.236  19.820  42.623  1.00 13.64           A
ATOM   1675  OG1 THR A 232      39.017  21.004  42.384  1.00 17.60           A
ATOM   1676  CG2 THR A 232      37.382  20.025  43.883  1.00 14.43           A
ATOM   1677  C   THR A 232      38.357  17.351  43.071  1.00  9.12           A
ATOM   1678  O   THR A 232      37.869  16.747  42.118  1.00 13.13           A
ATOM   1679  N   GLY A 233      38.240  16.934  44.332  1.00  9.55           A
ATOM   1680  CA  GLY A 233      37.466  15.739  44.636  1.00 13.57           A
ATOM   1681  C   GLY A 233      38.197  14.616  45.364  1.00 14.09           A
ATOM   1682  O   GLY A 233      37.634  13.556  45.591  1.00 16.30           A
ATOM   1683  N   LYS A 234      39.460  14.831  45.706  1.00 14.67           A
ATOM   1684  CA  LYS A 234      40.226  13.834  46.438  1.00 15.04           A
ATOM   1685  CB  LYS A 234      41.577  14.442  46.830  1.00 13.37           A
ATOM   1686  CG  LYS A 234      42.483  13.576  47.688  1.00 14.40           A
ATOM   1687  CD  LYS A 234      43.807  14.314  47.968  1.00 17.84           A
ATOM   1688  CE  LYS A 234      43.594  15.567  48.839  1.00 15.78           A
ATOM   1689  NZ  LYS A 234      44.766  16.501  48.832  1.00 12.74           A
ATOM   1690  C   LYS A 234      39.450  13.411  47.697  1.00 17.96           A
ATOM   1691  O   LYS A 234      38.826  14.240  48.369  1.00 13.45           A
ATOM   1692  N   GLY A 235      39.489  12.124  48.031  1.00 15.80           A
ATOM   1693  CA  GLY A 235      38.785  11.694  49.223  1.00 15.51           A
ATOM   1694  C   GLY A 235      38.764  10.191  49.402  1.00 19.91           A
ATOM   1695  O   GLY A 235      39.586   9.472  48.825  1.00 21.77           A
ATOM   1696  N   SER A 236      37.811   9.731  50.204  1.00 21.18           A
ATOM   1697  CA  SER A 236      37.624   8.311  50.489  1.00 24.63           A
ATOM   1698  CB  SER A 236      38.018   8.004  51.929  1.00 25.33           A
ATOM   1699  OG  SER A 236      39.359   8.397  52.161  1.00 33.33           A
ATOM   1700  C   SER A 236      36.159   7.969  50.291  1.00 26.45           A
ATOM   1701  O   SER A 236      35.282   8.624  50.855  1.00 27.89           A
ATOM   1702  N   SER A 237      35.891   6.947  49.488  1.00 22.58           A
ATOM   1703  CA  SER A 237      34.522   6.520  49.238  1.00 23.79           A
ATOM   1704  CB  SER A 237      34.123   6.799  47.786  1.00 25.37           A
ATOM   1705  OG  SER A 237      34.019   8.197  47.578  1.00 38.24           A
ATOM   1706  C   SER A 237      34.429   5.036  49.514  1.00 21.92           A
ATOM   1707  O   SER A 237      35.244   4.267  49.009  1.00 20.25           A
ATOM   1708  N   SER A 238      33.423   4.640  50.295  1.00 25.14           A
ATOM   1709  CA  SER A 238      33.233   3.236  50.662  1.00 24.45           A
ATOM   1710  CB  SER A 238      32.716   2.427  49.471  1.00 27.22           A
ATOM   1711  OG  SER A 238      31.371   2.785  49.163  1.00 39.35           A
ATOM   1712  C   SER A 238      34.559   2.670  51.159  1.00 23.39           A
ATOM   1713  O   SER A 238      34.961   1.557  50.809  1.00 24.29           A
ATOM   1714  N   GLY A 239      35.249   3.468  51.966  1.00 24.50           A
ATOM   1715  CA  GLY A 239      36.519   3.040  52.524  1.00 25.11           A
ATOM   1716  C   GLY A 239      37.705   2.973  51.584  1.00 28.40           A
ATOM   1717  O   GLY A 239      38.755   2.452  51.969  1.00 28.03           A
ATOM   1718  N   GLY A 240      37.563   3.495  50.365  1.00 21.59           A
ATOM   1719  CA  GLY A 240      38.677   3.459  49.431  1.00 26.05           A
ATOM   1720  C   GLY A 240      39.082   4.858  48.984  1.00 24.32           A
ATOM   1721  O   GLY A 240      38.218   5.685  48.714  1.00 23.70           A
ATOM   1722  N   GLY A 241      40.386   5.121  48.920  1.00 21.49           A
ATOM   1723  CA  GLY A 241      40.873   6.422  48.500  1.00 27.38           A
ATOM   1724  C   GLY A 241      40.495   6.715  47.058  1.00 28.81           A
ATOM   1725  O   GLY A 241      40.585   5.840  46.200  1.00 28.58           A
ATOM   1726  N   ALA A 242      40.057   7.939  46.784  1.00 24.66           A
ATOM   1727  CA  ALA A 242      39.663   8.303  45.434  1.00 22.08           A
ATOM   1728  CB  ALA A 242      38.159   8.527  45.367  1.00 25.95           A
ATOM   1729  C   ALA A 242      40.385   9.573  45.043  1.00 22.46           A
ATOM   1730  O   ALA A 242      40.541  10.472  45.869  1.00 16.67           A
ATOM   1731  N   GLU A 243      40.813   9.647  43.785  1.00 16.24           A
ATOM   1732  CA  GLU A 243      41.502  10.830  43.289  1.00 18.78           A
ATOM   1733  CB  GLU A 243      42.444  10.473  42.132  1.00 23.30           A
ATOM   1734  CG  GLU A 243      43.643   9.624  42.499  1.00 31.37           A
ATOM   1735  CD  GLU A 243      44.658   9.584  41.368  1.00 37.64           A
ATOM   1736  OE1 GLU A 243      44.234   9.507  40.195  1.00 38.59           A
ATOM   1737  OE2 GLU A 243      45.876   9.628  41.644  1.00 41.94           A
ATOM   1738  C   GLU A 243      40.469  11.817  42.757  1.00 15.80           A
ATOM   1739  O   GLU A 243      39.417  11.406  42.285  1.00 17.65           A
ATOM   1740  N   GLY A 244      40.765  13.111  42.827  1.00 15.34           A
ATOM   1741  CA  GLY A 244      39.832  14.101  42.286  1.00 16.23           A
ATOM   1742  C   GLY A 244      39.994  14.161  40.770  1.00 16.48           A
ATOM   1743  O   GLY A 244      40.894  13.528  40.228  1.00 14.37           A
```

FIGURE 5 (continued)

```
ATOM   1744  N    LYS A 245      39.148  14.939  40.096  1.00 14.99           A
ATOM   1745  CA   LYS A 245      39.186  15.079  38.632  1.00 14.88           A
ATOM   1746  CB   LYS A 245      37.792  14.795  38.060  1.00 13.06           A
ATOM   1747  CG   LYS A 245      37.294  13.363  38.289  1.00 22.95           A
ATOM   1748  CD   LYS A 245      38.174  12.353  37.540  1.00 27.44           A
ATOM   1749  CE   LYS A 245      37.596  10.939  37.643  1.00 27.64           A
ATOM   1750  NZ   LYS A 245      37.298  10.599  39.063  1.00 36.34           A
ATOM   1751  C    LYS A 245      39.617  16.471  38.165  1.00 13.81           A
ATOM   1752  O    LYS A 245      39.580  17.431  38.932  1.00 10.66           A
ATOM   1753  N    SER A 246      40.022  16.572  36.902  1.00 14.72           A
ATOM   1754  CA   SER A 246      40.405  17.856  36.344  1.00 11.87           A
ATOM   1755  CB   SER A 246      41.299  17.687  35.104  1.00 12.31           A
ATOM   1756  OG   SER A 246      40.515  17.215  34.011  1.00  9.67           A
ATOM   1757  C    SER A 246      39.095  18.500  35.913  1.00 10.79           A
ATOM   1758  O    SER A 246      38.076  17.815  35.735  1.00 10.08           A
ATOM   1759  N    PRO A 247      39.114  19.825  35.698  1.00 10.98           A
ATOM   1760  CD   PRO A 247      40.243  20.747  35.947  1.00  7.03           A
ATOM   1761  CA   PRO A 247      37.909  20.545  35.275  1.00  9.29           A
ATOM   1762  CB   PRO A 247      38.210  21.988  35.692  1.00  7.19           A
ATOM   1763  CG   PRO A 247      39.737  22.094  35.385  1.00  9.12           A
ATOM   1764  C    PRO A 247      37.632  20.416  33.765  1.00  9.99           A
ATOM   1765  O    PRO A 247      36.865  21.197  33.222  1.00 11.54           A
ATOM   1766  N    ALA A 248      38.253  19.449  33.083  1.00  9.23           A
ATOM   1767  CA   ALA A 248      37.992  19.278  31.638  1.00 12.63           A
ATOM   1768  CB   ALA A 248      38.832  18.097  31.069  1.00 10.35           A
ATOM   1769  C    ALA A 248      36.487  19.021  31.431  1.00 15.07           A
ATOM   1770  O    ALA A 248      35.838  18.390  32.278  1.00 11.60           A
ATOM   1771  N    ALA A 249      35.935  19.497  30.311  1.00 12.95           A
ATOM   1772  CA   ALA A 249      34.498  19.332  30.037  1.00 11.90           A
ATOM   1773  CB   ALA A 249      34.141  19.886  28.633  1.00 12.61           A
ATOM   1774  C    ALA A 249      34.037  17.890  30.149  1.00 15.30           A
ATOM   1775  O    ALA A 249      32.953  17.617  30.666  1.00 14.63           A
ATOM   1776  N    ALA A 250      34.845  16.949  29.672  1.00 14.76           A
ATOM   1777  CA   ALA A 250      34.426  15.542  29.769  1.00 18.41           A
ATOM   1778  CB   ALA A 250      35.486  14.623  29.168  1.00 15.53           A
ATOM   1779  C    ALA A 250      34.118  15.102  31.200  1.00 15.76           A
ATOM   1780  O    ALA A 250      33.366  14.154  31.410  1.00 14.59           A
ATOM   1781  N    ASN A 251      34.677  15.785  32.190  1.00 14.82           A
ATOM   1782  CA   ASN A 251      34.433  15.380  33.575  1.00 13.85           A
ATOM   1783  CB   ASN A 251      35.665  15.696  34.441  1.00 12.26           A
ATOM   1784  CG   ASN A 251      36.880  14.885  34.022  1.00 14.85           A
ATOM   1785  OD1  ASN A 251      36.755  13.712  33.653  1.00 14.23           A
ATOM   1786  ND2  ASN A 251      38.056  15.487  34.091  1.00 13.09           A
ATOM   1787  C    ASN A 251      33.168  15.968  34.210  1.00 16.10           A
ATOM   1788  O    ASN A 251      32.877  15.686  35.357  1.00 14.41           A
ATOM   1789  N    SER A 252      32.431  16.806  33.482  1.00 13.25           A
ATOM   1790  CA   SER A 252      31.191  17.346  34.039  1.00 10.81           A
ATOM   1791  CB   SER A 252      31.262  18.868  34.209  1.00 22.32           A
ATOM   1792  OG   SER A 252      31.266  19.536  32.953  1.00 23.58           A
ATOM   1793  C    SER A 252      30.027  16.982  33.101  1.00 11.68           A
ATOM   1794  O    SER A 252      28.862  17.077  33.479  1.00 12.18           A
ATOM   1795  N    SER A 253      30.365  16.501  31.904  1.00 11.74           A
ATOM   1796  CA   SER A 253      29.367  16.138  30.918  1.00 10.64           A
ATOM   1797  CB   SER A 253      30.048  15.572  29.665  1.00 18.81           A
ATOM   1798  OG   SER A 253      29.052  15.263  28.704  1.00 27.87           A
ATOM   1799  C    SER A 253      28.294  15.139  31.382  1.00 15.51           A
ATOM   1800  O    SER A 253      27.112  15.319  31.102  1.00 11.29           A
ATOM   1801  N    ALA A 254      28.692  14.080  32.081  1.00 12.85           A
ATOM   1802  CA   ALA A 254      27.700  13.084  32.525  1.00 14.75           A
ATOM   1803  CB   ALA A 254      28.423  11.868  33.216  1.00 13.94           A
ATOM   1804  C    ALA A 254      26.656  13.667  33.472  1.00 14.13           A
ATOM   1805  O    ALA A 254      25.457  13.394  33.342  1.00 14.40           A
ATOM   1806  N    ALA A 255      27.111  14.457  34.441  1.00 11.77           A
ATOM   1807  CA   ALA A 255      26.205  15.070  35.401  1.00 13.30           A
ATOM   1808  CB   ALA A 255      27.009  15.838  36.460  1.00 12.60           A
ATOM   1809  C    ALA A 255      25.223  16.017  34.698  1.00 15.34           A
ATOM   1810  O    ALA A 255      24.068  16.162  35.113  1.00 14.03           A
ATOM   1811  N    ILE A 256      25.684  16.680  33.644  1.00 13.10           A
ATOM   1812  CA   ILE A 256      24.812  17.599  32.920  1.00 14.09           A
ATOM   1813  CB   ILE A 256      25.614  18.445  31.900  1.00 11.60           A
ATOM   1814  CG2  ILE A 256      24.655  19.233  30.987  1.00 13.12           A
ATOM   1815  CG1  ILE A 256      26.577  19.378  32.657  1.00  8.87           A
ATOM   1816  CD1  ILE A 256      25.878  20.335  33.703  1.00  6.00           A
ATOM   1817  C    ILE A 256      23.716  16.813  32.195  1.00 12.88           A
ATOM   1818  O    ILE A 256      22.569  17.268  32.118  1.00 12.14           A
ATOM   1819  N    SER A 257      24.069  15.639  31.678  1.00 12.01           A
```

FIGURE 5 (continued)

```
ATOM   1820  CA   SER A 257      23.105  14.793  30.960  1.00 17.17      A
ATOM   1821  CB   SER A 257      23.773  13.529  30.418  1.00 20.37      A
ATOM   1822  OG   SER A 257      24.331  13.802  29.157  1.00 27.40      A
ATOM   1823  C    SER A 257      21.886  14.359  31.750  1.00 21.46      A
ATOM   1824  O    SER A 257      20.885  13.975  31.161  1.00 25.54      A
ATOM   1825  N    VAL A 258      21.949  14.417  33.070  1.00 18.37      A
ATOM   1826  CA   VAL A 258      20.803  13.983  33.849  1.00 22.61      A
ATOM   1827  CB   VAL A 258      21.230  13.049  34.996  1.00 23.45      A
ATOM   1828  CG1  VAL A 258      22.055  11.887  34.443  1.00 28.56      A
ATOM   1829  CG2  VAL A 258      22.004  13.831  36.041  1.00 29.85      A
ATOM   1830  C    VAL A 258      20.002  15.133  34.436  1.00 20.13      A
ATOM   1831  O    VAL A 258      19.056  14.907  35.193  1.00 19.13      A
ATOM   1832  N    VAL A 259      20.367  16.365  34.092  1.00 17.82      A
ATOM   1833  CA   VAL A 259      19.628  17.503  34.621  1.00 12.10      A
ATOM   1834  CB   VAL A 259      20.345  18.816  34.305  1.00  9.61      A
ATOM   1835  CG1  VAL A 259      19.448  20.009  34.655  1.00  9.95      A
ATOM   1836  CG2  VAL A 259      21.661  18.870  35.110  1.00  9.60      A
ATOM   1837  C    VAL A 259      18.257  17.470  33.946  1.00 10.93      A
ATOM   1838  O    VAL A 259      18.154  17.543  32.719  1.00 12.34      A
ATOM   1839  N    PRO A 260      17.185  17.372  34.746  1.00 12.49      A
ATOM   1840  CD   PRO A 260      17.178  17.349  36.227  1.00 15.54      A
ATOM   1841  CA   PRO A 260      15.823  17.321  34.204  1.00 12.14      A
ATOM   1842  CB   PRO A 260      14.992  16.881  35.415  1.00 18.68      A
ATOM   1843  CG   PRO A 260      15.705  17.553  36.556  1.00 20.90      A
ATOM   1844  C    PRO A 260      15.326  18.629  33.592  1.00 13.33      A
ATOM   1845  O    PRO A 260      15.719  19.704  34.025  1.00 11.59      A
ATOM   1846  N    LEU A 261      14.462  18.517  32.583  1.00 10.89      A
ATOM   1847  CA   LEU A 261      13.906  19.697  31.899  1.00 14.89      A
ATOM   1848  CB   LEU A 261      13.190  19.272  30.612  1.00 14.36      A
ATOM   1849  CG   LEU A 261      14.033  18.724  29.470  1.00 23.33      A
ATOM   1850  CD1  LEU A 261      13.132  18.115  28.388  1.00 17.91      A
ATOM   1851  CD2  LEU A 261      14.860  19.854  28.927  1.00 21.86      A
ATOM   1852  C    LEU A 261      12.868  20.354  32.782  1.00 14.14      A
ATOM   1853  O    LEU A 261      12.313  19.715  33.667  1.00 13.00      A
ATOM   1854  N    PRO A 262      12.598  21.646  32.570  1.00 16.56      A
ATOM   1855  CD   PRO A 262      13.154  22.620  31.613  1.00 18.10      A
ATOM   1856  CA   PRO A 262      11.576  22.260  33.421  1.00 16.86      A
ATOM   1857  CB   PRO A 262      11.753  23.752  33.137  1.00 16.37      A
ATOM   1858  CG   PRO A 262      12.147  23.764  31.698  1.00 22.55      A
ATOM   1859  C    PRO A 262      10.239  21.709  32.911  1.00 14.68      A
ATOM   1860  O    PRO A 262      10.136  21.357  31.743  1.00 14.32      A
ATOM   1861  N    ALA A 263       9.234  21.605  33.776  1.00 13.42      A
ATOM   1862  CA   ALA A 263       7.943  21.085  33.344  1.00 16.60      A
ATOM   1863  CB   ALA A 263       6.994  20.952  34.539  1.00 20.02      A
ATOM   1864  C    ALA A 263       7.343  22.011  32.292  1.00 16.04      A
ATOM   1865  O    ALA A 263       7.480  23.235  32.377  1.00 14.70      A
ATOM   1866  N    ALA A 264       6.664  21.426  31.309  1.00 15.42      A
ATOM   1867  CA   ALA A 264       6.050  22.206  30.239  1.00 12.74      A
ATOM   1868  CB   ALA A 264       5.248  21.287  29.308  1.00 19.88      A
ATOM   1869  C    ALA A 264       5.149  23.329  30.747  1.00 15.82      A
ATOM   1870  O    ALA A 264       5.247  24.461  30.264  1.00 17.34      A
ATOM   1871  N    ALA A 265       4.284  23.037  31.721  1.00 13.78      A
ATOM   1872  CA   ALA A 265       3.370  24.071  32.242  1.00 15.17      A
ATOM   1873  CB   ALA A 265       2.464  23.478  33.363  1.00 15.42      A
ATOM   1874  C    ALA A 265       4.057  25.333  32.772  1.00 15.06      A
ATOM   1875  O    ALA A 265       3.437  26.398  32.838  1.00 13.78      A
ATOM   1876  N    ASN A 266       5.320  25.212  33.175  1.00 13.85      A
ATOM   1877  CA   ASN A 266       6.057  26.343  33.733  1.00 12.11      A
ATOM   1878  CB   ASN A 266       6.987  25.895  34.873  1.00 13.94      A
ATOM   1879  CG   ASN A 266       6.253  25.239  36.028  1.00 23.25      A
ATOM   1880  OD1  ASN A 266       5.175  25.676  36.425  1.00 21.92      A
ATOM   1881  ND2  ASN A 266       6.856  24.200  36.592  1.00 19.37      A
ATOM   1882  C    ASN A 266       6.969  27.039  32.730  1.00 12.06      A
ATOM   1883  O    ASN A 266       7.662  27.965  33.100  1.00 13.88      A
ATOM   1884  N    ARG A 267       6.980  26.600  31.483  1.00 10.11      A
ATOM   1885  CA   ARG A 267       7.933  27.162  30.534  1.00 12.44      A
ATOM   1886  CB   ARG A 267       8.029  26.254  29.306  1.00 10.57      A
ATOM   1887  CG   ARG A 267       8.746  24.945  29.675  1.00 12.04      A
ATOM   1888  CD   ARG A 267       8.892  23.924  28.540  1.00  9.95      A
ATOM   1889  NE   ARG A 267       9.275  22.637  29.124  1.00 14.76      A
ATOM   1890  CZ   ARG A 267       9.533  21.530  28.439  1.00 14.94      A
ATOM   1891  NH1  ARG A 267       9.477  21.543  27.118  1.00 16.59      A
ATOM   1892  NH2  ARG A 267       9.782  20.387  29.084  1.00 12.17      A
ATOM   1893  C    ARG A 267       7.785  28.629  30.168  1.00 13.15      A
ATOM   1894  O    ARG A 267       8.658  29.207  29.505  1.00 13.32      A
ATOM   1895  N    GLY A 268       6.711  29.240  30.663  1.00 11.13      A
```

FIGURE 5 (continued)

```
ATOM   1896  CA   GLY A 268       6.491  30.653  30.439  1.00 13.33           A
ATOM   1897  C    GLY A 268       7.212  31.457  31.507  1.00 13.92           A
ATOM   1898  O    GLY A 268       7.219  32.679  31.452  1.00 14.39           A
ATOM   1899  N    ASP A 269       7.804  30.767  32.486  1.00 11.00           A
ATOM   1900  CA   ASP A 269       8.554  31.398  33.594  1.00 14.58           A
ATOM   1901  CB   ASP A 269       8.233  30.665  34.914  1.00 13.17           A
ATOM   1902  CG   ASP A 269       8.943  31.263  36.117  1.00 16.24           A
ATOM   1903  OD1  ASP A 269       9.767  32.179  35.944  1.00 17.40           A
ATOM   1904  OD2  ASP A 269       8.667  30.804  37.244  1.00 19.44           A
ATOM   1905  C    ASP A 269      10.064  31.290  33.303  1.00 10.72           A
ATOM   1906  O    ASP A 269      10.616  30.196  33.348  1.00 11.39           A
ATOM   1907  N    PRO A 270      10.742  32.417  33.010  1.00 11.52           A
ATOM   1908  CD   PRO A 270      10.217  33.796  32.924  1.00 11.48           A
ATOM   1909  CA   PRO A 270      12.184  32.394  32.709  1.00 10.44           A
ATOM   1910  CB   PRO A 270      12.523  33.867  32.491  1.00 11.04           A
ATOM   1911  CG   PRO A 270      11.225  34.465  32.026  1.00 13.30           A
ATOM   1912  C    PRO A 270      13.042  31.786  33.793  1.00 12.77           A
ATOM   1913  O    PRO A 270      14.097  31.243  33.521  1.00 10.58           A
ATOM   1914  N    ASN A 271      12.578  31.870  35.032  1.00 11.41           A
ATOM   1915  CA   ASN A 271      13.337  31.332  36.145  1.00 11.19           A
ATOM   1916  CB   ASN A 271      12.660  31.729  37.463  1.00 14.43           A
ATOM   1917  CG   ASN A 271      13.533  31.434  38.683  1.00 22.14           A
ATOM   1918  OD1  ASN A 271      14.734  31.726  38.696  1.00 16.89           A
ATOM   1919  ND2  ASN A 271      12.934  30.854  39.703  1.00 16.43           A
ATOM   1920  C    ASN A 271      13.545  29.816  36.090  1.00 16.21           A
ATOM   1921  O    ASN A 271      14.595  29.319  36.510  1.00 15.74           A
ATOM   1922  N    VAL A 272      12.574  29.065  35.575  1.00 10.21           A
ATOM   1923  CA   VAL A 272      12.749  27.613  35.547  1.00 11.32           A
ATOM   1924  CB   VAL A 272      11.378  26.849  35.440  1.00 13.38           A
ATOM   1925  CG1  VAL A 272      10.450  27.297  36.548  1.00 14.31           A
ATOM   1926  CG2  VAL A 272      10.759  27.074  34.078  1.00 11.03           A
ATOM   1927  C    VAL A 272      13.651  27.086  34.434  1.00 12.71           A
ATOM   1928  O    VAL A 272      14.028  25.907  34.459  1.00 10.89           A
ATOM   1929  N    TRP A 273      13.991  27.930  33.461  1.00  7.57           A
ATOM   1930  CA   TRP A 273      14.862  27.465  32.366  1.00  7.83           A
ATOM   1931  CB   TRP A 273      14.741  28.403  31.150  1.00  7.08           A
ATOM   1932  CG   TRP A 273      13.496  28.126  30.364  1.00 10.87           A
ATOM   1933  CD2  TRP A 273      13.359  27.161  29.325  1.00  9.80           A
ATOM   1934  CE2  TRP A 273      12.020  27.228  28.860  1.00  9.21           A
ATOM   1935  CE3  TRP A 273      14.241  26.240  28.732  1.00 10.74           A
ATOM   1936  CD1  TRP A 273      12.271  28.728  30.500  1.00  7.74           A
ATOM   1937  NE1  TRP A 273      11.375  28.192  29.590  1.00 12.31           A
ATOM   1938  CZ2  TRP A 273      11.545  26.412  27.838  1.00 10.97           A
ATOM   1939  CZ3  TRP A 273      13.764  25.428  27.700  1.00 10.91           A
ATOM   1940  CH2  TRP A 273      12.427  25.522  27.267  1.00 14.13           A
ATOM   1941  C    TRP A 273      16.338  27.311  32.755  1.00  9.26           A
ATOM   1942  O    TRP A 273      17.119  26.663  32.042  1.00  9.73           A
ATOM   1943  N    THR A 274      16.736  27.893  33.880  1.00  8.74           A
ATOM   1944  CA   THR A 274      18.123  27.769  34.281  1.00 11.71           A
ATOM   1945  CB   THR A 274      18.759  29.147  34.542  1.00 12.87           A
ATOM   1946  OG1  THR A 274      18.701  29.940  33.334  1.00 16.61           A
ATOM   1947  CG2  THR A 274      20.240  28.973  34.959  1.00  9.96           A
ATOM   1948  C    THR A 274      18.271  26.918  35.535  1.00 10.53           A
ATOM   1949  O    THR A 274      18.020  27.378  36.645  1.00 11.96           A
ATOM   1950  N    PRO A 275      18.673  25.657  35.373  1.00 11.80           A
ATOM   1951  CD   PRO A 275      18.885  24.916  34.119  1.00 13.30           A
ATOM   1952  CA   PRO A 275      18.841  24.782  36.543  1.00 11.14           A
ATOM   1953  CB   PRO A 275      19.180  23.424  35.921  1.00 15.21           A
ATOM   1954  CG   PRO A 275      18.600  23.506  34.528  1.00 15.39           A
ATOM   1955  C    PRO A 275      20.004  25.253  37.445  1.00 12.51           A
ATOM   1956  O    PRO A 275      21.007  25.723  36.950  1.00 12.15           A
ATOM   1957  N    VAL A 276      19.869  25.148  38.764  1.00  9.91           A
ATOM   1958  CA   VAL A 276      20.999  25.502  39.615  1.00 10.08           A
ATOM   1959  CB   VAL A 276      20.738  26.762  40.478  1.00 15.02           A
ATOM   1960  CG1  VAL A 276      20.534  27.990  39.568  1.00 16.57           A
ATOM   1961  CG2  VAL A 276      19.551  26.543  41.388  1.00 17.45           A
ATOM   1962  C    VAL A 276      21.236  24.293  40.500  1.00 12.75           A
ATOM   1963  O    VAL A 276      20.315  23.498  40.743  1.00  7.21           A
ATOM   1964  N    PHE A 277      22.472  24.149  40.969  1.00 13.38           A
ATOM   1965  CA   PHE A 277      22.848  23.017  41.798  1.00 12.43           A
ATOM   1966  CB   PHE A 277      24.231  22.491  41.373  1.00  8.49           A
ATOM   1967  CG   PHE A 277      24.229  21.828  40.017  1.00  8.19           A
ATOM   1968  CD1  PHE A 277      24.404  22.568  38.858  1.00  9.76           A
ATOM   1969  CD2  PHE A 277      23.999  20.461  39.909  1.00  8.15           A
ATOM   1970  CE1  PHE A 277      24.350  21.934  37.585  1.00 13.41           A
ATOM   1971  CE2  PHE A 277      23.938  19.825  38.654  1.00 13.62           A
```

FIGURE 5 (continued)

```
ATOM   1972  CZ   PHE A 277      24.114  20.555  37.499  1.00  8.74      A
ATOM   1973  C    PHE A 277      22.848  23.377  43.272  1.00 12.19      A
ATOM   1974  O    PHE A 277      22.892  24.553  43.634  1.00 12.80      A
ATOM   1975  N    GLY A 278      22.781  22.356  44.116  1.00 12.01      A
ATOM   1976  CA   GLY A 278      22.767  22.601  45.547  1.00 10.29      A
ATOM   1977  C    GLY A 278      23.113  21.342  46.309  1.00  9.39      A
ATOM   1978  O    GLY A 278      23.379  20.302  45.704  1.00 12.45      A
ATOM   1979  N    ALA A 279      23.087  21.414  47.637  1.00 11.15      A
ATOM   1980  CA   ALA A 279      23.436  20.246  48.450  1.00 14.32      A
ATOM   1981  CB   ALA A 279      23.362  20.604  49.930  1.00 16.91      A
ATOM   1982  C    ALA A 279      22.542  19.029  48.157  1.00 20.18      A
ATOM   1983  O    ALA A 279      23.038  17.896  48.017  1.00 18.69      A
ATOM   1984  N    VAL A 280      21.238  19.262  48.040  1.00 14.35      A
ATOM   1985  CA   VAL A 280      20.302  18.176  47.796  1.00 19.81      A
ATOM   1986  CB   VAL A 280      19.500  17.847  49.076  1.00 23.28      A
ATOM   1987  CG1  VAL A 280      20.457  17.579  50.225  1.00 23.97      A
ATOM   1988  CG2  VAL A 280      18.603  18.992  49.436  1.00 21.87      A
ATOM   1989  C    VAL A 280      19.311  18.483  46.686  1.00 20.63      A
ATOM   1990  O    VAL A 280      19.004  19.635  46.407  1.00 21.63      A
ATOM   1991  N    THR A 281      18.812  17.436  46.055  1.00 20.03      A
ATOM   1992  CA   THR A 281      17.838  17.599  44.982  1.00 19.32      A
ATOM   1993  CB   THR A 281      17.732  16.327  44.136  1.00 20.70      A
ATOM   1994  OG1  THR A 281      18.989  16.096  43.493  1.00 24.83      A
ATOM   1995  CG2  THR A 281      16.637  16.473  43.062  1.00 20.23      A
ATOM   1996  C    THR A 281      16.500  17.882  45.618  1.00 24.45      A
ATOM   1997  O    THR A 281      16.073  17.159  46.520  1.00 22.56      A
ATOM   1998  N    GLY A 282      15.854  18.949  45.164  1.00 22.37      A
ATOM   1999  CA   GLY A 282      14.564  19.316  45.706  1.00 26.62      A
ATOM   2000  C    GLY A 282      14.183  20.735  45.343  1.00 31.11      A
ATOM   2001  O    GLY A 282      15.048  21.603  45.206  1.00 27.54      A
ATOM   2002  N    GLY A 283      12.883  20.971  45.181  1.00 32.42      A
ATOM   2003  CA   GLY A 283      12.401  22.301  44.855  1.00 30.56      A
ATOM   2004  C    GLY A 283      13.051  22.950  43.654  1.00 30.47      A
ATOM   2005  O    GLY A 283      13.307  24.154  43.666  1.00 33.57      A
ATOM   2006  N    GLY A 284      13.298  22.171  42.607  1.00 26.82      A
ATOM   2007  CA   GLY A 284      13.925  22.723  41.415  1.00 26.01      A
ATOM   2008  C    GLY A 284      15.450  22.687  41.439  1.00 26.04      A
ATOM   2009  O    GLY A 284      16.115  22.822  40.406  1.00 25.82      A
ATOM   2010  N    VAL A 285      16.022  22.521  42.622  1.00 19.46      A
ATOM   2011  CA   VAL A 285      17.467  22.461  42.722  1.00 19.85      A
ATOM   2012  CB   VAL A 285      17.903  22.894  44.135  1.00 19.90      A
ATOM   2013  CG1  VAL A 285      19.389  22.673  44.319  1.00 16.38      A
ATOM   2014  CG2  VAL A 285      17.521  24.376  44.360  1.00 20.29      A
ATOM   2015  C    VAL A 285      17.958  21.037  42.428  1.00 18.72      A
ATOM   2016  O    VAL A 285      17.298  20.055  42.794  1.00 18.51      A
ATOM   2017  N    VAL A 286      19.103  20.932  41.755  1.00 14.01      A
ATOM   2018  CA   VAL A 286      19.706  19.645  41.423  1.00 16.59      A
ATOM   2019  CB   VAL A 286      20.200  19.625  39.964  1.00 14.25      A
ATOM   2020  CG1  VAL A 286      20.729  18.254  39.623  1.00 19.16      A
ATOM   2021  CG2  VAL A 286      19.068  19.997  39.036  1.00 20.67      A
ATOM   2022  C    VAL A 286      20.917  19.416  42.325  1.00 17.27      A
ATOM   2023  O    VAL A 286      21.757  20.302  42.484  1.00 13.49      A
ATOM   2024  N    ALA A 287      21.041  18.229  42.896  1.00 15.01      A
ATOM   2025  CA   ALA A 287      22.188  18.000  43.778  1.00 17.78      A
ATOM   2026  CB   ALA A 287      22.039  16.649  44.527  1.00 16.62      A
ATOM   2027  C    ALA A 287      23.483  18.011  42.999  1.00 12.88      A
ATOM   2028  O    ALA A 287      23.520  17.533  41.854  1.00 10.29      A
ATOM   2029  N    TYR A 288      24.538  18.576  43.603  1.00 11.08      A
ATOM   2030  CA   TYR A 288      25.867  18.554  42.979  1.00  8.88      A
ATOM   2031  CB   TYR A 288      26.877  19.297  43.862  1.00 12.41      A
ATOM   2032  CG   TYR A 288      26.891  20.803  43.649  1.00  9.59      A
ATOM   2033  CD1  TYR A 288      26.329  21.677  44.589  1.00  8.82      A
ATOM   2034  CE1  TYR A 288      26.320  23.086  44.382  1.00 10.11      A
ATOM   2035  CD2  TYR A 288      27.463  21.356  42.491  1.00 10.87      A
ATOM   2036  CE2  TYR A 288      27.464  22.744  42.275  1.00  6.63      A
ATOM   2037  CZ   TYR A 288      26.883  23.601  43.223  1.00  7.60      A
ATOM   2038  OH   TYR A 288      26.842  24.960  42.960  1.00  7.46      A
ATOM   2039  C    TYR A 288      26.263  17.061  42.851  1.00 12.67      A
ATOM   2040  O    TYR A 288      25.989  16.265  43.750  1.00 10.55      A
ATOM   2041  N    PRO A 289      26.929  16.672  41.746  1.00 12.61      A
ATOM   2042  CD   PRO A 289      27.338  17.560  40.625  1.00 13.50      A
ATOM   2043  CA   PRO A 289      27.346  15.280  41.495  1.00 12.99      A
ATOM   2044  CB   PRO A 289      27.863  15.328  40.051  1.00 15.51      A
ATOM   2045  CG   PRO A 289      28.424  16.734  39.920  1.00 10.53      A
ATOM   2046  C    PRO A 289      28.366  14.644  42.439  1.00 17.46      A
ATOM   2047  O    PRO A 289      29.342  15.282  42.835  1.00 15.29      A
```

FIGURE 5 (continued)

| | | | | | | | | | |
|---|---|---|---|---|---|---|---|---|---|
| ATOM | 2048 | N | ASP | A | 290 | 28.149 | 13.372 | 42.782 | 1.00 16.57 A |
| ATOM | 2049 | CA | ASP | A | 290 | 29.092 | 12.691 | 43.652 | 1.00 20.97 A |
| ATOM | 2050 | CB | ASP | A | 290 | 28.360 | 11.751 | 44.628 | 1.00 25.52 A |
| ATOM | 2051 | CG | ASP | A | 290 | 27.489 | 10.723 | 43.929 | 1.00 34.64 A |
| ATOM | 2052 | OD1 | ASP | A | 290 | 26.599 | 10.146 | 44.604 | 1.00 38.07 A |
| ATOM | 2053 | OD2 | ASP | A | 290 | 27.693 | 10.478 | 42.716 | 1.00 39.24 A |
| ATOM | 2054 | C | ASP | A | 290 | 30.154 | 11.952 | 42.824 | 1.00 21.23 A |
| ATOM | 2055 | O | ASP | A | 290 | 30.990 | 11.231 | 43.362 | 1.00 21.11 A |
| ATOM | 2056 | N | SER | A | 291 | 30.136 | 12.152 | 41.509 | 1.00 14.24 A |
| ATOM | 2057 | CA | SER | A | 291 | 31.143 | 11.538 | 40.645 | 1.00 16.28 A |
| ATOM | 2058 | CB | SER | A | 291 | 30.592 | 10.290 | 39.925 | 1.00 16.14 A |
| ATOM | 2059 | OG | SER | A | 291 | 29.549 | 10.625 | 39.031 | 1.00 22.17 A |
| ATOM | 2060 | C | SER | A | 291 | 31.555 | 12.609 | 39.643 | 1.00 14.75 A |
| ATOM | 2061 | O | SER | A | 291 | 30.842 | 13.605 | 39.493 | 1.00 13.50 A |
| ATOM | 2062 | N | GLY | A | 292 | 32.692 | 12.419 | 38.971 | 1.00 13.79 A |
| ATOM | 2063 | CA | GLY | A | 292 | 33.181 | 13.423 | 38.019 | 1.00 14.60 A |
| ATOM | 2064 | C | GLY | A | 292 | 33.713 | 14.688 | 38.707 | 1.00 11.05 A |
| ATOM | 2065 | O | GLY | A | 292 | 33.964 | 14.669 | 39.909 | 1.00 14.10 A |
| ATOM | 2066 | N | TYR | A | 293 | 33.904 | 15.779 | 37.955 | 1.00 10.56 A |
| ATOM | 2067 | CA | TYR | A | 293 | 34.380 | 17.049 | 38.529 | 1.00 9.23 A |
| ATOM | 2068 | CB | TYR | A | 293 | 34.838 | 18.014 | 37.443 | 1.00 10.30 A |
| ATOM | 2069 | CG | TYR | A | 293 | 35.535 | 19.229 | 38.012 | 1.00 11.13 A |
| ATOM | 2070 | CD1 | TYR | A | 293 | 36.829 | 19.138 | 38.526 | 1.00 7.85 A |
| ATOM | 2071 | CE1 | TYR | A | 293 | 37.482 | 20.269 | 39.049 | 1.00 8.64 A |
| ATOM | 2072 | CD2 | TYR | A | 293 | 34.900 | 20.470 | 38.038 | 1.00 11.82 A |
| ATOM | 2073 | CE2 | TYR | A | 293 | 35.547 | 21.601 | 38.554 | 1.00 11.43 A |
| ATOM | 2074 | CZ | TYR | A | 293 | 36.839 | 21.488 | 39.052 | 1.00 8.40 A |
| ATOM | 2075 | OH | TYR | A | 293 | 37.488 | 22.625 | 39.496 | 1.00 8.49 A |
| ATOM | 2076 | C | TYR | A | 293 | 33.183 | 17.645 | 39.252 | 1.00 9.71 A |
| ATOM | 2077 | O | TYR | A | 293 | 32.142 | 17.834 | 38.657 | 1.00 12.02 A |
| ATOM | 2078 | N | PRO | A | 294 | 33.347 | 18.021 | 40.531 | 1.00 12.25 A |
| ATOM | 2079 | CD | PRO | A | 294 | 34.575 | 17.923 | 41.350 | 1.00 12.44 A |
| ATOM | 2080 | CA | PRO | A | 294 | 32.229 | 18.559 | 41.302 | 1.00 14.24 A |
| ATOM | 2081 | CB | PRO | A | 294 | 32.644 | 18.263 | 42.748 | 1.00 12.15 A |
| ATOM | 2082 | CG | PRO | A | 294 | 34.132 | 18.499 | 42.712 | 1.00 15.49 A |
| ATOM | 2083 | C | PRO | A | 294 | 31.682 | 19.963 | 41.133 | 1.00 13.85 A |
| ATOM | 2084 | O | PRO | A | 294 | 30.511 | 20.171 | 41.429 | 1.00 11.37 A |
| ATOM | 2085 | N | ILE | A | 295 | 32.476 | 20.907 | 40.628 | 1.00 10.88 A |
| ATOM | 2086 | CA | ILE | A | 295 | 31.990 | 22.280 | 40.510 | 1.00 9.12 A |
| ATOM | 2087 | CB | ILE | A | 295 | 33.062 | 23.301 | 40.934 | 1.00 10.07 A |
| ATOM | 2088 | CG2 | ILE | A | 295 | 32.375 | 24.666 | 41.232 | 1.00 10.52 A |
| ATOM | 2089 | CG1 | ILE | A | 295 | 33.733 | 22.853 | 42.236 | 1.00 12.06 A |
| ATOM | 2090 | CD1 | ILE | A | 295 | 34.841 | 23.801 | 42.703 | 1.00 12.46 A |
| ATOM | 2091 | C | ILE | A | 295 | 31.564 | 22.574 | 39.087 | 1.00 12.87 A |
| ATOM | 2092 | O | ILE | A | 295 | 32.397 | 22.660 | 38.182 | 1.00 10.57 A |
| ATOM | 2093 | N | LEU | A | 296 | 30.257 | 22.743 | 38.902 | 1.00 10.82 A |
| ATOM | 2094 | CA | LEU | A | 296 | 29.703 | 22.951 | 37.570 | 1.00 8.61 A |
| ATOM | 2095 | CB | LEU | A | 296 | 29.370 | 21.578 | 36.949 | 1.00 9.63 A |
| ATOM | 2096 | CG | LEU | A | 296 | 28.032 | 20.884 | 37.276 | 1.00 7.75 A |
| ATOM | 2097 | CD1 | LEU | A | 296 | 27.971 | 19.517 | 36.572 | 1.00 11.60 A |
| ATOM | 2098 | CD2 | LEU | A | 296 | 27.852 | 20.690 | 38.784 | 1.00 10.20 A |
| ATOM | 2099 | C | LEU | A | 296 | 28.461 | 23.828 | 37.612 | 1.00 7.00 A |
| ATOM | 2100 | O | LEU | A | 296 | 27.945 | 24.137 | 38.690 | 1.00 11.47 A |
| ATOM | 2101 | N | GLY | A | 297 | 27.988 | 24.236 | 36.436 | 1.00 8.98 A |
| ATOM | 2102 | CA | GLY | A | 297 | 26.812 | 25.093 | 36.353 | 1.00 8.75 A |
| ATOM | 2103 | C | GLY | A | 297 | 26.503 | 25.452 | 34.906 | 1.00 14.03 A |
| ATOM | 2104 | O | GLY | A | 297 | 27.128 | 24.917 | 33.979 | 1.00 9.23 A |
| ATOM | 2105 | N | PHE | A | 298 | 25.544 | 26.353 | 34.700 | 1.00 7.40 A |
| ATOM | 2106 | CA | PHE | A | 298 | 25.177 | 26.758 | 33.350 | 1.00 7.84 A |
| ATOM | 2107 | CB | PHE | A | 298 | 23.666 | 26.550 | 33.105 | 1.00 6.30 A |
| ATOM | 2108 | CG | PHE | A | 298 | 23.249 | 25.102 | 32.984 | 1.00 10.10 A |
| ATOM | 2109 | CD1 | PHE | A | 298 | 22.775 | 24.398 | 34.094 | 1.00 9.62 A |
| ATOM | 2110 | CD2 | PHE | A | 298 | 23.356 | 24.444 | 31.763 | 1.00 8.37 A |
| ATOM | 2111 | CE1 | PHE | A | 298 | 22.414 | 23.038 | 33.988 | 1.00 13.84 A |
| ATOM | 2112 | CE2 | PHE | A | 298 | 23.005 | 23.087 | 31.630 | 1.00 7.19 A |
| ATOM | 2113 | CZ | PHE | A | 298 | 22.533 | 22.379 | 32.747 | 1.00 12.00 A |
| ATOM | 2114 | C | PHE | A | 298 | 25.469 | 28.235 | 33.145 | 1.00 10.22 A |
| ATOM | 2115 | O | PHE | A | 298 | 25.431 | 29.007 | 34.114 | 1.00 9.27 A |
| ATOM | 2116 | N | THR | A | 299 | 25.811 | 28.615 | 31.910 | 1.00 7.04 A |
| ATOM | 2117 | CA | THR | A | 299 | 25.961 | 30.029 | 31.594 | 1.00 8.99 A |
| ATOM | 2118 | CB | THR | A | 299 | 27.319 | 30.414 | 30.975 | 1.00 12.65 A |
| ATOM | 2119 | OG1 | THR | A | 299 | 27.293 | 31.818 | 30.682 | 1.00 10.67 A |
| ATOM | 2120 | CG2 | THR | A | 299 | 27.616 | 29.617 | 29.740 | 1.00 12.18 A |
| ATOM | 2121 | C | THR | A | 299 | 24.798 | 30.220 | 30.616 | 1.00 8.12 A |
| ATOM | 2122 | O | THR | A | 299 | 24.482 | 29.325 | 29.810 | 1.00 9.48 A |
| ATOM | 2123 | N | ASP | A | 300 | 24.173 | 31.392 | 30.677 | 1.00 8.49 A |

FIGURE 5 (continued)

| | | | | | | | | | | |
|---|---|---|---|---|---|---|---|---|---|---|
|ATOM|2124|CA|ASP|A|300|22.930|31.636|29.950|1.00 10.66|A|
|ATOM|2125|CB|ASP|A|300|21.849|31.816|31.023|1.00  8.23|A|
|ATOM|2126|CG|ASP|A|300|22.055|30.877|32.193|1.00 14.11|A|
|ATOM|2127|OD1|ASP|A|300|22.141|29.660|31.928|1.00  8.23|A|
|ATOM|2128|OD2|ASP|A|300|22.149|31.341|33.373|1.00 15.65|A|
|ATOM|2129|C|ASP|A|300|22.828|32.790|28.975|1.00 10.65|A|
|ATOM|2130|O|ASP|A|300|23.690|33.669|28.931|1.00  8.49|A|
|ATOM|2131|N|LEU|A|301|21.740|32.765|28.202|1.00  8.77|A|
|ATOM|2132|CA|LEU|A|301|21.407|33.819|27.246|1.00 10.49|A|
|ATOM|2133|CB|LEU|A|301|21.121|33.226|25.850|1.00 10.57|A|
|ATOM|2134|CG|LEU|A|301|22.189|32.371|25.157|1.00 17.61|A|
|ATOM|2135|CD1|LEU|A|301|21.699|31.951|23.775|1.00 16.46|A|
|ATOM|2136|CD2|LEU|A|301|23.456|33.151|25.057|1.00 12.96|A|
|ATOM|2137|C|LEU|A|301|20.128|34.533|27.689|1.00  7.85|A|
|ATOM|2138|O|LEU|A|301|19.179|33.889|28.127|1.00  7.63|A|
|ATOM|2139|N|ILE|A|302|20.101|35.855|27.564|1.00  8.91|A|
|ATOM|2140|CA|ILE|A|302|18.897|36.614|27.879|1.00  7.82|A|
|ATOM|2141|CB|ILE|A|302|19.146|37.648|29.000|1.00 10.36|A|
|ATOM|2142|CG2|ILE|A|302|17.848|38.429|29.261|1.00 12.51|A|
|ATOM|2143|CG1|ILE|A|302|19.588|36.918|30.287|1.00  8.81|A|
|ATOM|2144|CD1|ILE|A|302|20.089|37.867|31.411|1.00  7.82|A|
|ATOM|2145|C|ILE|A|302|18.517|37.368|26.602|1.00  9.48|A|
|ATOM|2146|O|ILE|A|302|19.320|38.158|26.096|1.00  8.44|A|
|ATOM|2147|N|PHE|A|303|17.311|37.120|26.081|1.00  8.80|A|
|ATOM|2148|CA|PHE|A|303|16.843|37.786|24.854|1.00  8.37|A|
|ATOM|2149|CB|PHE|A|303|16.751|36.821|23.651|1.00  7.07|A|
|ATOM|2150|CG|PHE|A|303|18.054|36.583|22.944|1.00  8.30|A|
|ATOM|2151|CD1|PHE|A|303|19.027|35.770|23.500|1.00  8.48|A|
|ATOM|2152|CD2|PHE|A|303|18.316|37.205|21.725|1.00  7.08|A|
|ATOM|2153|CE1|PHE|A|303|20.265|35.582|22.851|1.00  7.30|A|
|ATOM|2154|CE2|PHE|A|303|19.559|37.023|21.065|1.00  9.28|A|
|ATOM|2155|CZ|PHE|A|303|20.528|36.210|21.637|1.00 11.64|A|
|ATOM|2156|C|PHE|A|303|15.437|38.305|25.032|1.00  9.03|A|
|ATOM|2157|O|PHE|A|303|14.797|38.052|26.031|1.00  9.30|A|
|ATOM|2158|N|SER|A|304|14.947|39.002|24.014|1.00  7.56|A|
|ATOM|2159|CA|SER|A|304|13.566|39.465|24.044|1.00  9.72|A|
|ATOM|2160|CB|SER|A|304|13.470|40.870|23.444|1.00 11.08|A|
|ATOM|2161|OG|SER|A|304|12.117|41.291|23.498|1.00 10.08|A|
|ATOM|2162|C|SER|A|304|12.707|38.530|23.170|1.00  6.80|A|
|ATOM|2163|O|SER|A|304|13.198|38.018|22.162|1.00 10.90|A|
|ATOM|2164|N|GLU|A|305|11.451|38.293|23.534|1.00  8.14|A|
|ATOM|2165|CA|GLU|A|305|10.605|37.482|22.655|1.00 11.11|A|
|ATOM|2166|CB|GLU|A|305| 9.268|37.125|23.316|1.00 10.66|A|
|ATOM|2167|CG|GLU|A|305| 8.447|36.161|22.439|1.00 11.71|A|
|ATOM|2168|CD|GLU|A|305| 7.073|35.820|22.985|1.00 12.77|A|
|ATOM|2169|OE1|GLU|A|305| 6.767|36.154|24.147|1.00 14.12|A|
|ATOM|2170|OE2|GLU|A|305| 6.288|35.192|22.228|1.00 16.70|A|
|ATOM|2171|C|GLU|A|305|10.305|38.329|21.399|1.00 15.34|A|
|ATOM|2172|O|GLU|A|305|10.154|37.800|20.283|1.00 10.74|A|
|ATOM|2173|N|CYS|A|306|10.239|39.649|21.574|1.00 11.86|A|
|ATOM|2174|CA|CYS|A|306| 9.889|40.534|20.450|1.00 12.96|A|
|ATOM|2175|C|CYS|A|306|10.859|41.666|20.140|1.00 14.14|A|
|ATOM|2176|O|CYS|A|306|11.434|42.270|21.046|1.00 11.98|A|
|ATOM|2177|CB|CYS|A|306| 8.531|41.185|20.726|1.00 11.40|A|
|ATOM|2178|SG|CYS|A|306| 7.188|40.111|21.313|1.00 15.63|A|
|ATOM|2179|N|TYR|A|307|11.017|41.956|18.854|1.00 12.82|A|
|ATOM|2180|CA|TYR|A|307|11.872|43.060|18.397|1.00 10.85|A|
|ATOM|2181|CB|TYR|A|307|13.143|42.533|17.712|1.00  8.88|A|
|ATOM|2182|CG|TYR|A|307|14.066|41.850|18.703|1.00 13.96|A|
|ATOM|2183|CD1|TYR|A|307|13.902|40.499|19.020|1.00 13.44|A|
|ATOM|2184|CE1|TYR|A|307|14.683|39.882|20.020|1.00 13.43|A|
|ATOM|2185|CD2|TYR|A|307|15.035|42.579|19.401|1.00 11.32|A|
|ATOM|2186|CE2|TYR|A|307|15.821|41.972|20.410|1.00 11.99|A|
|ATOM|2187|CZ|TYR|A|307|15.637|40.625|20.712|1.00 12.10|A|
|ATOM|2188|OH|TYR|A|307|16.379|40.019|21.724|1.00 12.32|A|
|ATOM|2189|C|TYR|A|307|11.056|43.908|17.424|1.00 13.04|A|
|ATOM|2190|O|TYR|A|307|10.318|43.370|16.588|1.00 11.71|A|
|ATOM|2191|N|ALA|A|308|11.161|45.229|17.546|1.00 13.47|A|
|ATOM|2192|CA|ALA|A|308|10.420|46.123|16.660|1.00 19.16|A|
|ATOM|2193|CB|ALA|A|308|10.623|47.583|17.116|1.00 19.39|A|
|ATOM|2194|C|ALA|A|308|10.827|45.960|15.176|1.00 16.58|A|
|ATOM|2195|O|ALA|A|308| 9.990|46.011|14.290|1.00 15.94|A|
|ATOM|2196|N|ASN|A|309|12.109|45.752|14.919|1.00 16.56|A|
|ATOM|2197|CA|ASN|A|309|12.621|45.602|13.565|1.00 15.71|A|
|ATOM|2198|CB|ASN|A|309|14.084|46.052|13.558|1.00 11.74|A|
|ATOM|2199|CG|ASN|A|309|14.704|46.002|12.183|1.00 20.62|A|

FIGURE 5 (continued)

```
ATOM   2200  OD1 ASN A 309      15.130  44.946  11.713  1.00 17.26           A
ATOM   2201  ND2 ASN A 309      14.741  47.153  11.517  1.00 13.84           A
ATOM   2202  C   ASN A 309      12.493  44.142  13.066  1.00 16.39           A
ATOM   2203  O   ASN A 309      13.031  43.221  13.678  1.00 11.54           A
ATOM   2204  N   ALA A 310      11.806  43.942  11.941  1.00 12.69           A
ATOM   2205  CA  ALA A 310      11.583  42.584  11.430  1.00 16.06           A
ATOM   2206  CB  ALA A 310      10.564  42.618  10.281  1.00 16.44           A
ATOM   2207  C   ALA A 310      12.836  41.828  10.997  1.00 14.76           A
ATOM   2208  O   ALA A 310      12.907  40.599  11.128  1.00 15.90           A
ATOM   2209  N   THR A 311      13.827  42.546  10.485  1.00 13.61           A
ATOM   2210  CA  THR A 311      15.074  41.922  10.069  1.00 14.28           A
ATOM   2211  CB  THR A 311      15.949  42.927   9.314  1.00 15.47           A
ATOM   2212  OG1 THR A 311      15.284  43.307   8.097  1.00 18.10           A
ATOM   2213  CG2 THR A 311      17.291  42.322   8.977  1.00 16.40           A
ATOM   2214  C   THR A 311      15.813  41.407  11.324  1.00 15.00           A
ATOM   2215  O   THR A 311      16.371  40.313  11.318  1.00 12.29           A
ATOM   2216  N   GLN A 312      15.798  42.180  12.409  1.00 13.08           A
ATOM   2217  CA  GLN A 312      16.477  41.717  13.623  1.00 12.35           A
ATOM   2218  CB  GLN A 312      16.545  42.827  14.682  1.00 10.08           A
ATOM   2219  CG  GLN A 312      17.501  43.960  14.273  1.00  7.89           A
ATOM   2220  CD  GLN A 312      17.696  44.997  15.377  1.00 13.93           A
ATOM   2221  OE1 GLN A 312      16.897  45.087  16.311  1.00 14.28           A
ATOM   2222  NE2 GLN A 312      18.743  45.799  15.255  1.00 16.18           A
ATOM   2223  C   GLN A 312      15.768  40.486  14.191  1.00 11.19           A
ATOM   2224  O   GLN A 312      16.418  39.537  14.639  1.00 14.09           A
ATOM   2225  N   THR A 313      14.439  40.507  14.189  1.00  9.72           A
ATOM   2226  CA  THR A 313      13.670  39.363  14.685  1.00  8.88           A
ATOM   2227  CB  THR A 313      12.149  39.541  14.449  1.00 13.95           A
ATOM   2228  OG1 THR A 313      11.660  40.660  15.197  1.00 14.46           A
ATOM   2229  CG2 THR A 313      11.398  38.288  14.882  1.00 12.76           A
ATOM   2230  C   THR A 313      14.108  38.096  13.935  1.00 10.80           A
ATOM   2231  O   THR A 313      14.318  37.042  14.538  1.00 11.41           A
ATOM   2232  N   GLY A 314      14.218  38.204  12.615  1.00 11.55           A
ATOM   2233  CA  GLY A 314      14.628  37.067  11.810  1.00 12.96           A
ATOM   2234  C   GLY A 314      16.060  36.638  12.090  1.00 10.31           A
ATOM   2235  O   GLY A 314      16.370  35.439  12.111  1.00 11.80           A
ATOM   2236  N   GLN A 315      16.952  37.603  12.291  1.00 10.00           A
ATOM   2237  CA  GLN A 315      18.360  37.280  12.586  1.00 10.98           A
ATOM   2238  CB  GLN A 315      19.219  38.542  12.512  1.00 12.34           A
ATOM   2239  CG  GLN A 315      19.286  39.069  11.071  1.00 13.86           A
ATOM   2240  CD  GLN A 315      20.014  40.385  10.958  1.00 16.05           A
ATOM   2241  OE1 GLN A 315      19.868  41.254  11.818  1.00 15.65           A
ATOM   2242  NE2 GLN A 315      20.787  40.552   9.880  1.00 15.34           A
ATOM   2243  C   GLN A 315      18.518  36.613  13.952  1.00 11.33           A
ATOM   2244  O   GLN A 315      19.385  35.743  14.136  1.00 12.86           A
ATOM   2245  N   VAL A 316      17.677  37.006  14.909  1.00 11.99           A
ATOM   2246  CA  VAL A 316      17.719  36.389  16.238  1.00 11.29           A
ATOM   2247  CB  VAL A 316      16.803  37.131  17.251  1.00 12.97           A
ATOM   2248  CG1 VAL A 316      16.658  36.292  18.541  1.00 12.95           A
ATOM   2249  CG2 VAL A 316      17.401  38.493  17.602  1.00 11.75           A
ATOM   2250  C   VAL A 316      17.232  34.929  16.092  1.00 13.11           A
ATOM   2251  O   VAL A 316      17.813  33.996  16.667  1.00 12.64           A
ATOM   2252  N   ARG A 317      16.164  34.723  15.327  1.00  9.04           A
ATOM   2253  CA  ARG A 317      15.672  33.364  15.115  1.00 12.87           A
ATOM   2254  CB  ARG A 317      14.348  33.372  14.303  1.00 14.06           A
ATOM   2255  CG  ARG A 317      13.148 -33.951  15.076  1.00 13.07           A
ATOM   2256  CD  ARG A 317      11.823  33.964  14.243  1.00 14.93           A
ATOM   2257  NE  ARG A 317      11.520  32.611  13.765  1.00 14.57           A
ATOM   2258  CZ  ARG A 317      10.894  31.677  14.480  1.00 10.03           A
ATOM   2259  NH1 ARG A 317      10.470  31.934  15.704  1.00  9.62           A
ATOM   2260  NH2 ARG A 317      10.730  30.461  13.983  1.00 13.56           A
ATOM   2261  C   ARG A 317      16.730  32.491  14.434  1.00 12.01           A
ATOM   2262  O   ARG A 317      16.879  31.320  14.783  1.00 12.09           A
ATOM   2263  N   ASN A 318      17.462  33.033  13.464  1.00 11.68           A
ATOM   2264  CA  ASN A 318      18.503  32.246  12.796  1.00 13.18           A
ATOM   2265  CB  ASN A 318      19.123  33.028  11.629  1.00 11.52           A
ATOM   2266  CG  ASN A 318      18.145  33.249  10.500  1.00 15.15           A
ATOM   2267  OD1 ASN A 318      17.140  32.557  10.402  1.00 13.70           A
ATOM   2268  ND2 ASN A 318      18.438  34.211   9.638  1.00 17.31           A
ATOM   2269  C   ASN A 318      19.613  31.841  13.771  1.00 12.19           A
ATOM   2270  O   ASN A 318      20.207  30.753  13.658  1.00  9.01           A
ATOM   2271  N   PHE A 319      19.904  32.715  14.733  1.00 10.68           A
ATOM   2272  CA  PHE A 319      20.936  32.376  15.707  1.00  9.90           A
ATOM   2273  CB  PHE A 319      21.274  33.577  16.584  1.00  7.66           A
ATOM   2274  CG  PHE A 319      22.105  33.212  17.794  1.00 10.09           A
ATOM   2275  CD1 PHE A 319      23.351  32.644  17.631  1.00  6.01           A
```

FIGURE 5 (continued)

| | | | | | | | | | | |
|---|---|---|---|---|---|---|---|---|---|---|
| ATOM | 2276 | CD2 | PHE | A | 319 | 21.593 | 33.356 | 19.087 | 1.00 | 10.54 | A |
| ATOM | 2277 | CE1 | PHE | A | 319 | 24.102 | 32.203 | 18.738 | 1.00 | 12.72 | A |
| ATOM | 2278 | CE2 | PHE | A | 319 | 22.333 | 32.919 | 20.212 | 1.00 | 15.07 | A |
| ATOM | 2279 | CZ | PHE | A | 319 | 23.589 | 32.338 | 20.027 | 1.00 | 12.59 | A |
| ATOM | 2280 | C | PHE | A | 319 | 20.449 | 31.222 | 16.587 | 1.00 | 10.27 | A |
| ATOM | 2281 | O | PHE | A | 319 | 21.203 | 30.282 | 16.868 | 1.00 | 12.47 | A |
| ATOM | 2282 | N | PHE | A | 320 | 19.188 | 31.275 | 17.013 | 1.00 | 10.21 | A |
| ATOM | 2283 | CA | PHE | A | 320 | 18.649 | 30.213 | 17.860 | 1.00 | 10.79 | A |
| ATOM | 2284 | CB | PHE | A | 320 | 17.247 | 30.581 | 18.363 | 1.00 | 9.11 | A |
| ATOM | 2285 | CG | PHE | A | 320 | 17.246 | 31.285 | 19.698 | 1.00 | 7.96 | A |
| ATOM | 2286 | CD1 | PHE | A | 320 | 16.762 | 30.642 | 20.833 | 1.00 | 9.52 | A |
| ATOM | 2287 | CD2 | PHE | A | 320 | 17.723 | 32.583 | 19.822 | 1.00 | 12.60 | A |
| ATOM | 2288 | CE1 | PHE | A | 320 | 16.750 | 31.282 | 22.082 | 1.00 | 6.69 | A |
| ATOM | 2289 | CE2 | PHE | A | 320 | 17.712 | 33.244 | 21.075 | 1.00 | 9.45 | A |
| ATOM | 2290 | CZ | PHE | A | 320 | 17.220 | 32.579 | 22.209 | 1.00 | 8.89 | A |
| ATOM | 2291 | C | PHE | A | 320 | 18.598 | 28.912 | 17.089 | 1.00 | 7.76 | A |
| ATOM | 2292 | O | PHE | A | 320 | 18.856 | 27.838 | 17.634 | 1.00 | 9.90 | A |
| ATOM | 2293 | N | THR | A | 321 | 18.274 | 29.013 | 15.801 | 1.00 | 8.04 | A |
| ATOM | 2294 | CA | THR | A | 321 | 18.199 | 27.829 | 14.950 | 1.00 | 6.79 | A |
| ATOM | 2295 | CB | THR | A | 321 | 17.687 | 28.224 | 13.551 | 1.00 | 7.01 | A |
| ATOM | 2296 | OG1 | THR | A | 321 | 16.334 | 28.695 | 13.691 | 1.00 | 11.25 | A |
| ATOM | 2297 | CG2 | THR | A | 321 | 17.731 | 27.032 | 12.573 | 1.00 | 9.32 | A |
| ATOM | 2298 | C | THR | A | 321 | 19.535 | 27.128 | 14.872 | 1.00 | 11.09 | A |
| ATOM | 2299 | O | THR | A | 321 | 19.594 | 25.896 | 14.823 | 1.00 | 10.46 | A |
| ATOM | 2300 | N | LYS | A | 322 | 20.617 | 27.904 | 14.873 | 1.00 | 8.41 | A |
| ATOM | 2301 | CA | LYS | A | 322 | 21.950 | 27.319 | 14.849 | 1.00 | 8.00 | A |
| ATOM | 2302 | CB | LYS | A | 322 | 22.970 | 28.329 | 14.299 | 1.00 | 6.38 | A |
| ATOM | 2303 | CG | LYS | A | 322 | 24.410 | 27.805 | 14.359 | 1.00 | 10.15 | A |
| ATOM | 2304 | CD | LYS | A | 322 | 25.396 | 28.712 | 13.615 | 1.00 | 8.08 | A |
| ATOM | 2305 | CE | LYS | A | 322 | 26.665 | 27.922 | 13.317 | 1.00 | 11.78 | A |
| ATOM | 2306 | NZ | LYS | A | 322 | 27.577 | 28.702 | 12.437 | 1.00 | 18.79 | A |
| ATOM | 2307 | C | LYS | A | 322 | 22.415 | 26.857 | 16.242 | 1.00 | 9.52 | A |
| ATOM | 2308 | O | LYS | A | 322 | 22.864 | 25.711 | 16.425 | 1.00 | 9.02 | A |
| ATOM | 2309 | N | HIS | A | 323 | 22.289 | 27.735 | 17.231 | 1.00 | 10.06 | A |
| ATOM | 2310 | CA | HIS | A | 323 | 22.793 | 27.420 | 18.569 | 1.00 | 9.00 | A |
| ATOM | 2311 | CB | HIS | A | 323 | 22.710 | 28.677 | 19.469 | 1.00 | 7.78 | A |
| ATOM | 2312 | CG | HIS | A | 323 | 23.655 | 28.657 | 20.637 | 1.00 | 9.56 | A |
| ATOM | 2313 | CD2 | HIS | A | 323 | 23.426 | 28.762 | 21.970 | 1.00 | 9.53 | A |
| ATOM | 2314 | ND1 | HIS | A | 323 | 25.028 | 28.560 | 20.494 | 1.00 | 7.88 | A |
| ATOM | 2315 | CE1 | HIS | A | 323 | 25.602 | 28.615 | 21.683 | 1.00 | 9.47 | A |
| ATOM | 2316 | NE2 | HIS | A | 323 | 24.653 | 28.736 | 22.598 | 1.00 | 12.97 | A |
| ATOM | 2317 | C | HIS | A | 323 | 22.082 | 26.230 | 19.222 | 1.00 | 9.52 | A |
| ATOM | 2318 | O | HIS | A | 323 | 22.687 | 25.507 | 20.019 | 1.00 | 8.65 | A |
| ATOM | 2319 | N | TYR | A | 324 | 20.808 | 26.034 | 18.877 | 1.00 | 9.61 | A |
| ATOM | 2320 | CA | TYR | A | 324 | 20.024 | 24.911 | 19.427 | 1.00 | 10.38 | A |
| ATOM | 2321 | CB | TYR | A | 324 | 18.767 | 25.434 | 20.149 | 1.00 | 6.95 | A |
| ATOM | 2322 | CG | TYR | A | 324 | 19.137 | 26.376 | 21.277 | 1.00 | 7.33 | A |
| ATOM | 2323 | CD1 | TYR | A | 324 | 19.195 | 27.752 | 21.072 | 1.00 | 5.99 | A |
| ATOM | 2324 | CE1 | TYR | A | 324 | 19.656 | 28.618 | 22.097 | 1.00 | 8.99 | A |
| ATOM | 2325 | CD2 | TYR | A | 324 | 19.533 | 25.882 | 22.513 | 1.00 | 7.61 | A |
| ATOM | 2326 | CE2 | TYR | A | 324 | 19.994 | 26.731 | 23.525 | 1.00 | 5.98 | A |
| ATOM | 2327 | CZ | TYR | A | 324 | 20.052 | 28.094 | 23.303 | 1.00 | 7.54 | A |
| ATOM | 2328 | OH | TYR | A | 324 | 20.547 | 28.926 | 24.294 | 1.00 | 7.56 | A |
| ATOM | 2329 | C | TYR | A | 324 | 19.627 | 23.893 | 18.338 | 1.00 | 7.02 | A |
| ATOM | 2330 | O | TYR | A | 324 | 18.677 | 23.118 | 18.498 | 1.00 | 10.94 | A |
| ATOM | 2331 | N | GLY | A | 325 | 20.387 | 23.868 | 17.254 | 1.00 | 7.94 | A |
| ATOM | 2332 | CA | GLY | A | 325 | 20.064 | 22.938 | 16.181 | 1.00 | 7.51 | A |
| ATOM | 2333 | C | GLY | A | 325 | 20.514 | 21.493 | 16.386 | 1.00 | 12.01 | A |
| ATOM | 2334 | O | GLY | A | 325 | 21.492 | 21.227 | 17.097 | 1.00 | 10.59 | A |
| ATOM | 2335 | N | THR | A | 326 | 19.788 | 20.564 | 15.752 | 1.00 | 8.75 | A |
| ATOM | 2336 | CA | THR | A | 326 | 20.113 | 19.132 | 15.790 | 1.00 | 10.25 | A |
| ATOM | 2337 | CB | THR | A | 326 | 19.005 | 18.311 | 15.135 | 1.00 | 9.46 | A |
| ATOM | 2338 | OG1 | THR | A | 326 | 17.759 | 18.707 | 15.708 | 1.00 | 10.73 | A |
| ATOM | 2339 | CG2 | THR | A | 326 | 19.212 | 16.788 | 15.369 | 1.00 | 7.67 | A |
| ATOM | 2340 | C | THR | A | 326 | 21.432 | 18.937 | 15.038 | 1.00 | 9.78 | A |
| ATOM | 2341 | O | THR | A | 326 | 22.278 | 18.131 | 15.452 | 1.00 | 10.90 | A |
| ATOM | 2342 | N | SER | A | 327 | 21.614 | 19.688 | 13.953 | 1.00 | 12.37 | A |
| ATOM | 2343 | CA | SER | A | 327 | 22.858 | 19.666 | 13.176 | 1.00 | 11.58 | A |
| ATOM | 2344 | CB | SER | A | 327 | 22.743 | 18.752 | 11.935 | 1.00 | 14.65 | A |
| ATOM | 2345 | OG | SER | A | 327 | 21.725 | 19.192 | 11.051 | 1.00 | 10.13 | A |
| ATOM | 2346 | C | SER | A | 327 | 23.158 | 21.118 | 12.764 | 1.00 | 10.87 | A |
| ATOM | 2347 | O | SER | A | 327 | 22.419 | 22.031 | 13.149 | 1.00 | 9.05 | A |
| ATOM | 2348 | N | ALA | A | 328 | 24.228 | 21.331 | 12.000 | 1.00 | 11.22 | A |
| ATOM | 2349 | CA | ALA | A | 328 | 24.637 | 22.690 | 11.567 | 1.00 | 10.30 | A |
| ATOM | 2350 | CB | ALA | A | 328 | 23.682 | 23.234 | 10.518 | 1.00 | 12.01 | A |
| ATOM | 2351 | C | ALA | A | 328 | 24.602 | 23.592 | 12.790 | 1.00 | 11.88 | A |

FIGURE 5 (continued)

```
ATOM   2352  O   ALA A 328      24.046  24.674  12.742  1.00 13.69           A
ATOM   2353  N   ASN A 329      25.197  23.140  13.887  1.00 11.26           A
ATOM   2354  CA  ASN A 329      25.150  23.910  15.123  1.00 10.51           A
ATOM   2355  CB  ASN A 329      24.422  23.083  16.205  1.00  8.81           A
ATOM   2356  CG  ASN A 329      25.132  21.771  16.536  1.00  9.32           A
ATOM   2357  OD1 ASN A 329      26.352  21.717  16.573  1.00 11.49           A
ATOM   2358  ND2 ASN A 329      24.360  20.714  16.792  1.00 10.75           A
ATOM   2359  C   ASN A 329      26.526  24.402  15.604  1.00 12.21           A
ATOM   2360  O   ASN A 329      27.515  24.381  14.849  1.00  9.35           A
ATOM   2361  N   ASP A 330      26.586  24.863  16.851  1.00 10.38           A
ATOM   2362  CA  ASP A 330      27.837  25.386  17.412  1.00  9.41           A
ATOM   2363  CB  ASP A 330      27.575  26.677  18.208  1.00 10.91           A
ATOM   2364  CG  ASP A 330      27.239  27.852  17.331  1.00 13.71           A
ATOM   2365  OD1 ASP A 330      26.333  28.653  17.720  1.00 14.93           A
ATOM   2366  OD2 ASP A 330      27.880  27.981  16.261  1.00 10.16           A
ATOM   2367  C   ASP A 330      28.536  24.416  18.346  1.00 10.31           A
ATOM   2368  O   ASP A 330      29.484  24.809  19.029  1.00  8.29           A
ATOM   2369  N   ASN A 331      28.111  23.153  18.363  1.00  8.79           A
ATOM   2370  CA  ASN A 331      28.698  22.217  19.311  1.00 10.91           A
ATOM   2371  CB  ASN A 331      27.942  20.869  19.267  1.00 11.40           A
ATOM   2372  CG  ASN A 331      26.579  20.924  19.989  1.00 15.36           A
ATOM   2373  OD1 ASN A 331      25.926  19.893  20.194  1.00 12.09           A
ATOM   2374  ND2 ASN A 331      26.156  22.115  20.372  1.00  9.71           A
ATOM   2375  C   ASN A 331      30.220  22.012  19.218  1.00 12.28           A
ATOM   2376  O   ASN A 331      30.877  21.866  20.255  1.00 12.57           A
ATOM   2377  N   ALA A 332      30.795  22.001  18.012  1.00 10.00           A
ATOM   2378  CA  ALA A 332      32.252  21.842  17.903  1.00 12.41           A
ATOM   2379  CB  ALA A 332      32.677  21.733  16.445  1.00 12.06           A
ATOM   2380  C   ALA A 332      32.964  23.028  18.548  1.00  8.53           A
ATOM   2381  O   ALA A 332      33.973  22.872  19.247  1.00 11.75           A
ATOM   2382  N   ALA A 333      32.447  24.216  18.297  1.00  9.64           A
ATOM   2383  CA  ALA A 333      33.057  25.422  18.858  1.00 10.83           A
ATOM   2384  CB  ALA A 333      32.424  26.655  18.223  1.00  9.42           A
ATOM   2385  C   ALA A 333      32.910  25.473  20.379  1.00 10.44           A
ATOM   2386  O   ALA A 333      33.787  25.982  21.096  1.00  9.81           A
ATOM   2387  N   ILE A 334      31.787  24.963  20.869  1.00  9.49           A
ATOM   2388  CA  ILE A 334      31.536  24.919  22.305  1.00 10.34           A
ATOM   2389  CB  ILE A 334      30.099  24.404  22.567  1.00  7.35           A
ATOM   2390  CG2 ILE A 334      29.902  24.030  24.056  1.00  4.48           A
ATOM   2391  CG1 ILE A 334      29.093  25.467  22.091  1.00  8.68           A
ATOM   2392  CD1 ILE A 334      27.628  24.953  22.043  1.00  8.29           A
ATOM   2393  C   ILE A 334      32.593  24.003  22.946  1.00  9.03           A
ATOM   2394  O   ILE A 334      33.239  24.352  23.954  1.00  6.82           A
ATOM   2395  N   GLN A 335      32.805  22.847  22.333  1.00  6.99           A
ATOM   2396  CA  GLN A 335      33.800  21.903  22.831  1.00  8.99           A
ATOM   2397  CB  GLN A 335      33.695  20.589  22.053  1.00 11.58           A
ATOM   2398  CG  GLN A 335      32.448  19.784  22.446  1.00 21.44           A
ATOM   2399  CD  GLN A 335      32.279  18.518  21.598  1.00 30.71           A
ATOM   2400  OE1 GLN A 335      33.212  18.083  20.927  1.00 34.68           A
ATOM   2401  NE2 GLN A 335      31.089  17.926  21.638  1.00 37.34           A
ATOM   2402  C   GLN A 335      35.223  22.438  22.774  1.00 12.27           A
ATOM   2403  O   GLN A 335      36.014  22.219  23.704  1.00 10.25           A
ATOM   2404  N   ALA A 336      35.547  23.143  21.690  1.00 10.75           A
ATOM   2405  CA  ALA A 336      36.868  23.726  21.514  1.00 12.71           A
ATOM   2406  CB  ALA A 336      36.989  24.375  20.091  1.00  9.35           A
ATOM   2407  C   ALA A 336      37.109  24.794  22.591  1.00 11.11           A
ATOM   2408  O   ALA A 336      38.247  25.134  22.894  1.00 11.00           A
ATOM   2409  N   ASN A 337      36.025  25.310  23.164  1.00  8.06           A
ATOM   2410  CA  ASN A 337      36.125  26.342  24.185  1.00  9.10           A
ATOM   2411  CB  ASN A 337      35.098  27.440  23.887  1.00  8.86           A
ATOM   2412  CG  ASN A 337      35.621  28.457  22.874  1.00 12.21           A
ATOM   2413  OD1 ASN A 337      36.333  29.417  23.230  1.00 12.38           A
ATOM   2414  ND2 ASN A 337      35.301  28.237  21.605  1.00 13.95           A
ATOM   2415  C   ASN A 337      35.979  25.816  25.622  1.00  9.52           A
ATOM   2416  O   ASN A 337      35.647  26.565  26.534  1.00  7.92           A
ATOM   2417  N   ALA A 338      36.242  24.523  25.806  1.00  8.29           A
ATOM   2418  CA  ALA A 338      36.194  23.863  27.117  1.00  8.92           A
ATOM   2419  CB  ALA A 338      37.188  24.526  28.069  1.00 10.50           A
ATOM   2420  C   ALA A 338      34.825  23.786  27.785  1.00  8.55           A
ATOM   2421  O   ALA A 338      34.732  23.671  29.000  1.00 10.41           A
ATOM   2422  N   PHE A 339      33.765  23.844  27.002  1.00  7.84           A
ATOM   2423  CA  PHE A 339      32.410  23.781  27.553  1.00  8.93           A
ATOM   2424  CB  PHE A 339      31.624  25.034  27.120  1.00  7.76           A
ATOM   2425  CG  PHE A 339      32.258  26.345  27.576  1.00 10.23           A
ATOM   2426  CD1 PHE A 339      32.566  26.557  28.923  1.00 11.28           A
ATOM   2427  CD2 PHE A 339      32.497  27.369  26.664  1.00  9.75           A
```

FIGURE 5 (continued)

```
ATOM   2428  CE1 PHE A 339      33.108  27.795  29.360  1.00 11.58           A
ATOM   2429  CE2 PHE A 339      33.033  28.613  27.077  1.00  8.17           A
ATOM   2430  CZ  PHE A 339      33.339  28.820  28.437  1.00  8.56           A
ATOM   2431  C   PHE A 339      31.647  22.514  27.151  1.00  9.93           A
ATOM   2432  O   PHE A 339      32.084  21.742  26.279  1.00  9.23           A
ATOM   2433  N   VAL A 340      30.508  22.304  27.797  1.00  8.19           A
ATOM   2434  CA  VAL A 340      29.669  21.139  27.531  1.00 10.26           A
ATOM   2435  CB  VAL A 340      29.169  20.468  28.851  1.00 11.72           A
ATOM   2436  CG1 VAL A 340      28.219  19.269  28.538  1.00  8.46           A
ATOM   2437  CG2 VAL A 340      30.346  19.998  29.679  1.00  8.91           A
ATOM   2438  C   VAL A 340      28.439  21.577  26.742  1.00  6.33           A
ATOM   2439  O   VAL A 340      27.675  22.433  27.186  1.00  6.81           A
ATOM   2440  N   PRO A 341      28.255  21.021  25.547  1.00  6.85           A
ATOM   2441  CD  PRO A 341      29.193  20.162  24.797  1.00 10.26           A
ATOM   2442  CA  PRO A 341      27.082  21.373  24.736  1.00  9.67           A
ATOM   2443  CB  PRO A 341      27.275  20.537  23.468  1.00 11.39           A
ATOM   2444  CG  PRO A 341      28.752  20.386  23.363  1.00 14.97           A
ATOM   2445  C   PRO A 341      25.807  20.931  25.497  1.00 10.96           A
ATOM   2446  O   PRO A 341      25.851  20.024  26.342  1.00 10.96           A
ATOM   2447  N   LEU A 342      24.673  21.558  25.211  1.00  8.13           A
ATOM   2448  CA  LEU A 342      23.435  21.157  25.870  1.00 10.08           A
ATOM   2449  CB  LEU A 342      22.326  22.194  25.646  1.00 12.81           A
ATOM   2450  CG  LEU A 342      22.558  23.605  26.207  1.00 16.13           A
ATOM   2451  CD1 LEU A 342      21.280  24.428  26.007  1.00 10.84           A
ATOM   2452  CD2 LEU A 342      22.908  23.542  27.715  1.00 14.00           A
ATOM   2453  C   LEU A 342      22.981  19.821  25.288  1.00 11.91           A
ATOM   2454  O   LEU A 342      23.142  19.565  24.072  1.00 10.04           A
ATOM   2455  N   PRO A 343      22.437  18.937  26.147  1.00 10.12           A
ATOM   2456  CD  PRO A 343      22.407  19.074  27.618  1.00  8.23           A
ATOM   2457  CA  PRO A 343      21.947  17.622  25.721  1.00 11.60           A
ATOM   2458  CB  PRO A 343      21.407  17.006  27.021  1.00 11.29           A
ATOM   2459  CG  PRO A 343      22.287  17.643  28.083  1.00 12.10           A
ATOM   2460  C   PRO A 343      20.850  17.839  24.688  1.00 11.38           A
ATOM   2461  O   PRO A 343      20.229  18.896  24.648  1.00 10.75           A
ATOM   2462  N   SER A 344      20.590  16.836  23.861  1.00  9.55           A
ATOM   2463  CA  SER A 344      19.592  16.995  22.801  1.00  8.34           A
ATOM   2464  CB  SER A 344      19.547  15.741  21.940  1.00 15.39           A
ATOM   2465  OG  SER A 344      19.245  14.625  22.760  1.00 23.25           A
ATOM   2466  C   SER A 344      18.185  17.315  23.281  1.00  8.79           A
ATOM   2467  O   SER A 344      17.474  18.051  22.615  1.00 11.06           A
ATOM   2468  N   ASN A 345      17.751  16.744  24.410  1.00 11.97           A
ATOM   2469  CA  ASN A 345      16.403  17.061  24.874  1.00 13.51           A
ATOM   2470  CB  ASN A 345      15.962  16.128  26.015  1.00 11.25           A
ATOM   2471  CG  ASN A 345      16.896  16.145  27.206  1.00 19.63           A
ATOM   2472  OD1 ASN A 345      18.105  16.399  27.083  1.00 15.65           A
ATOM   2473  ND2 ASN A 345      16.343  15.822  28.379  1.00 15.03           A
ATOM   2474  C   ASN A 345      16.296  18.532  25.277  1.00 12.03           A
ATOM   2475  O   ASN A 345      15.236  19.131  25.167  1.00 11.72           A
ATOM   2476  N   TRP A 346      17.397  19.115  25.739  1.00 10.97           A
ATOM   2477  CA  TRP A 346      17.397  20.533  26.097  1.00  9.55           A
ATOM   2478  CB  TRP A 346      18.663  20.890  26.881  1.00  8.50           A
ATOM   2479  CG  TRP A 346      18.475  20.695  28.372  1.00  9.10           A
ATOM   2480  CD2 TRP A 346      17.927  21.660  29.285  1.00 10.08           A
ATOM   2481  CE2 TRP A 346      17.831  21.036  30.549  1.00 12.11           A
ATOM   2482  CE3 TRP A 346      17.502  22.994  29.149  1.00  9.60           A
ATOM   2483  CD1 TRP A 346      18.694  19.553  29.099  1.00  9.06           A
ATOM   2484  NE1 TRP A 346      18.304  19.752  30.411  1.00  9.93           A
ATOM   2485  CZ2 TRP A 346      17.323  21.705  31.682  1.00  9.30           A
ATOM   2486  CZ3 TRP A 346      17.004  23.662  30.261  1.00 10.14           A
ATOM   2487  CH2 TRP A 346      16.917  23.012  31.522  1.00 12.99           A
ATOM   2488  C   TRP A 346      17.298  21.390  24.824  1.00 10.69           A
ATOM   2489  O   TRP A 346      16.509  22.333  24.769  1.00 13.16           A
ATOM   2490  N   LYS A 347      18.087  21.074  23.804  1.00  9.34           A
ATOM   2491  CA  LYS A 347      17.984  21.852  22.557  1.00  8.27           A
ATOM   2492  CB  LYS A 347      18.902  21.287  21.466  1.00 12.86           A
ATOM   2493  CG  LYS A 347      20.416  21.357  21.748  1.00 11.51           A
ATOM   2494  CD  LYS A 347      21.221  21.071  20.440  1.00 14.73           A
ATOM   2495  CE  LYS A 347      22.733  21.317  20.590  1.00 14.12           A
ATOM   2496  NZ  LYS A 347      23.467  20.312  21.462  1.00 10.37           A
ATOM   2497  C   LYS A 347      16.549  21.789  22.030  1.00 10.83           A
ATOM   2498  O   LYS A 347      15.956  22.814  21.631  1.00  8.78           A
ATOM   2499  N   ALA A 348      15.987  20.583  21.997  1.00  9.70           A
ATOM   2500  CA  ALA A 348      14.627  20.418  21.472  1.00  9.41           A
ATOM   2501  CB  ALA A 348      14.238  18.928  21.448  1.00 12.04           A
ATOM   2502  C   ALA A 348      13.589  21.224  22.251  1.00 10.82           A
ATOM   2503  O   ALA A 348      12.678  21.830  21.657  1.00  9.58           A
```

FIGURE 5 (continued)

```
ATOM   2504  N    ALA A 349      13.735  21.261  23.569  1.00   9.39           A
ATOM   2505  CA   ALA A 349      12.791  22.018  24.392  1.00   8.51           A
ATOM   2506  CB   ALA A 349      13.045  21.750  25.891  1.00   8.51           A
ATOM   2507  C    ALA A 349      12.909  23.518  24.095  1.00  10.22           A
ATOM   2508  O    ALA A 349      11.888  24.224  24.012  1.00   8.91           A
ATOM   2509  N    VAL A 350      14.140  24.002  23.930  1.00  12.16           A
ATOM   2510  CA   VAL A 350      14.347  25.423  23.649  1.00   8.94           A
ATOM   2511  CB   VAL A 350      15.863  25.794  23.629  1.00   8.30           A
ATOM   2512  CG1  VAL A 350      16.075  27.221  23.071  1.00   8.00           A
ATOM   2513  CG2  VAL A 350      16.439  25.729  25.075  1.00   8.81           A
ATOM   2514  C    VAL A 350      13.709  25.763  22.305  1.00  10.89           A
ATOM   2515  O    VAL A 350      13.046  26.787  22.177  1.00  11.46           A
ATOM   2516  N    ARG A 351      13.890  24.895  21.313  1.00  10.91           A
ATOM   2517  CA   ARG A 351      13.289  25.144  20.002  1.00  11.54           A
ATOM   2518  CB   ARG A 351      13.765  24.106  18.988  1.00  10.07           A
ATOM   2519  CG   ARG A 351      15.237  24.167  18.647  1.00  10.05           A
ATOM   2520  CD   ARG A 351      15.527  23.433  17.312  1.00  14.16           A
ATOM   2521  NE   ARG A 351      14.971  22.067  17.282  1.00  17.52           A
ATOM   2522  CZ   ARG A 351      15.577  20.991  17.780  1.00  14.15           A
ATOM   2523  NH1  ARG A 351      14.993  19.802  17.708  1.00  14.19           A
ATOM   2524  NH2  ARG A 351      16.775  21.097  18.338  1.00  15.54           A
ATOM   2525  C    ARG A 351      11.750  25.097  20.069  1.00  13.24           A
ATOM   2526  O    ARG A 351      11.061  25.925  19.477  1.00  10.64           A
ATOM   2527  N    ALA A 352      11.221  24.112  20.786  1.00  10.94           A
ATOM   2528  CA   ALA A 352       9.772  23.942  20.890  1.00  13.45           A
ATOM   2529  CB   ALA A 352       9.447  22.656  21.636  1.00  14.54           A
ATOM   2530  C    ALA A 352       9.028  25.112  21.527  1.00  14.05           A
ATOM   2531  O    ALA A 352       7.875  25.385  21.193  1.00   9.92           A
ATOM   2532  N    SER A 353       9.669  25.802  22.454  1.00   9.51           A
ATOM   2533  CA   SER A 353       9.024  26.932  23.094  1.00  10.39           A
ATOM   2534  CB   SER A 353       9.503  27.088  24.548  1.00  11.56           A
ATOM   2535  OG   SER A 353       8.802  26.220  25.436  1.00  14.83           A
ATOM   2536  C    SER A 353       9.308  28.245  22.386  1.00  12.07           A
ATOM   2537  O    SER A 353       8.403  29.033  22.178  1.00  12.33           A
ATOM   2538  N    TYR A 354      10.568  28.459  22.015  1.00  10.56           A
ATOM   2539  CA   TYR A 354      10.955  29.733  21.455  1.00   8.65           A
ATOM   2540  CB   TYR A 354      12.240  30.188  22.159  1.00  11.42           A
ATOM   2541  CG   TYR A 354      12.077  30.164  23.670  1.00  11.26           A
ATOM   2542  CD1  TYR A 354      11.168  31.007  24.296  1.00  11.16           A
ATOM   2543  CE1  TYR A 354      10.962  30.955  25.673  1.00  13.86           A
ATOM   2544  CD2  TYR A 354      12.795  29.265  24.455  1.00  12.94           A
ATOM   2545  CE2  TYR A 354      12.608  29.204  25.846  1.00  13.83           A
ATOM   2546  CZ   TYR A 354      11.692  30.048  26.437  1.00  15.93           A
ATOM   2547  OH   TYR A 354      11.496  29.985  27.784  1.00  31.84           A
ATOM   2548  C    TYR A 354      11.069  29.882  19.951  1.00  11.12           A
ATOM   2549  O    TYR A 354      11.137  31.011  19.456  1.00  11.00           A
ATOM   2550  N    LEU A 355      11.097  28.778  19.218  1.00   9.87           A
ATOM   2551  CA   LEU A 355      11.156  28.896  17.757  1.00  11.35           A
ATOM   2552  CB   LEU A 355      12.292  28.069  17.185  1.00  12.01           A
ATOM   2553  CG   LEU A 355      13.697  28.633  17.424  1.00  18.77           A
ATOM   2554  CD1  LEU A 355      14.731  27.617  16.930  1.00  13.44           A
ATOM   2555  CD2  LEU A 355      13.856  29.963  16.666  1.00  19.42           A
ATOM   2556  C    LEU A 355       9.848  28.484  17.086  1.00  12.49           A
ATOM   2557  O    LEU A 355       9.337  29.208  16.231  1.00  13.91           A
ATOM   2558  N    THR A 356       9.300  27.331  17.458  1.00  13.88           A
ATOM   2559  CA   THR A 356       8.036  26.866  16.849  1.00  16.44           A
ATOM   2560  CB   THR A 356       7.414  25.759  17.704  1.00  19.06           A
ATOM   2561  OG1  THR A 356       8.352  24.678  17.794  1.00  22.02           A
ATOM   2562  CG2  THR A 356       6.108  25.265  17.077  1.00  20.44           A
ATOM   2563  C    THR A 356       7.058  28.040  16.684  1.00  15.88           A
ATOM   2564  O    THR A 356       6.609  28.642  17.658  1.00  14.53           A
ATOM   2565  N    ALA A 357       6.720  28.362  15.441  1.00  16.53           A
ATOM   2566  CA   ALA A 357       5.892  29.536  15.175  1.00  15.13           A
ATOM   2567  CB   ALA A 357       5.654  29.669  13.662  1.00  17.87           A
ATOM   2568  C    ALA A 357       4.569  29.630  15.918  1.00  18.27           A
ATOM   2569  O    ALA A 357       4.141  30.714  16.295  1.00  19.17           A
ATOM   2570  N    SER A 358       3.930  28.492  16.127  1.00  18.84           A
ATOM   2571  CA   SER A 358       2.643  28.444  16.800  1.00  22.62           A
ATOM   2572  CB   SER A 358       1.953  27.125  16.459  1.00  18.79           A
ATOM   2573  OG   SER A 358       2.853  26.049  16.654  1.00  21.93           A
ATOM   2574  C    SER A 358       2.716  28.607  18.318  1.00  22.54           A
ATOM   2575  O    SER A 358       1.719  28.918  18.949  1.00  19.82           A
ATOM   2576  N    ASN A 359       3.886  28.410  18.916  1.00  20.48           A
ATOM   2577  CA   ASN A 359       3.950  28.550  20.358  1.00  16.65           A
ATOM   2578  CB   ASN A 359       5.249  27.956  20.909  1.00  12.27           A
ATOM   2579  CG   ASN A 359       5.180  27.718  22.387  1.00  11.80           A
```

FIGURE 5 (continued)

```
ATOM  2580  OD1  ASN A 359       4.992  28.652  23.170  1.00 16.11       A
ATOM  2581  ND2  ASN A 359       5.329  26.451  22.793  1.00 14.58       A
ATOM  2582  C    ASN A 359       3.844  30.019  20.745  1.00 16.93       A
ATOM  2583  O    ASN A 359       4.550  30.861  20.194  1.00 15.08       A
ATOM  2584  N    ALA A 360       2.972  30.306  21.712  1.00 15.71       A
ATOM  2585  CA   ALA A 360       2.759  31.664  22.208  1.00 18.67       A
ATOM  2586  CB   ALA A 360       1.688  31.651  23.320  1.00 22.67       A
ATOM  2587  C    ALA A 360       4.041  32.309  22.744  1.00 18.59       A
ATOM  2588  O    ALA A 360       4.138  33.532  22.825  1.00 16.11       A
ATOM  2589  N    LEU A 361       5.010  31.488  23.144  1.00 14.62       A
ATOM  2590  CA   LEU A 361       6.276  32.021  23.653  1.00 11.27       A
ATOM  2591  CB   LEU A 361       6.863  31.060  24.685  1.00 15.51       A
ATOM  2592  CG   LEU A 361       6.087  30.788  25.971  1.00 15.37       A
ATOM  2593  CD1  LEU A 361       6.713  29.586  26.688  1.00 15.50       A
ATOM  2594  CD2  LEU A 361       6.086  32.030  26.849  1.00 14.07       A
ATOM  2595  C    LEU A 361       7.334  32.219  22.545  1.00 12.87       A
ATOM  2596  O    LEU A 361       8.430  32.716  22.818  1.00 12.41       A
ATOM  2597  N    SER A 362       7.036  31.821  21.314  1.00  9.97       A
ATOM  2598  CA   SER A 362       8.044  31.936  20.257  1.00 10.76       A
ATOM  2599  CB   SER A 362       7.627  31.145  19.011  1.00 15.72       A
ATOM  2600  OG   SER A 362       6.470  31.707  18.416  1.00 18.79       A
ATOM  2601  C    SER A 362       8.454  33.338  19.822  1.00 12.29       A
ATOM  2602  O    SER A 362       7.637  34.258  19.742  1.00 12.85       A
ATOM  2603  N    ILE A 363       9.741  33.457  19.512  1.00 10.84       A
ATOM  2604  CA   ILE A 363      10.353  34.698  19.072  1.00 14.99       A
ATOM  2605  CB   ILE A 363      11.850  34.461  18.777  1.00 13.05       A
ATOM  2606  CG2  ILE A 363      12.483  35.713  18.198  1.00 12.46       A
ATOM  2607  CG1  ILE A 363      12.578  34.071  20.064  1.00 15.60       A
ATOM  2608  CD1  ILE A 363      13.960  33.442  19.815  1.00 11.48       A
ATOM  2609  C    ILE A 363       9.639  35.206  17.807  1.00 14.29       A
ATOM  2610  O    ILE A 363       9.509  34.481  16.830  1.00 12.01       A
ATOM  2611  N    GLY A 364       9.176  36.451  17.848  1.00 15.53       A
ATOM  2612  CA   GLY A 364       8.477  37.034  16.717  1.00 14.88       A
ATOM  2613  C    GLY A 364       7.040  36.567  16.514  1.00 19.34       A
ATOM  2614  O    GLY A 364       6.436  36.872  15.487  1.00 19.36       A
ATOM  2615  N    ASP A 365       6.471  35.842  17.474  1.00 15.42       A
ATOM  2616  CA   ASP A 365       5.094  35.360  17.323  1.00 16.08       A
ATOM  2617  CB   ASP A 365       4.625  34.691  18.613  1.00 17.24       A
ATOM  2618  CG   ASP A 365       3.195  34.201  18.516  1.00 22.13       A
ATOM  2619  OD1  ASP A 365       2.992  33.003  18.238  1.00 24.97       A
ATOM  2620  OD2  ASP A 365       2.272  35.025  18.698  1.00 22.46       A
ATOM  2621  C    ASP A 365       4.100  36.490  16.954  1.00 20.12       A
ATOM  2622  O    ASP A 365       3.979  37.482  17.668  1.00 17.92       A
ATOM  2623  N    SER A 366       3.379  36.317  15.848  1.00 21.25       A
ATOM  2624  CA   SER A 366       2.419  37.319  15.360  1.00 19.32       A
ATOM  2625  CB   SER A 366       1.704  36.787  14.108  1.00 21.13       A
ATOM  2626  OG   SER A 366       2.640  36.400  13.125  1.00 29.92       A
ATOM  2627  C    SER A 366       1.359  37.814  16.342  1.00 15.84       A
ATOM  2628  O    SER A 366       1.155  39.010  16.461  1.00 22.39       A
ATOM  2629  N    ALA A 367       0.655  36.920  17.024  1.00 18.40       A
ATOM  2630  CA   ALA A 367      -0.384  37.363  17.965  1.00 22.33       A
ATOM  2631  CB   ALA A 367      -1.220  36.175  18.431  1.00 19.13       A
ATOM  2632  C    ALA A 367       0.182  38.093  19.187  1.00 25.24       A
ATOM  2633  O    ALA A 367      -0.402  39.066  19.682  1.00 26.45       A
ATOM  2634  N    VAL A 368       1.311  37.612  19.692  1.00 24.39       A
ATOM  2635  CA   VAL A 368       1.903  38.229  20.864  1.00 21.43       A
ATOM  2636  CB   VAL A 368       2.729  37.182  21.657  1.00 23.84       A
ATOM  2637  CG1  VAL A 368       3.447  37.838  22.850  1.00 19.42       A
ATOM  2638  CG2  VAL A 368       1.810  36.094  22.148  1.00 25.28       A
ATOM  2639  C    VAL A 368       2.770  39.447  20.558  1.00 19.50       A
ATOM  2640  O    VAL A 368       2.713  40.440  21.277  1.00 22.77       A
ATOM  2641  N    CYS A 369       3.557  39.396  19.491  1.00 17.47       A
ATOM  2642  CA   CYS A 369       4.448  40.505  19.195  1.00 20.32       A
ATOM  2643  C    CYS A 369       3.919  41.648  18.322  1.00 23.64       A
ATOM  2644  O    CYS A 369       4.617  42.639  18.120  1.00 26.98       A
ATOM  2645  CB   CYS A 369       5.746  39.977  18.581  1.00 22.42       A
ATOM  2646  SG   CYS A 369       6.819  38.961  19.671  1.00 19.53       A
ATOM  2647  N    GLY A 370       2.698  41.521  17.812  1.00 25.38       A
ATOM  2648  CA   GLY A 370       2.154  42.575  16.966  1.00 27.80       A
ATOM  2649  C    GLY A 370       2.190  43.938  17.627  1.00 21.46       A
ATOM  2650  O    GLY A 370       1.631  44.112  18.705  1.00 25.76       A
ATOM  2651  N    GLY A 371       2.872  44.885  16.988  1.00 20.44       A
ATOM  2652  CA   GLY A 371       2.970  46.237  17.516  1.00 23.12       A
ATOM  2653  C    GLY A 371       3.913  46.463  18.695  1.00 26.63       A
ATOM  2654  O    GLY A 371       3.946  47.561  19.263  1.00 23.97       A
ATOM  2655  N    LYS A 372       4.689  45.443  19.057  1.00 23.24       A
```

FIGURE 5 (continued)

```
ATOM   2656  CA  LYS A 372       5.612  45.537  20.197  1.00 21.66      A
ATOM   2657  CB  LYS A 372       5.141  44.605  21.296  1.00 19.20      A
ATOM   2658  CG  LYS A 372       3.715  44.856  21.675  1.00 25.31      A
ATOM   2659  CD  LYS A 372       3.278  43.936  22.769  1.00 24.34      A
ATOM   2660  CE  LYS A 372       1.884  44.315  23.208  1.00 29.63      A
ATOM   2661  NZ  LYS A 372       1.426  43.423  24.285  1.00 25.95      A
ATOM   2662  C   LYS A 372       7.037  45.167  19.855  1.00 18.74      A
ATOM   2663  O   LYS A 372       7.337  44.799  18.721  1.00 17.43      A
ATOM   2664  N   GLY A 373       7.917  45.247  20.852  1.00 15.44      A
ATOM   2665  CA  GLY A 373       9.297  44.876  20.616  1.00 12.87      A
ATOM   2666  C   GLY A 373      10.366  45.876  21.015  1.00 17.42      A
ATOM   2667  O   GLY A 373      10.168  47.106  20.965  1.00 13.70      A
ATOM   2668  N   ARG A 374      11.517  45.342  21.419  1.00 14.49      A
ATOM   2669  CA  ARG A 374      12.639  46.187  21.792  1.00 13.29      A
ATOM   2670  CB  ARG A 374      13.786  45.339  22.333  1.00 15.72      A
ATOM   2671  CG  ARG A 374      13.456  44.710  23.692  1.00 18.10      A
ATOM   2672  CD  ARG A 374      14.668  44.080  24.332  1.00 20.11      A
ATOM   2673  NE  ARG A 374      15.729  45.034  24.665  1.00 13.47      A
ATOM   2674  CZ  ARG A 374      16.143  45.296  25.899  1.00 13.50      A
ATOM   2675  NH1 ARG A 374      15.564  44.694  26.928  1.00 11.14      A
ATOM   2676  NH2 ARG A 374      17.206  46.082  26.100  1.00  9.65      A
ATOM   2677  C   ARG A 374      13.097  46.989  20.563  1.00 14.09      A
ATOM   2678  O   ARG A 374      13.008  46.517  19.411  1.00 13.90      A
ATOM   2679  N   PRO A 375      13.575  48.225  20.797  1.00 13.52      A
ATOM   2680  CD  PRO A 375      13.680  48.834  22.133  1.00 12.37      A
ATOM   2681  CA  PRO A 375      14.051  49.137  19.753  1.00 15.51      A
ATOM   2682  CB  PRO A 375      14.304  50.445  20.516  1.00 18.56      A
ATOM   2683  CG  PRO A 375      14.669  49.958  21.903  1.00 16.56      A
ATOM   2684  C   PRO A 375      15.282  48.622  19.017  1.00 16.94      A
ATOM   2685  O   PRO A 375      16.130  47.953  19.605  1.00 16.29      A
ATOM   2686  N   GLU A 376      15.384  48.956  17.733  1.00 14.83      A
ATOM   2687  CA  GLU A 376      16.501  48.480  16.928  1.00 14.54      A
ATOM   2688  CB  GLU A 376      16.191  48.638  15.429  1.00 20.94      A
ATOM   2689  CG  GLU A 376      15.989  50.054  14.930  1.00 25.93      A
ATOM   2690  CD  GLU A 376      15.840  50.093  13.408  1.00 28.12      A
ATOM   2691  OE1 GLU A 376      16.852  50.265  12.693  1.00 27.73      A
ATOM   2692  OE2 GLU A 376      14.706  49.921  12.926  1.00 22.85      A
ATOM   2693  C   GLU A 376      17.818  49.144  17.258  1.00 15.46      A
ATOM   2694  O   GLU A 376      17.779  50.308  17.715  1.00 20.34      A
ATOM   2695  OXT GLU A 376      18.870  48.501  17.040  1.00 17.16      A
ATOM   2696  OH2 WAT S1500      35.620  33.372  34.950  1.00  7.74      S
ATOM   2697  OH2 WAT S1501      26.719  26.585  54.115  1.00 13.35      S
ATOM   2698  OH2 WAT S1502      32.910  38.720  42.612  1.00 11.02      S
ATOM   2699  OH2 WAT S1503      25.842  40.990  19.393  1.00 10.30      S
ATOM   2700  OH2 WAT S1504      47.855  24.508  32.439  1.00 11.64      S
ATOM   2701  OH2 WAT S1505      37.575  38.877  30.460  1.00 13.25      S
ATOM   2702  OH2 WAT S1506      43.970  19.166  36.360  1.00 11.89      S
ATOM   2703  OH2 WAT S1507      51.431  26.280  38.870  1.00 11.08      S
ATOM   2704  OH2 WAT S1508      21.180  34.238  33.496  1.00 10.94      S
ATOM   2705  OH2 WAT S1509      34.016  23.145  55.150  1.00  7.21      S
ATOM   2706  OH2 WAT S1510      34.137  35.767  50.996  1.00 14.32      S
ATOM   2707  OH2 WAT S1511      29.833  31.064  61.815  1.00 12.62      S
ATOM   2708  OH2 WAT S1512      36.421  34.348  51.750  1.00  8.81      S
ATOM   2709  OH2 WAT S1513      24.593  22.841  22.601  1.00 14.49      S
ATOM   2710  OH2 WAT S1514      33.875  20.919  53.336  1.00 15.73      S
ATOM   2711  OH2 WAT S1515      55.590  18.894  44.228  1.00 20.22      S
ATOM   2712  OH2 WAT S1516      25.163  24.507  19.298  1.00  7.32      S
ATOM   2713  OH2 WAT S1517      29.287  27.565  53.584  1.00 10.43      S
ATOM   2714  OH2 WAT S1518      27.630  35.157  54.573  1.00 11.84      S
ATOM   2715  OH2 WAT S1519      34.308  40.814  45.314  1.00  9.91      S
ATOM   2716  OH2 WAT S1520      24.097  26.340  47.444  1.00 12.35      S
ATOM   2717  OH2 WAT S1521      26.289  17.353  26.191  1.00 14.15      S
ATOM   2718  OH2 WAT S1522      31.025  26.248  57.309  1.00  9.97      S
ATOM   2719  OH2 WAT S1523      16.012  33.323  36.822  1.00 10.61      S
ATOM   2720  OH2 WAT S1524      35.079  31.981  26.882  1.00  7.27      S
ATOM   2721  OH2 WAT S1525      48.948  16.302  35.666  1.00 22.32      S
ATOM   2722  OH2 WAT S1526      23.036  32.247  50.228  1.00 12.80      S
ATOM   2723  OH2 WAT S1527      41.445  42.204  48.819  1.00 16.71      S
ATOM   2724  OH2 WAT S1528      30.777  34.835  16.827  1.00 12.96      S
ATOM   2725  OH2 WAT S1529       9.482  33.895  27.983  1.00 10.22      S
ATOM   2726  OH2 WAT S1530      10.107  31.646  29.601  1.00 12.12      S
ATOM   2727  OH2 WAT S1531      37.836  31.446  58.127  1.00 18.63      S
ATOM   2728  OH2 WAT S1532      23.419  29.528  35.937  1.00 10.10      S
ATOM   2729  OH2 WAT S1533      36.234  16.727  51.505  1.00  9.28      S
ATOM   2730  OH2 WAT S1534       5.728  38.503  24.985  1.00 13.33      S
ATOM   2731  OH2 WAT S1535      29.914  14.295  35.432  1.00 16.41      S
```

FIGURE 5 (continued)

```
ATOM   2732  OH2 WAT S1536      31.310  38.281  18.695  1.00  9.93      S
ATOM   2733  OH2 WAT S1537      44.863  16.606  36.022  1.00 15.09      S
ATOM   2734  OH2 WAT S1538      40.186  22.869  38.700  1.00  9.90      S
ATOM   2735  OH2 WAT S1539      37.549  20.501  28.090  1.00 13.36      S
ATOM   2736  OH2 WAT S1540      12.913  31.829  29.436  1.00  9.36      S
ATOM   2737  OH2 WAT S1541      30.589  15.671  37.530  1.00 12.47      S
ATOM   2738  OH2 WAT S1542      23.885  35.406  43.402  1.00 18.37      S
ATOM   2739  OH2 WAT S1543       8.663  34.010  25.289  1.00 13.37      S
ATOM   2740  OH2 WAT S1544      13.484  46.444  33.757  1.00 12.24      S
ATOM   2741  OH2 WAT S1545      27.923  19.477  57.944  1.00 11.68      S
ATOM   2742  OH2 WAT S1546      17.540  33.345   7.715  1.00 19.22      S
ATOM   2743  OH2 WAT S1547      51.552  13.602  41.885  1.00 25.84      S
ATOM   2744  OH2 WAT S1548      27.270  26.074  40.675  1.00 10.51      S
ATOM   2745  OH2 WAT S1549      27.760  43.771  20.816  1.00 13.46      S
ATOM   2746  OH2 WAT S1550      37.046  17.292  27.914  1.00 14.34      S
ATOM   2747  OH2 WAT S1551      37.573  33.819  20.741  1.00 23.07      S
ATOM   2748  OH2 WAT S1552      40.930  14.067  35.565  1.00 17.08      S
ATOM   2749  OH2 WAT S1553       4.472  29.061  32.567  1.00 18.41      S
ATOM   2750  OH2 WAT S1554      26.302  32.912  28.375  1.00 10.00      S
ATOM   2751  OH2 WAT S1555      14.165  45.737  16.934  1.00 13.06      S
ATOM   2752  OH2 WAT S1556      29.555  43.029  36.030  1.00  7.32      S
ATOM   2753  OH2 WAT S1557      36.451  34.819  37.298  1.00 11.33      S
ATOM   2754  OH2 WAT S1558      31.931  17.255  49.603  1.00 39.16      S
ATOM   2755  OH2 WAT S1559      23.622  26.926  37.001  1.00 11.87      S
ATOM   2756  OH2 WAT S1560      31.327  13.311  33.059  1.00 12.47      S
ATOM   2757  OH2 WAT S1561      44.899  41.787  36.741  1.00 23.25      S
ATOM   2758  OH2 WAT S1562      44.879  35.365  50.334  1.00  9.60      S
ATOM   2759  OH2 WAT S1563      20.827  50.011  18.100  1.00 15.06      S
ATOM   2760  OH2 WAT S1564      24.374  31.041  38.304  1.00 12.38      S
ATOM   2761  OH2 WAT S1565      11.411  42.003  26.114  1.00 14.55      S
ATOM   2762  OH2 WAT S1566      21.341  35.751  40.722  1.00 12.16      S
ATOM   2763  OH2 WAT S1567      10.175  31.393  39.888  1.00 37.76      S
ATOM   2764  OH2 WAT S1568      47.181  26.945  33.704  1.00 12.30      S
ATOM   2765  OH2 WAT S1569      42.028  43.488  36.919  1.00 25.46      S
ATOM   2766  OH2 WAT S1570      31.053  24.724  15.706  1.00 12.46      S
ATOM   2767  OH2 WAT S1571      10.314  39.156  33.480  1.00 10.32      S
ATOM   2768  OH2 WAT S1572      51.433  20.485  50.130  1.00 15.09      S
ATOM   2769  OH2 WAT S1573      43.925  30.656  51.790  1.00 17.28      S
ATOM   2770  OH2 WAT S1574      23.091  53.758  28.375  1.00 12.50      S
ATOM   2771  OH2 WAT S1575      34.977  41.183  53.019  1.00 15.31      S
ATOM   2772  OH2 WAT S1576      29.766  26.781  12.309  1.00 18.82      S
ATOM   2773  OH2 WAT S1577       9.190  36.561  30.593  1.00 11.25      S
ATOM   2774  OH2 WAT S1578      36.599  15.728  48.666  1.00 21.18      S
ATOM   2775  OH2 WAT S1579      37.724  34.865  54.143  1.00 11.62      S
ATOM   2776  OH2 WAT S1580      21.457  35.713  12.303  1.00 13.24      S
ATOM   2777  OH2 WAT S1581      27.734  31.073  59.797  1.00 14.78      S
ATOM   2778  OH2 WAT S1582      51.536  35.554  40.163  1.00 14.52      S
ATOM   2779  OH2 WAT S1583      29.933  42.651  53.057  1.00 14.55      S
ATOM   2780  OH2 WAT S1584       9.469  23.677  25.125  1.00 12.14      S
ATOM   2781  OH2 WAT S1585      20.704  29.372  11.334  1.00 17.80      S
ATOM   2782  OH2 WAT S1586      56.481  22.975  38.435  1.00 29.16      S
ATOM   2783  OH2 WAT S1587       9.572  40.421  17.037  1.00 14.99      S
ATOM   2784  OH2 WAT S1588      20.542  42.224  40.862  1.00 13.90      S
ATOM   2785  OH2 WAT S1589       9.567  37.848  39.841  1.00 15.10      S
ATOM   2786  OH2 WAT S1590       6.391  48.835  28.636  1.00 19.52      S
ATOM   2787  OH2 WAT S1591      41.492  20.894  55.469  1.00 16.40      S
ATOM   2788  OH2 WAT S1592      22.505  28.556  52.952  1.00 24.23      S
ATOM   2789  OH2 WAT S1593      27.720  46.441  20.204  1.00 15.40      S
ATOM   2790  OH2 WAT S1594      37.216  41.499  30.864  1.00 19.68      S
ATOM   2791  OH2 WAT S1595      30.199  27.159  15.034  1.00 11.19      S
ATOM   2792  OH2 WAT S1596      25.139  30.964  53.858  1.00 21.47      S
ATOM   2793  OH2 WAT S1597      35.730  20.698  18.767  1.00 15.15      S
ATOM   2794  OH2 WAT S1598      44.994  20.666  23.797  1.00 17.67      S
ATOM   2795  OH2 WAT S1599      28.802  58.069  26.514  1.00 17.28      S
ATOM   2796  OH2 WAT S1600      16.767  47.104  22.319  1.00 11.98      S
ATOM   2797  OH2 WAT S1601      30.159  33.756  60.797  1.00  9.19      S
ATOM   2798  OH2 WAT S1602      48.106  27.997  36.005  1.00 14.93      S
ATOM   2799  OH2 WAT S1603      40.650  24.407  21.552  1.00 17.12      S
ATOM   2800  OH2 WAT S1604      22.968  17.449  18.008  1.00 17.85      S
ATOM   2801  OH2 WAT S1605      16.621  15.788  18.605  1.00 25.68      S
ATOM   2802  OH2 WAT S1606       7.206  32.992  16.005  1.00 14.53      S
ATOM   2803  OH2 WAT S1607      57.149  24.564  47.629  1.00 18.35      S
ATOM   2804  OH2 WAT S1608      24.205  26.840  10.350  1.00 23.21      S
ATOM   2805  OH2 WAT S1609      33.745  22.604  31.364  1.00 14.24      S
ATOM   2806  OH2 WAT S1610      21.687  28.608  49.750  1.00 41.13      S
ATOM   2807  OH2 WAT S1611      25.572  18.289  18.085  1.00 18.47      S
```

FIGURE 5 (continued)

```
ATOM   2808  OH2 WAT S1612      29.378  22.049  15.378  1.00 18.53      S
ATOM   2809  OH2 WAT S1613      47.580  17.180  46.156  1.00 18.00      S
ATOM   2810  OH2 WAT S1614      23.216  43.309  37.644  1.00 13.17      S
ATOM   2811  OH2 WAT S1615      22.669  24.274  48.564  1.00 24.15      S
ATOM   2812  OH2 WAT S1616       0.336  31.433  18.582  1.00 27.87      S
ATOM   2813  OH2 WAT S1617      45.294  33.053  51.773  1.00 13.88      S
ATOM   2814  OH2 WAT S1618      44.363  26.868  22.624  1.00 23.01      S
ATOM   2815  OH2 WAT S1619      24.023  16.291  14.532  1.00 14.28      S
ATOM   2816  OH2 WAT S1620      25.803  16.259  28.626  1.00 18.77      S
ATOM   2817  OH2 WAT S1621      10.423  51.944  32.078  1.00 36.29      S
ATOM   2818  OH2 WAT S1622      26.115  58.809  27.014  1.00 15.64      S
ATOM   2819  OH2 WAT S1623       1.344  28.356  22.672  1.00 26.37      S
ATOM   2820  OH2 WAT S1624      26.639  58.198  21.115  1.00 25.02      S
ATOM   2821  OH2 WAT S1625      26.622  32.997  55.284  1.00 16.24      S
ATOM   2822  OH2 WAT S1626      15.027  52.473  26.183  1.00 21.76      S
ATOM   2823  OH2 WAT S1627      57.187  25.783  44.900  1.00 20.20      S
ATOM   2824  OH2 WAT S1628      44.922  43.322  47.514  1.00 18.96      S
ATOM   2825  OH2 WAT S1629      32.001  38.779  53.199  1.00 17.42      S
ATOM   2826  OH2 WAT S1630      30.741  52.390  22.108  1.00 18.11      S
ATOM   2827  OH2 WAT S1631      14.999  39.258  44.162  1.00 19.15      S
ATOM   2828  OH2 WAT S1632      44.210  20.606  55.552  1.00 17.79      S
ATOM   2829  OH2 WAT S1633      21.471  43.377  12.416  1.00 19.05      S
ATOM   2830  OH2 WAT S1634      13.869  15.823  31.777  1.00 25.21      S
ATOM   2831  OH2 WAT S1635      52.620  30.612  55.173  1.00 30.08      S
ATOM   2832  OH2 WAT S1636      26.556  19.486  52.050  1.00 29.07      S
ATOM   2833  OH2 WAT S1637      21.965  25.980  45.841  1.00 19.07      S
ATOM   2834  OH2 WAT S1638      51.617  33.897  42.473  1.00  9.81      S
ATOM   2835  OH2 WAT S1639      11.552  20.655  19.351  1.00 16.68      S
ATOM   2836  OH2 WAT S1640      30.899  45.201  19.222  1.00 26.19      S
ATOM   2837  OH2 WAT S1641      31.709  48.342  31.000  1.00 18.10      S
ATOM   2838  OH2 WAT S1642      23.676  25.327  22.818  1.00 14.28      S
ATOM   2839  OH2 WAT S1643      25.577  17.219  46.479  1.00 20.91      S
ATOM   2840  OH2 WAT S1644      18.005  18.283  19.152  1.00 24.14      S
ATOM   2841  OH2 WAT S1645      52.881  16.705  50.095  1.00 20.16      S
ATOM   2842  OH2 WAT S1646       5.848  42.562  37.856  1.00 19.01      S
ATOM   2843  OH2 WAT S1647      43.582  14.659  34.565  1.00 28.17      S
ATOM   2844  OH2 WAT S1648      22.374  17.743  20.886  1.00 18.81      S
ATOM   2845  OH2 WAT S1649       8.712  48.989  27.030  1.00 23.87      S
ATOM   2846  OH2 WAT S1650       2.521  47.157  34.228  1.00 30.10      S
ATOM   2847  OH2 WAT S1651      44.220  43.064  40.109  1.00 29.97      S
ATOM   2848  OH2 WAT S1652      27.919  24.353  12.179  1.00 16.62      S
ATOM   2849  OH2 WAT S1653       3.523  42.077  26.249  1.00 22.83      S
ATOM   2850  OH2 WAT S1654      20.380  44.291  37.672  1.00 17.30      S
ATOM   2851  OH2 WAT S1655      57.034  28.423  45.056  1.00 27.44      S
ATOM   2852  OH2 WAT S1656      49.668  24.467  30.455  1.00 22.73      S
ATOM   2853  OH2 WAT S1657      51.259  13.409  45.586  1.00 34.23      S
ATOM   2854  OH2 WAT S1658       9.456  23.136  36.163  1.00 24.71      S
ATOM   2855  OH2 WAT S1659      52.331  23.665  57.905  1.00 18.92      S
ATOM   2856  OH2 WAT S1660      43.381  40.535  56.268  1.00 30.03      S
ATOM   2857  OH2 WAT S1661      13.806  46.776  43.159  1.00 30.72      S
ATOM   2858  OH2 WAT S1662      53.981  30.491  48.223  1.00 13.32      S
ATOM   2859  OH2 WAT S1663      41.765  26.570  28.744  1.00 27.76      S
ATOM   2860  OH2 WAT S1664      40.737  17.318  53.732  1.00 24.67      S
ATOM   2861  OH2 WAT S1665      13.225  44.990   8.674  1.00 28.84      S
ATOM   2862  OH2 WAT S1666      49.013  41.254  39.651  1.00 28.00      S
ATOM   2863  OH2 WAT S1667      44.805  37.426  30.933  1.00 16.56      S
ATOM   2864  OH2 WAT S1668      43.625  18.020  54.500  1.00 24.62      S
ATOM   2865  OH2 WAT S1669      14.317  25.699  46.118  1.00 34.64      S
ATOM   2866  OH2 WAT S1670       3.256  42.913  32.109  1.00 29.06      S
ATOM   2867  OH2 WAT S1671      10.555  49.763  20.725  1.00 28.19      S
ATOM   2868  OH2 WAT S1672      10.096  51.223  27.611  1.00 23.49      S
ATOM   2869  OH2 WAT S1673      14.363  23.946  36.209  1.00 40.49      S
ATOM   2870  OH2 WAT S1674      25.126  59.432  22.831  1.00 22.37      S
ATOM   2871  OH2 WAT S1675      36.093   4.004  46.425  1.00 41.05      S
ATOM   2872  OH2 WAT S1676      58.346  33.177  43.906  1.00 32.25      S
ATOM   2873  OH2 WAT S1677      48.932  35.192  51.801  1.00 26.68      S
ATOM   2874  OH2 WAT S1678      58.902  19.301  43.107  1.00 25.48      S
ATOM   2875  OH2 WAT S1679      44.340  42.085  50.822  1.00 28.00      S
ATOM   2876  OH2 WAT S1680      50.480  38.266  34.016  1.00 31.92      S
ATOM   2877  OH2 WAT S1681      32.259  20.178  55.706  1.00 22.68      S
ATOM   2878  OH2 WAT S1682       5.907  48.823  21.778  1.00 41.37      S
ATOM   2879  OH2 WAT S1683      50.286  29.738  36.205  1.00 41.24      S
ATOM   2880  OH2 WAT S1684      48.359  24.392  27.682  1.00 21.59      S
ATOM   2881  OH2 WAT S1685      28.819  16.491  25.944  1.00 22.91      S
ATOM   2882  OH2 WAT S1686      27.814  39.366  53.598  1.00 22.13      S
ATOM   2883  OH2 WAT S1687      23.282  56.182  29.647  1.00 21.73      S
```

FIGURE 5 (continued)

```
ATOM   2884  OH2  WAT  S1688    11.176  51.488  23.245  1.00  39.40      S
ATOM   2885  OH2  WAT  S1689    19.333  13.893  25.470  1.00  16.29      S
ATOM   2886  OH2  WAT  S1690    15.528  35.966  43.442  1.00  24.55      S
ATOM   2887  OH2  WAT  S1691    28.485  18.098  54.189  1.00  38.82      S
ATOM   2888  OH2  WAT  S1692    49.461  42.346  42.415  1.00  29.71      S
ATOM   2889  OH2  WAT  S1693     6.986  51.318  31.491  1.00  38.19      S
ATOM   2890  OH2  WAT  S1694    45.805  30.330  30.352  1.00  31.74      S
ATOM   2891  OH2  WAT  S1695    12.688  17.949  24.810  1.00  24.29      S
ATOM   2892  OH2  WAT  S1696    10.481  44.192  41.405  1.00  30.36      S
ATOM   2893  OH2  WAT  S1697    36.497  25.163  61.042  1.00  22.75      S
ATOM   2894  OH2  WAT  S1698    38.997   8.895  40.582  1.00  35.83      S
ATOM   2895  OH2  WAT  S1699    34.429  41.271  24.603  1.00  25.66      S
ATOM   2896  OH2  WAT  S1700     9.264  39.356  31.031  1.00  12.79      S
ATOM   2897  OH2  WAT  S1701    10.070  23.977  42.971  1.00  38.68      S
ATOM   2898  OH2  WAT  S1702    18.383  29.372   9.706  1.00  36.59      S
ATOM   2899  OH2  WAT  S1703    49.044  14.511  44.663  1.00  29.13      S
ATOM   2900  OH2  WAT  S1704    24.559  26.271  39.612  1.00   9.57      S
ATOM   2901  OH2  WAT  S1705    20.114  45.757  12.779  1.00  24.18      S
ATOM   2902  OH2  WAT  S1706    40.248  22.113  20.074  1.00  29.44      S
ATOM   2903  OH2  WAT  S1707    18.194  41.869  42.229  1.00  17.46      S
ATOM   2904  OH2  WAT  S1708    37.847  20.546  20.498  1.00  18.73      S
ATOM   2905  OH2  WAT  S1709    16.821  29.280  41.001  1.00  24.06      S
ATOM   2906  OH2  WAT  S1710    27.294  42.193  52.815  1.00  19.46      S
ATOM   2907  OH2  WAT  S1711    40.821  42.347  51.556  1.00  22.66      S
ATOM   2908  OH2  WAT  S1712    26.156  40.106  48.095  1.00  24.85      S
ATOM   2909  OH2  WAT  S1713    20.103  24.718  47.608  1.00  30.63      S
ATOM   2910  OH2  WAT  S1714    24.148  33.741  56.397  1.00  19.34      S
ATOM   2911  OH2  WAT  S1715    18.973  45.993  36.285  1.00  18.68      S
ATOM   2912  OH2  WAT  S1716    14.529  44.714  35.623  1.00  11.98      S
ATOM   2913  OH2  WAT  S1717    38.781  35.753  22.003  1.00  28.14      S
ATOM   2914  OH2  WAT  S1718     9.031  37.190  34.220  1.00  30.97      S
ATOM   2915  OH2  WAT  S1719    35.994  16.311  25.745  1.00  28.93      S
ATOM   2916  OH2  WAT  S1720    13.544  49.140  34.673  1.00  19.62      S
ATOM   2917  OH2  WAT  S1721    22.265  37.832  42.637  1.00  21.65      S
ATOM   2918  OH2  WAT  S1722     9.246  42.739  13.991  1.00  23.76      S
ATOM   2919  OH2  WAT  S1723    46.901  14.013  46.528  1.00  24.08      S
ATOM   2920  OH2  WAT  S1724    27.124  17.124  56.373  1.00  20.76      S
ATOM   2921  OH2  WAT  S1725     5.808  39.927  37.880  1.00  30.10      S
ATOM   2922  OH2  WAT  S1726    42.361  20.811  20.431  1.00  24.61      S
ATOM   2923  OH2  WAT  S1727    26.665  17.537  21.374  1.00  22.27      S
ATOM   2924  OH2  WAT  S1728    57.473  29.684  48.797  1.00  33.94      S
ATOM   2925  OH2  WAT  S1729     0.205  29.580  11.300  1.00  28.38      S
ATOM   2926  OH2  WAT  S1730    28.982  12.144  36.663  1.00  22.16      S
ATOM   2927  OH2  WAT  S1731    -2.247  31.885  18.386  1.00  37.56      S
ATOM   2928  OH2  WAT  S1732    19.593  14.821  28.910  1.00  29.82      S
ATOM   2929  OH2  WAT  S1733     1.174  27.052  34.363  1.00  22.10      S
ATOM   2930  OH2  WAT  S1734    35.909  11.924  47.248  1.00  27.93      S
ATOM   2931  OH2  WAT  S1735    41.887  40.436  52.838  1.00  28.22      S
ATOM   2932  OH2  WAT  S1736    26.213  19.454  10.997  1.00  22.64      S
ATOM   2933  OH2  WAT  S1737    34.114  42.884  34.175  1.00  28.42      S
ATOM   2934  OH2  WAT  S1738    22.945  32.302  53.065  1.00  25.85      S
ATOM   2935  OH2  WAT  S1739    39.089  15.172  28.466  1.00  31.20      S
ATOM   2936  OH2  WAT  S1740    47.610  43.601  46.621  1.00  36.15      S
ATOM   2937  OH2  WAT  S1741    16.327  45.853  37.179  1.00  17.39      S
ATOM   2938  OH2  WAT  S1742    55.363  25.260  59.367  1.00  29.21      S
ATOM   2939  OH2  WAT  S1743    30.641  36.731  14.630  1.00  26.83      S
ATOM   2940  OH2  WAT  S1744    10.864  46.250  10.531  1.00  23.96      S
ATOM   2941  OH2  WAT  S1745    33.170  48.399  28.312  1.00  27.45      S
ATOM   2942  OH2  WAT  S1746    32.054  14.892  42.067  1.00  24.32      S
ATOM   2943  OH2  WAT  S1747    42.724  28.782  21.018  1.00  34.32      S
ATOM   2944  OH2  WAT  S1748    51.123  15.697  52.194  1.00  27.97      S
ATOM   2945  OH2  WAT  S1749    42.354  43.166  56.140  1.00  29.49      S
ATOM   2946  OH2  WAT  S1750    28.037  37.891  13.736  1.00  33.67      S
ATOM   2947  OH2  WAT  S1751    51.086  26.646  30.768  1.00  30.84      S
ATOM   2948  OH2  WAT  S1752    10.931  38.592  10.467  1.00  25.71      S
ATOM   2949  OH2  WAT  S1753    25.655  29.886  60.929  1.00  19.64      S
ATOM   2950  OH2  WAT  S1754    17.145  13.376  23.383  1.00  34.23      S
ATOM   2951  OH2  WAT  S1755    44.748  12.372  45.391  1.00  18.99      S
ATOM   2952  OH2  WAT  S1756    24.658  10.868  33.101  1.00  39.56      S
ATOM   2953  OH2  WAT  S1757    10.322  35.265  39.792  1.00  31.55      S
ATOM   2954  OH2  WAT  S1758    57.341  22.537  45.377  1.00  16.36      S
ATOM   2955  OH2  WAT  S1759     9.420  34.820  36.963  1.00  32.92      S
ATOM   2956  OH2  WAT  S1760    32.502  28.596  14.854  1.00  21.37      S
ATOM   2957  OH2  WAT  S1761    39.205  22.929  17.441  1.00  35.60      S
ATOM   2958  OH2  WAT  S1762    20.840  52.812  17.278  1.00  31.30      S
ATOM   2959  OH2  WAT  S1763    34.711  11.735  35.138  1.00  32.11      S
```

FIGURE 5 (continued)

```
ATOM   2960  OH2 WAT S1764      51.666  34.131  47.365  1.00 35.34      S
ATOM   2961  OH2 WAT S1765      -2.014  36.180  15.830  1.00 28.16      S
ATOM   2962  OH2 WAT S1766      15.482  48.721  37.060  1.00 29.26      S
ATOM   2963  OH2 WAT S1767      40.630  14.716  31.062  1.00 40.40      S
ATOM   2964  OH2 WAT S1768      23.698  61.256  21.533  1.00 16.86      S
ATOM   2965  OH2 WAT S1769      24.781  28.532  54.977  1.00 16.20      S
ATOM   2966  OH2 WAT S1770      26.852  25.257  10.061  1.00 30.41      S
ATOM   2967  OH2 WAT S1771      43.726  10.405  46.878  1.00 29.13      S
ATOM   2968  OH2 WAT S1772      25.837  37.362  54.027  1.00 21.97      S
ATOM   2969  OH2 WAT S1773      33.373  46.686  32.566  1.00 26.20      S
ATOM   2970  OH2 WAT S1774      27.264  20.817  13.545  1.00 22.02      S
ATOM   2971  OH2 WAT S1775      47.925  30.806  31.477  1.00 33.49      S
ATOM   2972  OH2 WAT S1776       8.238  38.202  37.592  1.00 26.28      S
ATOM   2973  OH2 WAT S1777      21.090  51.641  25.222  1.00 18.54      S
ATOM   2974  OH2 WAT S1778       6.267  38.069  32.873  1.00 22.17      S
ATOM   2975  OH2 WAT S1779      23.234  49.347  16.745  1.00 24.08      S
ATOM   2976  OH2 WAT S1780      22.134  39.856  40.656  1.00 21.00      S
ATOM   2977  OH2 WAT S1781      20.856  35.405   9.637  1.00 23.13      S
ATOM   2978  OH2 WAT S1782      21.475  53.999  26.047  1.00 27.01      S
ATOM   2979  OH2 WAT S1783      34.915  27.212  15.190  1.00 31.71      S
ATOM   2980  OH2 WAT S1784      45.211  12.993  42.137  1.00 21.38      S
ATOM   2981  OH2 WAT S1785      38.126  34.805  40.034  1.00 17.57      S
ATOM   2982  OH2 WAT S1786      30.962  49.798  21.332  1.00 32.31      S
ATOM   2983  OH2 WAT S1787      33.222  19.319  25.705  1.00 29.22      S
ATOM   2984  OH2 WAT S1788      40.144  19.662  28.253  1.00 33.93      S
ATOM   2985  OH2 WAT S1789       6.555  28.590  37.281  1.00 28.90      S
ATOM   2986  OH2 WAT S1790      43.426  43.935  45.155  1.00 34.35      S
ATOM   2987  OH2 WAT S1791       3.263  33.201  14.705  1.00 33.11      S
ATOM   2988  OH2 WAT S1792      20.149  16.998  31.047  1.00 26.99      S
ATOM   2989  OH2 WAT S1793      34.123  42.842  21.180  1.00 24.49      S
ATOM   2990  OH2 WAT S1794      49.929  18.274  53.829  1.00 39.26      S
ATOM   2991  OH2 WAT S1795      14.815  31.617   9.739  1.00 35.94      S
ATOM   2992  OH2 WAT S1796      45.588  41.539  53.753  1.00 35.01      S
ATOM   2993  OH2 WAT S1797      33.245  52.433  24.002  1.00 34.85      S
ATOM   2994  OH2 WAT S1798      43.010  24.276  22.909  1.00 21.38      S
ATOM   2995  OH2 WAT S1799      19.769  14.826  46.718  1.00 30.67      S
ATOM   2996  OH2 WAT S1800      29.812  17.873  43.458  1.00 28.85      S
ATOM   2997  OH2 WAT S1801       7.028  22.438  24.718  1.00 30.13      S
ATOM   2998  OH2 WAT S1802       7.451  42.723  16.836  1.00 34.86      S
ATOM   2999  OH2 WAT S1803      13.062  50.532  16.899  1.00 27.23      S
ATOM   3000  OH2 WAT S1804      31.535  17.528  46.115  1.00 21.48      S
ATOM   3001  OH2 WAT S1805       1.214  41.199  23.409  1.00 33.03      S
ATOM   3002  OH2 WAT S1806      12.350  33.958  40.836  1.00 34.82      S
ATOM   3003  OH2 WAT S1807      33.164  41.928  54.755  1.00 33.81      S
ATOM   3004  OH2 WAT S1808       4.467  50.285  27.482  1.00 36.79      S
ATOM   3005  OH2 WAT S1809      60.702  26.732  42.684  1.00 35.13      S
ATOM   3006  OH2 WAT S1810      22.799  31.560  57.795  1.00 32.80      S
ATOM   3007  OH2 WAT S1811      16.630  35.862   8.507  1.00 29.92      S
ATOM   3008  OH2 WAT S1812      58.212  35.487  40.540  1.00 33.76      S
ATOM   3009  OH2 WAT S1813      31.566  17.525  26.426  1.00 39.01      S
ATOM   3010  OH2 WAT S1814      38.884  37.614  20.120  1.00 33.89      S
ATOM   3011  OH2 WAT S1815      58.154  24.777  37.822  1.00 35.73      S
ATOM   3012  OH2 WAT S1816      34.384  14.783  47.649  1.00 37.28      S
ATOM   3013  OH2 WAT S1817       3.439  43.153  36.372  1.00 30.78      S
ATOM   3014  OH2 WAT S1818      47.394  12.444  43.290  1.00 30.32      S
ATOM   3015  OH2 WAT S1819      24.644  13.829  44.044  1.00 32.65      S
ATOM   3016  OH2 WAT S1820      35.990  42.985  32.322  1.00 29.66      S
ATOM   3017  OH2 WAT S1821      26.914  40.212   9.947  1.00 33.58      S
ATOM   3018  OH2 WAT S1822      40.296  29.386  23.361  1.00 44.10      S
ATOM   3019  OH2 WAT S1823      42.915  30.163  27.417  1.00 33.23      S
ATOM   3020  OH2 WAT S1824      14.322  38.428   8.032  1.00 35.73      S
ATOM   3021  OH2 WAT S1825      33.329  16.000  45.385  1.00 29.78      S
ATOM   3022  OH2 WAT S1826      55.683  28.168  38.449  1.00 30.81      S
ATOM   3023  OH2 WAT S1827      18.514  45.706   9.695  1.00 34.33      S
ATOM   3024  OH2 WAT S1828      19.453  54.788  22.809  1.00 42.02      S
ATOM   3025  OH2 WAT S1829      46.686  27.005  20.816  1.00 31.17      S
ATOM   3026  OH2 WAT S1830      50.779  32.327  54.666  1.00 44.04      S
ATOM   3027  OH2 WAT S1831       5.243  43.614  40.262  1.00 40.69      S
ATOM   3028  OH2 WAT S1832      45.151  43.041  33.919  1.00 28.47      S
ATOM   3029  OH2 WAT S1833      26.385  11.949  41.104  1.00 33.70      S
ATOM   3030  OH2 WAT S1834      36.104  26.756  17.653  1.00 32.43      S
ATOM   3031  OH2 WAT S1835      40.585   7.298  41.894  1.00 32.97      S
ATOM   3032  OH2 WAT S1836      22.940  54.196  16.985  1.00 39.88      S
ATOM   3033  OH2 WAT S1837      53.968  24.450  37.442  1.00 39.29      S
ATOM   3034  OH2 WAT S1838      16.318  26.973  42.179  1.00 32.94      S
ATOM   3035  OH2 WAT S1839      14.513  48.940  39.307  1.00 29.97      S
```

FIGURE 5 (continued)

| | | | | | | | | | |
|---|---|---|---|---|---|---|---|---|---|
| ATOM | 3036 | OH2 | WAT | S1840 | 31.652 | 6.945 | 51.493 | 1.00 27.66 | S |
| ATOM | 3037 | OH2 | WAT | S1841 | 41.996 | 11.677 | 38.039 | 1.00 37.88 | S |
| ATOM | 3038 | OH2 | WAT | S1842 | 7.510 | 48.642 | 19.668 | 1.00 35.11 | S |
| ATOM | 3039 | OH2 | WAT | S1843 | 42.467 | 3.493 | 49.912 | 1.00 33.41 | S |
| ATOM | 3040 | OH2 | WAT | S1844 | 59.776 | 22.501 | 42.412 | 1.00 44.37 | S |
| ATOM | 3041 | OH2 | WAT | S1845 | 7.867 | 44.473 | 12.687 | 1.00 34.20 | S |
| ATOM | 3042 | OH2 | WAT | S1846 | 15.405 | 45.353 | 39.658 | 1.00 38.08 | S |
| ATOM | 3043 | OH2 | WAT | S1847 | 13.585 | 15.183 | 28.501 | 1.00 36.58 | S |
| ATOM | 3044 | OH2 | WAT | S1848 | 48.442 | 41.492 | 47.985 | 1.00 26.95 | S |
| ATOM | 3045 | OH2 | WAT | S1849 | 50.374 | 40.886 | 46.017 | 1.00 34.93 | S |
| ATOM | 3046 | OH2 | WAT | S1850 | 44.568 | 8.030 | 45.822 | 1.00 42.34 | S |
| ATOM | 3047 | OH2 | WAT | S1851 | 48.705 | 28.443 | 22.632 | 1.00 34.87 | S |
| ATOM | 3048 | OH2 | WAT | S1852 | 38.217 | 33.408 | 18.268 | 1.00 40.91 | S |
| ATOM | 3049 | OH2 | WAT | S1853 | 26.698 | 47.866 | 16.749 | 1.00 26.87 | S |
| ATOM | 3050 | OH2 | WAT | S1854 | 36.624 | 40.405 | 57.361 | 1.00 30.57 | S |
| ATOM | 3051 | OH2 | WAT | S1855 | 44.243 | 22.209 | 21.682 | 1.00 25.97 | S |
| ATOM | 3052 | OH2 | WAT | S1856 | 50.807 | 22.291 | 30.826 | 1.00 30.01 | S |
| ATOM | 3053 | OH2 | WAT | S1857 | 2.113 | 19.175 | 16.420 | 1.00 39.64 | S |
| ATOM | 3054 | OH2 | WAT | S1858 | 35.799 | 20.261 | 25.717 | 1.00 29.95 | S |
| ATOM | 3055 | OH2 | WAT | S1859 | 10.845 | 51.013 | 18.474 | 1.00 29.30 | S |
| ATOM | 3056 | OH2 | WAT | S1860 | 13.036 | 16.982 | 18.603 | 1.00 35.56 | S |
| ATOM | 3057 | OH2 | WAT | S1861 | 48.755 | 33.466 | 53.529 | 1.00 32.19 | S |
| ATOM | 3058 | OH2 | WAT | S1862 | 28.542 | 12.640 | 28.777 | 1.00 32.37 | S |
| ATOM | 3059 | OH2 | WAT | S1863 | 15.582 | 33.781 | 40.294 | 1.00 31.38 | S |
| ATOM | 3060 | OH2 | WAT | S1864 | 15.389 | 51.736 | 31.264 | 1.00 35.97 | S |
| ATOM | 3061 | OH2 | WAT | S1865 | 59.586 | 24.576 | 44.154 | 1.00 38.45 | S |
| ATOM | 3062 | OH2 | WAT | S1866 | 33.931 | 18.197 | 52.470 | 1.00 31.45 | S |
| ATOM | 3063 | OH2 | WAT | S1867 | 33.400 | 24.810 | 14.487 | 1.00 31.43 | S |
| ATOM | 3064 | OH2 | WAT | S1868 | 2.939 | 39.474 | 28.464 | 1.00 42.13 | S |
| ATOM | 3065 | OH2 | WAT | S1869 | 52.149 | 36.661 | 45.439 | 1.00 34.90 | S |
| ATOM | 3066 | OH2 | WAT | S1870 | 45.901 | 34.119 | 54.146 | 1.00 28.55 | S |
| ATOM | 3067 | OH2 | WAT | S1871 | 21.485 | 29.372 | 44.666 | 1.00 37.03 | S |
| ATOM | 3068 | OH2 | WAT | S1872 | 10.455 | 19.175 | 23.705 | 1.00 36.18 | S |
| ATOM | 3069 | OH2 | WAT | S1873 | 29.820 | 54.141 | 17.625 | 1.00 37.56 | S |
| ATOM | 3070 | OH2 | WAT | S1874 | 36.824 | 12.036 | 41.616 | 1.00 36.62 | S |
| ATOM | 3071 | OH2 | WAT | S1875 | 35.575 | 29.695 | 13.582 | 1.00 31.58 | S |
| ATOM | 3072 | OH2 | WAT | S1876 | 47.689 | 26.645 | 56.483 | 1.00 29.75 | S |
| ATOM | 3073 | OH2 | WAT | S1877 | 25.923 | 24.021 | 7.877 | 1.00 35.32 | S |
| ATOM | 3074 | OH2 | WAT | S1878 | 35.914 | 42.663 | 19.444 | 1.00 38.13 | S |
| ATOM | 3075 | OH2 | WAT | S1879 | 53.553 | 27.199 | 37.462 | 1.00 34.02 | S |
| ATOM | 3076 | OH2 | WAT | S1880 | 31.012 | 18.989 | 51.960 | 1.00 32.14 | S |
| ATOM | 3077 | OH2 | WAT | S1881 | 5.543 | 24.207 | 39.126 | 1.00 33.92 | S |
| ATOM | 3078 | OH2 | WAT | S1882 | 12.515 | 49.450 | 14.280 | 1.00 38.32 | S |
| ATOM | 3079 | OH2 | WAT | S1883 | 19.621 | 34.441 | 42.264 | 1.00 32.10 | S |
| ATOM | 3080 | OH2 | WAT | S1884 | 0.567 | 34.443 | 15.606 | 1.00 41.76 | S |
| ATOM | 3081 | OH2 | WAT | S1885 | 19.842 | 21.597 | 48.228 | 1.00 38.20 | S |
| ATOM | 3082 | OH2 | WAT | S1886 | 17.245 | 44.489 | 41.443 | 1.00 36.34 | S |
| ATOM | 3083 | OH2 | WAT | S1887 | 31.241 | 17.703 | 18.315 | 1.00 43.85 | S |
| ATOM | 3084 | OH2 | WAT | S1888 | 47.120 | 35.974 | 31.511 | 1.00 44.95 | S |
| ATOM | 3085 | OH2 | WAT | S1889 | 16.721 | 12.447 | 25.646 | 1.00 42.81 | S |
| ATOM | 3086 | OH2 | WAT | S1890 | 17.002 | 21.309 | 47.530 | 1.00 35.74 | S |
| ATOM | 3087 | OH2 | WAT | S1891 | 11.124 | 36.224 | 11.415 | 1.00 28.23 | S |
| ATOM | 3088 | OH2 | WAT | S1892 | 31.476 | 35.439 | 12.666 | 1.00 29.98 | S |
| ATOM | 3089 | OH2 | WAT | S1893 | 20.313 | 44.798 | 8.239 | 1.00 38.49 | S |
| ATOM | 3090 | OH2 | WAT | S1894 | 49.492 | 37.692 | 31.490 | 1.00 34.21 | S |
| ATOM | 3091 | OH2 | WAT | S1895 | 11.168 | 48.631 | 11.775 | 1.00 35.00 | S |
| ATOM | 3092 | OH2 | WAT | S1896 | 8.149 | 35.174 | 12.830 | 1.00 43.18 | S |
| ATOM | 3093 | OH2 | WAT | S1897 | 42.985 | 36.028 | 29.277 | 1.00 37.84 | S |
| ATOM | 3094 | OH2 | WAT | S1898 | 15.722 | 26.088 | 38.269 | 1.00 40.56 | S |
| ATOM | 3095 | OH2 | WAT | S1899 | 9.466 | 42.584 | 43.325 | 1.00 38.58 | S |
| ATOM | 3096 | OH2 | WAT | S1900 | 55.683 | 27.859 | 55.011 | 1.00 40.16 | S |
| ATOM | 3097 | OH2 | WAT | S1901 | 16.412 | 44.824 | 6.088 | 1.00 35.00 | S |
| ATOM | 3098 | OH2 | WAT | S1902 | 30.819 | 20.863 | 13.376 | 1.00 36.12 | S |
| ATOM | 3099 | OH2 | WAT | S1903 | 20.083 | 45.050 | 40.249 | 1.00 46.55 | S |
| ATOM | 3100 | OH2 | WAT | S1904 | 55.216 | 16.767 | 37.256 | 1.00 32.34 | S |
| ATOM | 3101 | OH2 | WAT | S1905 | 17.194 | 15.633 | 31.289 | 1.00 41.92 | S |
| ATOM | 3102 | OH2 | WAT | S1906 | 55.468 | 39.305 | 45.956 | 1.00 33.48 | S |
| ATOM | 3103 | OH2 | WAT | S1907 | 34.073 | 59.171 | 22.880 | 1.00 29.68 | S |
| ATOM | 3104 | OH2 | WAT | S1908 | 11.696 | 23.487 | 37.533 | 1.00 44.83 | S |
| ATOM | 3105 | OH2 | WAT | S1909 | 37.193 | 57.700 | 24.645 | 1.00 29.20 | S |
| ATOM | 3106 | OH2 | WAT | S1910 | 4.958 | 20.071 | 12.971 | 1.00 38.75 | S |
| ATOM | 3107 | OH2 | WAT | S1911 | 28.212 | 15.651 | 46.090 | 1.00 44.28 | S |
| ATOM | 3108 | OH2 | WAT | S1912 | 25.791 | 17.881 | 50.101 | 1.00 44.07 | S |
| ATOM | 3109 | OH2 | WAT | S1913 | 44.830 | 16.225 | 28.015 | 1.00 37.34 | S |
| ATOM | 3110 | OH2 | WAT | S1914 | 45.538 | 25.603 | 58.524 | 1.00 31.60 | S |
| ATOM | 3111 | OH2 | WAT | S1915 | 31.849 | 53.832 | 20.135 | 1.00 44.08 | S |

FIGURE 5 (continued)

| | | | | | | | | | |
|---|---|---|---|---|---|---|---|---|---|
| ATOM | 3112 | OH2 | WAT | S1916 | 55.981 | 32.376 | 47.108 | 1.00 41.65 | S |
| ATOM | 3113 | OH2 | WAT | S1917 | 35.699 | 24.353 | 16.736 | 1.00 43.04 | S |
| ATOM | 3114 | OH2 | WAT | S1918 | 3.252 | 25.157 | 38.490 | 1.00 42.38 | S |
| ATOM | 3115 | OH2 | WAT | S1919 | 34.711 | 10.496 | 39.861 | 1.00 36.97 | S |
| ATOM | 3116 | OS4 | PLA | P1001 | 8.781 | 29.613 | 10.689 | 1.00 35.34 | P |
| ATOM | 3117 | S2 | PLA | P1001 | 9.783 | 28.546 | 11.256 | 1.00 33.57 | P |
| ATOM | 3118 | OS5 | PLA | P1001 | 10.409 | 27.663 | 9.867 | 1.00 40.37 | P |
| ATOM | 3119 | OS6 | PLA | P1001 | 11.159 | 29.189 | 12.135 | 1.00 41.03 | P |
| ATOM | 3120 | C15 | PLA | P1001 | 9.058 | 27.351 | 12.199 | 1.00 30.49 | P |
| ATOM | 3121 | C14 | PLA | P1001 | 7.662 | 27.126 | 12.015 | 1.00 23.35 | P |
| ATOM | 3122 | C16 | PLA | P1001 | 9.978 | 26.532 | 12.898 | 1.00 28.94 | P |
| ATOM | 3123 | C10 | PLA | P1001 | 9.499 | 25.436 | 13.634 | 1.00 30.90 | P |
| ATOM | 3124 | C11 | PLA | P1001 | 8.025 | 25.127 | 13.485 | 1.00 25.22 | P |
| ATOM | 3125 | C13 | PLA | P1001 | 7.134 | 25.968 | 12.614 | 1.00 21.41 | P |
| ATOM | 3126 | O3 | PLA | P1001 | 5.837 | 25.588 | 12.437 | 1.00 24.00 | P |
| ATOM | 3127 | C12 | PLA | P1001 | 7.519 | 23.932 | 14.212 | 1.00 27.53 | P |
| ATOM | 3128 | O2 | PLA | P1001 | 6.235 | 23.585 | 13.967 | 1.00 21.97 | P |
| ATOM | 3129 | C9 | PLA | P1001 | 10.366 | 24.618 | 14.415 | 1.00 32.13 | P |
| ATOM | 3130 | C8 | PLA | P1001 | 9.876 | 23.541 | 15.205 | 1.00 31.56 | P |
| ATOM | 3131 | S1 | PLA | P1001 | 10.846 | 22.324 | 15.981 | 1.00 31.16 | P |
| ATOM | 3132 | OS3 | PLA | P1001 | 12.358 | 22.881 | 16.679 | 1.00 39.44 | P |
| ATOM | 3133 | OS2 | PLA | P1001 | 11.138 | 21.153 | 14.733 | 1.00 28.72 | P |
| ATOM | 3134 | OS1 | PLA | P1001 | 10.061 | 21.436 | 17.011 | 1.00 39.17 | P |
| ATOM | 3135 | C7 | PLA | P1001 | 8.424 | 23.154 | 15.086 | 1.00 20.93 | P |
| ATOM | 3136 | N2 | PLA | P1001 | 7.947 | 21.974 | 15.652 | 1.00 27.49 | P |
| ATOM | 3137 | N1 | PLA | P1001 | 6.731 | 21.270 | 15.708 | 1.00 26.74 | P |
| ATOM | 3138 | C2 | PLA | P1001 | 6.780 | 19.948 | 16.206 | 1.00 29.90 | P |
| ATOM | 3139 | C1 | PLA | P1001 | 7.938 | 19.230 | 16.659 | 1.00 26.11 | P |
| ATOM | 3140 | C3 | PLA | P1001 | 5.455 | 19.218 | 16.215 | 1.00 29.97 | P |
| ATOM | 3141 | O1 | PLA | P1001 | 4.329 | 19.881 | 15.839 | 1.00 27.77 | P |
| ATOM | 3142 | C4 | PLA | P1001 | 5.419 | 17.867 | 16.622 | 1.00 27.79 | P |
| ATOM | 3143 | C5 | PLA | P1001 | 6.617 | 17.226 | 17.060 | 1.00 24.04 | P |
| ATOM | 3144 | C6 | PLA | P1001 | 7.890 | 17.875 | 17.105 | 1.00 28.93 | P |
| ATOM | 3145 | CL1 | PLA | P1001 | 8.958 | 17.179 | 17.619 | 1.00 13.83 | P |
| ATOM | 3146 | OS4 | PLA | P1002 | -1.265 | 32.010 | 14.293 | 1.00 40.73 | P |
| ATOM | 3147 | S2 | PLA | P1002 | -2.593 | 31.401 | 14.907 | 1.00 34.43 | P |
| ATOM | 3148 | OS5 | PLA | P1002 | -3.293 | 32.318 | 16.225 | 1.00 36.70 | P |
| ATOM | 3149 | OS6 | PLA | P1002 | -3.702 | 31.417 | 13.545 | 1.00 38.28 | P |
| ATOM | 3150 | C15 | PLA | P1002 | -2.360 | 29.762 | 15.366 | 1.00 37.51 | P |
| ATOM | 3151 | C14 | PLA | P1002 | -1.339 | 29.023 | 14.693 | 1.00 32.35 | P |
| ATOM | 3152 | C16 | PLA | P1002 | -3.324 | 29.136 | 16.198 | 1.00 32.13 | P |
| ATOM | 3153 | C10 | PLA | P1002 | -3.227 | 27.770 | 16.534 | 1.00 32.57 | P |
| ATOM | 3154 | C11 | PLA | P1002 | -2.159 | 26.968 | 15.824 | 1.00 27.55 | P |
| ATOM | 3155 | C13 | PLA | P1002 | -1.219 | 27.623 | 14.849 | 1.00 32.76 | P |
| ATOM | 3156 | O3 | PLA | P1002 | -0.300 | 26.897 | 14.135 | 1.00 26.73 | P |
| ATOM | 3157 | C12 | PLA | P1002 | -2.103 | 25.533 | 16.170 | 1.00 29.76 | P |
| ATOM | 3158 | O2 | PLA | P1002 | -1.093 | 24.861 | 15.620 | 1.00 19.01 | P |
| ATOM | 3159 | C9 | PLA | P1002 | -4.076 | 27.177 | 17.503 | 1.00 28.28 | P |
| ATOM | 3160 | C8 | PLA | P1002 | -4.072 | 25.777 | 17.756 | 1.00 30.57 | P |
| ATOM | 3161 | S1 | PLA | P1002 | -4.937 | 25.049 | 19.065 | 1.00 30.09 | P |
| ATOM | 3162 | OS3 | PLA | P1002 | -6.417 | 25.925 | 19.382 | 1.00 26.32 | P |
| ATOM | 3163 | OS2 | PLA | P1002 | -3.886 | 25.328 | 20.444 | 1.00 39.20 | P |
| ATOM | 3164 | OS1 | PLA | P1002 | -5.060 | 23.483 | 18.960 | 1.00 35.43 | P |
| ATOM | 3165 | C7 | PLA | P1002 | -3.056 | 24.884 | 17.116 | 1.00 30.01 | P |
| ATOM | 3166 | N2 | PLA | P1002 | -2.942 | 23.547 | 17.510 | 1.00 30.83 | P |
| ATOM | 3167 | N1 | PLA | P1002 | -1.994 | 22.600 | 17.132 | 1.00 26.11 | P |
| ATOM | 3168 | C2 | PLA | P1002 | -2.109 | 21.347 | 17.777 | 1.00 33.57 | P |
| ATOM | 3169 | C1 | PLA | P1002 | -3.069 | 20.979 | 18.767 | 1.00 28.55 | P |
| ATOM | 3170 | C3 | PLA | P1002 | -1.126 | 20.289 | 17.352 | 1.00 32.70 | P |
| ATOM | 3171 | O1 | PLA | P1002 | -0.254 | 20.633 | 16.366 | 1.00 26.71 | P |
| ATOM | 3172 | C4 | PLA | P1002 | -1.181 | 19.011 | 17.978 | 1.00 35.63 | P |
| ATOM | 3173 | C5 | PLA | P1002 | -2.175 | 18.727 | 18.965 | 1.00 32.99 | P |
| ATOM | 3174 | C6 | PLA | P1002 | -3.137 | 19.696 | 19.364 | 1.00 34.82 | P |
| ATOM | 3175 | CL1 | PLA | P1002 | -4.110 | 19.418 | 20.286 | 1.00 26.50 | P |
| ATOM | 3176 | P | PO4 | I1000 | 31.378 | 36.578 | 34.442 | 1.00 7.30 | I |
| ATOM | 3177 | O1 | PO4 | I1000 | 30.121 | 37.237 | 34.900 | 1.00 8.97 | I |
| ATOM | 3178 | O2 | PO4 | I1000 | 32.276 | 37.583 | 33.795 | 1.00 6.24 | I |
| ATOM | 3179 | O3 | PO4 | I1000 | 31.043 | 35.497 | 33.462 | 1.00 6.45 | I |
| ATOM | 3180 | O4 | PO4 | I1000 | 32.089 | 35.965 | 35.624 | 1.00 7.79 | I |
| ATOM | 3181 | U | U | I1100 | 0.273 | 22.910 | 15.547 | 1.00 30.28 | I |
| ATOM | 3182 | U | U | I1101 | 4.450 | 22.112 | 14.520 | 1.00 29.14 | I |
| ATOM | 3183 | U | U | I1102 | 2.292 | 24.635 | 12.979 | 0.50 39.41 | I |
| ATOM | 3184 | NA | NA | I1200 | 37.019 | 13.768 | 54.963 | 1.00 21.53 | I |
| END | | | | | | | | | |

FIGURE 5 (continued)

ID NO: 1.

SEQUENCE LISTING

```
<160> NUMBER OF SEQ ID NOS: 11

<210> SEQ ID NO 1
<211> LENGTH: 376
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Asp or Ser
<220> FEATURE:
<221> NAME/KEY: MOD_RES
<222> LOCATION: (3)..(3)
<223> OTHER INFORMATION: Asn or Asp
<220> FEATURE:
<221> NAME/KEY: MOD_RES
<222> LOCATION: (11)..(11)
<223> OTHER INFORMATION: Gln or Glu
<220> FEATURE:
<221> NAME/KEY: MOD_RES
<222> LOCATION: (30)..(30)
<223> OTHER INFORMATION: Val or Thr
<220> FEATURE:
<221> NAME/KEY: MOD_RES
<222> LOCATION: (43)..(43)
<223> OTHER INFORMATION: Lys or Ser
<220> FEATURE:
<221> NAME/KEY: MOD_RES
<222> LOCATION: (50)..(50)
<223> OTHER INFORMATION: Asp or Asn
<220> FEATURE:
<221> NAME/KEY: MOD_RES
<222> LOCATION: (54)..(54)
<223> OTHER INFORMATION: Asn or Asp
<220> FEATURE:
<221> NAME/KEY: MOD_RES
<222> LOCATION: (67)..(67)
```

-continued

```
<223> OTHER INFORMATION: Thr or Ser
<220> FEATURE:
<221> NAME/KEY: MOD_RES
<222> LOCATION: (68)..(68)
<223> OTHER INFORMATION: Glu or Gln
<220> FEATURE:
<221> NAME/KEY: MOD_RES
<222> LOCATION: (75)..(75)
<223> OTHER INFORMATION: Asp or Asn
<220> FEATURE:
<221> NAME/KEY: MOD_RES
<222> LOCATION: (77)..(77)
<223> OTHER INFORMATION: Glu or Gln
<220> FEATURE:
<221> NAME/KEY: MOD_RES
<222> LOCATION: (85)..(85)
<223> OTHER INFORMATION: Gln or Glu
<220> FEATURE:
<221> NAME/KEY: MOD_RES
<222> LOCATION: (102)..(102)
<223> OTHER INFORMATION: Ala or Gly
<220> FEATURE:
<221> NAME/KEY: MOD_RES
<222> LOCATION: (122)..(122)
<223> OTHER INFORMATION: Asp or Asn
<220> FEATURE:
<221> NAME/KEY: MOD_RES
<222> LOCATION: (143)..(143)
<223> OTHER INFORMATION: Ser or Val
<220> FEATURE:
<221> NAME/KEY: MOD_RES
<222> LOCATION: (219)..(219)
<223> OTHER INFORMATION: Thr or Ser
<220> FEATURE:
<221> NAME/KEY: MOD_RES
<222> LOCATION: (224)..(224)
<223> OTHER INFORMATION: Asp or Asn
<220> FEATURE:
<221> NAME/KEY: MOD_RES
<222> LOCATION: (252)..(252)
<223> OTHER INFORMATION: Val or Ser
<220> FEATURE:
<221> NAME/KEY: MOD_RES
<222> LOCATION: (266)..(266)
<223> OTHER INFORMATION: Asp or Asn

<400> SEQUENCE: 1

Xaa Ile Xaa Gly Gly Gly Ala Thr Leu Pro Xaa Lys Leu Tyr Leu Thr
 1               5                  10                  15

Pro Asp Val Leu Thr Ala Gly Phe Ala Pro Tyr Ile Gly Xaa Gly Ser
             20                  25                  30

Gly Lys Gly Lys Ile Ala Phe Leu Glu Asn Xaa Tyr Asn Gln Phe Gly
         35                  40                  45

Thr Xaa Thr Thr Lys Xaa Val His Trp Ala Gly Ser Asp Ser Lys Leu
     50                  55                  60

Thr Ala Xaa Xaa Leu Ala Thr Tyr Ala Ala Xaa Lys Xaa Pro Gly Trp
65                  70                  75                  80

Gly Lys Leu Ile Xaa Val Pro Ser Val Ala Thr Ser Val Ala Ile Pro
                 85                  90                  95

Phe Arg Lys Ala Gly Xaa Asn Ala Val Asp Leu Ser Val Lys Glu Leu
            100                 105                 110

Cys Gly Val Phe Ser Gly Arg Ile Ala Xaa Trp Ser Gly Ile Thr Gly
        115                 120                 125

Ala Gly Arg Ser Gly Pro Ile Gln Val Val Tyr Arg Ala Glu Xaa Ser
    130                 135                 140

Gly Thr Thr Glu Leu Phe Thr Arg Phe Leu Asn Ala Lys Cys Thr Thr
145                 150                 155                 160

Gln Pro Gly Thr Phe Ala Val Thr Thr Val Phe Ala Asn Ser Tyr Ser
```

```
                        165                 170                 175
Leu Gly Leu Ser Pro Leu Ala Gly Ala Val Ala Ala Ile Gly Ser Val
                180                 185                 190
Gly Val Met Ala Ala Asp Asn Asp Val Thr Thr Ala Gln Gly Arg Ile
                195                 200                 205
Thr Tyr Ile Ser Pro Asp Phe Ala Ala Pro Xaa Leu Ala Gly Leu Xaa
                210                 215                 220
Asp Ala Thr Lys Val Ala Arg Thr Gly Lys Gly Ser Ser Ser Gly Gly
225                 230                 235                 240
Gly Ala Glu Gly Lys Ser Pro Ala Ala Asn Xaa Ser Ala Ala Ile
                245                 250                 255
Ser Val Val Pro Leu Pro Ala Ala Xaa Arg Gly Asp Pro Asn Val
                260                 265                 270
Trp Thr Pro Val Phe Gly Ala Val Thr Gly Gly Val Val Ala Tyr
                275                 280                 285
Pro Asp Ser Gly Tyr Pro Ile Leu Gly Phe Thr Asp Leu Ile Phe Ser
                290                 295                 300
Glu Cys Tyr Ala Asn Ala Thr Gln Thr Gly Gln Val Arg Asn Phe Phe
305                 310                 315                 320
Thr Lys His Tyr Gly Thr Ser Ala Asn Asp Asn Ala Ala Ile Gln Ala
                325                 330                 335
Asn Ala Phe Val Pro Leu Pro Ser Asn Trp Lys Ala Ala Val Arg Ala
                340                 345                 350
Ser Tyr Leu Thr Ala Ser Asn Ala Leu Ser Ile Gly Asp Ser Ala Val
                355                 360                 365
Cys Gly Gly Lys Gly Arg Pro Glu
                370                 375

<210> SEQ ID NO 2
<211> LENGTH: 376
<212> TYPE: PRT
<213> ORGANISM: Homo sapiens

<400> SEQUENCE: 2

Asp Ile Asn Gly Gly Ala Thr Leu Pro Gln Lys Leu Tyr Leu Thr
1               5                   10                  15
Pro Asp Val Leu Thr Ala Gly Phe Ala Pro Tyr Ile Gly Val Gly Ser
                20                  25                  30
Gly Lys Gly Lys Ile Ala Phe Leu Glu Asn Lys Tyr Asn Gln Phe Gly
                35                  40                  45
Thr Asp Thr Thr Lys Asn Val His Trp Ala Gly Ser Asp Ser Lys Leu
50                  55                  60
Thr Ala Thr Glu Leu Ala Thr Tyr Ala Ala Asp Lys Glu Pro Gly Trp
65                  70                  75                  80
Gly Lys Leu Ile Gln Val Pro Ser Val Ala Thr Ser Val Ala Ile Pro
                85                  90                  95
Phe Arg Lys Ala Gly Ala Asn Ala Val Asp Leu Ser Val Lys Glu Leu
                100                 105                 110
Cys Gly Val Phe Ser Gly Arg Ile Ala Asp Trp Ser Gly Ile Thr Gly
                115                 120                 125
Ala Gly Arg Ser Gly Pro Ile Gln Val Val Tyr Arg Ala Glu Ser Ser
                130                 135                 140
Gly Thr Thr Glu Leu Phe Thr Arg Phe Leu Asn Ala Lys Cys Thr Thr
145                 150                 155                 160
```

```
Gln Pro Gly Thr Phe Ala Val Thr Thr Val Phe Ala Asn Ser Tyr Ser
                165                 170                 175

Leu Gly Leu Ser Pro Leu Ala Gly Ala Val Ala Ala Ile Gly Ser Val
            180                 185                 190

Gly Val Met Ala Ala Asp Asn Asp Val Thr Thr Ala Gln Gly Arg Ile
        195                 200                 205

Thr Tyr Ile Ser Pro Asp Phe Ala Ala Pro Thr Leu Ala Gly Leu Asp
    210                 215                 220

Asp Ala Thr Lys Val Ala Arg Thr Gly Lys Gly Ser Ser Ser Gly Gly
225                 230                 235                 240

Gly Ala Glu Gly Lys Ser Pro Ala Ala Asn Val Ser Ala Ala Ile
                245                 250                 255

Ser Val Val Pro Leu Pro Ala Ala Ala Asp Arg Gly Asp Pro Asn Val
                260                 265                 270

Trp Thr Pro Val Phe Gly Ala Val Thr Gly Gly Val Val Ala Tyr
            275                 280                 285

Pro Asp Ser Gly Tyr Pro Ile Leu Gly Phe Thr Asp Leu Ile Phe Ser
        290                 295                 300

Glu Cys Tyr Ala Asn Ala Thr Gln Thr Gly Gln Val Arg Asn Phe Phe
305                 310                 315                 320

Thr Lys His Tyr Gly Thr Ser Ala Asn Asp Asn Ala Ala Ile Gln Ala
                325                 330                 335

Asn Ala Phe Val Pro Leu Pro Ser Asn Trp Lys Ala Ala Val Arg Ala
                340                 345                 350

Ser Tyr Leu Thr Ala Ser Asn Ala Leu Ser Ile Gly Asp Ser Ala Val
            355                 360                 365

Cys Gly Gly Lys Gly Arg Pro Glu
        370                 375

<210> SEQ ID NO 3
<211> LENGTH: 376
<212> TYPE: PRT
<213> ORGANISM: Homo sapiens

<400> SEQUENCE: 3

Ser Ile Asp Gly Gly Gly Ala Thr Leu Pro Glu Lys Leu Tyr Leu Thr
1               5                   10                  15

Pro Asp Val Leu Thr Ala Gly Phe Ala Pro Tyr Ile Gly Thr Gly Ser
            20                  25                  30

Gly Lys Gly Lys Ile Ala Phe Leu Glu Asn Ser Tyr Asn Gln Phe Gly
        35                  40                  45

Thr Asn Thr Thr Lys Asp Val His Trp Ala Gly Ser Asp Ser Lys Leu
    50                  55                  60

Thr Ala Ser Gln Leu Ala Thr Tyr Ala Ala Asn Lys Gln Pro Gly Trp
65                  70                  75                  80

Gly Lys Leu Ile Glu Val Pro Ser Val Ala Thr Ser Val Ala Ile Pro
                85                  90                  95

Phe Arg Lys Ala Gly Gly Asn Ala Val Asp Leu Ser Val Lys Glu Leu
            100                 105                 110

Cys Gly Val Phe Ser Gly Arg Ile Ala Asn Trp Ser Gly Ile Thr Gly
        115                 120                 125

Ala Gly Arg Ser Gly Pro Ile Gln Val Val Tyr Arg Ala Glu Val Ser
    130                 135                 140

Gly Thr Thr Glu Leu Phe Thr Arg Phe Leu Asn Ala Lys Cys Thr Thr
145                 150                 155                 160
```

```
Gln Pro Gly Thr Phe Ala Val Thr Thr Val Phe Ala Asn Ser Tyr Ser
            165                 170                 175

Leu Gly Leu Ser Pro Leu Ala Gly Ala Val Ala Ala Ile Gly Ser Val
            180                 185                 190

Gly Val Met Ala Ala Asp Asn Asp Val Thr Thr Ala Gln Gly Arg Ile
            195                 200                 205

Thr Tyr Ile Ser Pro Asp Phe Ala Ala Pro Ser Leu Ala Gly Leu Asn
            210                 215                 220

Asp Ala Thr Lys Val Ala Arg Thr Gly Lys Gly Ser Ser Gly Gly
225             230                 235                 240

Gly Ala Glu Gly Lys Ser Pro Ala Ala Asn Ser Ser Ala Ala Ile
                245                 250                 255

Ser Val Val Pro Leu Pro Ala Ala Asn Arg Gly Asp Pro Asn Val
            260                 265                 270

Trp Thr Pro Val Phe Gly Ala Val Thr Gly Gly Val Val Ala Tyr
            275                 280                 285

Pro Asp Ser Gly Tyr Pro Ile Leu Gly Phe Thr Asp Leu Ile Phe Ser
290             295                 300

Glu Cys Tyr Ala Asn Ala Thr Gln Thr Gly Gln Val Arg Asn Phe Phe
305             310                 315                 320

Thr Lys His Tyr Gly Thr Ser Ala Asn Asp Asn Ala Ala Ile Gln Ala
            325                 330                 335

Asn Ala Phe Val Pro Leu Pro Ser Asn Trp Lys Ala Val Arg Ala
                340                 345                 350

Ser Tyr Leu Thr Ala Ser Asn Ala Leu Ser Ile Gly Asp Ser Ala Val
            355                 360                 365

Cys Gly Gly Lys Gly Arg Pro Glu
            370                 375

<210> SEQ ID NO 4
<211> LENGTH: 355
<212> TYPE: PRT
<213> ORGANISM: Homo sapiens

<400> SEQUENCE: 4

Met Ala Lys Leu Ile Ala Leu Thr Leu Leu Gly Met Gly Leu Ala Leu
1               5                   10                  15

Phe Arg Asn His Gln Ser Ser Tyr Gln Thr Arg Leu Asn Ala Leu Arg
                20                  25                  30

Glu Val Gln Pro Val Glu Leu Pro Asn Cys Asn Leu Val Lys Gly Ile
            35                  40                  45

Glu Thr Gly Ser Glu Asp Met Glu Ile Leu Pro Asn Gly Leu Ala Phe
        50                  55                  60

Ile Ser Ser Gly Leu Lys Tyr Pro Gly Ile Lys Ser Phe Asn Pro Asn
65              70                  75                  80

Ser Pro Gly Lys Ile Leu Leu Met Asp Leu Asn Glu Glu Asp Pro Thr
                85                  90                  95

Val Leu Glu Leu Gly Ile Thr Gly Ser Lys Phe Asp Val Ser Ser Phe
            100                 105                 110

Asn Pro His Gly Ile Ser Thr Phe Thr Asp Glu Asp Asn Ala Met Tyr
        115                 120                 125

Leu Leu Val Val Asn His Pro Asp Ala Lys Ser Thr Val Glu Leu Phe
    130                 135                 140

Lys Phe Gln Glu Glu Glu Lys Ser Leu Leu His Leu Lys Thr Ile Arg
```

```
                145                 150                 155                 160
        His Lys Leu Leu Pro Asn Leu Asn Asp Ile Val Ala Val Gly Pro Glu
                        165                 170                 175

His Phe Tyr Gly Thr Asn Asp His Tyr Phe Leu Asp Pro Tyr Leu Gln
                        180                 185                 190

Ser Trp Glu Met Tyr Leu Gly Leu Ala Trp Ser Tyr Val Tyr Tyr
                        195                 200                 205

Ser Pro Ser Glu Val Arg Val Val Ala Glu Gly Phe Asp Phe Ala Asn
                        210                 215                 220

Gly Ile Asn Ile Ser Pro Asp Gly Lys Tyr Val Tyr Ile Ala Glu Leu
        225                 230                 235                 240

Leu Ala His Lys Ile His Val Tyr Glu Lys His Ala Asn Trp Thr Leu
                        245                 250                 255

Thr Pro Leu Lys Ser Leu Asp Phe Asn Thr Leu Val Asp Asn Ile Ser
                        260                 265                 270

Val Asp Pro Glu Thr Gly Asp Leu Trp Val Gly Cys His Pro Asn Gly
                        275                 280                 285

Met Lys Ile Phe Phe Tyr Asp Ser Glu Asn Pro Pro Ala Ser Glu Val
                        290                 295                 300

Leu Arg Ile Gln Asn Ile Leu Thr Glu Glu Pro Lys Val Thr Gln Val
        305                 310                 315                 320

Tyr Ala Glu Asn Gly Thr Val Leu Gln Gly Ser Thr Val Ala Ser Val
                        325                 330                 335

Tyr Lys Gly Lys Leu Leu Ile Gly Thr Val Phe His Lys Ala Leu Tyr
                        340                 345                 350

Cys Glu Leu
                355

<210> SEQ ID NO 5
<211> LENGTH: 354
<212> TYPE: PRT
<213> ORGANISM: Homo sapiens

<400> SEQUENCE: 5

Met Gly Ala Trp Val Gly Cys Gly Leu Ala Gly Asp Arg Ala Gly Phe
1               5                   10                  15

Leu Gly Glu Arg Leu Leu Ala Leu Arg Asn Arg Leu Lys Ala Ser Arg
                20                  25                  30

Glu Val Glu Ser Val Asp Leu Pro His Cys His Leu Ile Lys Gly Ile
                35                  40                  45

Glu Ala Gly Ser Glu Asp Ile Asp Ile Leu Pro Asn Gly Leu Ala Phe
        50                  55                  60

Phe Ser Val Gly Leu Lys Phe Pro Gly Leu His Ser Phe Ala Pro Asp
65                  70                  75                  80

Lys Pro Gly Gly Ile Leu Met Met Asp Leu Lys Glu Lys Pro Arg
                85                  90                  95

Ala Arg Glu Leu Arg Ile Ser Arg Gly Phe Asp Leu Ala Ser Phe Asn
                100                 105                 110

Pro His Gly Ile Ser Thr Phe Ile Asp Asn Asp Asp Thr Val Tyr Leu
                115                 120                 125

Phe Val Val Asn His Pro Glu Phe Lys Asn Thr Val Glu Ile Phe Lys
        130                 135                 140

Phe Glu Glu Ala Glu Asn Ser Leu Leu His Leu Lys Thr Val Lys His
145                 150                 155                 160
```

```
Glu Leu Leu Pro Ser Val Asn Asp Ile Thr Ala Val Gly Pro Ala His
            165                 170                 175
Phe Tyr Ala Thr Asn Asp His Tyr Phe Ser Asp Pro Phe Leu Lys Tyr
            180                 185                 190
Leu Glu Thr Tyr Leu Asn Leu His Trp Ala Asn Val Val Tyr Tyr Ser
            195                 200                 205
Pro Asn Glu Val Lys Val Val Ala Glu Gly Phe Asp Ser Ala Asn Gly
            210                 215                 220
Ile Asn Ile Ser Pro Asp Asp Lys Tyr Ile Tyr Val Ala Asp Ile Leu
225                 230                 235                 240
Ala His Glu Ile His Val Leu Glu Lys His Thr Asn Met Asn Leu Thr
            245                 250                 255
Gln Leu Lys Val Leu Glu Leu Asp Thr Leu Val Asp Asn Leu Ser Ile
            260                 265                 270
Asp Pro Ser Ser Gly Asp Ile Trp Val Gly Cys His Pro Asn Gly Gln
            275                 280                 285
Lys Leu Phe Val Tyr Asp Pro Asn Asn Pro Ser Ser Glu Val Leu
            290                 295                 300
Arg Ile Gln Asn Ile Leu Cys Glu Lys Pro Thr Val Thr Thr Val Tyr
305                 310                 315                 320
Ala Asn Asn Gly Ser Val Leu Gln Gly Ser Ser Val Ala Ser Val Tyr
            325                 330                 335
Asp Gly Lys Leu Leu Ile Gly Thr Leu Tyr His Arg Ala Leu Tyr Cys
            340                 345                 350
Glu Leu

<210> SEQ ID NO 6
<211> LENGTH: 354
<212> TYPE: PRT
<213> ORGANISM: Homo sapiens

<400> SEQUENCE: 6

Met Gly Lys Leu Val Ala Leu Val Leu Leu Gly Val Gly Leu Ser Leu
1               5                   10                  15
Val Gly Glu Met Phe Leu Ala Phe Arg Glu Arg Val Asn Ala Ser Arg
            20                  25                  30
Glu Val Glu Pro Val Glu Pro Glu Asn Cys His Leu Ile Glu Glu Leu
            35                  40                  45
Glu Ser Gly Ser Glu Asp Ile Asp Ile Leu Pro Ser Gly Leu Ala Phe
            50                  55                  60
Ile Ser Ser Gly Leu Lys Tyr Pro Gly Met Pro Asn Phe Ala Pro Asp
65                  70                  75                  80
Glu Pro Gly Lys Ile Phe Leu Met Asp Leu Asn Glu Gln Asn Pro Arg
            85                  90                  95
Ala Gln Ala Leu Glu Ile Ser Gly Gly Phe Asp Lys Glu Leu Phe Asn
            100                 105                 110
Pro His Gly Ile Ser Ile Phe Ile Asp Lys Asp Asn Thr Val Tyr Leu
            115                 120                 125
Tyr Val Val Asn His Pro His Met Lys Ser Thr Val Glu Ile Phe Lys
130                 135                 140
Phe Glu Glu Gln Gln Arg Ser Leu Val Tyr Leu Lys Thr Ile Lys His
145                 150                 155                 160
Glu Leu Leu Lys Ser Val Asn Asp Ile Val Val Leu Gly Pro Glu Gln
            165                 170                 175
```

```
Phe Tyr Ala Thr Arg Asp His Tyr Phe Thr Asn Ser Leu Leu Ser Phe
            180                 185                 190

Phe Glu Met Ile Leu Asp Leu Arg Trp Thr Tyr Val Leu Phe Tyr Ser
            195                 200                 205

Pro Arg Glu Val Lys Val Val Ala Lys Gly Phe Cys Ser Ala Asn Gly
            210                 215                 220

Ile Thr Val Ser Ala Asp Gln Lys Tyr Val Tyr Val Ala Asp Val Ala
225                 230                 235                 240

Ala Lys Asn Ile His Ile Met Glu Lys His Asp Asn Trp Asp Leu Thr
            245                 250                 255

Gln Leu Lys Val Ile Gln Leu Gly Thr Leu Val Asp Asn Leu Thr Val
            260                 265                 270

Asp Pro Ala Thr Gly Asp Ile Leu Ala Gly Cys His Pro Asn Pro Met
            275                 280                 285

Lys Leu Leu Asn Tyr Asn Pro Glu Asp Pro Pro Gly Ser Glu Val Leu
            290                 295                 300

Arg Ile Gln Asn Val Leu Ser Glu Lys Pro Arg Val Ser Thr Val Tyr
305                 310                 315                 320

Ala Asn Asn Gly Ser Val Leu Gln Gly Thr Ser Val Ala Ser Val Tyr
            325                 330                 335

His Gly Lys Ile Leu Ile Gly Thr Val Phe His Lys Thr Leu Tyr Cys
            340                 345                 350

Glu Leu

<210> SEQ ID NO 7
<211> LENGTH: 359
<212> TYPE: PRT
<213> ORGANISM: Oryctolagus cuniculus

<400> SEQUENCE: 7

Met Ala Lys Leu Thr Ala Leu Thr Leu Gly Leu Gly Leu Ala Leu
1               5                   10                  15

Phe Asp Gly Gln Lys Ser Ser Phe Gln Thr Arg Phe Asn Val His Arg
            20                  25                  30

Glu Val Thr Pro Val Glu Leu Pro Asn Cys Asn Leu Val Lys Gly Ile
            35                  40                  45

Asp Asn Gly Ser Glu Asp Leu Glu Ile Leu Pro Asn Gly Leu Ala Phe
        50                  55                  60

Ile Ser Ala Gly Leu Lys Tyr Pro Gly Ile Met Ser Phe Asp Pro Asp
65                  70                  75                  80

Lys Pro Gly Lys Ile Leu Leu Met Asp Leu Asn Glu Lys Asp Pro Val
            85                  90                  95

Val Leu Glu Leu Ser Ile Thr Gly Ser Thr Phe Asp Leu Ser Ser Phe
            100                 105                 110

Asn Pro His Gly Ile Ser Thr Phe Thr Asp Glu Asp Asn Ile Val Tyr
            115                 120                 125

Leu Met Val Val Asn His Pro Asp Ser Lys Ser Thr Val Glu Leu Phe
130                 135                 140

Lys Phe Gln Glu Lys Glu Lys Ser Leu Leu His Leu Lys Thr Ile Arg
145                 150                 155                 160

His Lys Leu Leu Pro Ser Val Asn Asp Ile Val Ala Val Gly Pro Glu
            165                 170                 175

His Phe Tyr Ala Thr Asn Asp His Tyr Phe Ile Asp Pro Tyr Leu Lys
            180                 185                 190
```

```
Ser Trp Glu Met His Leu Gly Leu Ala Trp Ser Phe Val Thr Tyr Tyr
    195                 200                 205

Ser Pro Asn Asp Val Arg Val Val Ala Glu Gly Phe Asp Phe Ala Asn
210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asn Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Ala Ser Glu Val
    290                 295                 300

Leu Arg Ile Gln Asp Ile Leu Ser Lys Glu Pro Lys Val Thr Val Ala
305                 310                 315                 320

Tyr Ala Glu Asn Gly Thr Val Leu Gln Gly Ser Thr Val Ala Ala Val
                325                 330                 335

Tyr Lys Gly Lys Met Leu Val Gly Thr Val Phe His Lys Ala Leu Tyr
            340                 345                 350

Cys Glu Leu Ser Gln Ala Asn
        355

<210> SEQ ID NO 8
<211> LENGTH: 355
<212> TYPE: PRT
<213> ORGANISM: Rattus rattus

<400> SEQUENCE: 8

Met Ala Lys Leu Leu Gly Leu Thr Leu Val Gly Leu Val Leu Ala Leu
1               5                   10                  15

Tyr Lys Asn His Arg Ser Ser Tyr Gln Thr Arg Leu Asn Ala Phe Arg
                20                  25                  30

Glu Val Thr Pro Val Asp Leu Pro Asn Cys Thr Leu Val Lys Gly Ile
            35                  40                  45

Glu Ala Gly Ala Glu Asp Leu Glu Ile Leu Pro Asn Gly Leu Thr Phe
50                  55                  60

Phe Ser Thr Phe Leu Lys Tyr Pro Gly Ile Lys Ser Phe Asp Pro Ser
65                  70                  75                  80

Lys Pro Gly Lys Ile Leu Leu Met Asp Leu Asn Glu Lys Glu Pro Ala
                85                  90                  95

Val Ser Glu Leu Ala Ile Met Gly Asn Thr Leu Asp Met Ser Ser Phe
            100                 105                 110

Asn Pro His Gly Ile Ser Thr Phe Ile Asp Glu Asp Asn Thr Val Tyr
        115                 120                 125

Leu Leu Val Val Ser His Pro Asp Ser Ser Thr Val Glu Val Phe
    130                 135                 140

Lys Phe Gln Glu Glu Arg Ser Leu Leu His Leu Lys Thr Ile Thr
145                 150                 155                 160

His Glu Leu Leu Pro Ser Ile Asn Asp Ile Ala Ala Val Gly Pro Glu
                165                 170                 175

Ser Phe Tyr Ala Thr Asn Asp His Tyr Phe Ala Asp Pro Tyr Leu Arg
            180                 185                 190

Ser Trp Glu Met Tyr Leu Gly Leu Ser Trp Ser Asn Val Val Tyr Tyr
        195                 200                 205
```

```
Ser Pro Asp Lys Val Arg Val Ala Asp Gly Phe Asp Phe Ala Asn
    210                 215                 220

Gly Ile Gly Ile Ser Leu Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Val Leu Ser Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Phe Tyr Asp Ser Glu Asn Pro Pro Gly Ser Glu Val
    290                 295                 300

Leu Arg Ile Gln Ser Ile Leu Ser Glu Asp Pro Lys Val Thr Val Val
305                 310                 315                 320

Tyr Ala Glu Asn Gly Thr Val Leu Gln Gly Thr Thr Val Ala Ala Val
                325                 330                 335

Tyr Lys Gly Lys Leu Leu Ile Gly Thr Val Phe His Arg Ala Leu Cys
            340                 345                 350

Cys Tyr Leu
        355

<210> SEQ ID NO 9
<211> LENGTH: 355
<212> TYPE: PRT
<213> ORGANISM: Mus musculus

<400> SEQUENCE: 9

Met Ala Lys Leu Leu Ala Leu Thr Leu Val Gly Leu Val Leu Ala Leu
1               5                   10                  15

Tyr Lys Asn His Arg Ser Ser Tyr Gln Thr Arg Leu Asn Ala Phe Arg
                20                  25                  30

Glu Val Thr Pro Val Glu Leu Pro Asn Cys Asn Leu Val Lys Gly Ile
            35                  40                  45

Glu Thr Gly Ala Glu Asp Leu Glu Ile Leu Pro Asn Gly Leu Thr Phe
        50                  55                  60

Phe Ser Thr Gly Leu Lys Tyr Pro Gly Ile Lys Ser Phe Asp Pro Ser
65                  70                  75                  80

Lys Pro Gly Lys Ile Leu Leu Met Asp Leu Asn Lys Lys Glu Pro Ala
                85                  90                  95

Val Ser Glu Leu Glu Ile Ile Gly Asn Thr Leu Asp Ile Ser Ser Phe
            100                 105                 110

Asn Pro His Gly Ile Ser Thr Phe Thr Asp Glu Asp Asn Thr Val Tyr
        115                 120                 125

Leu Leu Val Val Asn His Pro Asp Ser Ser Ser Thr Val Glu Val Phe
    130                 135                 140

Lys Phe Gln Glu Glu Glu Arg Ser Leu Leu His Leu Lys Thr Ile Thr
145                 150                 155                 160

His Glu Leu Leu Pro Ser Ile Asn Asp Ile Ala Ala Ile Gly Pro Glu
                165                 170                 175

Ser Phe Tyr Ala Thr Asn Asp His Tyr Phe Ala Asp Pro Tyr Leu Arg
            180                 185                 190

Ser Trp Glu Met Tyr Leu Gly Leu Ser Trp Ser Asn Val Val Tyr Tyr
        195                 200                 205

Ser Pro Asp Lys Val Gln Val Val Ala Glu Gly Phe Asp Phe Ala Asn
```

```
                210                 215                 220
Gly Ile Gly Ile Ser Leu Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Val Leu Asn Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Phe Tyr Asp Ala Glu Asn Pro Pro Gly Ser Glu Val
290                 295                 300

Leu Arg Ile Gln Asn Ile Leu Ser Glu Asp Pro Lys Ile Thr Val Val
305                 310                 315                 320

Tyr Ala Glu Asn Gly Thr Val Leu Gln Gly Thr Thr Val Ala Ser Val
                325                 330                 335

Tyr Lys Gly Lys Leu Leu Ile Gly Thr Val Phe His Lys Ala Leu Tyr
            340                 345                 350

Cys Asp Leu
        355

<210> SEQ ID NO 10
<211> LENGTH: 354
<212> TYPE: PRT
<213> ORGANISM: Mus musculus

<400> SEQUENCE: 10

Met Gly Arg Met Val Ala Leu Gly Phe Ala Gly His Arg Val Ala Leu
1               5                   10                  15

Leu Gly Glu Arg Phe Leu Ala Leu Ser Ser Arg Leu Lys Gly Ser Arg
                20                  25                  30

Glu Val Glu Ser Val Asp Leu Pro Asn Cys His Leu Ile Lys Gly Ile
            35                  40                  45

Glu Thr Gly Ala Glu Asp Ile Asp Ile Leu Pro Asn Gly Leu Ala Phe
        50                  55                  60

Phe Ser Val Gly Leu Lys Phe Pro Gly Leu His Ser Phe Ala Pro Asp
65                  70                  75                  80

Lys Pro Gly Gly Ile Leu Met Met Asp Leu Asp Glu Arg Pro Pro Ser
                85                  90                  95

Leu Glu Glu Leu Arg Val Ser Trp Gly Phe Asp Leu Ala Ser Phe Asn
                100                 105                 110

Pro His Gly Ile Ser Thr Phe Ile Asp Asp Asp Thr Val Tyr Leu
            115                 120                 125

Phe Val Val Asn His Pro Gln Phe Ser Asn Thr Val Glu Ile Phe Lys
        130                 135                 140

Phe Gln Glu Ala Glu Asn Ser Leu Leu His Leu Lys Thr Ile Lys His
145                 150                 155                 160

Glu Leu Leu Pro Ser Val Asn Asp Ile Ile Ala Val Gly Pro Ala His
                165                 170                 175

Phe Tyr Ala Thr Asn Asp His Tyr Phe Ser Asp Pro Phe Leu Lys Tyr
            180                 185                 190

Leu Glu Thr Tyr Leu Asn Leu His Trp Ala Asn Val Val Tyr Tyr Ser
        195                 200                 205

Pro Glu Glu Val Lys Leu Val Ala Glu Gly Phe Asp Ser Ala Asn Gly
    210                 215                 220
```

```
Ile Asn Ile Ser Pro Asp Lys Lys Tyr Val Tyr Val Ala Asp Ile Leu
225                 230                 235                 240

Ala His Glu Ile His Val Leu Glu Lys Gln Pro Asn Met Asn Leu Thr
            245                 250                 255

Gln Leu Lys Val Leu Gln Leu Gly Thr Leu Val Asp Asn Leu Ser Ile
                260                 265                 270

Asp Pro Ser Ser Gly Asp Ile Trp Val Gly Cys His Pro Asn Gly Gln
        275                 280                 285

Arg Leu Phe Val Tyr His Pro Asn His Pro Pro Thr Ser Glu Val Leu
        290                 295                 300

Arg Ile Gln Asn Ile Leu Ser Glu Lys Pro Ser Val Thr Thr Val Tyr
305                 310                 315                 320

Ile Asn Asn Gly Ser Val Leu Gln Gly Ser Ser Val Ala Thr Ile Tyr
                325                 330                 335

Asp Arg Lys Leu Leu Val Gly Thr Leu Tyr Gln Lys Ala Leu Tyr Cys
            340                 345                 350

Glu Leu

<210> SEQ ID NO 11
<211> LENGTH: 354
<212> TYPE: PRT
<213> ORGANISM: Mus musculus

<400> SEQUENCE: 11

Met Gly Lys Leu Val Ala Leu Thr Leu Leu Gly Ala Cys Leu Ala Leu
1               5                   10                  15

Ile Gly Glu Arg Leu Leu Asn Phe Arg Glu Arg Val Ser Thr Thr Arg
                20                  25                  30

Glu Ile Lys Ala Thr Glu Pro Gln Asn Cys His Leu Ile Glu Gly Leu
            35                  40                  45

Glu Asn Gly Ser Glu Asp Ile Asp Ile Leu Pro Ser Gly Leu Ala Phe
        50                  55                  60

Ile Ser Thr Gly Leu Lys Tyr Pro Gly Met Pro Ala Phe Ala Pro Asp
65                  70                  75                  80

Lys Pro Gly Arg Ile Phe Leu Met Asp Leu Asn Glu Gln Asn Pro Glu
                85                  90                  95

Ala Gln Ala Leu Glu Ile Ser Gly Gly Leu Asp Gln Glu Ser Leu Asn
            100                 105                 110

Pro His Gly Ile Ser Thr Phe Ile Asp Lys Asp Asn Thr Ala Tyr Leu
        115                 120                 125

Tyr Val Val Asn His Pro Asn Met Asp Ser Thr Val Glu Ile Phe Lys
130                 135                 140

Phe Glu Glu Gln Gln Arg Ser Leu Ile His Leu Lys Thr Leu Lys His
145                 150                 155                 160

Glu Leu Leu Lys Ser Val Asn Asp Ile Val Leu Gly Pro Glu Gln
                165                 170                 175

Phe Tyr Ala Thr Arg Asp His Tyr Phe Thr Ser Tyr Phe Leu Val Leu
            180                 185                 190

Leu Glu Met Ile Leu Asp Pro His Trp Thr Ser Val Val Phe Tyr Ser
        195                 200                 205

Pro Lys Glu Val Lys Val Ala Gln Gly Phe Ser Ser Ala Asn Gly
        210                 215                 220

Ile Thr Val Ser Leu Asp Gln Lys Phe Val Tyr Val Ala Asp Val Thr
225                 230                 235                 240
```

-continued

```
Ala Lys Asn Ile His Ile Met Lys Lys His Asp Asn Trp Asp Leu Thr
            245             250             255
Pro Val Lys Val Ile Gln Leu Gly Thr Leu Val Asp Asn Leu Thr Val
            260             265             270
Asp Pro Ala Thr Gly Asp Ile Leu Ala Gly Cys His Pro Asn Pro Met
            275             280             285
Lys Leu Leu Ile Tyr Asn Pro Glu Asp Pro Pro Gly Ser Glu Val Leu
        290             295             300
Arg Ile Gln Asp Ser Leu Ser Asp Lys Pro Arg Val Ser Thr Leu Tyr
305             310             315             320
Ala Asn Asn Gly Ser Val Leu Gln Gly Ser Thr Val Ala Ser Val Tyr
                325             330             335
His Lys Arg Met Leu Ile Gly Thr Ile Phe His Lys Ala Leu Tyr Cys
            340             345             350
Asp Leu
```

PHOSPHATE-BINDING PROTEIN, PHARMACEUTICAL COMPOSITIONS CONTAINING SAME AND USE THEREOF

A subject of the present invention is a novel phosphate-binding protein, obtained from human serum, pharmaceutical compositions containing it as well as uses thereof, in particular within the framework of the treatment of hyperphosphataemia and cardiovascular diseases or arthritis.

Phosphate is a very important molecule involved in numerous biological mechanisms. Phosphate is found in particular in the phospholipids, in the energy-production mechanism (ATP, ADP), in the cell signalling processes and in the composition of the genetic material in the bones (in the form of calcium phosphate).

Hyperphosphataemia is a pathology linked to an excess of phosphate in the organism and causes in particular an increase in the risks of cardiovascular diseases, by promoting the processes of atherosclerosis and calcification of the arteries (Dorozhkin and Epple, 2002; Amann et al., 2003; Blazheevich et al., 1975). As calcification takes place in the joints, hyperphosphataemia can also cause arthritis (pseudogout).

The calcium phosphate salts produced in the serum during hyperphosphataemia precipitate in the soft tissues with ectopic calcification in different tissues: vessels (cerebral or cardio vascular accidents), joints (pseudogout), lens, renal interstitium (nephrocalcinosis), sub-cutaneous (pruritis), pulmonary, and pancreatic.

Thus, half the deaths of individuals suffering from renal insufficiency is due to cardiovascular diseases linked to hyperphosphataemia. In this regard, certain phosphate chelating agents which complex the phosphate in the intestinal lumen are currently used as medicaments. However, not all these chelating agents are physiological. This results in certain complications or restrictions as to their use.

Preparations containing magnesium are limited by the appearance of digestive disorders (diarrhoea) and are to be proscribed because of the risk of hypermagnesaemia. Similarly, the prescription of aluminium hydroxide, long used because of its effectiveness, must be avoided, or at least limited to very short periods, because of the risk of aluminium intoxication (microcytic hypochromic anaemia, osteomalacia, myopathy, dementia).

The prescription of calcium salts is the best means for correcting both hypocalcaemia and hyperphosphoraemia, making it possible on the one hand to increase the quantity of calcium absorbed by the small intestine in spite of the calcitriol deficiency, and on the other hand to complex the phosphorus in the intestinal lumen in the form of calcium phosphate which is eliminated in the faeces. However, the major drawback of the chelating agents containing calcium is that of inducing hypercalcaemia, which, in certain series, has been noted in 20% of patients. This risk has lead to the development of other products capable of limiting hyperphosphoraemia.

The medicament most used at present is Renagel® (Ramsdell; 1999). This is a non-absorbable cationic polymer, capable of chelating phosphate.

The purpose of the present invention is to provide a novel physiological protein chelating agent binding to phosphate, not requiring the use of other ions which can lead to complications and offering wider use perspectives than current chelating agents.

The present invention relates to a protein characterized in that it comprises or is constituted by:
the sequence SEQ ID NO: 1,
or any sequence derived from the sequence SEQ ID NO: 1, in particular by substitution, suppression or addition of one or more amino acids, providing that said derived sequence binds to phosphate,
or any sequence homologous to the sequence SEQ ID NO: 1, preferably having a homology of at least approximately 80% with the sequence SEQ ID NO: 1, providing that said homologous sequence binds to phosphate,
or any fragment of one of the sequences defined above, providing that said fragment binds to phosphate, in particular any fragment being constituted by at least approximately 20 contiguous amino acids in the sequence SEQ ID NO: 1.

The present invention relates to a protein as defined above, characterized in that it comprises or is constituted by:
the sequence SEQ ID NO: 2 or the sequence SEQ ID NO: 3,
or any sequence derived from the sequence SEQ ID NO: 2 or SEQ ID NO: 3, in particular by substitution, suppression or addition of one or more amino acids, providing that said derived sequence binds to phosphate,
or any sequence homologous to the sequence SEQ ID NO: 2 or SEQ ID NO: 3, preferably having a homology of at least approximately 80% with the sequence SEQ ID NO: 2 or SEQ ID NO: 3, providing that said homologous sequence binds to phosphate,
or any fragment of one of the sequences defined above, providing that said fragment binds to phosphate, in particular any fragment being constituted by at least approximately 20 contiguous amino acids in the sequence SEQ ID NO: 2 or SEQ ID NO: 3.

The sequence SEQ ID NO: 2 corresponds to the human phosphate-binding protein. This novel protein has been isolated in human plasma and its three-dimensional structure shows that it belongs to the "phosphate binding protein" (PBP) class. It is also called hereafter HPBP (human phosphate binding protein).

The sequence SEQ ID NO: 3 corresponds to a protein homologous to the protein sequence SEQ ID NO: 2, having a percentage of identity of approximately 90% with the sequence SEQ ID NO: 2, and having the same phosphate-binding properties as the sequence SEQ ID NO: 2.

The phosphate-binding property of the sequences of the invention can be verified by the following phosphate-binding test by radioactive labelling:

The protein is bound to a nitrocellulose membrane (dot blot by aspiration). The membrane is left to incubate in a radioactive buffer ($^{32}P$ (10 mCi/ml, Amersham-Biosciences) 2M; Tris 50 mM; pH 8.0)

The membrane is rapidly rinsed 2×1 min in a Tris 50 mM buffer, pH 8.0. By exposing a photographic film with the membrane (approximately 45 min) it is possible to detect the zones which bind the radioactive phosphate (see FIG. 3 hereafter).

The present invention also relates to a nucleotide sequence encoding a protein as defined above.

The present invention also relates to a recombinant vector, in particular plasmid, cosmid, phage or virus DNA, containing a nucleotide sequence as defined above.

According to an advantageous embodiment, the present invention relates to a recombinant vector as defined above, containing the elements necessary for the expression in a host cell of the polypeptides encoded by the nucleotide sequence as defined above, inserted into said vector.

The present invention also relates to a host cell, chosen in particular from bacteria, viruses, yeasts, fungi, plants or mammal cells, said host cell being transformed, in particular using a recombinant vector as defined above.

The present invention also relates to a pharmaceutical composition comprising as active ingredient a protein as defined above, in particular SEQ ID NO: 2 or SEQ ID NO: 3, in combination with a pharmaceutically acceptable vehicle.

The present invention also relates to a pharmaceutical composition as defined above, in which the protein of the invention, in particular SEQ ID NO: 2 or SEQ ID NO: 3, is in combination with a variant of the paraoxonase protein, having a paraoxon hydrolysis activity.

Among the variants of paraoxonase, there can be mentioned the variants PON1, PON2, PON3, of human or non-human origin, such as SEQ ID NO: 4 (human PON1; Hassett et al. 1991), SEQ ID NO: 5 (human PON2; Primo-Parmo et al., 1996), SEQ ID NO: 6 (human PON3; Reddy et al., 2001), SEQ ID NO: 7 (rabbit PON1; Hassett et al., 1991), SEQ ID NO: 8 (rat PON1; Rodrigo et al., 1997), SEQ ID NO: 9 (mouse PON1; Sorenson et al., 1995), SEQ ID NO: 10 (mouse PON2; Primo-Parmo et al., 1996) and SEQ ID NO: 11 (mouse PON3; Primo-Parmo et al., 1996).

The present invention also relates to the use of a protein as defined above, in particular SEQ ID NO: 2 or SEQ ID NO: 3, for the preparation of a medicament intended for the prevention or treatment of diseases linked to hyperphosphataemia, such as cardiovascular diseases and arthritis (pseudogout).

The term "hyperphosphataemia" designates an excess of phosphate in the organism. More precisely, hyperphosphataemia is defined by an increase in the phosphate concentration in the plasma above 1.44 mmol/l (45 mg/l), said quantity being obtained by assay of the total phosphate (assay by colorimetric method is carried out after a mineralization process).

According to an advantageous embodiment, the protein of the invention can be administered in intravenous form in order to be able to bind a maximum quantity of phosphate over a long period, of the order of a week. By subsequently eliminating the protein, a large quantity of phosphate is thus rapidly eliminated. This makes it possible to space out and reduce the periods of dialysis.

The present invention relates more particularly to the use of a protein as defined above, in particular SEQ ID NO: 2 or SEQ ID NO: 3, within the framework of the prevention or treatment of cardiovascular diseases.

The present invention also relates to the use of a protein according to the invention, in particular of the protein represented by the sequence SEQ ID NO: 2 or SEQ ID NO: 3, in combination with a protein such as a variant of the paraoxonase protein, within the framework of the prophylaxis or treatment of intoxications caused by insecticides or nerve agents, such as soman, VX, tabun or sarin, or within the framework of the treatment of atherosclerosis.

The present invention also relates to a combination product comprising at least one protein as defined above, in particular SEQ ID NO: 2 or SEQ ID NO: 3, and at least one variant of the paraoxonase protein, for simultaneous or separate use or use spread over time intended for the prophylaxis or treatment of intoxications caused by insecticides or nerve agents, such as soman, VX, tabun or sarin.

The combined use of the protein of the invention, in particular SEQ ID NO: 2, with a variant of the paraoxonase protein, makes it possible to increase the stability of the paraoxonase, in particular within the framework of the prophylaxis or treatment of the intoxications caused by insecticides or nerve agents.

The present invention also relates to a protein assay method as defined above, characterized in that it comprises the following stages:

rabbit monoclonal antibodies directed against different epitopes of the protein of the invention (anti-HPB) are fixed on a plate and the human serum to be analyzed containing said protein (HPB) is applied to the above-mentioned plate, the plate is rinsed and washed, antibodies directed against rabbit antibodies (anti-IGrabbit-per) marked with peroxidase are applied to the plate over 30 minutes, in order to form a ternary complex between a rabbit monoclonal antibody, the protein according to the invention and an above-mentioned antibody directed against a rabbit antibody (anti-HPB-HPB-anti-IGrabbit-per), the plate is rinsed and washed, the peroxidase fixed to the plate is reacted with its substrate (commercially available kit, Chemiluminescent Peroxidase Substrate (Sigma)) and the reaction is stopped at the end of 30 minutes with 3,3',5,5'-tetramethylbenzidine (TMB, Sigma), the optical density of the product formed in the preceding stage is measured at 450 nm using a spectrophotometer, and comparison of this measurement with a standard curve makes it possible to determine the concentration of the protein according to the invention (HPB) present in the serum.

Thus, the above-mentioned assay method uses an ELISA-type immunoassay method (Engvall et al., 1971).

Other methods can be used to assay the concentration of the protein of the invention in the plasma such as:

electrophoretic methods, or the quantification of its activity.

The present invention also relates to the application of the assay method as defined above to the in vitro diagnosis of diseases linked to hyperphosphataemia in particular when the quantity of protein as defined above, in particular SEQ ID NO: 2 or SEQ ID NO: 3, assayed according to the method as defined above, is less than the quantity of this protein normally present in the blood of a healthy individual, or to the in vitro diagnosis of diseases linked to hypophosphataemia in particular when the quantity of protein as defined above, in particular SEQ ID NO: 2 or SEQ ID NO: 3, assayed according to the method as defined above, is greater than the quantity of this protein normally present in the blood of a healthy individual, or to the in vitro diagnosis of an individual's predisposition to such pathologies.

The level of the protein according to the invention is an indicator of predisposition to a risk of cardiovascular disease. Thus, individuals having a low level of said protein will have a higher level of free phosphate which will precipitate with the calcium in the plasma to form calcium phosphate plates, which is a factor aggravating in particular the risks of cardiovascular diseases or arthritis.

An abnormal level of this protein is also the sign of an existing pathology. For example hyperphosphataemia can trigger an increased production of protein in order to limit the phosphate level. A low level can also reveal a dysfunction.

The present invention also relates to the application as defined above to the in vitro diagnosis of diseases linked to hyperphosphataemia such as cardiovascular diseases, in particular cardiovascular diseases linked to the formation of atheroma plaques, or to the in vitro diagnosis of an individual's predisposition to develop one of the above-mentioned diseases.

The present invention also relates to the application as defined above to the in vitro diagnosis of diseases linked to hypophosphataemia, or to the in vitro diagnosis of an individual's predisposition to develop these diseases.

Among the clinical or physiological signs characterizing diseases linked to hypophosphataemia, there can be mentioned:
- a demineralization of the bones,
- the muscular manifestations of hypophosphataemia which comprise a proximal myopathy affecting the skeletal muscle and dysphagia and an ileus affecting the smooth muscles,
- cardiopulmonary deficiencies due to the lack of ATP, and metabolic encephalopathy.

LEGENDS TO THE FIGURES

FIG. 1 represents an SDS-PAGE gel of the final fractions within the framework of the purification of human paraoxonase and the protein of the invention SEQ ID NO: 2.

Column A corresponds to the molecular weight marker and columns B, C and D to three different purifications originating from different bags of human plasma. They all three contain human paraoxonase and the phosphate-binding protein.

FIG. 2 represents the diagrammatic structure of the protein of the invention SEQ ID NO: 2 to which a phosphate molecule is bound.

FIG. 3 corresponds to a test of phosphate binding by the protein of the invention SEQ ID NO: 2.

Columns A to F correspond to different batches of purification of the protein of the invention originating from different bags of human plasma; column G to lysozyme 1 mg/ml and column H to β-lactoglobulin.

FIG. 5 represents the molecular coordinates of the crystallized protein of the invention SEQ ID NO: 2.

EXPERIMENTAL PART

Isolation of the Protein

Figure 1:
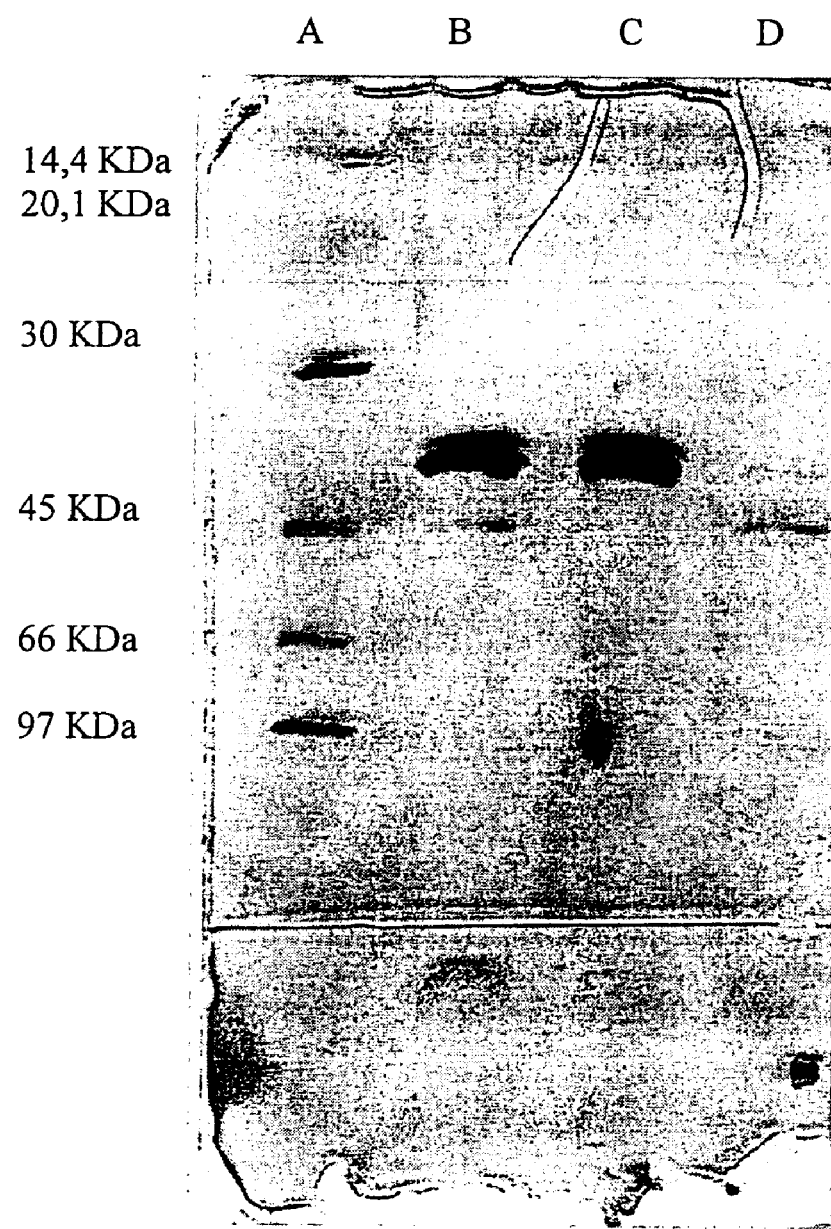

The protein SEQ ID NO: 2 is obtained from human plasma according to the following method of Gan et al. (1991):

The protein SEQ ID NO: 2 is purified from bags of frozen plasma (~200 ml) supplied by the Etablissement de Transfusion Sanguine of Lyon-Beynost. The fibrin clot, formed by the addition of 1 M (1% v/v) of $CaCl_2$ to the plasma is separated from the serum by filtration. The serum is then mixed with 400 ml of affinity gel (Cibacron 3GA-Agarose, C-1535, Sigma) equilibrated with a buffer A (Tris/HCl 50 mM, $CaCl_2$ 1 mM, NaCl 4M, pH 8). Under these conditions, mainly the HDLs ("high density lipoproteins") are adsorbed. After incubation for 6 to 8 hours, the proteins not adsorbed on the gel are eliminated by filtration on a fritted disc of porosity No. 2. This washing is carried out until no more protein is detected in the eluate (UV absorption at 280 nm). The gel is then equilibrated with a buffer B (Tris/HCl 50 mM, $CaCl_2$ 1 mM, pH 8) then placed in an XK 50/30 column (Pharmacia). The elution is carried out by adding 1 g/l of sodium deoxycholate and 0.1% of triton X-100 to buffer B. The fractions showing an arylesterase activity are injected onto 50 ml of an anion-exchange gel (DEAE Sepharose Fast Flow, Pharmacia) arranged in an XK 26/70 column (Pharmacia) and equilibrated with buffer B and 0.05% triton X-100. The elution is carried out by NaCl gradient. A first plateau is reached at 87.5 mM of NaCl in order to eliminate the apo A-I, a protein linked to paraoxonase, and the majority of the contaminating proteins. Human paraoxonase (PON1) is approximately eluted at a concentration of 140 mM of NaCl. All the fractions retained show a paraoxonase and arylesterase activity, these activities being verified according to the tests mentioned below. The eluted fractions are not brought back together. The SDS-PAGE gels of the fractions obtained show bands comprised between 38 kDa and 45 kDa (see FIG. 1). Each purification does not always result in the same apparent mass distribution. This slight heterogeneity can be explained by the presence of 2 glycosylated chains on the PON1.

In addition to the PON1 in these batches another protein has been isolated by crystallization, by substituting C12-maltoside for triton and using ammonium sulphate as precipitating agent. The crystals obtained are those of an unknown protein characterized by radiocrystallography and corresponding to the sequence SEQ ID NO: 2 of the invention. Crystallization is at present the only existing method for purifying this protein.

The paraoxonase activity is measured in a glycine 50 mM/NaOH, $CaCl_2$ 1 mM buffer, in the presence of 1 M NaCl, pH 10.5 and is determined by means of a double beam spectrophotometer (Shimadzu UV 160A) thermostatically controlled at 25° C. The speed of hydrolysis is determined according to the variation of absorbance at 412 nm, corresponding to the formation of p-nitrophenol released by the hydrolysis of paraoxon, as a function of time, $\epsilon=18290$ $M^{-1}cm^{-1}$ (Smolen, 1991).

The arylesterase activity is measured in a tris 50 mM/HCl, $CaCl_2$ 1 mM buffer, pH 8 and is determined by means of a double beam spectrophotometer (Shimadzu UV 160A) thermostatically controlled at 25° C. The speed of hydrolysis is determined according to the variation in absorbance at 270 nm, corresponding to the formation of phenol released by the hydrolysis of phenyl acetate, as a function of time, $\epsilon=1310$ $M^{-1}cm^{-1}$ (Smolen, 1991).

Structure

Figure 2:
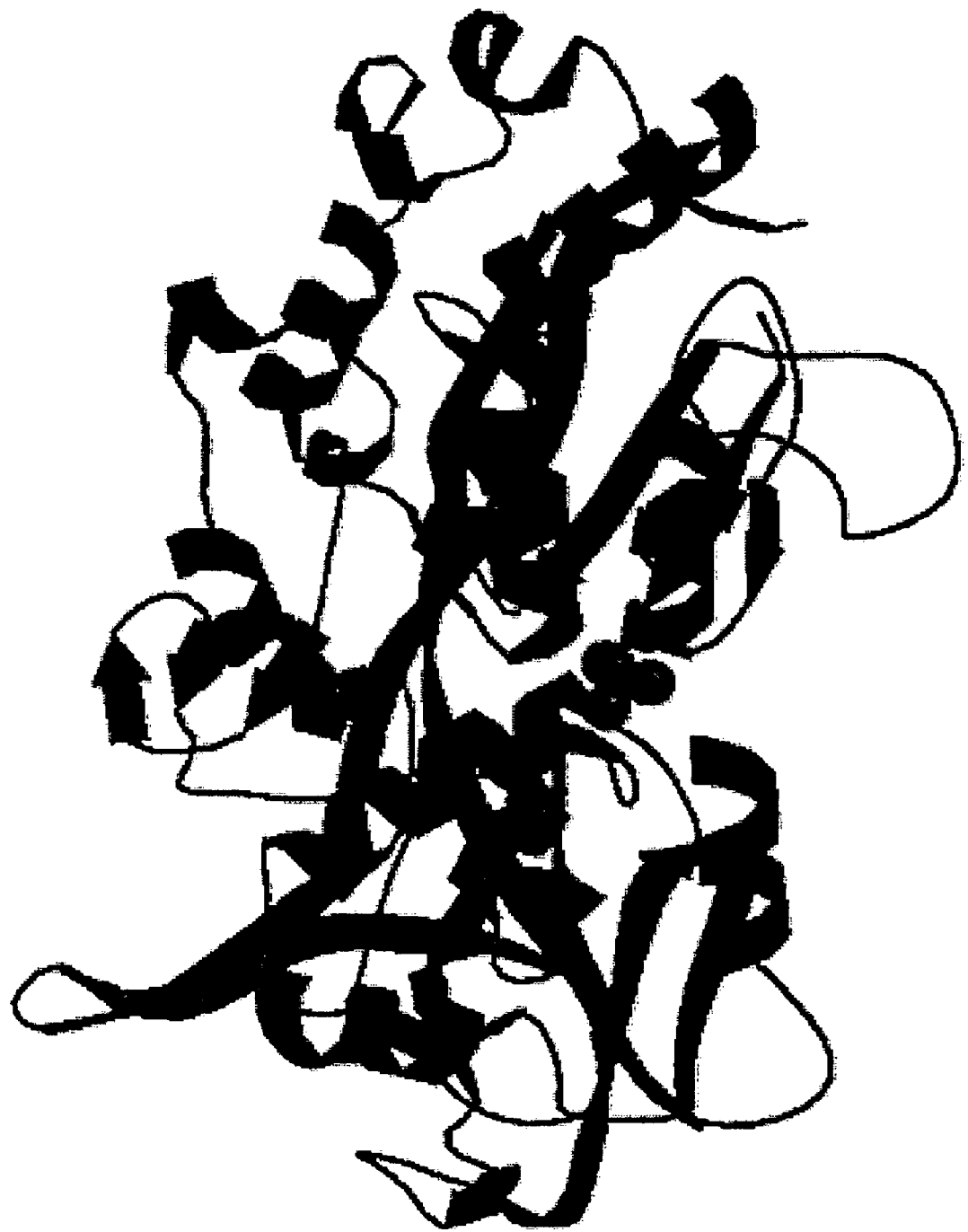

The structure of the crystallized protein SEQ ID NO: 2 was obtained by X-ray crystallography. The structure at 1.9 Å resolution was obtained by the SIRAS (Single Isomorphous Replacement and Anomalous Scattering) method (FIG. 2).

The X-ray diffraction data were collected on the BM30 line of the ESRF (Grenoble).

A heavy atom salt derivative was obtained by soaking a crystal in a solution containing uranium salts.

The images were integrated, scaled and combined with the XDS2000 programs (Kabsch, 1993) and the CCP4 suite (COLLABORATIVE COMPUTATIONAL PROJECT, NUMBER 4. 1994. "The CCP4 Suite: Programs for Protein Crystallography". Acta Cryst. D50, 760-763).

The CNS (BRUNGER, 1998) and SnB (Weeks, 1999) programs were used in order to locate the uranium atoms. The SHARP program (Copyright © 2001-2002 the Buster Development Group) was used in order to obtain the phases by the SIRAS technique.

372 amino acids were constructed automatically in the electronic density map by the ARP/wARP (Perrakis, 1997) program. This first model was then refined by the CNS program.

Because of the very good quality of the electronic density map, it was possible to assign 80% reliability to the primary sequence of the protein. It was also possible to locate a phosphate molecule.

The structure obtained does not at all correspond to human paraoxonase. The sequencing obtained by identifying the amino acids from the electronic density indicates that neither this human protein nor its gene have been described previously. It is therefore a novel protein.

The structure of the protein of the invention exhibits a very strong homology with the phosphate-binding protein of *Escherichia coli*. This protein in this bacterium serves to transport the phosphate across the periplasm. It is found in many prokaryotes but in no eukaryote.

The electronic density also showed that a phosphate molecule was bound to the novel protein of the invention, in the same manner as in that of *Escherichia coli*.

Thus, it can be concluded that the protein of the invention characterized from human plasma has a very strong homology with the bacterial protein and that it is capable of binding phosphate and transporting it.

Sequencing

Digestion in the Gel

The paraoxonase-HPBP mixture was separated by electrophoretic gel with SDS-PAGE (without heating). Several bands corresponding to HPBP in the region of 70 kDa were cut out.

The digestion of the protein contained in these bands was carried out by means of the automatic digestion system, MassPrep Station (Waters Manchester, UK). The gel bands were washed twice with 50 µl of a solution of 25 mM of ammonium bicarbonate ($NH_4HCO_3$) and 50 µl of acetonitrile. The cysteines were reduced with 50 µl of a 10 mM dithiothreitol solution at 57° C. and acylated with 50 µl of 55 mM iodoacetamide. After dehydration with acetonitrile, the protein was digested enzymatically with 10 µl of modified porcine trypsin at 12.5 ng/µl (Promega, Madisson, Wis., U.S.A) or with lys-C of Lysobacter enzymogenes (Roche Applied Science, Penzberg, Germany) in 25 mM of $NH_4HCO_3$. The digestion is carried out overnight at ambient temperature. The cleaved peptides were extracted with a 60% acetonitrile solution and 5% formic acid.

Mass Spectrometry Analysis

MALDI-MS and MALDI-MS/MS

MALDI-TOF mass measurements were carried out on an Ultraflex™ TOF/TOF (Bruker, Daltonik GmbH, Bremen, Germany). This instrument was used with a maximum acceleration voltage of 25 KV in reflectron mode. The sample was prepared with the standard drop preparation dried over the stainless steel target using α-cyano-4-hydroxycinnamic acid as matrix.

The external calibration of the MALDI-MS spectrum was carried out using only the peaks of the monoisotopic charges of a known solution of peptides (bradykinin 1-7 (m/z=757.400), human angiotensin II (m/z=1046.542), human angiotensin I (m/z=1296.685), substance P (m/z=1347.735), bombesin (m/z=1619.822), renin (m/z=1758.933), ACTH 1-17 (m/z=2093.087) and ACTH 18-39 (m/z=2465.199)). The masses of the monoisotopic peptides were automatically annotated using the Flexanalysis 2.0 program.

The MS/MS spectra were obtained by analysis of the metastable ions obtained by "Laser-Induced Decomposition" (LID) of a sectioned ion precursor, without additional collision in the gas phase. The ion precursor was accelerated to 8 kV and was selected by means of a timed ion gate. The fragments were further accelerated by 19 kV in the LIFT cell and their masses measured after passing the ion reflector.

The de novo sequencing of each of these MS/MS spectra was carried out with the Full DeNovo Sequencing program (Biotools, Bruker Daltonik GmbH, Bremen, Germany).

Nano LC-MS/MS

Nano LC-MS/MS analysis was carried out using a CapLC (Waters, Manchester, UK) coupled to a time-of-flight mass spectrometer accelerated by an Q-TOF II orthogonal hybrid quadrupole (Micromass, Manchester, UK). Separation by reversed-phase chromatography was carried out with capillaries (Pepmap C18, 75 µm i.d., 15 cm long, LC Packings) under a flow of 200 nL/min, kept constant by means of a partition pre-column. The calibration was carried out using 2 pmol/µl of GFP.

The mass data acquisition was controlled by the MassLynx program (Micromass, Manchester, UK) which automatically switches between the MS mode and the MS/MS mode.

The MS/MS spectra generated were individually sequenced de novo in order to obtain the partial or complete sequence. These interpretations were made using the PepSeq program (MassLynx, Micromass) and the PEAKS Studio program (Bioinformatics Solutions. Waterloo, Canada) which are capable of completely processing a .pkl file with a de novo automatic sequencing on each MS/MS spectrum.

Phosphate Binding

Figure 3:
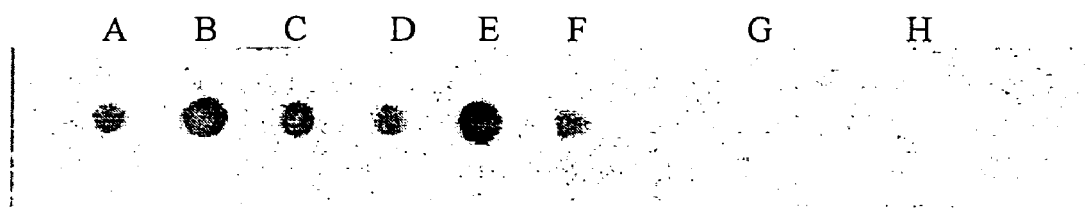

Phosphate binding by the protein of the invention SEQ ID NO: 2 was demonstrated according to the following test:

200 µl of the protein of the invention SEQ ID NO: 2 (columns A-F of FIG. 3), or 1 mg/ml lysozyme (column G) or of β-lactoglobulin was applied to nitrocellulose (dot blot by aspiration).

The mixture is incubated for 2 hours 30 minutes in a mixture comprising: tris 50 mM; pH 8.0; $^{32}P$ (10 mCi/ml) 2 mM.

Rinsing was then carried out twice for 1 minute with tris 50 mM at pH 8.0, then the mixture is exposed at ambient temperature for 45 minutes.

It is then noted (see FIG. 3) that the protein of the invention has bound the radioactive phosphate (columns A to F), whereas the test controls have not bound it (columns G and H).

Role and Use of the Protein SEQ ID NO: 2

For assaying the concentration of this protein in the plasma the methods which can be used are:
- the electrophoretic methods,
- the purification of the protein,
- the quantification of its activity,
- the immunoassay of the protein using polyclonal/monoclonal antibodies directed against the protein.

Combination with Paraoxonase

Two-Dimensional Electrophoresis

The purified proteins (40 µg) as described previously in the protocol are mixed with 100 µL of a solution containing 9.8 M of urea, 4% (v/v) triton X100, 2 mM tributyl phosphine, 0.2% (v/v) ampholine 3-10 (Bio-Lytes 3-10; Bio-Rad), and 0.001% (m/v) bromophenol blue. Ready-to-use polyacrylamide gel strips (IPG-Strips; Bio-Rad) (T: 4%; C: 3%) are used. Ampholines were bound to the polyacrylamide in a covalent manner so as to have a pre-established linear pH gradient. The pH gradient used is between 3.0 and 10.0.

1. Isoelectric Focusing (IEF)

The strips are placed in contact with the protein samples in the Protean IEF Cell device (Bio-Rad) and actively rehydrated (50 V constant) for 15 hours at 20° C. Isoelectric focusing is then carried out in 3 stages at 20° C. Firstly, a low voltage of 250 V is applied for 15 minutes; secondly, a rise in gradient from 250 to 4000 V (amperage limited by 50 µA strip) is programmed over 2 hours. Thirdly, the voltage is held constant at 4000 V for 4 hours. After migration, the strips are stored at −20° C.

Figure 4:
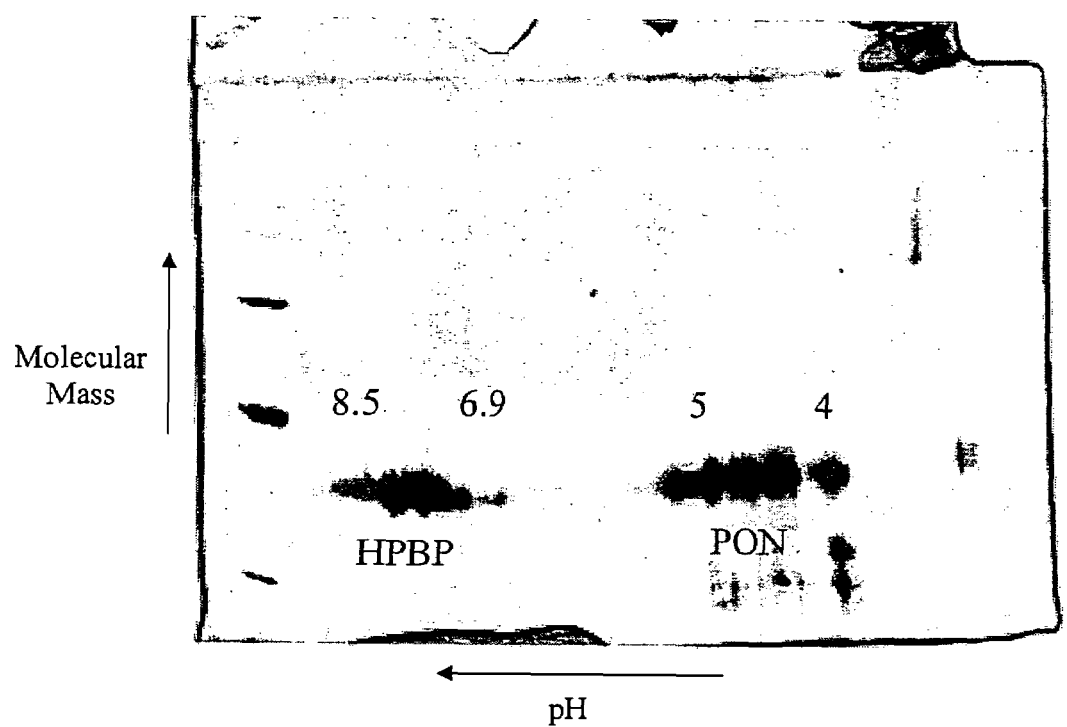
FIG. 4 represents a two-dimensional electrophoresis gel of a mixture of the protein of the invention SEQ ID NO: 2 and paraoxonase.

According to the preceding purification protocol, the HPBP protein of the invention is co-purified with human paraoxonase (PON) (Fokine et al., 2003). By making a two-dimensional gel with the above protocol, 2 spots were identified by N-terminal sequencing as being respectively the protein of the invention HPBP and human paraoxonase (see FIG. 4). The two proteins have approximately the same molecular mass (approximately 40 kDa) and distinct isoelectric points, 6.9-8.5 for HPBP and 4-5 for PON1. Taking account of the fact that it has been necessary to use drastic conditions in order to succeed in separating the 2 proteins (9M of urea and 4% triton) on gel and that the 2 proteins which have very different isoelectric points remain co-purified after passage through an anion exchange column (DEAE sepharose), it is concluded that they are combined by forming a complex.

BIBLIOGRAPHICAL REFERENCES

Amann K., Tornig J., Kugel B., Gross M. L., Tyralla K., El-Shakmak A., Szabo A., Ritz E. (2003) *Kidney Int.* 63(4): 1296-1301;
Blazheevich N. V., Spirichev V. B., Pozdniakov A. L. (1975) *Kardiologiia.* 15(6): 67-71;
Brunger A. T., Adams P. D., Clore G. M., Delano W. L., Gros P., Grosse-Kunstleve R. W., Jiang J.-S., Kuszewski J., Nilges N., Pannu N. S., Read R. J., Rice L. M., Simonson T. et Warren G. L. (1998) *Acta Cryst.* D54: 905-921;
Dorozhkin S. V., Epple M. (2002) *Angew Chem Int Ed Engl.* 41(17): 3130-46;
Engvall E., Jonsson K., Perlmann P. (1971) *Biochim Biophys Acta.* (1971) 251: 427-34;
Fokine A., Morales R., Contreras-Martel C., Carpentier P., Renault F., Rochu D., Chabriere E. (2003) *Acta Crystallogr D.* 59, 2083-7;
Gan, K. N., Smolen, A., Eckerson, H. W. & La Du, B. N. (1991). *Drug Metab Dispos.* 19, 100-106;
Hassett, C., Richter, R. J., Humbert, R., Chapline, C., Crabb, J. W., Omiecinski, C. J. et Furlong, C. E. (1991) *Biochemistry* 30(42), 10141-10149;
Kabsch W. (1993) *J. Appl. Cryst.* 26: 795-800;
Perrakis, A., Sixma, T. K., Wilson, K. S., et Lamzin, V. S. (1997) *Acta Cryst.* D53: 448-455;
Primo-Parmo, S. L., Sorenson, R. C., Teiber, J. et La Du, B. N. (1996) *Genomics* 33 (3), 498-507;
Ramsdell R. (1999) *Anna J.* 26(3): 346-7;
Reddy, S. T., Wadleigh, D. J., Grijalva, V., Ng, C., Hama, S., Gangopadhyay, A., Khorsan, R., Shih, D., Lusis, A. J., Navab, M. et Fogelman, A. M. (2001) *Arterioscler Thromb Vasc Biol* 21(4): 542-7;
Rodrigo, L., Gil, F., Hernandez, A. F., Marina, A., Vazquez, J. and Pla, A. (1997) *Biochem. J.* 321, 595-601;
Smolen A, Eckerson H W, Gan K N, Hailat N, La Du B N. (1991) *Drug Metab Dispos.,* 19: 107-112;
Sorenson, R. C., Primo-Parmo, S. L., Kuo, C. L., Adkins, S., Lockridge, O. and La Du, B. N. (1995) *Proc. Natl. Acad. Sci. U.S.A.* 92 (16), 7187-7191;
Weeks, C. M. & Miller, R. (1999) *J. Appl. Cryst.* 32, 120-124.

The invention claimed is:

1. An isolated protein that comprises or is constituted by the amino acid sequence of SEQ ID NO: 1.

2. The isolated protein of claim 1, wherein said protein comprises or is constituted by the amino acid sequence of SEQ ID NO: 2 or SEQ ID NO: 3.

3. A pharmaceutical composition comprising, as active ingredient, the isolated protein according to claim 1, in combination with a pharmaceutically acceptable vehicle.

4. The pharmaceutical composition according to claim 3, in which the isolated protein is in combination with a paraoxonase protein comprising an amino acid sequence selected from the group consisting of: SEQ ID NO: 4, SEQ ID NO: 5, and SEQ ID NO: 6.

5. The pharmaceutical composition according to claim 4, wherein the isolated protein is an isolated protein of SEQ ID NO: 2 or SEQ ID NO: 3.

6. A combination product comprising:
at least the isolated protein according to claim 1, and
at least one paraoxonase protein consisting of the amino acid sequence selected from the group consisting of: SEQ ID NO: 4, SEQ ID NO: 5, and SEQ ID NO: 6,
for simultaneous or separate use, or use spread over time, intended for the prophylaxis or treatment of intoxications caused by insecticides or nerve agents.

7. The combination product according to claim 6, wherein said isolated protein is an isolated protein of SEQ ID NO: 2 or SEQ ID NO: 3.

8. The combination product according to claim 6, wherein said nerve agents are soman, VX, sarin, or tabun.

9. A method for determining the concentration in human plasma of the isolated protein according to claim 1, said method being chosen from:
eletrophoretic methods;
purification of the protein;
quantification of protein activity; and
immunoassay of the protein using polyclonal/monoclonal antibodies directed against said protein.

10. The method for determining the concentration in human plasma of the isolated protein according to claim 9, wherein the immunoassay is an ELISA-type immunoassay.

11. The method according to claim 9, wherein said isolated protein is the isolated protein of SEQ ID NO: 2 or SEQ ID NO: 3.

12. A pharmaceutical composition, comprising as active ingredient, a protein represented by the amino acid sequence of SEQ ID NO: 2 or SEQ ID NO: 3, in combination with a pharmaceutically acceptable vehicle.

13. An isolated nucleotide sequence encoding the protein that comprises or is constituted by the amino acid sequence of SEQ ID NO: 1.

14. A recombinant vector comprising a nucleotide sequence encoding an isolated protein wherein the isolated protein comprises or is constituted by the amino acid sequence of SEQ ID NO: 1.

15. The recombinant vector according to claim 14, wherein said recombinant vector is a plasmid, a cosmid, a phage, or a virus DNA.

16. The recombinant vector according to claim 14, further comprising operable elements for expression in a host cell of the isolated protein encoded by the nucleotide sequence, inserted into said vector.

17. An isolated host cell transformed with a recombinant vector containing a nucleotide sequence encoding an isolated protein wherein the isolated protein comprises or is constituted by the amino acid sequence of SEQ ID NO: 1.

18. The host cell according to claim 17, said host cell being chosen from bacteria, yeast, fungi, plant cells, or mammalian cells.

* * * * *